United States Patent
Watabe et al.

(10) Patent No.: US 12,419,155 B2
(45) Date of Patent: Sep. 16, 2025

(54) HOLE-TRANSPORT LAYER MATERIAL, ELECTRON-BLOCKING LAYER MATERIAL, ELECTRON-TRANSPORT LAYER MATERIAL, HOLE-BLOCKING LAYER MATERIAL, LIGHT-EMITTING DEVICE, LIGHT-EMITTING APPARATUS, ELECTRONIC DEVICE, AND LIGHTING DEVICE

(71) Applicant: SEMICONDUCTOR ENERGY LABORATORY CO., LTD., Atsugi (JP)

(72) Inventors: Takeyoshi Watabe, Kanagawa (JP); Hiromi Seo, Kanagawa (JP); Airi Ueda, Kanagawa (JP); Yuta Kawano, Kanagawa (JP); Tomohiro Kubota, Kanagawa (JP); Yasushi Kitano, Kanagawa (JP); Takao Tosu, Kanagawa (JP); Nobuharu Ohsawa, Kanagawa (JP); Satoshi Seo, Kanagawa (JP)

(73) Assignee: Semiconductor Energy Laboratory Co., Ltd., Atsugi (JP)

( * ) Notice: Subject to any disclaimer, the term of this patent is extended or adjusted under 35 U.S.C. 154(b) by 445 days.

(21) Appl. No.: 17/739,260

(22) Filed: May 9, 2022

(65) Prior Publication Data
US 2023/0029353 A1 Jan. 26, 2023

(30) Foreign Application Priority Data
May 13, 2021 (JP) .................................. 2021-081940

(51) Int. Cl.
*H10K 50/15* (2023.01)
*C07C 211/45* (2006.01)
(Continued)

(52) U.S. Cl.
CPC ............ *H10K 50/15* (2023.02); *C07C 211/45* (2013.01); *H10K 30/353* (2023.02); *H10K 50/18* (2023.02);
(Continued)

(58) Field of Classification Search
CPC ...... H10K 50/15; H10K 50/16; H10K 30/353; C07C 211/45
See application file for complete search history.

(56) References Cited

U.S. PATENT DOCUMENTS

| 9,412,962 B2 | 8/2016 | Hamada. et al. |
| 10,950,805 B2 | 3/2021 | Watabe et al. |

(Continued)

FOREIGN PATENT DOCUMENTS

WO  WO-2019/115577  6/2019

OTHER PUBLICATIONS

Dalasinski et al.; "Study of optical properties of TRIS (8-hydroxyquinoline) aluminum (III)"; Journal of Applied Physics 111, 114508 (2012) (Year: 2012).*

(Continued)

*Primary Examiner* — Syed I Gheyas
(74) *Attorney, Agent, or Firm* — Fish & Richardson P.C.

(57) ABSTRACT

An organic semiconductor device with low driving voltage is provided. The light-emitting device includes an anode, a cathode, and an EL layer between the anode and the cathode. The EL layer includes a hole-transport layer and a light-emitting layer. The hole-transport layer is positioned between the anode and the light-emitting layer. The hole-transport layer is not in contact with the anode. The hole-transport layer includes a transport layer material for a light-emitting device and the GSP_slope that is a potential gradient of a surface potential of an evaporated film of the material is higher than or equal to 20 (mV/nm).

21 Claims, 34 Drawing Sheets

(51) Int. Cl.
  *H10K 30/30* (2023.01)
  *H10K 50/18* (2023.01)
  *H10K 39/30* (2023.01)
  *H10K 101/00* (2023.01)

(52) U.S. Cl.
  CPC ........... *H10K 50/181* (2023.02); *H10K 39/30* (2023.02); *H10K 2101/00* (2023.02)

(56) References Cited

U.S. PATENT DOCUMENTS

| | | |
|---|---|---|
| 2007/0207346 A1 | 9/2007 | Saitoh et al. |
| 2009/0066227 A1 | 3/2009 | Okinaka et al. |
| 2009/0302758 A1 | 12/2009 | Saitoh et al. |
| 2010/0171417 A1 | 7/2010 | Kitamura. et al. |
| 2013/0207046 A1 | 8/2013 | Pflumm et al. |
| 2019/0016666 A1 | 1/2019 | Jeong et al. |
| 2020/0308129 A1 | 10/2020 | Montenegro et al. |
| 2021/0005814 A1 | 1/2021 | Watabe et al. |
| 2021/0143352 A1 | 5/2021 | Yamazaki et al. |
| 2021/0257562 A1 | 8/2021 | Watabe et al. |
| 2021/0317069 A1 | 10/2021 | Seo et al. |
| 2021/0336151 A1 | 10/2021 | Tosu et al. |
| 2021/0336176 A1 | 10/2021 | Kawano. et al. |
| 2022/0278292 A1 | 9/2022 | Watabe et al. |

OTHER PUBLICATIONS

Osada et al.; "Observation of spontaneous orientation polarization in evaporated films of organic light-emitting diode materials"; Organic Electronics 58 (2018) 313-317. (Year: 2018).*

Noguchi.Y et al., "Spontaneous Orientation Polarization of Polar Molecules and Interface Properties of Organic Electronic Devices", Journal of the Vacuum Society of Japan, Mar. 27, 2015, vol. 58, No. 3, pp. 109-116.

Noguch.Y et al., "Spontaneous orientation polarization in organic light-emitting diodes", Jpn. J. Appl. Phys. (Japanese Journal of Applied Physics), May 24, 2019, vol. 58, pp. SF0801-1-SF0801-10.

Noguchi.Y et al., "Charge accumulation at organic semiconductor interfaces due to a permanent dipole moment and its orientational order in bilayer devices", J. Appl. Phys. (Journal of Applied Physics), Jun. 5, 2012, vol. 111, No. 11, pp. 114508-1-114508-10.

Friederich.P et al., "Built-In Potentials Induced by Molecular Order in Amorphous Organic Thin Films", ACS Applied Materials & Interfaces, Jan. 5, 2018, vol. 10, No. 2, pp. 1881-1887.

* cited by examiner

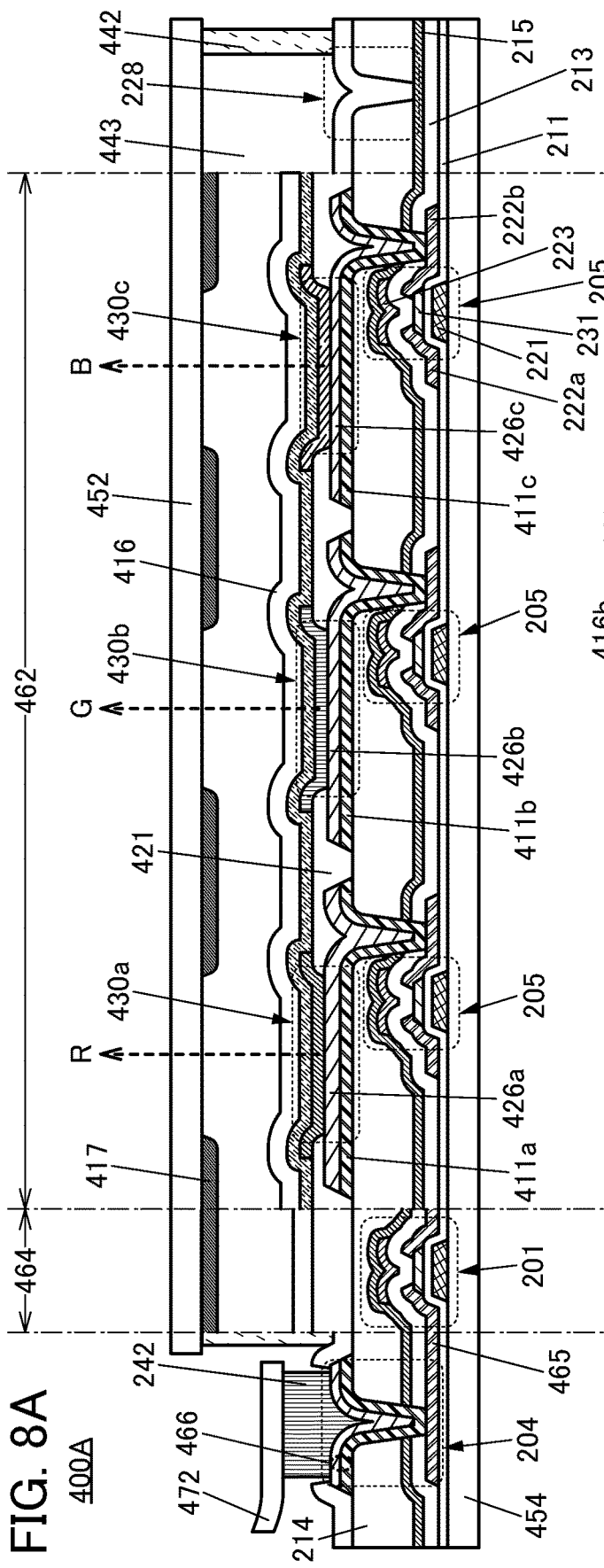
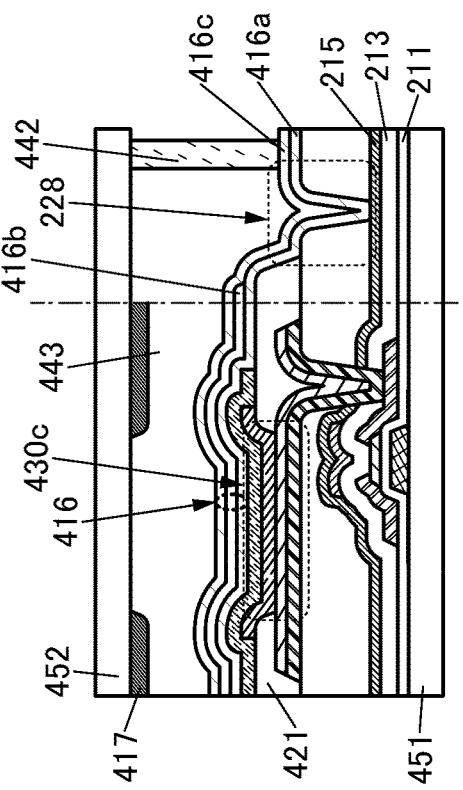
FIG. 8A
400A
FIG. 8B

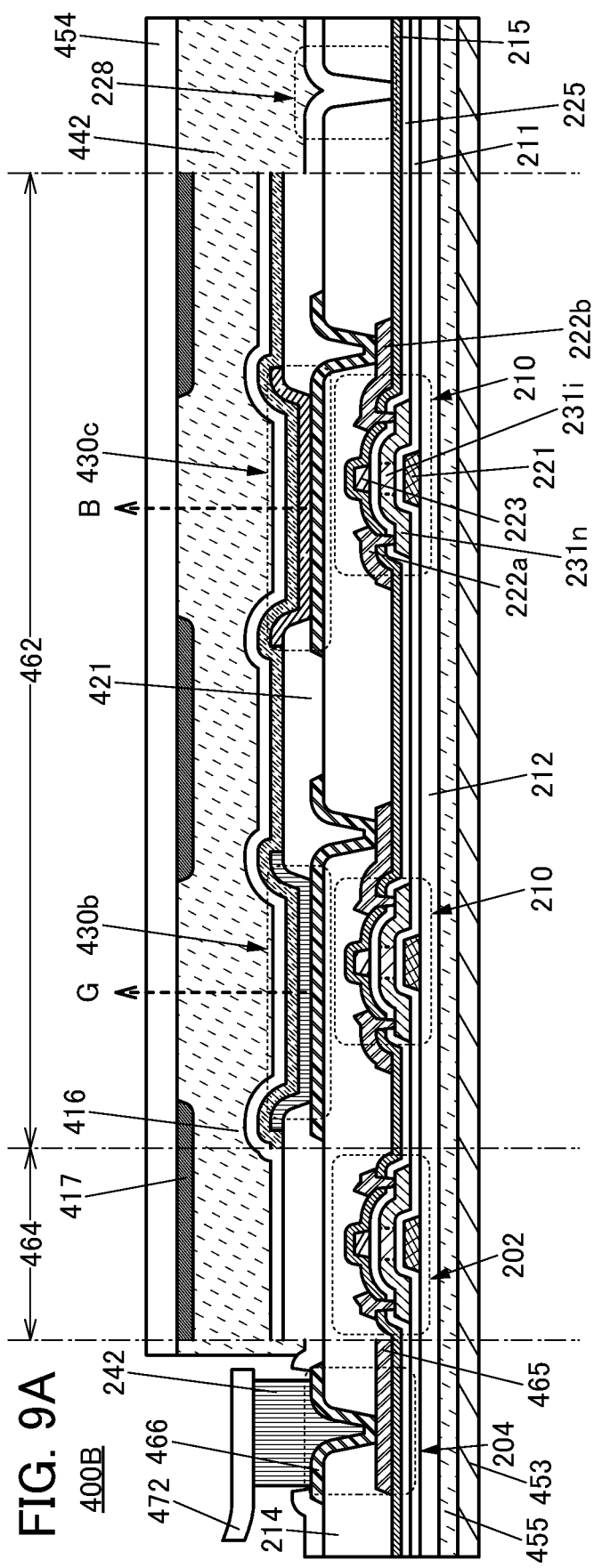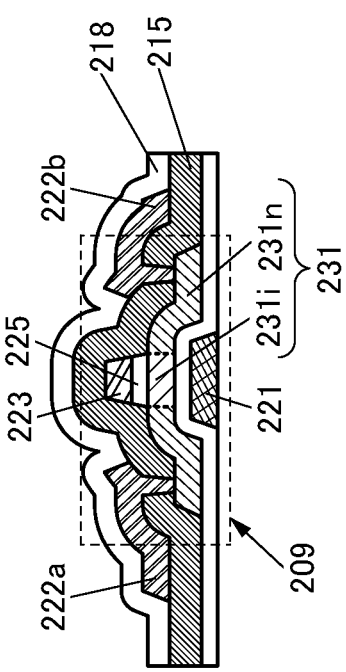

HOLE-TRANSPORT LAYER MATERIAL, ELECTRON-BLOCKING LAYER MATERIAL, ELECTRON-TRANSPORT LAYER MATERIAL, HOLE-BLOCKING LAYER MATERIAL, LIGHT-EMITTING DEVICE, LIGHT-EMITTING APPARATUS, ELECTRONIC DEVICE, AND LIGHTING DEVICE

BACKGROUND OF THE INVENTION

1. Field of the Invention

One embodiment of the present invention relates to an organic compound, an organic semiconductor device, a light-emitting element, a light-emitting device, an organic EL device, a photodiode sensor, a display module, a lighting module, a display device, a light-emitting apparatus, an electronic apparatus, a lighting device, and an electronic device. Note that one embodiment of the present invention is not limited to the above technical field. The technical field of one embodiment of the invention disclosed in this specification and the like relates to an object, a method, or a manufacturing method. One embodiment of the present invention relates to a process, a machine, manufacture, or a composition of matter. Specifically, examples of the technical field of one embodiment of the present invention disclosed in this specification include a semiconductor device, a display device, a liquid crystal display device, a light-emitting apparatus, a lighting device, a power storage device, a memory device, an imaging device, a driving method thereof, and a manufacturing method thereof.

2. Description of the Related Art

Light-emitting devices (organic EL devices) including organic compounds and utilizing electroluminescence (EL) have been put to more practical use. In the basic structure of such light-emitting devices, an organic compound layer containing a light-emitting material (an EL layer) is sandwiched between a pair of electrodes. Carriers are injected by application of voltage to the device, and recombination energy of the carriers is used, whereby light emission can be obtained from the light-emitting material.

Such light-emitting devices are of self-luminous type and thus have advantages over liquid crystal displays, such as high visibility and no need for backlight when used as pixels of a display, and are particularly suitable for flat panel displays. Displays including such light-emitting devices are also highly advantageous in that they can be thin and lightweight. Moreover, such light-emitting devices also have a feature that response speed is extremely fast.

Since light-emitting layers of such light-emitting devices can be successively formed in a planar shape, planar light emission can be achieved. This feature is difficult to realize with point light sources typified by incandescent lamps and LEDs or linear light sources typified by fluorescent lamps; thus, the light-emitting devices also have great potential as planar light sources, which can be used for lighting devices and the like.

Displays or lighting devices including light-emitting devices are suitable for a variety of electronic devices as described above, and research and development of light-emitting devices has progressed for more favorable characteristics (see Non-Patent Document 1, for example).

REFERENCE

Non-Patent Document

[Non-Patent Document 1] Y. Noguchi et al., "Spontaneous Orientation Polarization of Polar Molecules and Interface Properties of Organic Electronic Devices", Journal of the Vacuum Society of Japan, 2015, Vol. 58, No. 3.

SUMMARY OF THE INVENTION

An object of one embodiment of the present invention is to provide any of a transport layer material, a hole transport layer material, an electron transport layer material, an electron blocking layer material, and a hole blocking layer material, which can provide an organic semiconductor device with low driving voltage. Another object of one embodiment of the present invention is to provide any of a transport layer material, a hole transport layer material, an electron transport layer material, an electron blocking layer material, and a hole blocking layer material, which can provide a light-emitting device with low driving voltage. Another object of one embodiment of the present invention is to provide any of a transport layer material, a hole transport layer material, an electron transport layer material, an electron blocking layer material, and a hole blocking layer material, which can provide a photodiode sensor with low driving voltage. Another object of one embodiment of the present invention is to provide any of a transport layer material, a hole transport layer material, an electron transport layer material, an electron blocking layer material, and a hole blocking layer material, which can provide any of a light-emitting apparatus, an electronic device, a display device, and an electronic device having low power consumption.

An object of one embodiment of the present invention is to provide an organic semiconductor device with low driving voltage. Another object of one embodiment of the present invention is to provide a light-emitting device with low driving voltage. Another object of one embodiment of the present invention is to provide a photodiode sensor with low driving voltage. Another object of one embodiment of the present invention is to provide any of a light-emitting apparatus, an electronic apparatus, a display device, and an electronic device each having low power consumption.

It is only necessary that at least one of the above-described objects be achieved in the present invention.

One embodiment of the present invention is a hole transport layer material for alight-emitting device. The GSP_slope (mV/nm) that is a potential gradient of a surface potential of an evaporated film of the material is higher than or equal to 20 (mV/nm).

Another embodiment of the present invention is the hole transport layer material for a light-emitting device with a GSP_slope lower than or equal to 100 (mV/nm).

Another embodiment of the present invention is the above-described hole transport layer material for a light-emitting device. The ordinary ray refractive index of the material with respect to light with a wavelength of 450 nm is higher than or equal to 1.50 and lower than or equal to 1.75.

Another embodiment of the present invention is the above-described hole transport layer material for a light-emitting device. The ordinary ray refractive index of the material with respect to light with a wavelength of 633 nm is higher than or equal to 1.45 and lower than or equal to 1.70.

Another embodiment of the present invention is the above-described hole transport layer material for a light-emitting device. The glass transition temperature (Tg) of the material is higher than or equal to 100° C.

Another embodiment of the present invention is the above-described hole transport layer material for a light-emitting device. The material includes at least three substituents selected from a chain alkyl group having 2 to 5 carbon atoms and a cycloalkyl group having 6 to 12 carbon atoms.

Another embodiment of the present invention is the above-described hole transport layer material for a light-emitting device. The alkyl group is a branched-chain alkyl group having 3 to 5 carbon atoms.

Another embodiment of the present invention is the above-described hole transport layer material for a light-emitting device. The alkyl group is a t-butyl group.

Another embodiment of the present invention is the above-described hole transport layer material for a light-emitting device. The percentage of carbon atoms forming a bond by $sp^3$ hybrid orbitals in the total number of carbon atoms in a molecule is higher than or equal to 23% and lower than or equal to 55%.

Another embodiment of the present invention is the above-described hole transport layer material for a light-emitting device. The integral value of signals lower than 4 ppm exceeds the integral value of signals at 4 ppm or higher in a $^1$H-NMR measurement of the material.

Another embodiment of the present invention is the above-described hole transport layer material for a light-emitting device. The material has a hole-transport property.

Another embodiment of the present invention is the above-described hole transport layer material for a light-emitting device. The material is arylamine.

Another embodiment of the present invention is the above-described hole transport layer material for a light-emitting device. When the material includes a condensed aromatic hydrocarbon ring, the condensed aromatic hydrocarbon ring is a monocyclic condensed aromatic ring, a bicyclic condensed aromatic ring, or a tricyclic condensed aromatic ring and the total number of condensed aromatic hydrocarbon rings in a molecule of the material is preferably one or two.

Another embodiment of the present invention is the above-described hole transport layer material for a light-emitting device. The material includes two or less fluorene skeletons in a molecule.

Another embodiment of the present invention is an electron blocking layer material including the above-described hole transport layer material Another embodiment of the present invention is an electron transport layer material for a light-emitting device. The GSP_slope (mV/nm) that is a potential gradient of a surface potential of an evaporated film of the material is higher than or equal to 20 (mV/nm). The ordinary ray refractive index of the material with respect to light with a wavelength of 450 nm is higher than or equal to 1.50 and lower than or equal to 1.75.

Another embodiment of the present invention is an electron transport layer material for a light-emitting device. The GSP_slope that is a potential gradient of a surface potential of an evaporated film of the material is higher than or equal to 20 (mV/nm), and the ordinary ray refractive index of the material with respect to light with a wavelength of 633 nm is higher than or equal to 1.45 and lower than or equal to 1.70.

Another embodiment of the present invention is the above-described electron transport layer material for a light-emitting device. The GSP_slope is lower than or equal to 100 (mV/nm).

Another embodiment of the present invention is the above-described electron transport layer material for a light-emitting device. The glass transition temperature (Tg) of the material is higher than or equal to 100° C.

Another embodiment of the present invention is the above-described electron transport layer material for a light-emitting device. The material includes at least three substituents selected from a chain alkyl group having 2 to 5 carbon atoms and a cycloalkyl group having 6 to 12 carbon atoms.

Another embodiment of the present invention is the above-described electron transport layer material for a light-emitting device. The alkyl group is a branched-chain alkyl group having 3 to 5 carbon atoms.

Another embodiment of the present invention is the above-described electron transport layer material for a light-emitting device. The alkyl group is a t-butyl group.

Another embodiment of the present invention is the above-described electron transport layer material for a light-emitting device. The percentage of carbon atoms forming a bond by $sp^3$ hybrid orbitals in the total number of carbon atoms in a molecule is higher than or equal to 23% and lower than or equal to 55%.

Another embodiment of the present invention is the above-described electron transport layer material for alight-emitting device. The integral value of signals at lower than 4 ppm exceeds an integral value of signals at 4 ppm or higher in a $^1$H-NMR measurement of the material.

Another embodiment of the present invention is the above-described electron transport layer material for a light-emitting device. The material has an electron-transport property.

Another embodiment of the present invention is a hole blocking layer material including the above-described electron transport layer material.

Another embodiment of the present invention is a light-emitting device including an anode, a cathode, and an EL layer between the anode and the cathode. The EL layer includes a hole-transport layer and a light-emitting layer. The hole-transport layer is positioned between the anode and the light-emitting layer. The hole-transport layer is not in contact with the anode. The hole-transport layer includes the above-described hole transport layer material or the above-described electron transport layer material.

Another embodiment of the present invention is a light-emitting device including an anode, a cathode, and an EL layer between the anode and the cathode. The EL layer includes a hole-injection layer, a hole-transport layer, and a light-emitting layer. The hole-injection layer and the hole-transport layer are positioned between the anode and the light-emitting layer. The hole-transport layer is positioned between the hole-injection layer and the light-emitting layer. The hole-transport layer includes the above-described hole transport layer material.

Another embodiment of the present invention is the above-described light emitting device. The hole-transport layer is in contact with the light-emitting layer.

Another embodiment of the present invention is a light-emitting device including an anode, a cathode, and an EL layer between the anode and the cathode. The EL layer includes a hole-injection layer, a hole-transport layer, an electron-blocking layer, and a light-emitting layer. The hole-injection layer, the hole-transport layer, and the electron-blocking layer are positioned between the anode and the light-emitting layer. The electron-blocking layer is in contact with the light-emitting layer. The hole-injection layer is in contact with the anode. The electron-blocking layer includes the above-described electron blocking layer material.

Another embodiment of the present invention is the above-described light emitting device. The GSP_slope of an evaporated film of an organic compound included in the hole-transport layer is lower than the GSP_slope of an evaporated film of the electron blocking layer material.

Another embodiment of the present invention is the above-described light emitting device. The GSP_slope of an evaporated film of an organic compound included in the hole-injection layer is lower than 20 (mV/nm).

Another embodiment of the present invention is a light-emitting device including an anode, a cathode, and an EL layer between the anode and the cathode. The EL layer includes an electron-transport layer and a light-emitting layer. The electron-transport layer is positioned between the cathode and the light-emitting layer. The electron-transport layer is not in contact with the cathode. The electron-transport layer includes the above-described electron transport layer material.

Another embodiment of the present invention is a light-emitting device including an anode, a cathode, and an EL layer between the anode and the cathode. The EL layer includes an electron-injection layer, an electron-transport layer, and a light-emitting layer. The electron-injection layer and the electron-transport layer are positioned between the cathode and the light-emitting layer. The electron-transport layer is positioned between the electron-injection layer and the light-emitting layer and includes the above-described electron transport layer material Another embodiment of the present invention is the above-described light emitting device. The electron-transport layer is in contact with the light-emitting layer.

Another embodiment of the present invention is a light-emitting device including an anode, a cathode, and an EL layer between the anode and the cathode. The EL layer includes an electron-injection layer, an electron-transport layer, a hole-blocking layer, and a light-emitting layer. The electron-injection layer, the electron-transport layer, and the hole-blocking layer are positioned between the cathode and the light-emitting layer. The hole-blocking layer is in contact with the light-emitting layer. The electron-injection layer is in contact with the cathode. The hole-blocking layer includes the above-described hole blocking layer material.

Another embodiment of the present invention is an electronic device including any of the above light-emitting devices, and at least one of a sensor, an operation button, a speaker, and a microphone.

Another embodiment of the present invention is a light-emitting apparatus including any of the above light-emitting devices, and at least one of a transistor and a substrate.

Another embodiment of the present invention is a lighting device including any of the above light-emitting devices and a housing.

Note that the light-emitting apparatus in this specification includes, in its category, an image display device that uses a light-emitting device. The light-emitting apparatus may also include a module in which a light-emitting device is provided with a connector such as an anisotropic conductive film or a tape carrier package (TCP), a module in which a printed wiring board is provided at the end of a TCP, and a module in which an integrated circuit (IC) is directly mounted on a light-emitting device by a chip on glass (COG) method. Furthermore, a lighting device or the like may include the light-emitting apparatus.

One embodiment of the present invention can provide any of a hole transport layer material, an electron transport layer material, an electron blocking layer material, and a hole blocking layer material, which can provide an organic semiconductor device with low driving voltage. Another embodiment of the present invention can provide any of a transport layer material, a hole transport layer material, an electron transport layer material, an electron blocking layer material, and a hole blocking layer material, which can provide a light-emitting device with low driving voltage. Another embodiment of the present invention can provide any of a transport layer material, a hole transport layer material, an electron transport layer material, an electron blocking layer material, and a hole blocking layer material, which can provide a photodiode sensor with low driving voltage. Another embodiment of the present invention can provide any of a transport layer material, a hole transport layer material, an electron transport layer material, an electron blocking layer material, and a hole blocking layer material, which can provide any of a light-emitting apparatus, an electronic device, a display device, and an electronic device having low power consumption.

One embodiment of the present invention can provide an organic semiconductor device with low driving voltage. Another embodiment of the present invention can provide a light-emitting device with low driving voltage. Another embodiment of the present invention can provide a photodiode sensor with low driving voltage. Another embodiment of the present invention can provide any of a light-emitting apparatus, an electronic apparatus, a display device, and an electronic device each having low power consumption.

Note that the description of these effects does not preclude the existence of other effects. One embodiment of the present invention does not necessarily have all these effects. Other effects will be apparent from and can be derived from the description of the specification, the drawings, the claims, and the like.

BRIEF DESCRIPTION OF THE DRAWINGS

FIGS. 8A and 8B are cross-sectional views showing an example of a display device.

FIG. 9A is a cross-sectional view showing an example of a display device and FIG. 9B is a cross-sectional view showing an example of a transistor.

DETAILED DESCRIPTION OF THE INVENTION

Figure 1A:
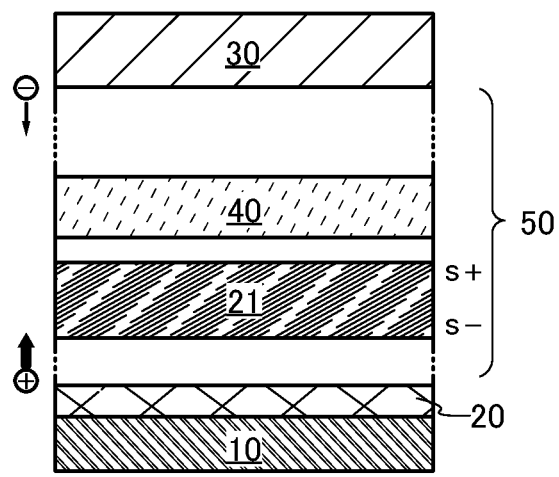
FIGS. 1A and 1B illustrate a light-emitting device of one embodiment of the present invention.

Embodiments of the present invention will be described in detail below with reference to the drawings. Note that the present invention is not limited to the following description, and it will be readily appreciated by those skilled in the art that modes and details of the present invention can be modified in various ways without departing from the spirit and scope of the present invention. Therefore, the present invention should not be construed as being limited to the description in the following embodiments.

In this specification and the like, a device formed using a metal mask or a fine metal mask (FMM) may be referred to as a device having a metal mask (MM) structure. In this specification and the like, a device formed without using a metal mask or an FMM may be referred to as a device having a metal maskless (MML) structure.

Embodiment 1

A light-emitting device is a kind of organic semiconductor device including an organic thin film. Typical examples of the organic semiconductor device include a photodiode sensor and an organic TFT.

Most of the organic thin films used for such organic semiconductor devices are formed by an evaporation method. The organic thin films, except for some films of materials that are easily crystallized, formed by an evaporation method in which sublimation is caused by application of energy such as heat to an organic compound to be deposited have been thought for a long time to be amorphous and have random orientation.

However, in recent years, many spectroscopic studies have revealed that modest molecular orientation sometimes exists also in an amorphous organic thin film and influences the device performance. It is known that, in a light-emitting device, easy light extraction from a substance in which dipole moments of a light-emitting substance are likely to be aligned parallel to a light-emitting surface makes it easier to provide a light-emitting element with high emission efficiency, and a substance in which overlap of π orbitals due to orientation easily occurs tends to have high conductivity, for example.

A polar molecule and a non-polar molecule exist in an organic compound, and the polar molecule has a permanent dipole moment. When the polar molecule is evaporated and the evaporated film has random orientation, unbalanced polarity is canceled out and polarization derived from the polarity of the molecule does not occur in the film. However, when the evaporated film has some imbalance, spontaneous polarization derived from the imbalance sometimes results in the giant surface potential.

The giant surface potential (GSP) refers to a phenomenon in which a surface potential of an evaporated film increases in proportion to a film thickness. In order to treat the surface potential as a value independent of a film thickness, a value obtained by dividing the surface potential of an evaporated film by the film thickness, that is, the potential gradient (slope) of a surface potential of an evaporated film, is used. In this specification, the potential gradient of a surface potential of an evaporated film is denoted by GSP_slope (mV/nm).

Owing to the giant surface potential, the surface potential of an evaporated film increases linearly with increasing thickness without saturation. For example, the surface potential of an evaporated film of tris(8-quinolinolato)aluminum (abbreviation: Alq$_3$) reaches approximately 28 V at a thickness of 560 nm. The electric field strength reaches $5 \times 10^5$ V/cm, which is approximately the same level as electric field strength during driving of a general organic thin film device.

The present inventors have found here that using a material with a high GSP_slope (higher than or equal to 20 mV/nm) as a material of a carrier-transport layer apart from an electrode significantly reduces the driving voltage of the light-emitting device. Note that in this specification, the value of a GSP_slope is obtained by measurement and calculation using an organic compound film to be measured with a thickness of approximately 80 nm.

FIG. 1A is a schematic view of a light-emitting device of one embodiment of the present invention. The light-emitting device of one embodiment of the present invention includes an EL layer 50 between a first electrode 10 and a second electrode 30. The EL layer 50 includes at least a light-emitting layer 40 and a layer 21 including a carrier transport layer material that exhibits a high GSP_slope (higher than or equal to 20 mV/nm) in an evaporated film.

Since the layer 21 includes the carrier transport layer material that exhibits a high GSP_slope (higher than or equal to 20 mV/nm) in an evaporated film, a potential difference derived from the polarization is generated in the layer. The negative polarization generated in the first electrode side of the layer 21 attracts holes to the interface, promoting hole injection and resulting in lower driving voltage.

The GSP_slope of the carrier transport layer material that exhibits a high GSP_slope (higher than or equal to 20 mV/nm) in an evaporated film is preferably lower than or equal to 100 mV/nm to reduce the driving voltage.

In FIG. TA, the layer 21 functions as a hole-transport layer and is not in contact with the first electrode 10. Thus, a carrier-injection layer 20 (a hole-injection layer in FIG. TA) which is a layer in contact with the electrode exists between the first electrode and the layer 21. In one embodiment of the present invention, the GSP_slope of a material included in the carrier-injection layer 20 is preferably low (lower than 20 mV/nm).

The layer 21 is preferably in contact with the light-emitting layer 40 to facilitate the carrier injection to the light-emitting layer; in this case, the layer 21 further preferably functions as a carrier-blocking layer (an electron-blocking layer in FIG. TA). In the case where the layer 21 functions as an electron-blocking layer, the LUMO level of a material included in the layer 21 is preferably higher than the lowest LUMO level among the material included in the light-emitting layer by 0.5 eV or more.

The hole-transport layer may have a stacked-layer structure of a plurality of layers. In this stacked-layer structure, the layer including a carrier transport layer material that exhibits a high GSP_slope (higher than or equal to 20 mV/nm) in an evaporated film (i.e. the layer 21) can be one of the layers. In the stacked-layer structure of the hole-transport layer, the layer 21 is preferably located closest to the light-emitting layer to facilitate the hole injection. In this case, the layer 21 further preferably functions as an electron-blocking layer. The GSP_slope of any of the other layers included in the hole-transport layer is preferably lower than the GSP_slope of the layer 21 to further facilitate the hole injection. Note that the GSP_slope of any layer other than the layer 21 in the hole-transport layer may be lower than 20 (mV/nm).

When the layer 21 is the hole-transport layer between the first electrode 10 serving as an anode and the light-emitting layer 40, as illustrated in FIG. 1A, the carrier transport layer material that is included in the layer 21 and has a high GSP_slope in an evaporated film preferably has a hole-transport property, and is further preferably arylamine to improve the hole-transport property.

Figure 1B:
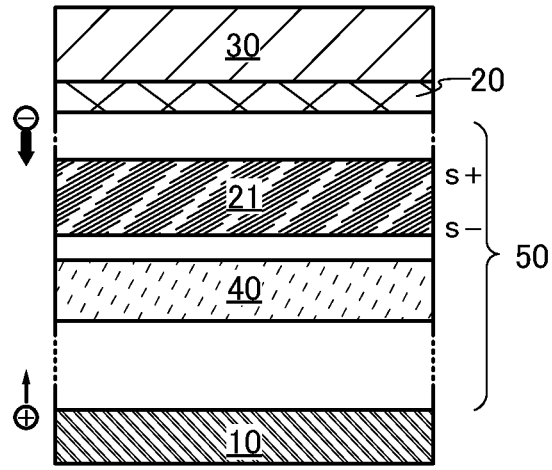

FIG. 1B is a schematic view of a light-emitting device of one embodiment of the present invention. FIG. 1B is different from FIG. 1A in that the layer 21 is provided between the light-emitting layer 40 and the second electrode 30 and functions as an electron-transport layer. The layer 21 is not in contact with the second electrode 30, and the carrier-injection layer 20 (an electron-injection layer in FIG. 1B) exists between the layer 21 and the second electrode 30. In one embodiment of the present invention, the GSP_slope of a material included in the carrier-injection layer 20 is preferably low (lower than 20 mV/nm) to reduce the driving voltage.

Since the layer 21 includes the carrier transport layer material that exhibits a high GSP_slope (higher than or equal to 20 mV/nm) in an evaporated film, a potential difference derived from the polarization is generated in the layer. The positive polarization generated in the second electrode side of the layer 21 attracts electrons to the interface, promoting electron injection and resulting in lower driving voltage.

The layer 21 is preferably in contact with the light-emitting layer 40 to facilitate the carrier injection to the light-emitting layer 40; in this case, the layer 21 further preferably functions as a carrier-blocking layer (a hole-blocking layer in FIG. 1B). In the case where the layer 21 functions as a hole-blocking layer, the HOMO level of a material included in the layer 21 is deeper than the HOMO level of the material included in the light-emitting layer by 0.5 eV or more.

The electron-transport layer may have a stacked-layer structure of a plurality of layers. In this stacked-layer structure, the layer including a carrier transport layer material that exhibits a high GSP_slope (higher than or equal to 20 mV/nm) in an evaporated film (i.e. the layer 21) can be one of the layers. In the stacked-layer structure of the electron-transport layer, the layer 21 is preferably located closest to the light-emitting layer to facilitate the hole injection. In this case, the layer 21 further preferably functions as a hole-blocking layer. The GSP_slope of any of the layers included in the electron-transport layer is preferably lower than the GSP_slope of the layer 21 to further facilitate the electron injection. Note that the GSP_slope of any layer other than the layer 21 in the electron-transport layer may be lower than 20 (mV/nm).

The light-emitting device of one embodiment of the present invention having the above-described structure can have favorable characteristics with low driving voltage.

It is known that a low refractive index layer is provided in an EL layer of a light-emitting device to increase the outcoupling efficiency and accordingly the light-emitting device can have high efficiency. The low refractive index layer is preferably provided in a layer close to the light-emitting layer to obtain a larger effect.

However, there is a trade-off between a high carrier-transport property and a low refractive index. This is because the carrier-transport properties of organic compounds largely depend on an unsaturated bond and organic compounds having many unsaturated bonds tend to have high refractive indexes. Hence, despite the improved current efficiency, the effect of reducing power consumption might have not been as sufficient as expected owing to the increased driving voltage when a carrier-transport material with a low refractive index is used in a light-emitting device.

Here, the present inventors have found that using a material with a low refractive index and a high GSP_slope in an area close to the light-emitting layer enables the light-emitting device to have high current efficiency and suppresses an increase in driving voltage. Both a layer with a low refractive index and a layer with a high GSP_slope are more effective when located in an area closer to the light-emitting layer. Hence, with the structure employing the material with a low refractive index and a high GSP_slope in an area close to the light-emitting layer, the light-emitting device can have low power consumption and extremely high power efficiency.

In view of the above, the refractive index of the carrier transport layer material that exhibits a high GSP_slope in an evaporated film is preferably low. Specifically, an ordinary ray refractive index of the material with respect to light with a wavelength of 450 nm is preferably higher than or equal to 1.50 and lower than or equal to 1.75, or an ordinary ray refractive index of the material with respect to light with a wavelength of 633 nm is preferably higher than or equal to 1.45 and lower than or equal to 1.70.

When the material has a condensed aromatic hydrocarbon ring, to keep its low refractive index, the condensed aromatic hydrocarbon ring is preferably a monocyclic condensed aromatic ring, a bicyclic condensed aromatic ring, or a tricyclic condensed aromatic ring (e.g., an anthracene ring, a naphthalene ring, or a fluorene ring) and the total number of condensed aromatic hydrocarbon rings in a molecule of the material is preferably one or two. Although a fluorene skeleton is preferably included in the molecule to improve the hole-transport property, the number of the fluorene skeletons in the molecule of the material is preferably two or less to keep the low refractive index.

A substituent with low molecular refraction is preferably introduced into a molecule in order that the material can have a low refractive index. Examples of the substituent include a saturated hydrocarbon group and a cyclic saturated hydrocarbon group. Thus, at least three substituents selected from a chain alkyl group having 2 to 5 carbon atoms and a cycloalkyl group having 6 to 12 carbon atoms and, in particular, a branched-chain alkyl group having 3 to 5 carbon atoms, are preferably included in the carrier transport layer material that exhibits a high GSP_slope in an evaporated film. As the chain alkyl group having 2 to 5 carbon atoms or the cycloalkyl group having 6 to 12 carbon atoms, a t-butyl group or a cyclohexyl group is particularly preferable.

Including two or more t-butyl groups or cyclohexyl groups also improves the heat resistance. The glass transition temperature (Tg) of the carrier transport layer material that exhibits a high GSP_slope in an evaporated film is higher than or equal to 100° C., preferably higher than or equal to 110° C., and further preferably higher than or equal to 120° C.

The chain alkyl groups having 2 to 5 carbon atoms or the cycloalkyl groups having 6 to 12 carbon atoms have carbon atoms forming a bond by $sp^3$ hybrid orbitals. As the percentage of carbon atoms forming a bond by the $sp^3$ hybrid orbitals, which have a low refractive index, in the total carbon atoms in the molecule is higher, the refractive index of the material can be reduced. However, in consideration of the carrier-transport property, the percentage of carbon atoms forming a bond by the $sp^3$ hybrid orbitals in the total number of carbon atoms in the molecule is preferably higher than or equal to 23% and lower than or equal to 55%.

The signal of the carbon atoms forming a bond by $sp^3$ hybrid orbitals is lower than 4 ppm in the $^1$H-NMR measurement of the material. Hence, the integral value of signals lower than 4 ppm preferably exceeds the integral value of signals at 4 ppm or higher in the $^1$H-NMR measurement of the carrier transport layer material that exhibits a high GSP_slope in an evaporated film.

The above-described carrier transport layer material that exhibits a high GSP_slope in an evaporated film can be favorably used in a sensor such as a photodiode.

Here, a method for obtaining the GSP_slope of an organic compound will be described.

A phenomenon in which a surface potential of an evaporated film increases in proportion to a film thickness is called the giant surface potential as described above. In general, a slope of a plot of a surface potential of an evaporated film in the thickness direction by Kelvin probe measurement is assumed as the level of the giant surface potential, that is, GSP_slope (mV/nm); in the case where two different layers are stacked, a change in the density of polarization charges (mC/m$^2$) accumulated at the interface, which is in association with GSP_slope, can be utilized to estimate GSP_slope.

Non-Patent Document 1 discloses that the following formulae hold when current is made to flow through a stack of organic thin films (a thin film 1 positioned on the anode side and a thin film 2 positioned on the cathode side) with different kinds of spontaneous polarization.

[Formula 1]

$$\sigma_{if} = \frac{Q_{if}}{S} = (V_i - V_{bi})\frac{\varepsilon_2}{d_2} \quad (1)$$

[Formula 2]

$$\sigma_{if} = P_1 - P_2 = \frac{\varepsilon_1 V_1}{d_1} - \frac{\varepsilon_2 V_2}{d_2} \quad (2)$$

In Formula (1), $\sigma_{if}$ is a polarization charge density, $V_i$ is a hole-injection voltage, $V_{bi}$ is a threshold voltage, $d_2$ is a thickness of the thin film 2, and $\varepsilon_2$ is a dielectric constant of the thin film 2. Note that $V_i$ and $V_{bi}$ can be estimated from the capacity-voltage characteristics of a device. The square of an ordinary refractive index $n_o$(633 nm) can be used as the dielectric constant. As described above, according to Formula (1), the polarization charge density $\sigma_{if}$ can be calculated using $V_i$ and $V_{bi}$ estimated from the capacity-voltage characteristics, the dielectric constant $\varepsilon_2$ of the thin film 2 calculated from the refractive index, and the thickness $d_2$ of the thin film 2.

Next, in Formula (2), $\sigma_{if}$ is a polarization charge density, $P_n$ is a GSP_slope of a thin film n, and $\varepsilon_n$ is a dielectric constant of the thin film n. Since the polarization charge density $\sigma_{if}$ can be obtained from Formula (1), the use of a substance with known GSP_slope for the thin film 2 enables the GSP_slope of the thin film 1 to be estimated.

Thus, Alq$_3$ whose GSP_slope is known to be 48 (mV/nm) is used for the thin film 2, Devices 1 and 2 are fabricated as measurement devices, and GSP_slope of mmtBumTPoFBi-02 in Device 1 and GSP_slope of NPB in Device 2 are calculated below, for example.

The following table lists device structures of Devices 1 and 2. Note that layers 1_1 to 4_1 and a cathode in each of Devices 1 and 2 are formed from the anode side by a vacuum evaporation method under the conditions where the substrate temperature is set to room temperature and the deposition rate is within the range from 0.2 nm/sec to 0.4 nm/sec. One layer is formed without interruption of evaporation. In each of Devices 1 and 2, the layer 2_1 corresponds to the thin film 1 and the layer 3_1 corresponds to the thin film 2.

Figure 2:
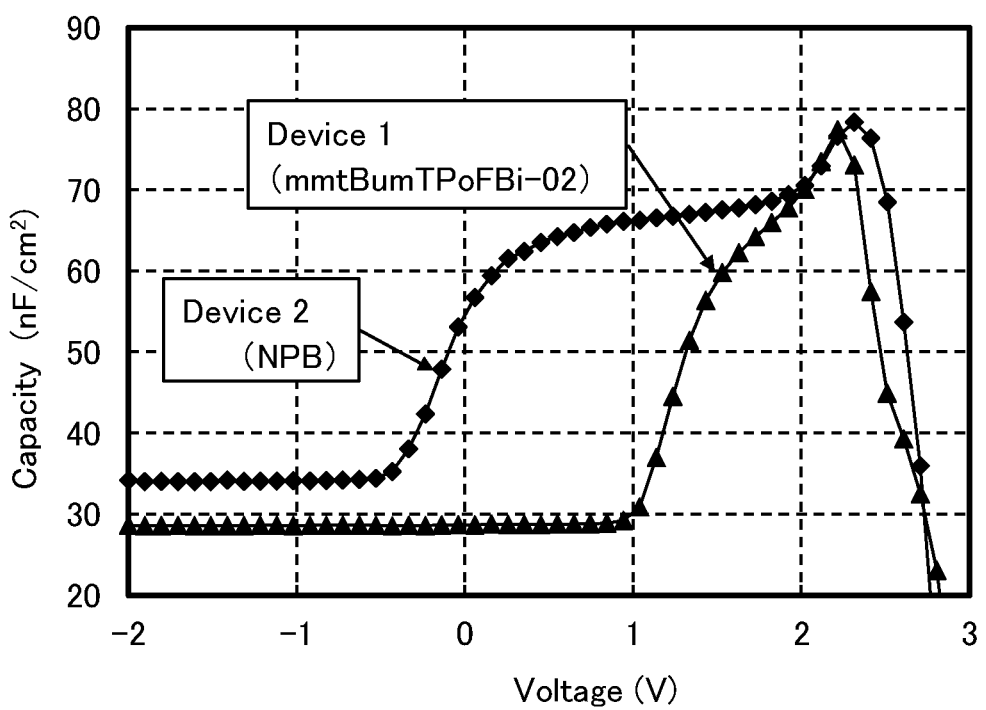
FIG. 2 shows the capacity-voltage characteristics of Device 1 and Device 2.

FIG. 2 shows the capacity-voltage characteristics of Devices 1 and 2.

TABLE 1

|  | Thickness | Device 1 | Device 2 |
|---|---|---|---|
| Cathode | 200 nm | Al | |
| Layer 4_1 | 1 nm | LiF | |
| Layer 3_1 | 60 nm | Alq$_3$ | |
| Layer 2_1 | 80 nm | mmtBumTPoFBi-02 | NPB |
| Layer 1_1 | 10 nm | mmtBumTPoFBi-02:<br>OCHD-003<br>(1:0.1) | NPB:<br>OCHD-003<br>(1:0.1) |
| Anode | 70 nm | ITSO | |

Table 2 shows the hole-injection voltage $V_i$, the threshold voltage $V_{bi}$, the polarization charge density air, and GSP_slope of Device 1 (mmtBumTPoFBi-02) and Device 2 (NPB) that are obtained from FIG. 2 and Formulae (1) and (2) and the refractive indices $n_o$ of the materials used in the calculation.

TABLE 2

|  | Device 1<br>(mmtBumTPoFBi-02) | Device 2<br>(NPB) |
|---|---|---|
| Hole-injection voltage $V_i$ (V) | 0.94 | −0.53 |
| Threshold voltage $V_{bi}$ (V) | 2.02 | 2.02 |
| Polarization charge density $\sigma_{if}$ (mC/m$^2$) | −0.47 | −1.1 |
| Ordinary refractive index $n_o$ (@ 633 nm) | 1.64 | 1.77 |
| GSP (mV/nm) | 32.6 | 5.2 |

Note that Devices 3 and 4 having substantially the same structures as Devices 1 and 2 except that the thickness of Alq$_3$ is 80 nm are fabricated. It is confirmed that the hole-injection voltages of Devices 3 and 4 shift to a lower voltage side than those of Devices 1 and 2. That is, it is presumed that holes are injected first and polarization charges are accumulated at the interface with Alq$_3$ in such devices. Furthermore, the GSP_slope is estimated for Devices 3 and 4 in a manner similar to that for Devices 1 and 2, and the same results as those of Devices 1 and 2 are obtained.

In this manner, a device in which Alq$_3$ with known GSP_slope and an organic compound whose GSP_slope is to be obtained are stacked is fabricated and the capacity-voltage characteristics are measured, so that the GSP_slope of the organic compound can be estimated.

Note that in the case where the thin film 1 or the thin film 2 contains a plurality of organic compounds, GSP_slope of the major organic compound (e.g., the material contained in the largest proportion) can be regarded as "GSP_slope of an organic compound in a layer". Alternatively, in the case where the thin film 1 or the thin film 2 contains a plurality of organic compounds, GSP_slope and contents of the organic compounds are calculated, and a weighted average (GSP_slope_ave) may be defined as "GSP_slope of a material in a layer".

Embodiment 2

Figure 3A:
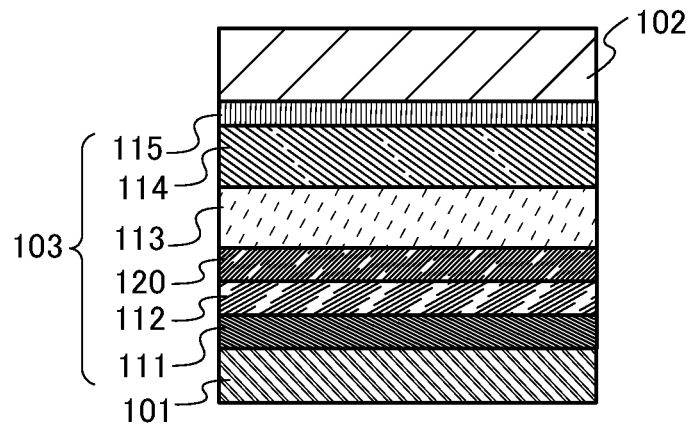
FIGS. 3A to 3C are schematic views of light-emitting devices of one embodiment of the present invention.

In this embodiment, the light-emitting device of one embodiment of the present invention will be described in detail. FIG. 3A illustrates the light-emitting device of one embodiment of the present invention. The light-emitting device of one embodiment of the present invention includes an EL layer 103 between a first electrode 101 and a second electrode 102. The EL layer 103 includes a light-emitting layer 113 and a layer including a material that exhibits a high GSP_slope in an evaporated film (an electron-blocking layer 120 in this embodiment).

A region between the light-emitting layer 113 and the first electrode 101 is a hole-transport region where holes serve as carriers, and a region between the light-emitting layer 113 and the second electrode 102 is an electron-transport region where electrons serve as carriers. The layer including a material that exhibits a high GSP_slope in an evaporated film functions as the electron-blocking layer when included in the hole-transport region, and the layer functions as the electron-transport layer and the hole-blocking layer when included in the electron-transport region.

In the light-emitting device, the layers are formed sequentially from the first electrode 101 side, which functions as an anode.

Between the hole-transport layer 112 and the first electrode 101, the hole-injection layer 111 is provided in contact with the first electrode 101, and the hole-transport layer and the electron-blocking layer 120 are not in contact with either electrode in the present invention. When the layer including a material that exhibits a high GSP_slope in an evaporated film is formed in the electron-transport region, the light-emitting device includes the electron-injection layer 115 in contact with the second electrode 102 serving as a cathode, and the electron-transport layer and the hole-blocking layer are not in contact with the second electrode.

Although FIG. 3A illustrates an electron-transport layer 114 and an electron-injection layer 115 in addition to these layers, the structure of the light-emitting device is not limited thereto, and other functional layers such as a carrier-blocking layer, an exciton-blocking layer, and a charge-generation layer may be provided.

Next, examples of specific structures and materials of the above-described light-emitting device will be described.

The first electrode 101 serving as an anode is preferably formed using any of metals, alloys, and conductive compounds with a high work function (specifically, higher than or equal to 4.0 eV), mixtures thereof, and the like. Specific examples include indium oxide-tin oxide (ITO: indium tin oxide), indium oxide-tin oxide containing silicon or silicon oxide, indium oxide-zinc oxide, and indium oxide containing tungsten oxide and zinc oxide (IWZO). Such conductive metal oxide films are usually formed by a sputtering method, but may be formed by application of a sol-gel method or the like. In an example of the formation method, indium oxide-zinc oxide is deposited by a sputtering method using a target obtained by adding 1 wt % to 20 wt % of zinc oxide to indium oxide. Furthermore, a film of indium oxide containing tungsten oxide and zinc oxide (IWZO) can be formed by a sputtering method using a target in which tungsten oxide and zinc oxide are added to indium oxide at 0.5 wt % to 5 wt % and 0.1 wt % to 1 wt %, respectively. Alternatively, gold (Au), platinum (Pt), nickel (Ni), tungsten (W), chromium (Cr), molybdenum (Mo), iron (Fe), cobalt (Co), copper (Cu), palladium (Pd), nitride of a metal material (e.g., titanium nitride), or the like can be used. Graphene can also be used. Note that when a composite material described later is used for the hole-injection layer 111, an electrode material can be selected regardless of its work function.

The hole-injection layer 111, which is in contact with the first electrode 101, contains a substance having an acceptor property. Either an organic compound or an inorganic compound can be used as the substance having an acceptor property.

As the substance having an acceptor property, it is possible to use a compound having an electron-withdrawing group (e.g., a halogen group or a cyano group); for example, 7,7,8,8-tetracyano-2,3,5,6-tetrafluoroquinodimethane (abbreviation: $F_4$-TCNQ), chloranil, 2,3,6,7,10,11-hexacyano-1,4,5,8,9,12-hexaazatriphenylene (abbreviation: HAT-CN), 1,3,4,5,7,8-hexafluorotetracyano-naphthoquinodimethane (abbreviation: F6-TCNNQ), or 2-(7-dicyanomethylene-1,3,4,5,6,8,9,10-octafluoro-7H-pyren-2-ylidene)malononitrile can be used. A compound in which electron-withdrawing groups are bonded to a condensed aromatic ring having a plurality of heteroatoms, such as HAT-CN, is particularly preferable because it is thermally stable. A [3]radialene derivative having an electron-withdrawing group (in particular, a cyano group, a halogen group such as a fluoro group, or the like) has a very high electron-accepting property and thus is preferable. Specific examples include α,α', α"-1,2,3-cyclopropanetriylidenetris[4-cyano-2,3,5,6-tetrafluorobenzeneacetonitrile], α,α',α"-1,2,3-cyclopropanetriylidenetris[2,6-dichloro-3,5-difluoro-4-(trifluoromethyl)benzeneacetonitrile], and α,α',α"-1,2,3-cyclopropanetriylidenetris[2,3,4,5,6-pentafluorobenzeneacetonitrile]. As the substance having an acceptor property, molybdenum oxide, vanadium oxide, ruthenium oxide, tungsten oxide, manganese oxide, or the like can be used, other than the above-described organic compounds. Alternatively, the hole-injection layer 111 can be formed using a phthalocyanine-based complex compound such as phthalocyanine (abbreviation: H2Pc) and copper phthalocyanine (CuPc), an aromatic amine compound such as 4,4'-bis[N-(4-diphenylaminophenyl)-N-phenylamino]biphenyl (abbreviation: DPAB) and N,N-bis{4-[bis(3-methylphenyl)amino]phenyl}-N,N-diphenyl-(1,1'-biphenyl)-4,4'-diamine (abbreviation: DNTPD), or a high molecular compound such as poly(3,4-ethylenedioxythiophene)/poly(styrenesulfonic acid) (PEDOT/PSS). The substance having an acceptor property can extract electrons from an adjacent hole-transport layer (or hole-transport material) by application of an electric field.

Alternatively, a composite material in which a material having a hole-transport property contains any of the aforementioned substances having an acceptor property can be used for the hole-injection layer 111. By using a composite material in which a material having a hole-transport property contains an acceptor substance, a material used to form an electrode can be selected regardless of its work function. In other words, besides a material having a high work function, a material having a low work function can be used for the first electrode 101.

As the material having a hole-transport property used for the composite material, any of a variety of organic compounds such as aromatic amine compounds, carbazole derivatives, aromatic hydrocarbons, and high molecular compounds (e.g., oligomers, dendrimers, or polymers) can be used. Note that the material having a hole-transport property used for the composite material preferably has a hole mobility of $1\times10^{-6}$ cm²/Vs or higher. Organic compounds that can be used as the material having a hole-transport property in the composite material are specifically given below.

Examples of the aromatic amine compounds that can be used for the composite material include N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), and 1,3,5-tris[N-(4-diphenylaminophenyl)-N-phenylamino]benzene (abbreviation: DPA3B). Specific examples of the carbazole derivative include 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 4,4'-di(N-carbazolyl)biphenyl (abbreviation: CBP), 1,3,5-tris[4-(N-carbazolyl)phenyl]benzene (abbreviation: TCPB), 9-[4-(10-phenylanthracen-9-yl)phenyl]-9H-carbazole (abbreviation: CzPA), and 1,4-bis[4-(N-carbazolyl)phenyl]-2,3,5,6-tetraphenylbenzene.

Examples of the aromatic hydrocarbon include 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, and 2,5,8,11-tetra(tert-butyl)perylene. Other examples include pentacene and coronene. The aromatic hydrocarbon may have a vinyl skeleton. Examples of the aromatic hydrocarbon having a vinyl group include 4,4'-bis(2,2-diphenylvinyl)biphenyl (abbreviation: DPVBi) and 9,10-bis[4-(2,2-diphenylvinyl)phenyl]anthracene (abbreviation: DPVPA).

Other examples include high molecular compounds such as poly(N-vinylcarbazole) (abbreviation: PVK), poly(4-vinyltriphenylamine) (abbreviation: PVTPA), poly[N-(4-{NM-[4-(4-diphenylamino)phenyl]phenyl-N-phenylamino}phenyl)methacrylamide] (abbreviation: PTPDMA), and poly[N,N-bis(4-butylphenyl)-N,N-bis(phenyl)benzidine] (abbreviation: poly-TPD).

The material having a hole-transport property that is used in the composite material further preferably has any of a carbazole skeleton, a dibenzofuran skeleton, a dibenzothiophene skeleton, and an anthracene skeleton. In particular, an aromatic amine having a substituent that includes a dibenzofuran ring or a dibenzothiophene ring, an aromatic monoamine that includes a naphthalene ring, or an aromatic monoamine in which a 9-fluorenyl group is bonded to nitrogen of amine through an arylene group may be used. Note that the hole-transport material having an N,N-bis(4-biphenyl)amino group is preferable because a light-emitting device having a long lifetime can be fabricated. Specific examples of the hole-transport material include N-(4-biphenyl)-6,N-diphenylbenzo[b]naphtho[1,2-d]furan-8-amine (abbreviation: BnfABP), N,N-bis(4-biphenyl)-6-phenyl-benzo[b]naphtho[1,2-d]furan-8-amine (abbreviation: BBABnf), 4,4'-bis(6-phenylbenzo[b]naphtho[1,2-d]furan-8-yl)-4"-phenyltriphenylamine (abbreviation: BnfBB1BP), N,N-bis(4-biphenyl)benzo[b]naphtho[1,2-d]furan-6-amine (abbreviation: BBABnf(6)), N,N-bis(4-biphenyl)benzo[b]naphtho[1,2-d]furan-8-amine (abbreviation: BBABnf(8)), N,N-bis(4-biphenyl)benzo[b]naphtho[2,3-d]furan-4-amine (abbreviation: BBABnf(II) (4)), N,N-bis[4-(dibenzofuran-4-yl)phenyl]-4-amino-p-terphenyl (abbreviation: DBfBB1TP), N-[4-(dibenzothiophen-4-yl)phenyl]-N-phenyl-4-biphenylamine (abbreviation: ThBA1BP), 4-(2-naphthyl)-4',4"-diphenyltriphenylamine (abbreviation: BBAβNB), 4-[4-(2-naphthyl)phenyl]-4',4"-diphenyltriphenylamine (abbreviation: BBAβNBi), 4,4'-diphenyl-4''-(6;1'-binaphthyl-2-yl)triphenylamine (abbreviation: BBAαNPNB), 4,4'-diphenyl-4''-(7;1'-binaphthyl-2-yl)triphenylamine (abbreviation: BBAαNPNB-03), 4,4'-diphenyl-4''-(7-phenyl)naphthyl-2-yltriphenylamine (abbreviation: BBAPβNB-03), 4,4'-diphenyl-4''-(6;2'-binaphthyl-2-yl)triphenylamine (abbreviation: BBA(βN2)B), 4,4'-diphenyl-4''-(7;2'-binaphthyl-2-yl)triphenylamine (abbreviation: BBA(βN2)B-03), 4,4'-diphenyl-4''-(4;2'-binaphthyl-1-yl)triphenylamine (abbreviation: BBAβNαNB), 4,4'-diphenyl-4''-(5;2'-binaphthyl-1-yl)triphenylamine (abbreviation: BBAβNαNB-02), 4-(4-biphenylyl)-4'-(2-naphthyl)-4''-phenyltriphenylamine (abbreviation: TPBiAβNB), 4-(3-biphenylyl)-4'-[4-(2-naphthyl)phenyl]-4''-phenyltriphenylamine (abbreviation: mTPBiAβNBi), 4-(4-biphenylyl)-4'-[4-(2-naphthyl)phenyl]-4''-phenyltriphenylamine (abbreviation: TPBiAβNBi), 4-phenyl-4'-(1-naphthyl)triphenylamine (abbreviation: αNBA1BP), 4,4'-bis(1-naphthyl)triphenylamine (abbreviation: αNBB1BP), 4,4'-diphenyl-4''-[4'-(carbazol-9-yl)biphenyl-4-yl]triphenylamine (abbreviation: YGTBi1BP), 4'-[4-(3-phenyl-9H-carbazol-9-yl)phenyl]tris(1,1'-biphenyl-4-yl)amine (abbreviation: YGTBiTBP-02), 4-diphenyl-4'-(2-naphthyl)-4''-{9-(4-biphenylyl)carbazole}triphenylamine (abbreviation: YGTBiβNB), N-[4-(9-phenyl-9H-carbazol-3-yl)phenyl]-N-[4-(1-naphthyl)phenyl]-9,9'-spirobi(9H-fluoren)-2-amine (abbreviation: PCBNBSF), N,N-bis(4-biphenylyl)-9,9'-spirobi[9H-fluoren]-2-amine (abbreviation: BBASF), N,N-bis(1,1'-biphenyl-4-yl)-9,9'-spirobi[9H-fluoren]-4-amine (abbreviation: BBASF(4)), N-(1,1'-biphenyl-2-yl)-N-(9,9-dimethyl-9H-fluoren-2-yl)-9,9'-spirobi[9H-fluoren]-4-amine (abbreviation: oFBiSF), N-(4-biphenyl)-N-(dibenzofuran-4-yl)-9,9-dimethyl-9H-fluoren-2-amine (abbreviation: FrBiF), N-[4-(1-naphthyl)phenyl]-N-[3-(6-phenyldibenzofuran-4-yl)phenyl]-1-naphthylamine (abbreviation: mPDBfBNBN), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-[4-(9-phenylfluoren-9-yl)phenyl]triphenylamine (abbreviation: BPAFLBi), 4-phenyl-4'-(9-phenyl-9H-carbazol-3-yl)triphenylamine (abbreviation: PCBA1BP), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4''-(9-phenyl-9H-carbazol-3-yl)triphenylamine (abbreviation: PCBNBB), N-phenyl-N-[4-(9-phenyl-9H-carbazol-3-yl)phenyl]spiro-9,9'-bifluoren-2-amine (abbreviation: PCBASF), N-(1,1'-biphenyl-4-yl)-N-[4-(9-phenyl-9H-carbazol-3-yl)phenyl]-9,9-dimethyl-9H-fluoren-2-amine (abbreviation: PCBBiF), N,N-bis(9,9-dimethyl-9H-fluoren-2-yl)-9,9'-spirobi-9H-fluoren-4-amine, N,N-bis(9,9-dimethyl-9H-fluoren-2-yl)-9,9'-spirobi-9H-fluoren-3-amine, N,N-bis(9,9-dimethyl-9H-fluoren-2-yl)-9,9'-spirobi-9H-fluoren-2-amine, and N,N-bis(9,9-dimethyl-9H-fluoren-2-yl)-9,9'-spirobi-9H-fluoren-1-amine.

Note that it is further preferable that the material having a hole-transport property to be used in the composite material have a relatively deep HOMO level higher than or equal to −5.7 eV and lower than or equal to −5.4 eV. Using the material with a hole-transport property which has a relatively deep HOMO level in the composite material makes it easy to inject holes into the hole-transport layer 112 and to obtain a light-emitting device having a long lifetime.

Note that mixing the above composite material with a fluoride of an alkali metal or an alkaline earth metal (the proportion of fluorine atoms in a layer using the mixed material is preferably greater than or equal to 20%) can lower the refractive index of the layer. This also enables a layer with a low refractive index to be formed in the EL layer 103, leading to higher external quantum efficiency of the light-emitting device.

The formation of the hole-injection layer 111 can improve the hole-injection property, which allows the light-emitting device to be driven at a low voltage. In addition, the organic compound having an acceptor property is easy to use because it is easily deposited by vapor deposition.

A material used for the hole-injection layer 111 is preferably a material with a GSP_slope lower than 20 mV/nm, in which case the driving voltage of the light-emitting device can be further reduced. Thus, the hole-injection layer 111 is preferably formed using a material with a GSP_slope lower than 20 mV/nm, among the above-described materials.

The hole-transport layer 112 is formed using a material having a hole-transport property. The material having a hole-transport property preferably has a hole mobility higher than or equal to $1 \times 10^{-6}$ cm$^2$/Vs.

In the light-emitting device of one embodiment of the present invention, the hole-transport layer 112 preferably includes a material with a GSP_slope higher than or equal to 20 mV/nm. The hole-transport layer 112 may be formed of a plurality of layers of different materials. In this case, the hole-transport layer 112 includes at least one layer including a material with a GSP_slope higher than or equal to 20 mV/nm, or preferably, at least one layer composed of a material with a GSP_slope higher than or equal to 20 mV/nm. The layer including a material with a GSP_slope higher than or equal to 20 mV/nm is preferably located close to the light-emitting layer, and further preferably in contact with the light-emitting layer. Furthermore, in that case, the layer including a material with a GSP_slope higher than or equal to 20 mV/nm further preferably functions as an electron-blocking layer.

A light-emitting device having such a structure can easily inject holes and thus can have low driving voltage.

Examples of the organic compound that can be used for the hole-transport layer 112 include compounds having an aromatic amine skeleton, such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4''-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), and N-phenyl-N-[4-(9-phenyl-9H-carbazol-3-yl)phenyl]spiro-9,9'-bifluoren-2-amine (abbreviation: PCBASF); compounds having a carbazole skeleton, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), and 3,3'-bis(9-phenyl-9H-carbazole) (abbreviation: PCCP); compounds having a thiophene skeleton, such as 4,4',4''-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)

phenyl]-6-phenyldibenzothiophene (abbreviation: DBTFLP-IV); and compounds having a furan skeleton, such as 4,4',4''-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II). Among the above materials, the compound having an aromatic amine skeleton and the compound having a carbazole skeleton are preferable because these compounds are highly reliable and have high hole-transport properties to contribute to a reduction in driving voltage. Note that any of the substances given as examples of the organic compound that can be used for the composite material in the hole-injection layer 111 can also be suitably used as the material included in the hole-transport layer 112. To form the layer including a material with a high GSP_slope, a material with a GSP_slope higher than or equal to 20 mV/nm can be selected from the above materials.

The material used for the hole-transport layer preferably includes, as alkyl groups, at least three substituents selected from a chain alkyl group having 2 to 5 carbon atoms and a cycloalkyl group having 6 to 12 carbon atoms, and particularly preferably includes a branched-chain alkyl group having 3 to 5 carbon atoms. In that case, the refractive index of the hole-transport layer 112 can be lowered and light extraction efficiency can be improved. Preferable examples of such a material include N,N-bis(4-cyclohexylphenyl)-9,9-dimethyl-9H-fluoren-2-amine (abbreviation: dchPAF), N-[(4'-cyclohexyl)-1,1'-biphenyl-4-yl]-N-(4-cyclohexylphenyl)-9,9-dimethyl-9H-fluoren-2-amine (abbreviation: chBichPAF), N,N-bis(4-cyclohexylphenyl)-N-(spiro[cyclohexane-1,9'-[9H]fluoren]-2'yl)amine (abbreviation: dchPASchF), N-[(4'-cyclohexyl)-1,1'-biphenyl-4-yl]-N-(4-cyclohexylphenyl)-N-(spiro[cyclohexane-1,9'-[9H]fluoren]-2'yl)amine (abbreviation: chBichPASchF), N-(4-cyclohexylphenyl)-bis(spiro[cyclohexane-1,9'-[9H]fluoren]-2'-yl)amine (abbreviation: SchFB1chP), N-[(3',5'-ditertiarybutyl)-1,1'-biphenyl-4-yl]-N-(4-cyclohexylphenyl)-9,9-dimethyl-9H-fluoren-2-amine (abbreviation: mmtBuBichPAF), N,N-bis(3',5'-ditertiarybutyl-1,1'-biphenyl-4-yl)-9,9-dimethyl-9H-fluoren-2-amine (abbreviation: dmmtBuBiAF), N-(3,5-ditertiarybutylphenyl)-N-(3',5'-ditertiarybutyl-1,1'-biphenyl-4-yl)-9,9-dimethyl-9H-fluoren-2-amine (abbreviation: mmtBuBimmtBuPAF), N,N-bis(4-cyclohexylphenyl)-9,9-dipropyl-9H-fluoren-2-amine (abbreviation: dchPAPrF), N-[(3',5'-dicyclohexyl)-1,1'-biphenyl-4-yl]-N-(4-cyclohexylphenyl)-9,9-dimethyl-9H-fluoren-2-amine (abbreviation: mmchBichPAF), N-(3,3'',5,5''-tetra-t-butyl-1,1':3',1''-terphenyl-5'-yl)-N-(4-cyclohexylphenyl)-9,9-dimethyl-9H-fluoren-2-amine (abbreviation: mmtBumTPchPAF), N-(4-cyclododecylphenyl)-N-(4-cyclohexylphenyl)-9,9-dimethyl-9H-fluoren-2-amine (abbreviation: CdoPchPAF), N-(3,3'',5,5''-tetra-t-butyl-1,1':3',1''-terphenyl-5'-yl)-N-phenyl-9,9-dimethyl-9H-fluoren-2-amine (abbreviation: mmtBumTPFA), N-(1,1'-biphenyl-4-yl)-N-(3,3'',5,5''-tetra-t-butyl-1,1':3',1''-terphenyl-5'-yl)-9,9-dimethyl-9H-fluoren-2-amine (abbreviation: mmtBumTPFBi), N-(1,1'-biphenyl-2-yl)-N-(3,3'',5,5''-tetra-t-butyl-1,1':3',1''-terphenyl-5'-yl)-9,9-dimethyl-9H-fluoren-2-amine (abbreviation: mmtBumTPoFBi), N-[(3,3',5'-tri-t-butyl)-1,1'-biphenyl-5-yl]-N-(4-cyclohexylphenyl)-9,9-dimethyl-9H-fluoren-2-amine (abbreviation: mmtBumBichPAF), N-(1,1'-biphenyl-2-yl)-N-[(3,3',5'-tri-t-butyl)-1,1'-biphenyl-5-yl]-9,9-dimethyl-9H-fluoren-2-amine (abbreviation: mmtBumBioFBi), N-(4-tert-butylphenyl)-N-(3,3'',5,5''-tetra-t-butyl-1,1':3',1''-terphenyl-5'-yl)-9,9-dimethyl-9H-fluoren-2-amine (abbreviation: mmtBumTPtBuPAF), N-(3,3'',5,5''-tetra-tert-butyl-1,1':3',1''-terphenyl-5-yl)-N-phenyl-9,9-dimethyl-9H-fluoren-2-amine (abbreviation: mmtBumTPFA-02), N-(1,1'-biphenyl-4-yl)-N-(3,3'',5,5''-tetra-tert-butyl-1,1':3',1''-terphenyl-5-yl)-9,9-dimethyl-9H-fluoren-2-amine (abbreviation: mmtBumTPFBi-02), N-(1,1'-biphenyl-2-yl)-N-(3,3'',5,5''-tetra-tert-butyl-1,1':3',1''-terphenyl-5-yl)-9,9-dimethyl-9H-fluoren-2-amine (abbreviation: mmtBumTPoFBi-02), N-(4-cyclohexylphenyl)-N-(3,3'',5,5''-tetra-tert-butyl-1,1':3',1''-terphenyl-5-yl)-9,9-dimethyl-9H-fluoren-2-amine (abbreviation: mmtBumTPchPAF-02), N-(1,1'-biphenyl-2-yl)-N-(3'',5'',5''-tri-tert-butyl-1,1':3',1''-terphenyl-5-yl)-9,9-dimethyl-9H-fluoren-2-amine (abbreviation: mmtBumTPoFBi-03), N-(4-cyclohexylphenyl)-N-(3'',5',5''-tri-tert-butyl-1,1':3',1''-terphenyl-5-yl)-9,9-dimethyl-9H-fluoren-2-amine (abbreviation: mmtBumTPchPAF-03), N-(1,1'-biphenyl-2-yl)-N-(3'',5',5''-tri-tert-butyl-1,1':3',1''-terphenyl-4-yl)-9,9-dimethyl-9H-fluoren-2-amine (abbreviation: mmtBumTPoFBi-04), N-(4-cyclohexylphenyl)-N-(3'',5',5''-tri-tert-butyl-1,1':3',1''-terphenyl-4-yl)-9,9-dimethyl-9H-fluoren-2-amine (abbreviation: mmtBumTPchPAF-04), N-(1,1'-biphenyl-2-yl)-N-(3,3'',5''-tri-tert-butyl-1,1':4',1''-terphenyl-5-yl)-9,9-dimethyl-9H-fluoren-2-amine (abbreviation: mmtBumTPoFBi-05), N-(4-cyclohexylphenyl)-N-(3,3'',5''-tri-tert-butyl-1,1':4',1''-terphenyl-5-yl)-9,9-dimethyl-9H-fluoren-2-amine (abbreviation: mmtBumTPchPAF-05), N-(3',5'-ditertiary-butyl-1,1'-biphenyl-4-yl)-N-(1,1'-biphenyl-2-yl)-9,9-dimethyl-9H-fluoren-2-amine (abbreviation: mmtBuBioFBi), N-2',4',6'-tricyclohexyl-1,1'-biphenyl-4-yl-N-(4-cyclohexylphenyl)-9,9-dimethyl-9H-fluoren-2-amine (abbreviation: ch3BichPAF), and N-3',5'-di-t-butylbiphenyl-4-yl)-N-(4-cyclohexyl-biphenyl-2-yl)-9,9-dimethyl-9H-fluoren-2-amine (abbreviation: mmtBuBichoBiF). To form the layer including a material with a high GSP_slope, a material with a GSP_slope higher than or equal to 20 mV/nm can be selected from the above materials.

Among the above materials, ch3BichPAF, mmtBuBichoBiF, mmtBuBiFF-02, mmtBumTPoFBi-02, mmtBuBichPAF, mmtBuBioBitBu2FLP(2), mmtBuBiFF, mmtBumTPchPAF-04, and mmtBuBioFBi each have a GSP_slope higher than or equal to 20 mV/nm. Thus, using any of these materials as the carrier-transport material with a high GSP_slope can easily reduce the driving voltage of the light-emitting device. Furthermore, since these materials have low refractive indexes, using any of them as a material forming the hole-transport layer or the electron-blocking layer enables the light-emitting device to have excellent characteristics with low driving voltage and high current efficiency.

The light-emitting layer 113 includes a light-emitting substance and a host material. The light-emitting layer 113 may additionally include other materials. Alternatively, the light-emitting layer 113 may be a stack of two layers with different compositions.

As the light-emitting substance, fluorescent substances, phosphorescent substances, substances exhibiting thermally activated delayed fluorescence (TADF), or other light-emitting substances may be used.

Examples of the material that can be used as a fluorescent substance in the light-emitting layer 113 are as follows. Other fluorescent substances can also be used.

The examples include 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-diphenyl-N,N-bis[4-(9-phenyl-9H-fluoren-9-yl)phenyl]pyrene-1,6-diamine (abbreviation: 1,6FLPAPm), N,N'-bis(3-methylphenyl)-N, N'-bis[3-(9-phenyl-9H-fluoren-9-yl)phenyl]pyrene-1,6-diamine (abbreviation: 1,6mMemFLPAPrn), N,N-bis[4-(9H-carbazol-9-yl)phenyl]-N,N-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N'-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), N,N-diphenyl-N,N'-(1,6-pyrene-diyl)bis[(6-phenylbenzo[b]naphtho[1,2-d]furan)-8-amine] (abbreviation: 1,6BnfAPrn-03), 3,10-bis[N-(9-phenyl-9H-carbazol-2-yl)-N-phenylamino]naphtho[2,3-b;6,7-b']bisbenzofuran (abbreviation: 3,10PCA2Nbf(IV)-02), and 3,10-bis[N-(dibenzofuran-3-yl)-N-phenylamino]naphtho[2,3-b;6,7-b']bisbenzofuran (abbreviation: 3,10FrA2Nbf(IV)-02). Condensed aromatic diamine compounds typified by pyrenediamine compounds such as 1,6FLPAPrn, 1,6mMemFLPAPrn, and 1,6BnfAPrn-03 are particularly preferable because of their high hole-trapping properties, high emission efficiency, and high reliability.

Examples of the material that can be used when a phosphorescent substance is used as the light-emitting substance in the light-emitting layer 113 are as follows.

The examples include an organometallic iridium complex having a 4H-triazole skeleton, such as tris{2-[5-(2-methylphenyl)-4-(2,6-dimethylphenyl)-4H-1,2,4-triazol-3-yl-κN$^2$]phenyl-xC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), and tris[4-(3-biphenyl)-5-isopropyl-3-phenyl-4H-1,2,4-triazolato]iridium(III) (abbreviation: [Ir(iPrptz-3b)$_3$]); an organometallic iridium complex having a 1H-triazole skeleton, such as tris[3-methyl-1-(2-methylphenyl)-5-phenyl-1H-1,2,4-triazolato]iridium(III) (abbreviation: [Ir(Mptz1-mp)$_3$]) and tris(1-methyl-5-phenyl-3-propyl-TH-1,2,4-triazolato)iridium(III) (abbreviation: [Ir(Prptzl-Me)$_3$]); an organometallic iridium complex having an imidazole skeleton, such as fac-tris[1-(2,6-diisopropylphenyl)-2-phenyl-TH-imidazole]iridium(III) (abbreviation: [Ir(iPrpmi)$_3$]) and tris[3-(2,6-dimethylphenyl)-7-methylimidazo[1,2-f]phenanthridinato]iridium(III) (abbreviation: [Ir(dmpimpt-Me)$_3$]); and an organometallic iridium complex in which a phenylpyridine derivative having an electron-withdrawing group is a ligand, such as bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis{2-[3',5'-bis(trifluoromethyl)phenyl]pyridinato-N,C$^{2'}$}iridium(III) picolinate (abbreviation: [Ir(CF$_3$ppy)$_2$(pic)]), and bis[2-(4',6'-difluorophenyl)pyridinato-N,C$^{2'}$]iridium(III) acetylacetonate (abbreviation: FIr(acac)). These compounds emit blue phosphorescence and have an emission peak at 440 nm to 520 nm.

Other examples include organometallic iridium complexes having a pyrimidine skeleton, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(tBuppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), and (acetylacetonato)bis(4,6-diphenylpyrimidinato)iridium(III) (abbreviation: [Ir(dppm)$_2$(acac)]); organometallic iridium complexes having a pyrazine skeleton, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); organometallic iridium complexes having a pyridine skeleton, such as tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation: [Ir(pq)$_3$]), and bis(2-phenylquinolinato-N,C$^{2'}$)iridium(III) acetylacetonate (abbreviation: [Ir(pq)$_2$(acac)]); and a rare earth metal complex such as tris(acetylacetonato) (monophenanthroline)terbium(III) (abbreviation: [Tb(acac)$_3$(Phen)]). These are mainly compounds that emit green phosphorescence and have an emission peak at 500 nm to 600 nm. Note that organometallic iridium complexes having a pyrimidine skeleton have distinctively high reliability and emission efficiency and thus are particularly preferable.

Other examples include organometallic iridium complexes having a pyrimidine skeleton, such as (diisobutyrylmethanato)bis[4,6-bis(3-methylphenyl)pyrimidinato]

iridium(III) (abbreviation: [Ir(5mdppm)₂(dibm)]), bis[4,6-bis(3-methylphenyl)pyrimidinato](dipivaloylmethanato)iridium(III) (abbreviation: [Ir(5mdppm)₂(dpm)]), and bis[4,6-di(naphthalen-1-yl)pyrimidinato](dipivaloylmethanato)iridium(III) (abbreviation: [Ir(dlnpm)₂(dpm)]); organometallic iridium complexes having a pyrazine skeleton, such as (acetylacetonato)bis(2,3,5-triphenylpyrazinato)iridium(III) (abbreviation: [Ir(tppr)₂(acac)]), bis(2,3,5-triphenylpyrazinato)(dipivaloylmethanato)iridium(III) (abbreviation: [Ir(tppr)₂(dpm)]), and (acetylacetonato)bis[2,3-bis(4-fluorophenyl)quinoxalinato]iridium(III) (abbreviation: [Ir(Fdpq)₂(acac)]); organometallic iridium complexes having a pyridine skeleton, such as tris(1-phenylisoquinolinato-N,C²')iridium(III) (abbreviation: [Ir(piq)₃]) and bis(1-phenylisoquinolinato-N,C²')iridium(III) acetylacetonate (abbreviation: [Ir(piq)₂(acac)]); platinum complexes such as 2,3,7,8,12,13,17,18-octaethyl-21H,23H-porphyrinplatinum(II) (abbreviation: PtOEP); and rare earth metal complexes such as tris(1,3-diphenyl-1,3-propanedionato)(monophenanthroline)europium(III) (abbreviation: [Eu(DBM)₃(Phen)]) and tris[1-(2-thenoyl)-3,3,3-trifluoroacetonato](monophenanthroline)europium(III) (abbreviation: [Eu(TTA)₃(Phen)]). These compounds emit red phosphorescence and have an emission peak at 600 nm to 700 nm. Furthermore, the organometallic iridium complexes having a pyrazine skeleton can provide red light emission with favorable chromaticity.

Besides the above phosphorescent compounds, known phosphorescent substances may be selected and used.

Examples of the TADF material include a fullerene, a derivative thereof, an acridine, a derivative thereof, and an eosin derivative. Furthermore, a metal-containing porphyrin, such as a porphyrin containing magnesium (Mg), zinc (Zn), cadmium (Cd), tin (Sn), platinum (Pt), indium (In), or palladium (Pd), can be given. Examples of the metal-containing porphyrin include a protoporphyrin-tin fluoride complex (SnF₂(Proto IX)), a mesoporphyrin-tin fluoride complex (SnF₂(Meso IX)), a hematoporphyrin-tin fluoride complex (SnF₂(Hemato IX)), a coproporphyrin tetramethyl ester-tin fluoride complex (SnF₂(Copro III-4Me)), an octaethylporphyrin-tin fluoride complex (SnF₂(OEP)), an etioporphyrin-tin fluoride complex (SnF₂(Etio I)), and an octaethylporphyrin-platinum chloride complex (PtCl₂OEP), which are represented by the following structural formulae.

[Chemical Formula 1]

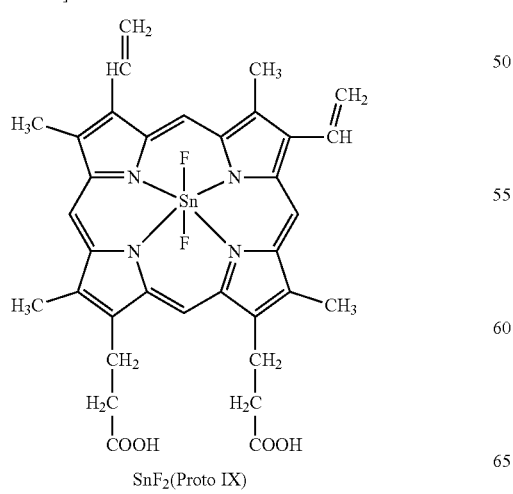

SnF₂(Proto IX)

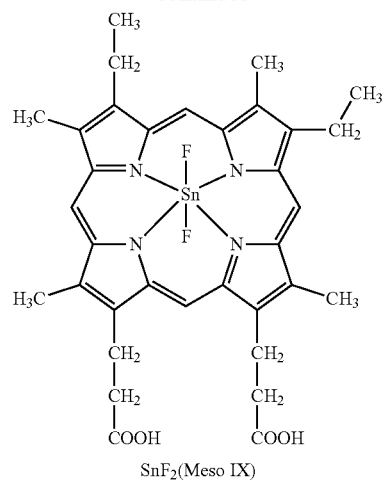

SnF₂(Meso IX)

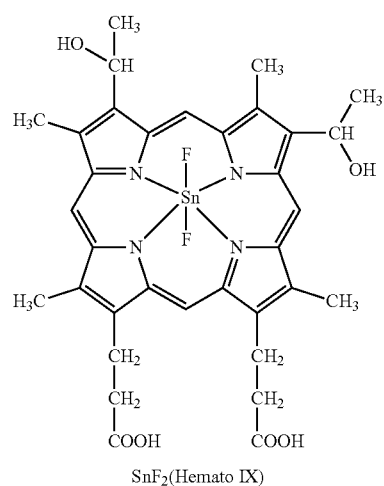

SnF₂(Hemato IX)

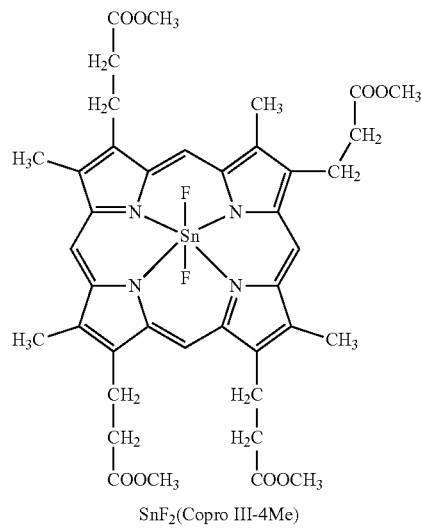

SnF₂(Copro III-4Me)

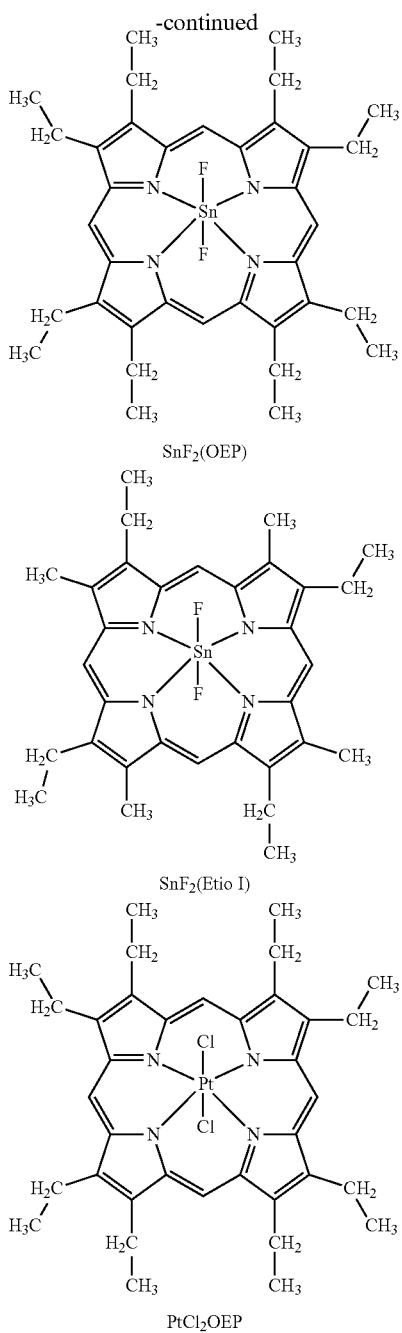

SnF₂(OEP)

SnF₂(Etio I)

PtCl₂OEP

Alternatively, a heterocyclic compound having one or both of a π-electron rich heteroaromatic ring and a π-electron deficient heteroaromatic ring that is represented by the following structural formulae, such as 2-(biphenyl-4-yl)-4,6-bis(12-phenylindolo[2,3-a]carbazol-11-yl)-1,3,5-triazine (abbreviation: PIC-TRZ), 9-(4,6-diphenyl-1,3,5-triazin-2-yl)-9'-phenyl-9H,9'H-3,3'-bicarbazole (abbreviation: PCCzTzn), 9-[4-(4,6-diphenyl-1,3,5-triazin-2-yl)phenyl]-9'-phenyl-9H,9'H-3,3'-bicarbazole (abbreviation: PCCzPTzn), 2-[4-(10H-phenoxazin-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-10'-one (abbreviation: ACRSA) can be used. Such a heterocyclic compound is preferable because of having excellent electron-transport and hole-transport properties owing to a π-electron rich heteroaromatic ring and a π-electron deficient heteroaromatic ring. Among skeletons having the π-electron deficient heteroaromatic ring, a pyridine skeleton, a diazine skeleton (a pyrimidine skeleton, a pyrazine skeleton, and a pyridazine skeleton), and a triazine skeleton are preferred because of their high stability and reliability. In particular, a benzofuropyrimidine skeleton, a benzothienopyrimidine skeleton, a benzofuropyrazine skeleton, and a benzothienopyrazine skeleton are preferred because of their high acceptor properties and high reliability. Among skeletons having the π-electron rich heteroaromatic ring, an acridine skeleton, a phenoxazine skeleton, a phenothiazine skeleton, a furan skeleton, a thiophene skeleton, and a pyrrole skeleton have high stability and reliability; thus, at least one of these skeletons is preferably included. A dibenzofuran skeleton is preferable as a furan skeleton, and a dibenzothiophene skeleton is preferable as a thiophene skeleton. As a pyrrole skeleton, an indole skeleton, a carbazole skeleton, an indolocarbazole skeleton, a bicarbazole skeleton, and a 3-(9-phenyl-9H-carbazol-3-yl)-9H-carbazole skeleton are particularly preferable. Note that a substance in which the π-electron rich heteroaromatic ring is directly bonded to the π-electron deficient heteroaromatic ring is particularly preferred because the electron-donating property of the π-electron rich heteroaromatic ring and the electron-accepting property of the π-electron deficient heteroaromatic ring are both improved, the energy difference between the S1 level and the T1 level becomes small, and thus thermally activated delayed fluorescence can be obtained with high efficiency. Note that an aromatic ring to which an electron-withdrawing group such as a cyano group is bonded may be used instead of the π-electron deficient heteroaromatic ring. As a π-electron rich skeleton, an aromatic amine skeleton, a phenazine skeleton, or the like can be used. As a π-electron deficient skeleton, a xanthene skeleton, a thioxanthene dioxide skeleton, an oxadiazole skeleton, a triazole skeleton, an imidazole skeleton, an anthraquinone skeleton, a skeleton containing boron such as phenylborane or boranthrene, an aromatic ring or a heteroaromatic ring having a cyano group or a nitrile group such as benzonitrile or cyanobenzene, a carbonyl skeleton such as benzophenone, a phosphine oxide skeleton, a sulfone skeleton, or the like can be used. As described above, a π-electron deficient skeleton and a π-electron rich skeleton can be used instead of at least one of the π-electron deficient heteroaromatic ring and the π-electron rich heteroaromatic ring.

[Chemical Formula 2]
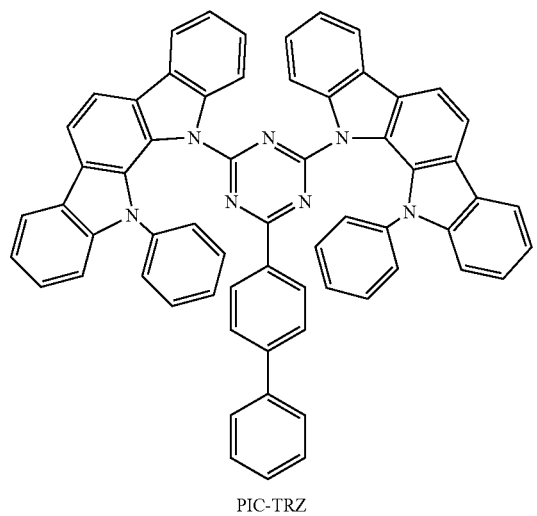
PIC-TRZ
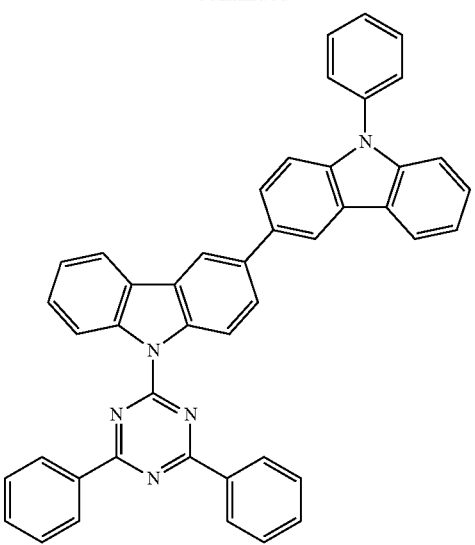
PCCzTzn
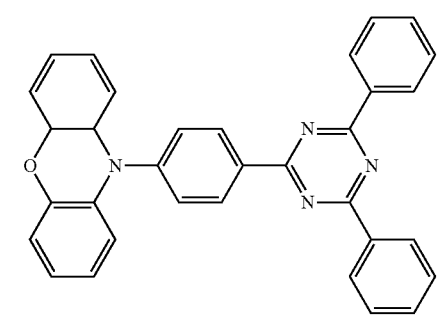
PXZ-TRZ
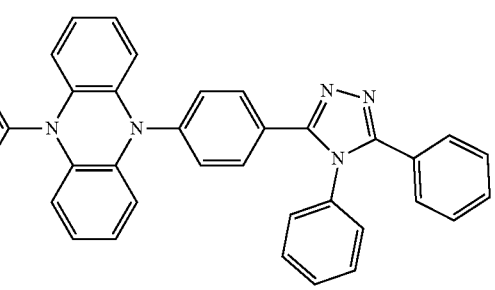
PPZ-3TPT
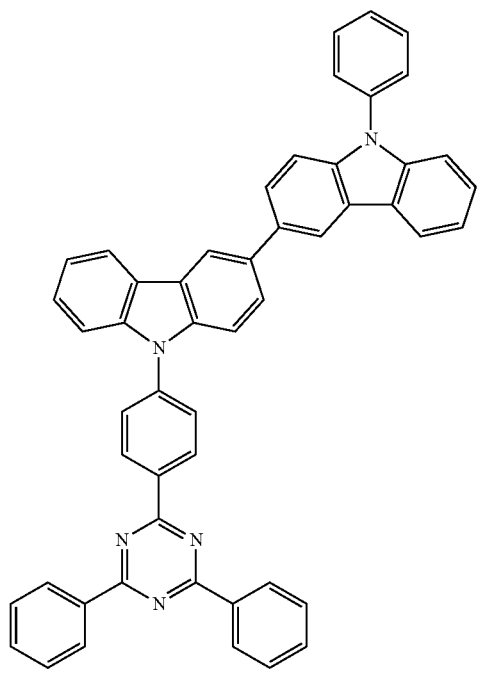
PCCzPTzn
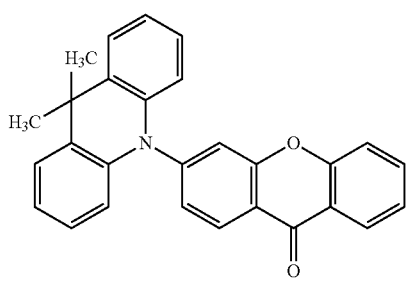
ACRXTN

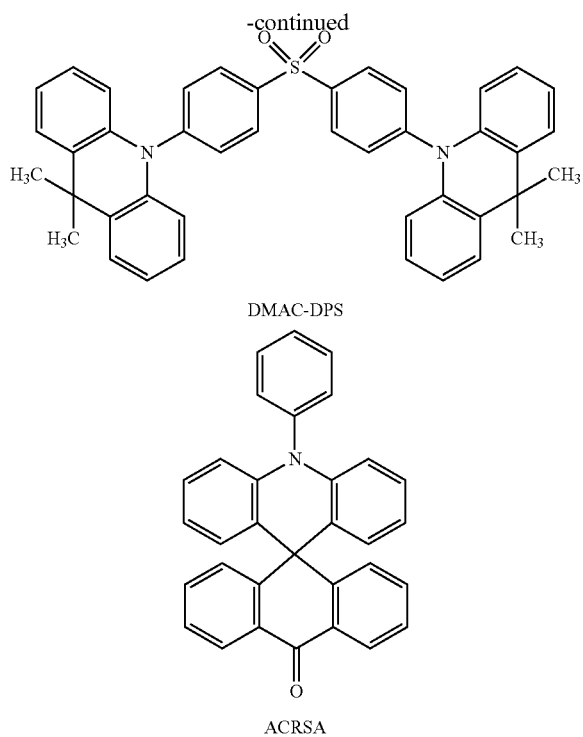

DMAC-DPS

ACRSA

Alternatively, a TADF material whose singlet excited state and triplet excited state are in a thermal equilibrium state may be used. Such a TADF material has a short emission lifetime (excitation lifetime), which allows inhibiting a decrease in efficiency in a high-luminance region of a light-emitting element. Specifically, a material having the following molecular structure can be used.

[Chemical Formula 3]

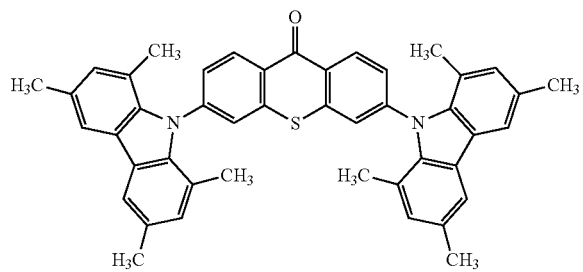

Note that a TADF material is a material having a small difference between the S1 level and the T1 level and a function of converting triplet excitation energy into singlet excitation energy by reverse intersystem crossing. Thus, a TADF material can upconvert triplet excitation energy into singlet excitation energy (i.e., reverse intersystem crossing) using a small amount of thermal energy and efficiently generate a singlet excited state. In addition, the triplet excitation energy can be converted into luminescence.

An exciplex whose excited state is formed of two kinds of substances has an extremely small difference between the S1 level and the T1 level and functions as a TADF material capable of converting triplet excitation energy into singlet excitation energy.

A phosphorescent spectrum observed at a low temperature (e.g., 77 K to 10 K) is used for an index of the T1 level. When the level of energy with a wavelength of the line obtained by extrapolating a tangent to the fluorescent spectrum at a tail on the short wavelength side is the S1 level and the level of energy with a wavelength of the line obtained by extrapolating a tangent to the phosphorescent spectrum at a tail on the short wavelength side is the T1 level, the difference between the S1 level and the T1 level of the TADF material is preferably smaller than or equal to 0.3 eV, further preferably smaller than or equal to 0.2 eV.

When a TADF material is used as the light-emitting substance, the S1 level of the host material is preferably higher than that of the TADF material. In addition, the T1 level of the host material is preferably higher than that of the TADF material.

As the host material in the light-emitting layer, various carrier-transport materials such as materials having an electron-transport property, materials having a hole-transport property, and the TADF materials can be used.

The material having a hole-transport property is preferably an organic compound having an amine skeleton or a π-electron rich heteroaromatic ring skeleton, for example. Examples of the material include compounds having an aromatic amine skeleton, such as 4,4'-bis[N-(1-naphthyl)-N-phenylamino]biphenyl (abbreviation: NPB), N,N-bis(3-methylphenyl)-N,N-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), and N-phenyl-N-[4-(9-phenyl-9H-carbazol-3-yl)phenyl]spiro-9,9'-bifluoren-2-amine (abbreviation: PCBASF); compounds having a carbazole skeleton, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), and 3,3'-bis(9-phenyl-9H-carbazole) (abbreviation: PCCP); compounds having a thiophene skeleton, such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having a furan skeleton, such as 4,4',4"-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II). Among the above materials, the compound having an aromatic amine skeleton and the compound having a carbazole skeleton are preferable because these compounds are highly reliable and have high hole-transport properties to contribute to a reduction in driving voltage. In addition, the organic compounds given as examples of the first substance can also be used.

As the material having an electron-transport property, for example, metal complexes such as bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); or an organic compound having a π-electron deficient heteroaromatic ring skeleton is preferable. Examples of the organic compound having a π-electron deficient heteroaromatic ring skeleton include heterocyclic compounds having a polyazole skeleton, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2''-(1,3,5-benzenetriyl)tris(1-phenyl-1H-benzimidazole) (abbreviation: TPBI), and 2-[3-(dibenzothiophen-4-yl)phenyl]-1-phenyl-1H-benzimidazole (abbreviation: mDBTBIm-II); heterocyclic compounds having a diazine skeleton, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl] dibenzo[f,h]quinoxaline (abbreviation: 2mCzBPDBq), 4,6-bis[3-(phenanthren-9-yl)phenyl]pyrimidine (abbreviation: 4,6mPnP2Pm), and 4,6-bis[3-(4-dibenzothienyl)phenyl]pyrimidine (abbreviation: 4,6mDBTP2Pm-II); heterocyclic compounds having a triazine skeleton, such as 2-[3'-(9,9-dimethyl-9H-fluoren-2-yl)-1,1'-biphenyl-3-yl]-4,6-diphenyl-1,3,5-triazine (abbreviation: mFBPTzn), 2-[(1,1'-biphenyl)-4-yl]-4-phenyl-6-[9,9'-spirobi(9H-fluoren)-2-yl]-1,3,5-triazine (abbreviation: BP-SFTzn), 2-{3-[3-(benzo[b]naphtho[1,2-d]furan-8-yl)phenyl]phenyl}-4,6-diphenyl-1,3,5-triazine (abbreviation: mBnfBPTzn), and 2-{3-[3-(benzo[b]naphtho[1,2-d]furan-6-yl)phenyl]phenyl}-4,6-diphenyl-1,3,5-triazine (abbreviation: mBnfBPTzn-02); and heterocyclic compounds having a pyridine skeleton, such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB). Among the above materials, the heterocyclic compound having a diazine skeleton, the heterocyclic compound having a triazine skeleton, and the heterocyclic compound having a pyridine skeleton have high reliability and thus are preferable. In particular, the heterocyclic compound having a diazine (e.g., pyrimidine or pyrazine) skeleton has a high electron-transport property to contribute to a reduction in driving voltage.

As the TADF material that can be used as the host material, the above materials mentioned as the TADF material can also be used. When the TADF material is used as the host material, triplet excitation energy generated in the TADF material is converted into singlet excitation energy by reverse intersystem crossing and transferred to the light-emitting substance, whereby the emission efficiency of the light-emitting device can be increased. Here, the TADF material functions as an energy donor, and the light-emitting substance functions as an energy acceptor.

This is very effective in the case where the light-emitting substance is a fluorescent substance. In that case, the S1 level of the TADF material is preferably higher than that of the fluorescent substance in order that high emission efficiency can be achieved. Furthermore, the T1 level of the TADF material is preferably higher than the S1 level of the fluorescent substance. Therefore, the T1 level of the TADF material is preferably higher than that of the fluorescent substance.

It is also preferable to use a TADF material that emits light whose wavelength overlaps with the wavelength on a lowest-energy-side absorption band of the fluorescent substance, in which case excitation energy is transferred smoothly from the TADF material to the fluorescent substance and light emission can be obtained efficiently.

In addition, in order to efficiently generate singlet excitation energy from the triplet excitation energy by reverse intersystem crossing, carrier recombination preferably occurs in the TADF material. It is also preferable that the triplet excitation energy generated in the TADF material not be transferred to the triplet excitation energy of the fluorescent substance. For that reason, the fluorescent substance preferably has a protective group around a luminophore (a skeleton which causes light emission) of the fluorescent substance. As the protective group, a substituent having no π bond and a saturated hydrocarbon are preferably used. Specific examples include an alkyl group having 3 to 10 carbon atoms, a substituted or unsubstituted cycloalkyl group having 3 to 10 carbon atoms, and a trialkylsilyl group having 3 to 10 carbon atoms. It is further preferable that the fluorescent substance have a plurality of protective groups. The substituents having no π bond are poor in carrier transport performance, whereby the TADF material and the luminophore of the fluorescent substance can be made away from each other with little influence on carrier transportation or carrier recombination. Here, the luminophore refers to an atomic group (skeleton) that causes light emission in a fluorescent substance. The luminophore is preferably a skeleton having a π bond, further preferably includes an aromatic ring, and still further preferably includes a condensed aromatic ring or a condensed heteroaromatic ring. Examples of the condensed aromatic ring or the condensed heteroaromatic ring include a phenanthrene skeleton, a stilbene skeleton, an acridone skeleton, a phenoxazine skeleton, and a phenothiazine skeleton. Specifically, a fluorescent substance having any of a naphthalene skeleton, an anthracene skeleton, a fluorene skeleton, a chrysene skeleton, a triphenylene skeleton, a tetracene skeleton, a pyrene skeleton, a perylene skeleton, a coumarin skeleton, a quinacridone skeleton, and a naphthobisbenzofuran skeleton is preferred because of its high fluorescence quantum yield.

In the case where a fluorescent substance is used as the light-emitting substance, a material having an anthracene skeleton is suitably used as the host material. The use of a substance having an anthracene skeleton as the host material for the fluorescent substance makes it possible to obtain a light-emitting layer with high emission efficiency and high durability. Among the substances having an anthracene skeleton, a substance having a diphenylanthracene skeleton, in particular, a substance having a 9,10-diphenylanthracene skeleton, is chemically stable and thus is preferably used as the host material. The host material preferably has a carbazole skeleton because the hole-injection and hole-transport properties are improved; further preferably, the host material has a benzocarbazole skeleton in which a benzene ring is further condensed to carbazole because the HOMO level thereof is shallower than that of carbazole by approximately 0.1 eV and thus holes enter the host material easily. In particular, the host material preferably has a dibenzocarbazole skeleton because the HOMO level thereof is shallower than that of carbazole by approximately 0.1 eV so that holes enter the host material easily, the hole-transport property is improved, and the heat resistance is increased. Accordingly, a substance that has both a 9,10-diphenylanthracene skeleton and a carbazole skeleton (or a benzocarbazole or dibenzocarbazole skeleton) is further preferable as the host material. Note that in terms of the hole-injection and hole-transport properties described above, instead of a carbazole skeleton, a benzofluorene skeleton or a dibenzofluorene skeleton may be used. Examples of such a substance include 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), 9-phenyl-10-{4-(9-phenyl-9H-fluoren-9-yl)biphenyl-4'-yl}anthracene (abbreviation: FLPPA), and 9-(1-naphthyl)-10-[4-(2-naphthyl)phenyl]anthracene (abbreviation: αN-βNPAnth). In particular, CzPA, cgDBCzPA, 2mBnfPPA, and PCzPA have excellent characteristics and thus are preferably selected.

Note that the host material may be a mixture of a plurality of kinds of substances; in the case of using a mixed host material, it is preferable to mix a material having an electron-transport property with a material having a hole-transport property. By mixing the material having an electron-transport property with the material having a hole-transport property, the transport property of the light-emitting layer 113 can be easily adjusted and a recombination region can be easily controlled. The weight ratio of the content of the material having a hole-transport property to the content of the material having an electron-transport property may be 1:19 to 19:1.

Note that a phosphorescent substance can be used as part of the mixed material. When a fluorescent substance is used as the light-emitting substance, a phosphorescent substance can be used as an energy donor for supplying excitation energy to the fluorescent substance.

An exciplex may be formed of these mixed materials. These mixed materials are preferably selected so as to form an exciplex that exhibits light emission whose wavelength overlaps with the wavelength on a lowest-energy-side absorption band of the light-emitting substance, in which case energy can be transferred smoothly and light emission can be obtained efficiently. The use of such a structure is preferable because the driving voltage can also be reduced.

Note that at least one of the materials forming an exciplex may be a phosphorescent substance. In this case, triplet excitation energy can be efficiently converted into singlet excitation energy by reverse intersystem crossing.

Combination of a material having an electron-transport property and a material having a hole-transport property whose HOMO level is higher than or equal to that of the material having an electron-transport property is preferable for forming an exciplex efficiently. In addition, the LUMO level of the material having a hole-transport property is preferably higher than or equal to that of the material having an electron-transport property. Note that the LUMO levels and the HOMO levels of the materials can be derived from the electrochemical characteristics (the reduction potentials and the oxidation potentials) of the materials that are measured by cyclic voltammetry (CV).

The formation of an exciplex can be confirmed by a phenomenon in which the emission spectrum of the mixed film in which the material having a hole-transport property and the material having an electron-transport property are mixed is shifted to the longer wavelength side than the emission spectra of each of the materials (or has another peak on the longer wavelength side) observed by comparison of the emission spectra of the material having a hole-transport property, the material having an electron-transport property, and the mixed film of these materials, for example. Alternatively, the formation of an exciplex can be confirmed by a difference in transient response, such as a phenomenon in which the transient PL lifetime of the mixed film has longer lifetime components or has a larger proportion of delayed components than that of each of the materials, observed by comparison of transient photoluminescence (PL) of the material having a hole-transport property, the material having an electron-transport property, and the mixed film of these materials. The transient PL can be rephrased as transient electroluminescence (EL). That is, the formation of an exciplex can also be confirmed by a difference in transient response observed by comparison of the transient EL of the material having a hole-transport property, the material having an electron-transport property, and the mixed film of these materials.

The electron-transport layer 114 contains a substance having an electron-transport property. As the substance having an electron-transport property, it is possible to use any of the above-listed substances having electron-transport properties that can be used as the host material. When the electron-transport layer 114 is formed using a material with a high GSP_slope, a material with a GSP_slope higher than or equal to 20 (mV/nm) can be selected.

The material used for the electron-transport layer preferably includes, as alkyl groups, at least three chain alkyl groups having 2 to 5 carbon atoms or cycloalkyl groups having 6 to 12 carbon atoms, and particularly preferably includes branched-chain alkyl groups having 3 to 5 carbon atoms. In that case, the refractive index of the hole-transport layer 112 can be lowered and light extraction efficiency can be improved. Preferable examples of such a material include 2-{(3',5'-di-tert-butyl)-1,1'-biphenyl-3-yl}-4,6-bis(3,5-di-tert-butylphenyl)-1,3,5-triazine (abbreviation: mmtBumBP-dmmtBuPTzn), 2-{(3',5'-di-tert-butyl)-1,1'-biphenyl-3-yl}-4,6-diphenyl-1,3,5-triazine (abbreviation: mmtBumBPTzn), 2-(3,3",5',5"-tetra-tert-butyl-1,1':3',1"-terphenyl-5'-yl)-4,6-diphenyl-1,3,5-triazine (abbreviation: mmtBumTPTzn), 2-(3',5'-di-tert-butylbiphenyl-3-yl)-4,6-bis(3,5-di-tert-butylphenyl)pyrimidine (abbreviation: mmtBumBP-dmmtBuPPm), 2-(3',5'-di-tert-butylbiphenyl-3-yl)-4,6-bis(3,5-di-tert-butylphenyl)pyrimidine (abbreviation: mmtBumBP-dmmtBuPPm), 2-(3,3",5',5"-tetra-tert-butyl-1,1':3',1"-terphenyl-5-yl)-4,6-diphenyl-1,3,5-triazine (abbreviation: mmtBumTPTzn-02), 2-{3-(3,5-dicyclohexylphenyl)phenyl}-4,6-diphenyl-1,3,5-triazine (abbreviation: mmchmBPTzn), 2-(3",5',5"-tri-tert-butyl-1,1':3',1"-terphenyl-4-yl)-4,6-diphenyl-1,3,5-triazine (abbreviation: mmt-BumTPTzn-04), 2-[3-(2,6-dimethylpyridin-3-yl)-5-{(3,5-di-tert-butyl) phenyl}phenyl]-4,6-diphenyl-1,3,5-triazine (abbreviation: mmtBuPh-mDMePyPTzn), 2-(3"',5',5"-tri-tert-butyl-1,1':3',1"-terphenyl-5-yl)-4,6-diphenyl-1,3,5-triazine (abbreviation: mmtBumTPTzn-03), 2,4-bis[(3',5'-di-tert-butyl)-1,1'-biphenyl-3-yl]-6-phenyl-1,3,5-triazine (abbreviation: mmtBumBP2Tzn), 2-{(1,1'-biphenyl)-2-yl}-4-{(3',5'-di-tert-butyl)-1,1'-biphenyl-3-yl}-6-phenyl-1,3,5-triazine (abbreviation: oBP-mmtBumBPTzn), 2-[(1,1'-biphenyl)-2-yl]-4-{(3',5'-di-tert-butyl)-1,1'-biphenyl-4-yl}-6-phenyl-1,3,5-triazine (abbreviation: oBP-mmtBuBPTzn), 2-[3-{(3,5-di-tert-butyl) phenyl}-5-(3-pyridyl) phenyl]-4,6-diphenyl-1,3,5-triazine (abbreviation: mmtBuPh-mPyPTzn), 2-[3-(2,6-dimethylpyridin-3-yl)-5-{3',5,5'-tri-tert-butylbiphenyl}phenyl]-4,6-diphenyl-1,3,5-triazine (abbreviation: mmtBuBP-mDMePyPTzn), 2-[3-(2,6-dimethylpyridin-3-yl)-5-{(3',5'-di-tert-butyl)-1,1'-biphenyl-3-yl}phenyl]-4,6-diphenyl-1,3,5-triazine (abbreviation: mmt-BuBP-mDMePyPTzn-02), 2,4-[(1,1'-biphenyl)-2-yl]-6-[3-(2,6-dimethylpyridin-3-yl)-5-{(3,5-di-tert-butyl) phenyl}] phenyl-1,3,5-triazine (abbreviation: oBP2-mmtBuPh-mDMePyPTzn), 2-[(1,1'-biphenyl)-2-yl]-4-[3-(2,6-dimethylpyridin-3-yl)-5-{(3,5-di-tert-butyl) phenyl}]

phenyl-6-phenyl-1,3,5-triazine (abbreviation: oBP-mmtBuPh-mDMePyPTzn), 2,4,6-tris{3'-(pyridin-3-yl)-5'-tert-butyl-1,1'-biphenyl-3-yl}-1,3,5-triazine (abbreviation: tBu-TmPPPyTz), and 2,4,6-tris{3'-(pyridin-3-yl)-5'-tert-butyl-1,1'-biphenyl-4-yl}-1,3,5-triazine (abbreviation: tBu-TmPPPyTz-02). To form the layer including a material with a high GSP_slope, a material with a GSP_slope higher than or equal to 20 mV/nm can be selected from the above materials.

Note that the electron-transport layer preferably includes a material having an electron-transport property and an alkali metal, an alkaline earth metal, a compound thereof, or a complex thereof. The electron mobility of the electron-transport layer 114 in the case where the square root of the electric field strength [V/cm] is 600 is preferably higher than or equal to $1 \times 10^1$ cm$^2$/Vs and lower than or equal to $5 \times 10^{-5}$ cm$^2$/Vs. The amount of electrons injected into the light-emitting layer can be controlled by the reduction in the electron-transport property of the electron-transport layer 114, whereby the light-emitting layer can be prevented from having excess electrons. It is particularly preferable to employ this structure when the hole-injection layer is formed using a composite material that includes a material having a hole-transport property with a relatively deep HOMO level of −5.7 eV or higher and −5.4 eV or lower, in which case a long lifetime can be achieved. In this case, the material having an electron-transport property preferably has a HOMO level of −6.0 eV or higher. The material having an electron-transport property is preferably an organic compound having an anthracene skeleton and further preferably an organic compound having both an anthracene skeleton and a heterocyclic skeleton. The heterocyclic skeleton is preferably a nitrogen-containing five-membered ring skeleton or a nitrogen-containing six-membered ring skeleton, and particularly preferably a nitrogen-containing five-membered ring skeleton or a nitrogen-containing six-membered ring skeleton including two heteroatoms in the ring, such as a pyrazole ring, an imidazole ring, an oxazole ring, a thiazole ring, a pyrazine ring, a pyrimidine ring, or a pyridazine ring. In addition, it is preferable that the alkali metal, the alkaline earth metal, the compound thereof, or the complex thereof have a 8-hydroxyquinolinato structure. Specific examples include 8-hydroxyquinolinato-lithium (abbreviation: Liq) and 8-hydroxyquinolinato-sodium (abbreviation: Naq). In particular, a complex of a monovalent metal ion, especially a complex of lithium is preferable, and Liq is further preferable. Note that in the case where the 8-hydroxyquinolinato structure is included, a methyl-substituted product (e.g., a 2-methyl-substituted product or a 5-methyl-substituted product) of the alkali metal, the alkaline earth metal, the compound, or the complex can also be used, for example. There is preferably a difference in the concentration (including 0) of the alkali metal, the alkaline earth metal, the compound thereof, or the complex thereof in the electron-transport layer in the thickness direction.

A layer containing an alkali metal, an alkaline earth metal, or a compound thereof such as lithium fluoride (LiF), cesium fluoride (CsF), calcium fluoride (CaF$_2$), or 8-hydroxyquinolinato-lithium (Liq) may be provided as the electron-injection layer 115 between the electron-transport layer 114 and the second electrode 102. An electride or a layer that is formed using a substance having an electron-transport property and that includes an alkali metal, an alkaline earth metal, or a compound thereof can be used as the electron-injection layer 115. Examples of the electride include a substance in which electrons are added at high concentration to calcium oxide-aluminum oxide.

Note that as the electron-injection layer 115, it is possible to use a layer containing a substance that has an electron-transport property (preferably an organic compound having a bipyridine skeleton) and contains a fluoride of the alkali metal or the alkaline earth metal at a concentration higher than that at which the electron-injection layer 115 becomes in a microcrystalline state (50 wt % or higher). Since the layer has a low refractive index, a light-emitting device including the layer can have high external quantum efficiency.

Figure 3B:
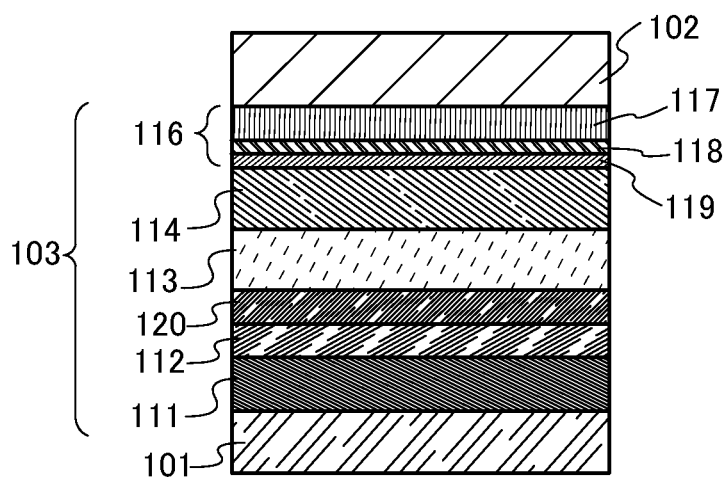

Instead of the electron-injection layer 115, a charge-generation layer 116 may be provided (FIG. 3B). The charge-generation layer 116 refers to a layer capable of injecting holes into a layer in contact with the cathode side of the charge-generation layer 116 and electrons into a layer in contact with the anode side thereof when a potential is applied. The charge-generation layer 116 includes at least a p-type layer 117. The p-type layer 117 is preferably formed using any of the composite materials given above as examples of materials that can be used for the hole-injection layer 111. The p-type layer 117 may be formed by stacking a film containing the above-described acceptor material as a material included in the composite material and a film containing a hole-transport material. When a potential is applied to the p-type layer 117, electrons are injected into the electron-transport layer 114 and holes are injected into the second electrode 102; thus, the light-emitting device operates. Since the organic compound of one embodiment of the present invention has a low refractive index, using the organic compound for the p-type layer 117 enables the light-emitting device to have high external quantum efficiency.

Note that the charge-generation layer 116 preferably includes an electron-relay layer 118 and/or an electron-injection buffer layer 119 in addition to the p-type layer 117.

The electron-relay layer 118 includes at least the substance having an electron-transport property and has a function of preventing an interaction between the electron-injection buffer layer 119 and the p-type layer 117 and smoothly transferring electrons. The LUMO level of the substance having an electron-transport property contained in the electron-relay layer 118 is preferably between the LUMO level of the acceptor substance in the p-type layer 117 and the LUMO level of a substance contained in a layer of the electron-transport layer 114 that is in contact with the charge-generation layer 116. As a specific value of the energy level, the LUMO level of the substance having an electron-transport property in the electron-relay layer 118 is preferably higher than or equal to −5.0 eV, further preferably higher than or equal to −5.0 eV and lower than or equal to −3.0 eV. Note that as the substance having an electron-transport property in the electron-relay layer 118, a phthalocyanine-based material or a metal complex having a metal-oxygen bond and an aromatic ligand is preferably used.

A substance having a high electron-injection property can be used for the electron-injection buffer layer 119. For example, an alkali metal, an alkaline earth metal, a rare earth metal, or a compound thereof (an alkali metal compound (including an oxide such as lithium oxide, a halide, and a carbonate such as lithium carbonate and cesium carbonate), an alkaline earth metal compound (including an oxide, a halide, and a carbonate), or a rare earth metal compound (including an oxide, a halide, and a carbonate)) can be used.

In the case where the electron-injection buffer layer 119 contains the substance having an electron-transport property and a donor substance, an organic compound such as tetrathianaphthacene (abbreviation: TTN), nickelocene, or decamethylnickelocene can be used as the donor substance, as well as an alkali metal, an alkaline earth metal, a rare earth metal, or a compound thereof (e.g., an alkali metal compound (including an oxide such as lithium oxide, a halide, and a carbonate such as lithium carbonate and cesium carbonate), an alkaline earth metal compound (including an oxide, a halide, and a carbonate), or a rare earth metal compound (including an oxide, a halide, and a carbonate)). As the substance having an electron-transport property, a material similar to the above-described material for the electron-transport layer 114 can be used.

For the second electrode 102, a metal, an alloy, an electrically conductive compound, or a mixture thereof each having a low work function (specifically, lower than or equal to 3.8 eV) or the like can be used. Specific examples of such a cathode material include elements belonging to Groups 1 and 2 of the periodic table, such as alkali metals (e.g., lithium (Li) and cesium (Cs)), magnesium (Mg), calcium (Ca), and strontium (Sr), alloys containing these elements (e.g., MgAg and AlLi), rare earth metals such as europium (Eu) and ytterbium (Yb), and alloys containing these rare earth metals. However, when the electron-injection layer is provided between the second electrode 102 and the electron-transport layer, a variety of conductive materials such as Al, Ag, ITO, or indium oxide-tin oxide containing silicon or silicon oxide can be used for the second electrode 102 regardless of the work function. Films of these conductive materials can be formed by a dry process such as a vacuum evaporation method or a sputtering method, an ink-jet method, a spin coating method, or the like. Alternatively, a wet process using a sol-gel method or a wet process using a paste of a metal material may be employed.

Furthermore, any of a variety of methods can be used for forming the EL layer 103, regardless of a dry method or a wet method. For example, a vacuum evaporation method, a gravure printing method, an offset printing method, a screen printing method, an ink-jet method, a spin coating method, or the like may be used.

Different methods may be used to form the electrodes or the layers described above.

The structure of the layers provided between the first electrode 101 and the second electrode 102 is not limited to the above-described structure. Preferably, a light-emitting region where holes and electrons recombine is positioned away from the first electrode 101 and the second electrode 102 so as to inhibit quenching due to the proximity of the light-emitting region and a metal used for electrodes or carrier-injection layers.

Furthermore, in order that transfer of energy from an exciton generated in the light-emitting layer can be suppressed, preferably, the hole-transport layer and the electron-transport layer which are in contact with the light-emitting layer 113, particularly a carrier-transport layer closer to the recombination region in the light-emitting layer 113, are formed using a substance having a wider band gap than the light-emitting material of the light-emitting layer or the light-emitting material included in the light-emitting layer.

Next, an embodiment of a light-emitting device with a structure in which a plurality of light-emitting units are stacked (this type of light-emitting device is also referred to as a stacked or tandem device) is described with reference to FIG. 3C. This light-emitting device includes a plurality of light-emitting units between an anode and a cathode. One light-emitting unit has substantially the same structure as the EL layer 103 illustrated in FIG. 3A. In other words, the light-emitting device illustrated in FIG. 3A or 3B includes a single light-emitting unit, and the light-emitting device illustrated in FIG. 3C includes a plurality of light-emitting units.

Figure 3C:
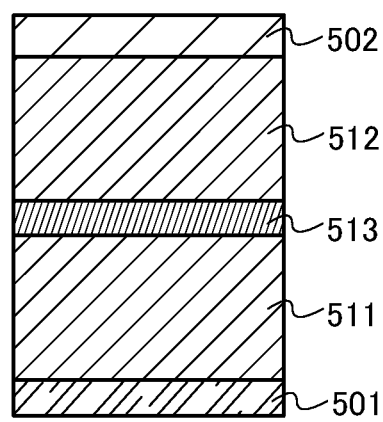

In FIG. 3C, a first light-emitting unit 511 and a second light-emitting unit 512 are stacked between a first electrode 501 and a second electrode 502, and a charge-generation layer 513 is provided between the first light-emitting unit 511 and the second light-emitting unit 512. The first electrode 501 and the second electrode 502 correspond, respectively, to the first electrode 101 and the second electrode 102 illustrated in FIG. 3A, and the materials given in the description for FIG. 3A can be used. Furthermore, the first light-emitting unit 511 and the second light-emitting unit 512 may have the same structure or different structures. Note that any or all of the hole-transport layers and electron-transport layers in the first light-emitting unit 511 and the second light-emitting unit 512 preferably include a material with a high GSP_slope.

The charge-generation layer 513 has a function of injecting electrons into one of the light-emitting units and injecting holes into the other of the light-emitting units when voltage is applied between the first electrode 501 and the second electrode 502. That is, in FIG. 3C, the charge-generation layer 513 injects electrons into the first light-emitting unit 511 and holes into the second light-emitting unit 512 when voltage is applied such that the potential of the anode becomes higher than the potential of the cathode.

The charge-generation layer 513 preferably has a structure similar to that of the charge-generation layer 116 described with reference to FIG. 3B. A composite material of an organic compound and a metal oxide has an excellent carrier-injection property and an excellent carrier-transport property; thus, low-voltage driving and low-current driving can be achieved. In the case where the anode-side surface of a light-emitting unit is in contact with the charge-generation layer 513, the charge-generation layer 513 can also function as a hole-injection layer of the light-emitting unit; therefore, a hole-injection layer is not necessarily provided in the light-emitting unit.

In the case where the charge-generation layer 513 includes the electron-injection buffer layer 119, the electron-injection buffer layer 119 functions as the electron-injection layer in the light-emitting unit on the anode side; thus, an electron-injection layer is not necessarily formed in the light-emitting unit on the anode side.

The light-emitting device having two light-emitting units is described with reference to FIG. 3C; however, one embodiment of the present invention can also be applied to a light-emitting device in which three or more light-emitting units are stacked. With a plurality of light-emitting units partitioned by the charge-generation layer 513 between a pair of electrodes as in the light-emitting device of this embodiment, it is possible to provide a long-life element that can emit light with high luminance at a low current density. A light-emitting apparatus that can be driven at a low voltage and has low power consumption can be provided.

When the emission colors of the light-emitting units are different, light emission of a desired color can be obtained from the light-emitting device as a whole. For example, in a light-emitting device having two light-emitting units, the emission colors of the first light-emitting unit may be red and green and the emission color of the second light-emitting unit may be blue, so that the light-emitting device can emit white light as the whole.

The above-described layers and electrodes such as the EL layer 103, the first light-emitting unit 511, the second light-emitting unit 512, and the charge-generation layer can be formed by a method such as an evaporation method (including a vacuum evaporation method), a droplet discharge method (also referred to as an ink-jet method), a coating method, or a gravure printing method. A low molecular material, a middle molecular material (including an oligomer and a dendrimer), or a high molecular material may be included in the layers and electrodes.

Embodiment 3

In this embodiment, a light-emitting apparatus including the light-emitting device described in Embodiments 1 and 2 will be described.

Figure 38A:
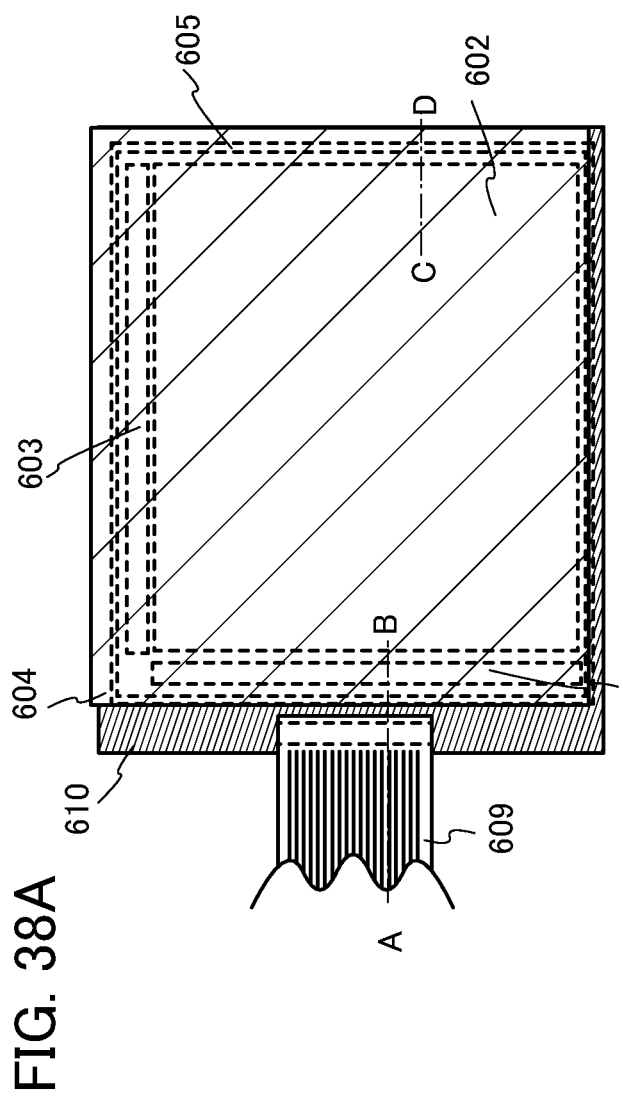
FIGS. 38A and 38B illustrate an active matrix light-emitting apparatus.
Figure 38B:
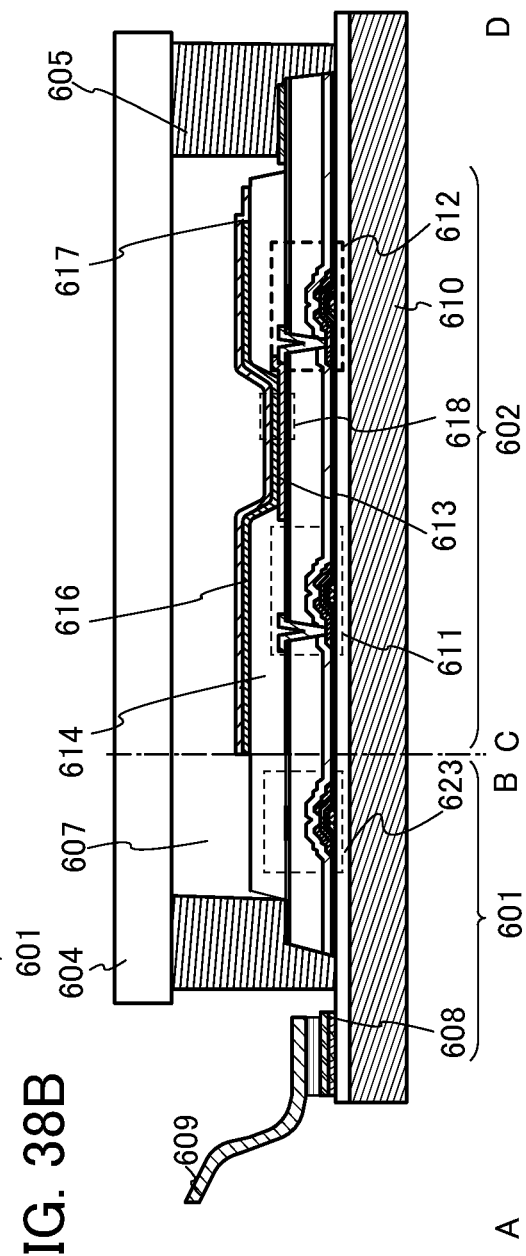

In this embodiment, the light-emitting apparatus manufactured using the light-emitting device described in Embodiments 1 and 2 is described with reference to FIGS. 38A and 38B. Note that FIG. 38A is a top view of the light-emitting apparatus and FIG. 38B is a cross-sectional view taken along the lines A-B and C-D in FIG. 38A. This light-emitting apparatus includes a driver circuit portion (source line driver circuit) 601, a pixel portion 602, and a driver circuit portion (gate line driver circuit) 603, which are to control light emission of a light-emitting device and illustrated with dotted lines. Reference numeral 604 denotes a sealing substrate; 605, a sealing material; and 607, a space surrounded by the sealing material 605.

Reference numeral 608 denotes a lead wiring for transmitting signals to be input to the source line driver circuit 601 and the gate line driver circuit 603 and receiving signals such as a video signal, a clock signal, a start signal, and a reset signal from a flexible printed circuit (FPC) 609 serving as an external input terminal. Although only the FPC is illustrated here, a printed wiring board (PWB) may be attached to the FPC. The light-emitting apparatus in this specification includes, in its category, not only the light-emitting apparatus itself but also the light-emitting apparatus provided with the FPC or the PWB.

Next, a cross-sectional structure is described with reference to FIG. 38B. The driver circuit portions and the pixel portion are formed over an element substrate 610; here, the source line driver circuit 601, which is a driver circuit portion, and one pixel in the pixel portion 602 are illustrated.

The element substrate 610 may be a substrate containing glass, quartz, an organic resin, a metal, an alloy, or a semiconductor or a plastic substrate formed of fiber reinforced plastics (FRP), poly(vinyl fluoride) (PVF), polyester, an acrylic resin, or the like.

The structure of transistors used in pixels and driver circuits is not particularly limited. For example, inverted staggered transistors may be used, or staggered transistors may be used. Furthermore, top-gate transistors or bottom-gate transistors may be used. A semiconductor material used for the transistors is not particularly limited, and for example, silicon, germanium, silicon carbide, gallium nitride, or the like can be used. Alternatively, an oxide semiconductor containing at least one of indium, gallium, and zinc, such as an In—Ga—Zn-based metal oxide, may be used.

There is no particular limitation on the crystallinity of a semiconductor material used for the transistors, and an amorphous semiconductor or a semiconductor having crystallinity (a microcrystalline semiconductor, a polycrystalline semiconductor, a single crystal semiconductor, or a semiconductor partly including crystal regions) may be used. It is preferable to use a semiconductor having crystallinity, in which case deterioration of the transistor characteristics can be suppressed.

Here, an oxide semiconductor is preferably used for semiconductor devices such as the transistors provided in the pixels and driver circuits and transistors used for touch sensors described later, and the like. In particular, an oxide semiconductor having a wider band gap than silicon is preferably used. When an oxide semiconductor having a wider band gap than silicon is used, off-state current of the transistors can be reduced.

The oxide semiconductor preferably contains at least indium (In) or zinc (Zn). Further preferably, the oxide semiconductor contains an oxide represented by an In-M-Zn-based oxide (M represents a metal such as Al, Ti, Ga, Ge, Y, Zr, Sn, La, Ce, or Hf).

As a semiconductor layer, it is particularly preferable to use an oxide semiconductor film including a plurality of crystal parts whose c-axes are aligned perpendicular to a surface on which the semiconductor layer is formed or the top surface of the semiconductor layer and in which the adjacent crystal parts have no grain boundary.

The use of such materials for the semiconductor layer makes it possible to provide a highly reliable transistor in which a change in the electrical characteristics is suppressed.

Charge accumulated in a capacitor through a transistor including the above-described semiconductor layer can be held for a long time because of the low off-state current of the transistor. When such a transistor is used in a pixel, operation of a driver circuit can be stopped while a gray scale of an image displayed in each display region is maintained. As a result, an electronic device with extremely low power consumption can be obtained.

For stable characteristics or the like of the transistor, a base film is preferably provided. The base film can be formed with a single-layer structure or a stacked-layer structure using an inorganic insulating film such as a silicon oxide film, a silicon nitride film, a silicon oxynitride film, or a silicon nitride oxide film. The base film can be formed by a sputtering method, a chemical vapor deposition (CVD) method (e.g., a plasma CVD method, a thermal CVD method, or a metal organic CVD (MOCVD) method), an atomic layer deposition (ALD) method, a coating method, a printing method, or the like. Note that the base film is not necessarily provided.

Note that an FET 623 is illustrated as a transistor formed in the driver circuit portion 601. In addition, the driver circuit may be formed with any of a variety of circuits such as a CMOS circuit, a PMOS circuit, or an NMOS circuit. Although a driver integrated type in which the driver circuit is formed over the substrate is illustrated in this embodiment, the driver circuit is not necessarily formed over the substrate, and the driver circuit can be formed outside.

The pixel portion 602 includes a plurality of pixels each including a switching FET 611, a current controlling FET 612, and a first electrode 613 electrically connected to a drain of the current controlling FET 612. One embodiment of the present invention is not limited to the structure. The pixel portion 602 may include three or more FETs and a capacitor in combination.

Note that an insulator 614 is formed to cover an end portion of the first electrode 613. Here, the insulator 614 can be formed using a positive photosensitive acrylic resin film.

In order to improve coverage with an EL layer or the like which is formed later, the insulator 614 is formed to have a curved surface with curvature at its upper or lower end portion. For example, in the case where a positive photosensitive acrylic resin is used as a material of the insulator 614, only the upper end portion of the insulator 614 preferably has a curved surface with a curvature radius (0.2 m to 3 m). As the insulator 614, either a negative photosensitive resin or a positive photosensitive resin can be used.

An EL layer 616 and a second electrode 617 are formed over the first electrode 613. Here, as a material used for the first electrode 613 functioning as an anode, a material having a high work function is preferably used. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like, a stack of a titanium nitride film and a film containing aluminum as its main component, a stack of three layers of a titanium nitride film, a film containing aluminum as its main component, and a titanium nitride film, or the like can be used. The stacked-layer structure enables low wiring resistance, favorable ohmic contact, and a function as an anode.

The EL layer 616 is formed by any of a variety of methods such as an evaporation method using an evaporation mask, an ink-jet method, and a spin coating method. The EL layer 616 has the structure described in Embodiments 1 and 2. As another material included in the EL layer 616, a low molecular compound or a high molecular compound (including an oligomer or a dendrimer) may be used.

As a material used for the second electrode 617, which is formed over the EL layer 616 and functions as a cathode, a material having a low work function (e.g., Al, Mg, Li, and Ca, or an alloy or a compound thereof, such as MgAg, MgIn, and AlLi) is preferably used. In the case where light generated in the EL layer 616 is transmitted through the second electrode 617, a stack of a thin metal film and a transparent conductive film (e.g., ITO, indium oxide containing zinc oxide at 2 wt % to 20 wt %, indium tin oxide containing silicon, or zinc oxide (ZnO)) is preferably used for the second electrode 617.

Note that the light-emitting device is formed with the first electrode 613, the EL layer 616, and the second electrode 617. The light-emitting device is the light-emitting device described in Embodiments 1 and 2. In the light-emitting apparatus of this embodiment, the pixel portion, which includes a plurality of light-emitting devices, may include both the light-emitting device described in Embodiments 1 and 2 and a light-emitting device having a different structure.

The sealing substrate 604 is attached to the element substrate 610 with the sealing material 605, so that a light-emitting device 618 is provided in the space 607 surrounded by the element substrate 610, the sealing substrate 604, and the sealing material 605. The space 607 may be filled with a filler, and may be filled with an inert gas (such as nitrogen or argon), or the sealing material. It is preferable that the sealing substrate be provided with a recessed portion and a drying agent be provided in the recessed portion, in which case deterioration due to influence of moisture can be suppressed.

An epoxy-based resin or glass frit is preferably used for the sealing material 605. It is preferable that such a material not be permeable to moisture or oxygen as much as possible. As the sealing substrate 604, a glass substrate, a quartz substrate, or a plastic substrate formed of fiber reinforced plastics (FRP), poly(vinyl fluoride) (PVF), polyester, an acrylic resin, or the like can be used.

Although not illustrated in FIGS. 38A and 38B, a protective film may be provided over the second electrode. As the protective film, an organic resin film or an inorganic insulating film may be formed. The protective film may be formed so as to cover an exposed portion of the sealing material 605. The protective film may be provided so as to cover surfaces and side surfaces of the pair of substrates and exposed side surfaces of a sealing layer, an insulating layer, and the like.

The protective film can be formed using a material through which an impurity such as water does not permeate easily. Thus, diffusion of an impurity such as water from the outside into the inside can be effectively suppressed.

As a material of the protective film, an oxide, a nitride, a fluoride, a sulfide, a ternary compound, a metal, a polymer, or the like can be used. For example, the material may contain aluminum oxide, hafnium oxide, hafnium silicate, lanthanum oxide, silicon oxide, strontium titanate, tantalum oxide, titanium oxide, zinc oxide, niobium oxide, zirconium oxide, tin oxide, yttrium oxide, cerium oxide, scandium oxide, erbium oxide, vanadium oxide, indium oxide, aluminum nitride, hafnium nitride, silicon nitride, tantalum nitride, titanium nitride, niobium nitride, molybdenum nitride, zirconium nitride, gallium nitride, a nitride containing titanium and aluminum, an oxide containing titanium and aluminum, an oxide containing aluminum and zinc, a sulfide containing manganese and zinc, a sulfide containing cerium and strontium, an oxide containing erbium and aluminum, an oxide containing yttrium and zirconium, or the like.

The protective film is preferably formed using a deposition method with favorable step coverage. One such method is an atomic layer deposition (ALD) method. A material that can be formed by an ALD method is preferably used for the protective film. A dense protective film having reduced defects such as cracks or pinholes or a uniform thickness can be formed by an ALD method. Furthermore, damage caused to a process member in forming the protective film can be reduced.

By an ALD method, a uniform protective film with few defects can be formed even on, for example, a surface with a complex uneven shape or upper, side, and lower surfaces of a touch panel.

As described above, the light-emitting apparatus manufactured using the light-emitting device described in Embodiments 1 and 2 can be obtained.

The light-emitting apparatus in this embodiment is manufactured using the light-emitting device described in Embodiments 1 and 2 and thus can have favorable characteristics. Specifically, since the light-emitting device described in Embodiments 1 and 2 has low driving voltage, the light-emitting apparatus can achieve low power consumption.

Figures 39A, 39B:
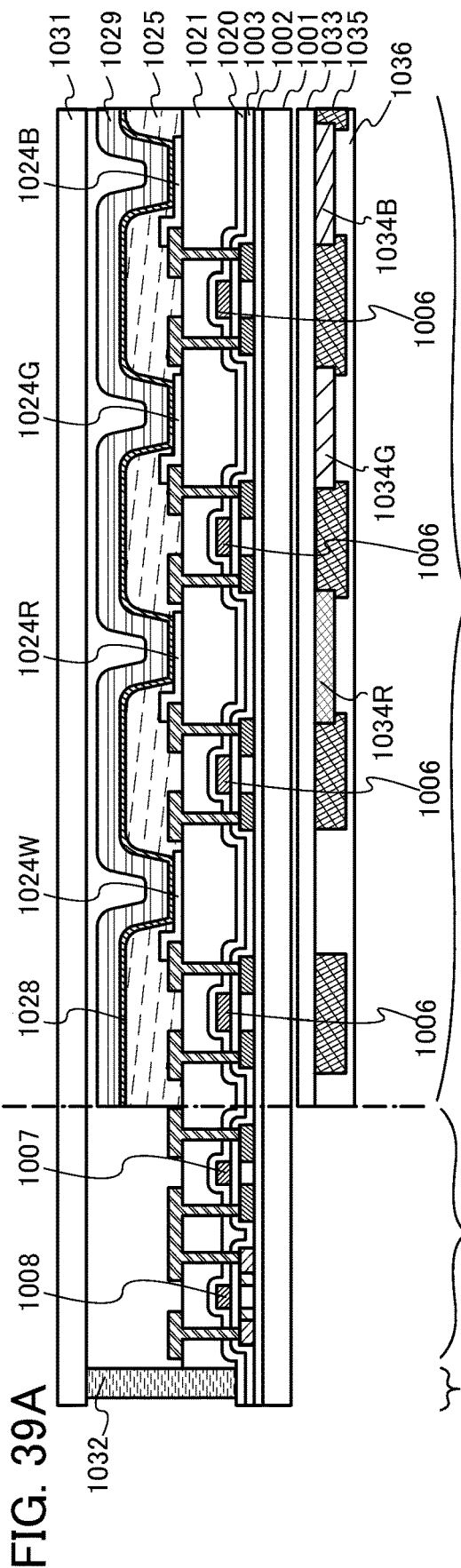
FIGS. 39A and 39B each illustrate an active matrix light-emitting apparatus.

FIGS. 39A and 39B each illustrate an example of a light-emitting apparatus in which full color display is achieved by formation of a light-emitting device exhibiting white light emission and with the use of coloring layers (color filters) and the like. In FIG. 39A, a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of light-emitting devices, a partition 1025, an EL layer 1028, a second electrode 1029 of the light-emitting devices, a sealing substrate 1031, a sealing material 1032, and the like are illustrated.

In FIG. 39A, coloring layers (a red coloring layer 1034R, a green coloring layer 1034G, and a blue coloring layer 1034B) are provided on a transparent base material 1033. A black matrix 1035 may be additionally provided. The transparent base material 1033 provided with the coloring layers and the black matrix is aligned and fixed to the substrate 1001. Note that the coloring layers and the black matrix 1035 are covered with an overcoat layer 1036. In FIG. 39A, light emitted from part of the light-emitting layer does not pass through the coloring layers, while light emitted from the other part of the light-emitting layer passes through the coloring layers. Since light which does not pass through the coloring layers is white and light which passes through any one of the coloring layers is red, green, or blue, an image can be displayed using pixels of the four colors.

FIG. 39B illustrates an example in which the coloring layers (the red coloring layer 1034R, the green coloring layer 1034G, and the blue coloring layer 1034B) are provided between the gate insulating film 1003 and the first interlayer insulating film 1020. As in the structure, the coloring layers may be provided between the substrate 1001 and the sealing substrate 1031.

Figure 40:
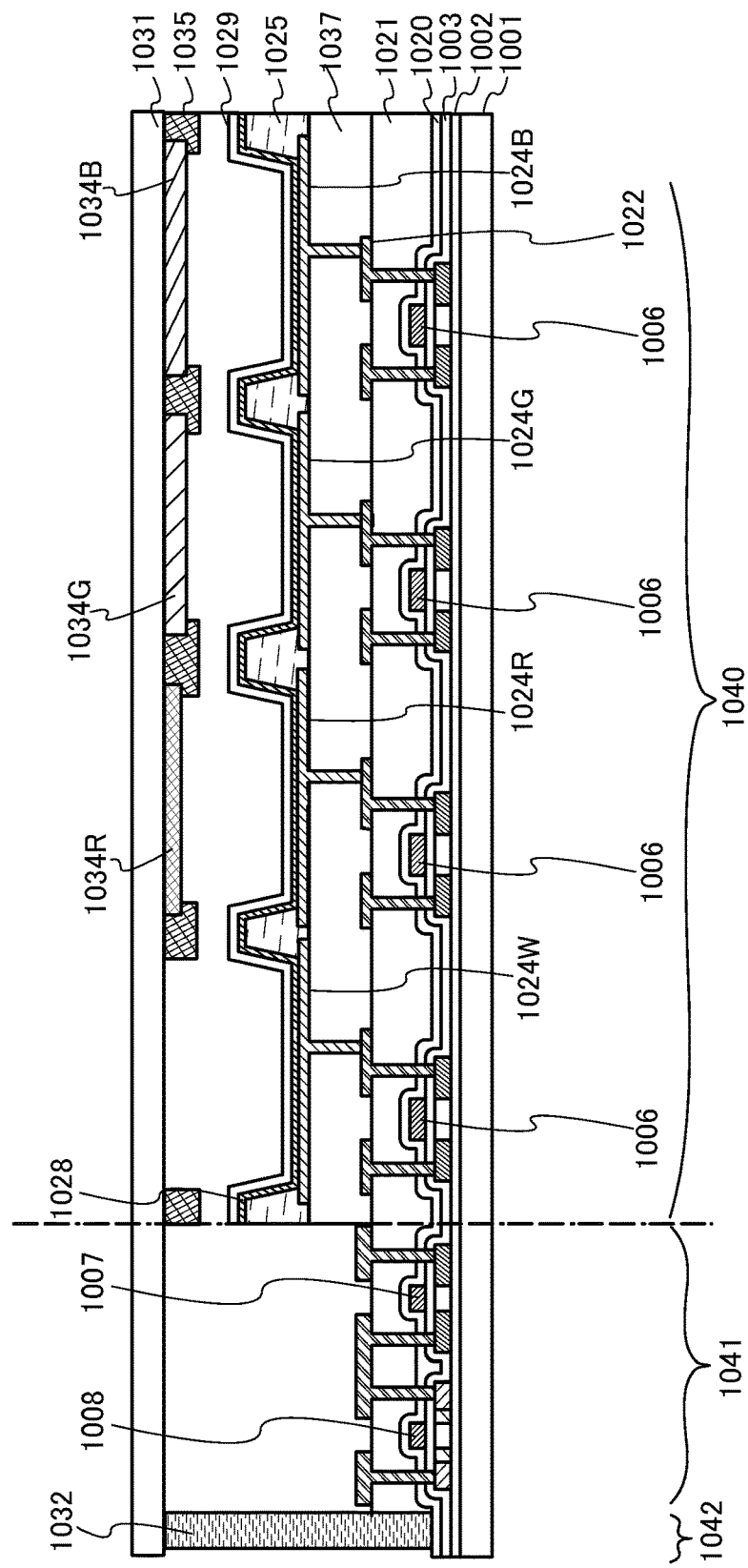
FIG. 40 illustrates an active matrix light-emitting apparatus.

The above-described light-emitting apparatus has a structure in which light is extracted from the substrate 1001 side where FETs are formed (a bottom emission structure), but may have a structure in which light is extracted from the sealing substrate 1031 side (atop emission structure). FIG. 40 is a cross-sectional view of a light-emitting apparatus having a top emission structure. In this case, a substrate that does not transmit light can be used as the substrate 1001. The process up to the step of forming a connection electrode that connects the FET and the anode of the light-emitting device is performed in a manner similar to that of the light-emitting apparatus having a bottom emission structure. Then, a third interlayer insulating film 1037 is formed to cover an electrode 1022. This insulating film may have a planarization function. The third interlayer insulating film 1037 can be formed using a material similar to that of the second interlayer insulating film, and can alternatively be formed using any of other known materials.

The first electrodes 1024W, 1024R, 1024G, and 1024B of the light-emitting devices each serve as an anode here, but may serve as a cathode. Furthermore, in the case of a light-emitting apparatus having a top emission structure as illustrated in FIG. 40, the first electrodes are preferably reflective electrodes. The EL layer 1028 is formed to have a structure similar to the structure of the EL layer 103, which is described in Embodiments 1 and 2, with which white light emission can be obtained.

In the case of a top emission structure as illustrated in FIG. 40, sealing can be performed with the sealing substrate 1031 on which the coloring layers (the red coloring layer 1034R, the green coloring layer 1034G, and the blue coloring layer 1034B) are provided. The sealing substrate 1031 may be provided with the black matrix 1035 which is positioned between pixels. The coloring layers (the red coloring layer 1034R, the green coloring layer 1034G, and the blue coloring layer 1034B) and the black matrix may be covered with the overcoat layer 1036. Note that a light-transmitting substrate is used as the sealing substrate 1031. Although an example in which full color display is performed using four colors of red, green, blue, and white is shown here, there is no particular limitation and full color display using four colors of red, yellow, green, and blue or three colors of red, green, and blue may be performed.

In the light-emitting apparatus having a top emission structure, a microcavity structure can be suitably employed. A light-emitting device with a microcavity structure is formed with the use of a reflective electrode as the first electrode and a transflective electrode as the second electrode. The light-emitting device with a microcavity structure includes at least an EL layer between the reflective electrode and the transflective electrode, which includes at least a light-emitting layer serving as a light-emitting region.

Note that the reflective electrode has a visible light reflectivity of 40% to 100%, preferably 70% to 100%, and a resistivity of $1 \times 10^{-2}$ $\Omega$cm or lower. In addition, the transflective electrode has a visible light reflectivity of 20% to 80%, preferably 40% to 70%, and a resistivity of $1 \times 10^{-2}$ $\Omega$cm or lower.

Light emitted from the light-emitting layer included in the EL layer is reflected and resonated by the reflective electrode and the transflective electrode.

In the light-emitting device, by changing thicknesses of the transparent conductive film, the composite material, the carrier-transport material, and the like, the optical path length between the reflective electrode and the transflective electrode can be changed. Thus, light with a wavelength that is resonated between the reflective electrode and the transflective electrode can be intensified while light with a wavelength that is not resonated therebetween can be attenuated.

Note that light that is reflected back by the reflective electrode (first reflected light) considerably interferes with light that directly enters the transflective electrode from the light-emitting layer (first incident light). For this reason, the optical path length between the reflective electrode and the light-emitting layer is preferably adjusted to $(2n-1)\lambda/4$ (n is a natural number of 1 or larger and $\lambda$ is a wavelength of light to be amplified). By adjusting the optical path length, the phases of the first reflected light and the first incident light can be aligned with each other and the light emitted from the light-emitting layer can be further amplified.

Note that in the above structure, the EL layer may include a plurality of light-emitting layers or may include a single light-emitting layer. The tandem light-emitting device described above may be combined with a plurality of EL layers; for example, a light-emitting device may have a structure in which a plurality of EL layers are provided, a charge-generation layer is provided between the EL layers, and each EL layer includes a plurality of light-emitting layers or a single light-emitting layer.

With the microcavity structure, emission intensity with a specific wavelength in the front direction can be increased, whereby power consumption can be reduced. Note that in the case of a light-emitting apparatus which displays images with subpixels of four colors, red, yellow, green, and blue, the light-emitting apparatus can have favorable characteristics because the luminance can be increased owing to yellow light emission and each subpixel can employ a microcavity structure suitable for wavelengths of the corresponding color.

The light-emitting apparatus in this embodiment is manufactured using the light-emitting device described in Embodiments 1 and 2 and thus can have favorable characteristics. Specifically, since the light-emitting device described in Embodiments 1 and 2 has low driving voltage, the light-emitting apparatus can achieve low power consumption.

Since many minute light-emitting devices arranged in a matrix in the light-emitting apparatus described above can each be controlled, the light-emitting apparatus can be suitably used as a display device for displaying images.

This embodiment can be freely combined with any of the other embodiments.

Embodiment 4

[Light-Emitting Apparatus]

An example of the light-emitting apparatus of one embodiment of the present invention using the above light-emitting device will be described below.

Figure 4A:
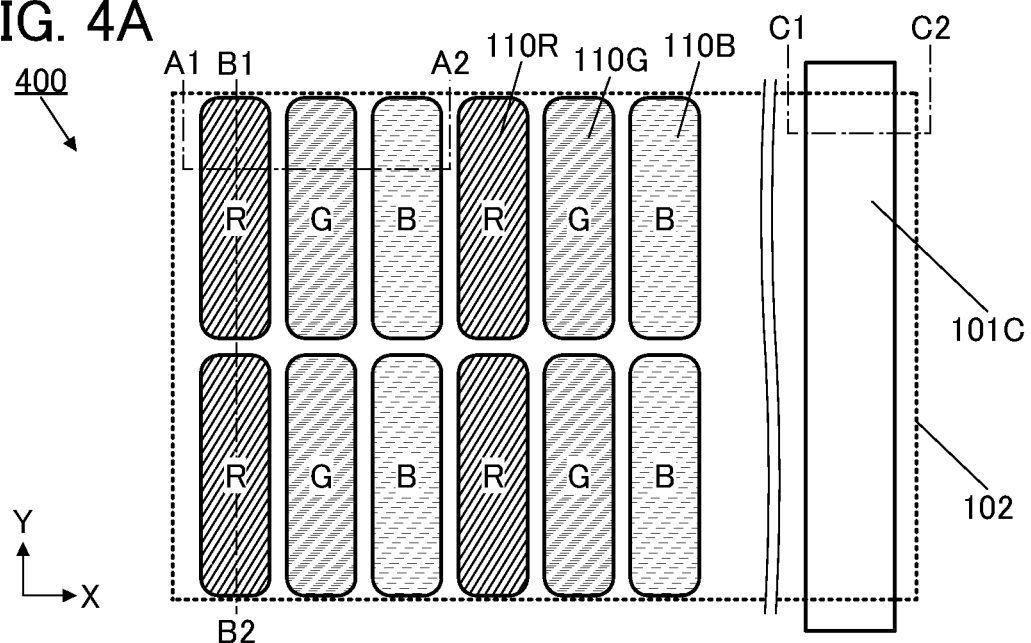
FIGS. 4A to 4D show a structure example of a display device.

FIG. 4A illustrates a schematic top view of a light-emitting apparatus 400 of one embodiment of the present invention. The light-emitting apparatus 400 includes a plurality of light-emitting devices 110R emitting red light, a plurality of light-emitting devices 110G emitting green light, and a plurality of light-emitting devices 110B emitting blue light. In FIG. 4A, light-emitting regions of the light-emitting devices are denoted by R, G, and B to easily differentiate the light-emitting devices.

The light-emitting devices 110R, the light-emitting devices 110G, and the light-emitting devices 110B are arranged in a matrix. FIG. 4A shows what is called a stripe arrangement, in which the light-emitting devices of the same color are arranged in one direction. Note that the arrangement of the light-emitting devices is not limited thereto; another arrangement such as a delta, zigzag, or PenTile pattern may also be used.

The light-emitting device 110R, the light-emitting device 110G, and the light-emitting device 1101B are arranged in the X direction. The light-emitting devices of the same color are arranged in the Y direction intersecting with the X direction.

The light-emitting device 110R, the light-emitting device 110G, and the light-emitting device 110B have the above structure.

Figure 4B:
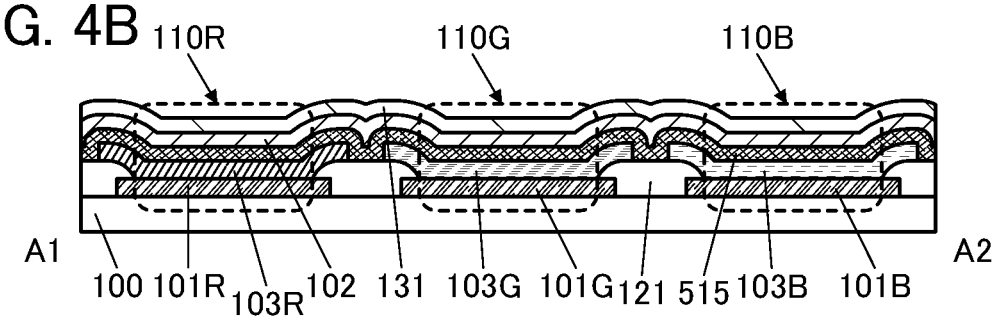
Figure 4C:
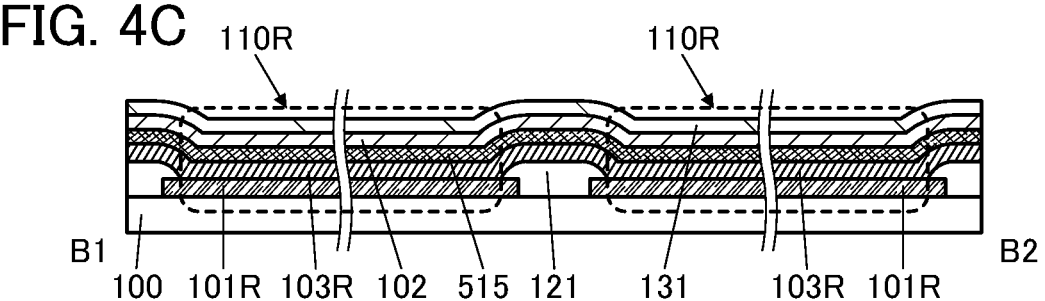

FIG. 4B is a cross-sectional schematic view taken along the dashed-dotted line A1-A2 in FIG. 4A. FIG. 4C is across-sectional schematic view taken along the dashed-dotted line B1-B2 in FIG. 4A.

FIG. 4B shows cross sections of the light-emitting device 110R, the light-emitting device 110G, and the light-emitting device 110B. The light-emitting device 110R includes a first electrode 101R serving as an anode, an EL layer 103R, an EL layer 515, and the second electrode 102 serving as a cathode. The light-emitting device 110G includes a first electrode 101G serving as an anode, an EL layer 103G, the EL layer 515, and the second electrode 102 serving as a cathode. The light-emitting device 110B includes a first electrode 101B serving as an anode, an EL layer 103B, the EL layer 515, and the second electrode 102 serving as a cathode. The EL layer 515 and the second electrode 102 are provided in common to the light-emitting device 110R, the light-emitting device 110G, and the light-emitting device 110B. The EL layer 515 can also be referred to as a common layer.

The EL layer 103R included in the light-emitting device 110R contains a light-emitting organic compound that emits light with intensity at least in a red wavelength range. The EL layer 103G included in the light-emitting device 110G contains a light-emitting organic compound that emits light with intensity at least in a green wavelength range. The EL layer 103B included in the light-emitting device 1101B contains a light-emitting organic compound that emits light with intensity at least in a blue wavelength range.

Note that the first light-emitting device and the second light-emitting device that are adjacent to each other correspond to the light-emitting devices 1110R and 110G and the light-emitting devices 110G and 110B in FIG. 4B, for example. Vertically arranged light-emitting devices of the same color in FIG. 4A can also be referred to as the light-emitting devices adjacent to each other.

Each of the EL layer 103R, the EL layer 103G, and the EL layer 103B may include one or more of a hole-injection layer, a hole-transport layer, a carrier-blocking layer, an exciton-blocking layer, and the like in addition to a layer containing a light-emitting organic compound (a light-emitting layer). The EL layer 515 does not include the light-emitting layer. In the light-emitting apparatus of one embodiment of the present invention, the EL layer 515 preferably serve as the electron-transport layer and the electron-injection layer.

The first electrode 101R, the first electrode 101G, and the first electrode 101B are provided for different light-emitting devices. The second electrode 102 and the EL layer 515 are each provided as a layer common to the light-emitting devices. A conductive film that transmits visible light is used for either the respective pixel electrodes or the second electrode 102, and a reflective conductive film is used for the other. When the respective pixel electrodes are light-transmitting electrodes and the second electrode 102 is a reflective electrode, a bottom-emission display device is obtained. When the respective pixel electrodes are reflective electrodes and the second electrode 102 is a light-transmitting electrode, a top-emission display device is obtained. Note that when both the respective pixel electrodes and the second electrode 102 transmit light, a dual-emission display device can be obtained.

An insulating layer 121 is provided to cover end portions of the first electrode 101R, the first electrode 101G, and the first electrode 101B. The end portions of the insulating layer 121 are preferably tapered. Note that the insulating layer 121 is not necessarily provided.

The EL layer 103R, the EL layer 103G, and the EL layer 103B each include a region in contact with a top surface of a pixel electrode and a region in contact with a surface of the insulating layer 121. End portions of the EL layer 103R, the EL layer 103G, and the EL layer 103B are positioned over the insulating layer 121.

As shown in FIG. 4B, there is a gap between the EL layers of two light-emitting devices with different colors. The EL layer 103R, the EL layer 103G, and the EL layer 103B are thus preferably provided so as not to be in contact with each other. This effectively prevents unintentional light emission from being caused by current flowing through two adjacent EL layers. As a result, the contrast can be increased to achieve a display device with high display quality.

FIG. 4C shows an example in which the EL layer 103R is formed in a band shape so as to be continuous in the Y direction. When the EL layer 103R and the like are formed in a band shape, no space for dividing the layer is needed to reduce a non-light-emitting area between the light-emitting devices, resulting in a higher aperture ratio. FIG. 4C shows the cross section of the light-emitting device 110R as an example; the light-emitting device 110G and the light-emitting device 110B can have a similar shape. Note that the EL layer may be divided for the light-emitting devices in the Y direction.

A protective layer 131 is provided over the second electrode 102 so as to cover the light-emitting device 110R, the light-emitting device 110G, and the light-emitting device 110B. The protective layer 131 has a function of preventing diffusion of impurities such as water into each light-emitting device from the above.

The protective layer 131 can have, for example, a single-layer structure or a stacked-layer structure at least including an inorganic insulating film. Examples of the inorganic insulating film include an oxide film or a nitride film such as a silicon oxide film, a silicon oxynitride film, a silicon nitride oxide film, a silicon nitride film, an aluminum oxide film, an aluminum oxynitride film, or a hafnium oxide film. Alternatively, a semiconductor material such as indium gallium oxide or indium gallium zinc oxide may be used for the protective layer 131.

As the protective layer 131, a stacked film of an inorganic insulating film and an organic insulating film can be used. For example, a structure in which an organic insulating film is sandwiched between a pair of inorganic insulating films is preferable. Furthermore, it is preferable that the organic insulating film function as a planarization film. With this structure, the top surface of the organic insulating film can be flat, and accordingly, coverage with the inorganic insulating film over the organic insulating film is improved, leading to an improvement in barrier properties. Moreover, since the top surface of the protective layer 131 is flat, a preferable effect can be obtained; when a component (e.g., a color filter, an electrode of a touch sensor, a lens array, or the like) is provided above the protective layer 131, the component is less affected by an uneven shape caused by the lower structure.

FIG. 4A also illustrates a connection electrode 101C that is electrically connected to the second electrode 102. The connection electrode 101C is supplied with a potential (e.g., an anode potential or a cathode potential) that is to be supplied to the second electrode 102. The connection electrode 101C is provided outside a display region where the light-emitting devices 110R and the like are arranged. In FIG. 4A, the second electrode 102 is denoted by a dashed line.

The connection electrode 101C can be provided along the outer periphery of the display region. For example, the connection electrode 101C may be provided along one side of the outer periphery of the display region or two or more sides of the outer periphery of the display region. That is, in the case where the display region has a rectangular top surface, the top surface of the connection electrode 101C can have a band shape, an L shape, a square bracket shape, a quadrangular shape, or the like.

Figure 4D:
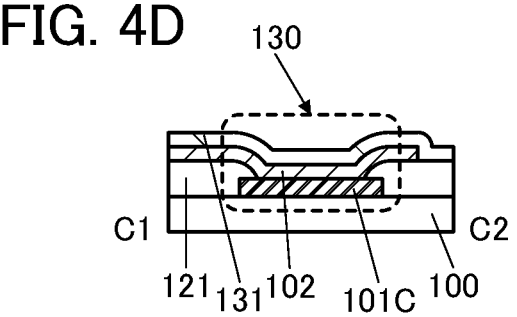

FIG. 4D is a cross-sectional schematic view taken along the dashed-dotted line C1-C2 in FIG. 4A. FIG. 4D illustrates a connection portion 130 at which the connection electrode 101C is electrically connected to the second electrode 102. In the connection portion 130, the second electrode 102 is provided on and in contact with the connection electrode 101C and the protective layer 131 is provided to cover the second electrode 102. In addition, the insulating layer 121 is provided to cover end portions of the connection electrode 101C.

[Manufacturing Method Example 1]

Figure 5A:
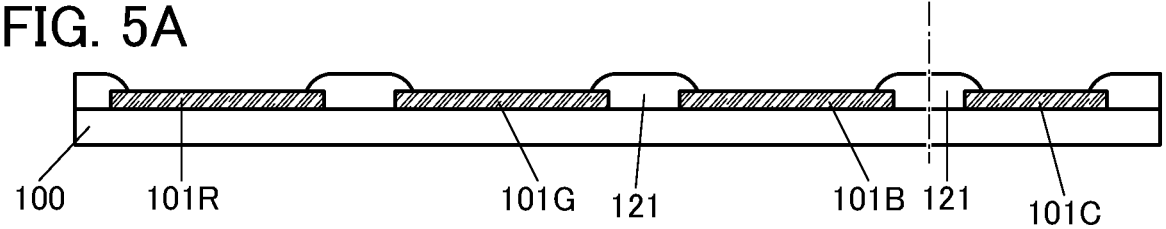
FIGS. 5A to 5F show a manufacturing method example of a display device.

An example of a method for manufacturing the display device of one embodiment of the present invention is described below with reference to the drawings. Here, description is made with use of the light-emitting apparatus 400 shown in the above structure example. FIGS. 5A to 5F are cross-sectional schematic views of steps in a manufacturing method of a display device described below. In FIG. 5A and the like, the cross-sectional schematic views of the connection portion 130 and the periphery thereof are also illustrated on the right side.

Note that thin films included in the display device (e.g., insulating films, semiconductor films, or conductive films) can be formed by any of a sputtering method, a chemical vapor deposition (CVD) method, a vacuum evaporation method, a pulsed laser deposition (PLD) method, an atomic layer deposition (ALD) method, and the like. Examples of the CVD method include a plasma-enhanced chemical vapor deposition (PECVD) method and a thermal CVD method. An example of a thermal CVD method is a metal organic CVD (MOCVD) method.

Alternatively, thin films included in the display device (e.g., insulating films, semiconductor films, and conductive films) can be formed by a method such as spin coating, dipping, spray coating, ink-jetting, dispensing, screen printing, or offset printing or with a doctor knife, a slit coater, a roll coater, a curtain coater, or a knife coater.

Thin films included in the display device can be processed by a photolithography method or the like. Besides, a nanoimprinting method, a sandblasting method, a lift-off method, or the like may be used to process thin films. Alternatively, island-shaped thin films may be directly formed by a film formation method using a shielding mask such as a metal mask.

There are two typical examples of photolithography methods. In one of the methods, a resist mask is formed over a thin film that is to be processed, the thin film is processed by etching or the like, and then the resist mask is removed. In the other method, a photosensitive thin film is formed and then processed into a desired shape by light exposure and development.

As light for exposure in a photolithography method, light with an i-line (with a wavelength of 365 nm), light with a g-line (with a wavelength of 436 nm), light with an h-line (with a wavelength of 405 nm), or light in which the i-line, the g-line, and the h-line are mixed can be used. Alternatively, ultraviolet light, KrF laser light, ArF laser light, or the like can be used. Exposure may be performed by liquid immersion exposure technique. As the light for exposure, extreme ultraviolet (EUV) light or X-rays may also be used. Furthermore, instead of the light used for the exposure, an electron beam can also be used. It is preferable to use EUV, X-rays, or an electron beam because extremely minute processing can be performed. Note that a photomask is not needed when exposure is performed by scanning with a beam such as an electron beam.

For etching of thin films, a dry etching method, a wet etching method, a sandblast method, or the like can be used.

[Preparation for Substrate 100]

A substrate that has heat resistance high enough to withstand at least heat treatment performed later can be used as the substrate 100. When an insulating substrate is used as the substrate 100, a glass substrate, a quartz substrate, a sapphire substrate, a ceramic substrate, an organic resin substrate, or the like can be used. Alternatively, a semiconductor substrate can be used. For example, a single crystal semiconductor substrate or a polycrystalline semiconductor substrate of silicon, silicon carbide, or the like; a compound semiconductor substrate of silicon germanium or the like; an SOI substrate; or the like can be used.

As the substrate 100, it is particularly preferable to use the semiconductor substrate or the insulating substrate over which a semiconductor circuit including a semiconductor element such as a transistor is formed. The semiconductor circuit preferably forms a pixel circuit, a gate line driver circuit (a gate driver), a source line driver circuit (a source driver), or the like. In addition to the above, an arithmetic circuit, a memory circuit, or the like may be formed.

[Formation of First Electrodes 101R, 101G, and 101B, and Connection Electrode 101C]

Next, the first electrodes 101R, 101G, and 101B, and the connection electrode 101C are formed over the substrate 100. First, a conductive film to be an anode (a pixel electrode) is formed, a resist mask is formed by a photolithography method, and an unnecessary portion of the conductive film is removed by etching. After that, the resist mask is removed to form the first electrodes 101R, 101G, and 101B.

In the case where a conductive film that reflects visible light is used as each pixel electrode, it is preferable to use a material (e.g., silver or aluminum) having reflectance as high as possible in the whole wavelength range of visible light. This can increase both light extraction efficiency of the light-emitting devices and color reproducibility. In the case where a conductive film that reflects visible light is used as each pixel electrode, what is called a top-emission light-emitting apparatus in which light is extracted in the direction opposite to the substrate can be obtained. In the case where a conductive film that transmits light is used as each pixel electrode, what is called a bottom-emission light-emitting apparatus in which light is extracted in the direction of the substrate can be obtained.

[Formation of Insulating Layer 121]

Then, the insulating layer 121 is provided to cover end portions of the first electrode 101R, the first electrode 101G, and the first electrode 101B (FIG. 5A). An organic insulating film or an inorganic insulating film can be used as the insulating layer 121. The end portions of the insulating layer 121 are preferably tapered to improve step coverage with an EL film. In particular, when an organic insulating film is used, a photosensitive material is preferably used so that the shape of the end portions can be easily controlled by the conditions of light exposure and development. In the case where the insulating layer 121 is not provided, the distance between the light-emitting devices can be further reduced to offer a light-emitting apparatus with higher resolution.

[Formation of EL Film 103Rb]

Subsequently, the EL film 103Rb, which is to be the EL layer 103R, is formed over the first electrode 101R, the first electrode 101G, the first electrode 101B, and the insulating layer 121.

The EL film 103Rb includes at least a film containing a light-emitting compound. The EL film 103Rb may have a structure in which one or more films functioning as a hole-transport layer, a hole-injection layer, an electron-blocking layer, an electron-transport layer, and an electron-injection layer are further stacked. The EL film 103Rb can be formed by, for example, an evaporation method, a sputtering method, an inkjet method, or the like. Without limitation to this, the above-described film-formation method can be used as appropriate.

For example, the EL film 103Rb is preferably a stacked film in which a hole-injection layer, a hole-transport layer, a light-emitting layer, and an electron-transport layer are stacked in this order. In that case, a film including the electron-injection layer 115 can be used as the EL layer formed later.

The EL film 103Rb is preferably formed so as not to overlap with the connection electrode 101C. For example, in the case where the EL film 103Rb is formed by an evaporation method (or a sputtering method), it is preferable that the EL film 103Rb be formed using a shielding mask so as not to be formed over the connection electrode 101C, or the EL film 103Rb be removed in a later etching step.

[Formation of Sacrificial Film 144a]

Then, the sacrificial film 144a is formed to cover the EL film 103Rb. The sacrificial film 144a is provided in contact with a top surface of the connection electrode 101C.

As the sacrificial film 144a, it is possible to use a film highly resistant to etching treatment performed on various EL films such as the EL film 103Rb, i.e., a film having high etching selectivity with respect to the EL film. Furthermore, as the sacrificial film 144a, it is possible to use a film having high etching selectivity with respect to a protective film such as a protective film 146a described later. Moreover, as the sacrificial film 144a, it is possible to use a film that can be removed by a wet etching method less likely to cause damage to the EL film.

The sacrificial film 144a can be formed using an inorganic film such as a metal film, an alloy film, a metal oxide film, a semiconductor film, or an inorganic insulating film, for example. The sacrificial film 144a can be formed by any of a variety of film formation methods such as a sputtering method, an evaporation method, a CVD method, and an ALD method.

The sacrificial film 144a can be formed using a metal material such as gold, silver, platinum, magnesium, nickel, tungsten, chromium, molybdenum, iron, cobalt, copper, palladium, titanium, aluminum, yttrium, zirconium, or tantalum or an alloy material containing the metal material. It is particularly preferable to use a low-melting-point material such as aluminum or silver.

Alternatively, the sacrificial film 144a can be formed using a metal oxide such as an indium-gallium-zinc oxide (In—Ga—Zn oxide, also referred to as IGZO). It is also possible to use indium oxide, indium zinc oxide (In—Zn oxide), indium tin oxide (In—Sn oxide), indium titanium oxide (In—Ti oxide), indium tin zinc oxide (In—Sn—Zn oxide), indium titanium zinc oxide (In—Ti—Zn oxide), indium gallium tin zinc oxide (In—Ga—Sn—Zn oxide), or the like. Indium tin oxide containing silicon, or the like can also be used.

An element M (M is one or more of aluminum, silicon, boron, yttrium, copper, vanadium, beryllium, titanium, iron, nickel, germanium, zirconium, molybdenum, lanthanum, cerium, neodymium, hafnium, tantalum, tungsten, and magnesium) may be used instead of gallium. In particular, M is preferably one or more of gallium, aluminum, and yttrium.

Alternatively, the sacrificial film 144a can be formed using an inorganic insulating material such as aluminum oxide, hafnium oxide, or silicon oxide.

The sacrificial film 144a is preferably formed using a material that can be dissolved in a solvent chemically stable with respect to at least the uppermost film of the EL film 103Rb. Specifically, a material that will be dissolved in water or alcohol can be suitably used for the sacrificial film 144a. In formation of the sacrificial film 144a, it is preferable that application of such a material dissolved in a solvent such as water or alcohol be performed by a wet process and followed by heat treatment for evaporating the solvent. At this time, the heat treatment is preferably performed under a reduced-pressure atmosphere, in which case the solvent can be removed at a low temperature in a short time and thermal damage to the EL film 103Rb can be accordingly minimized.

The sacrificial film 144a can be formed by spin coating, dipping, spray coating, ink-jetting, dispensing, screen printing, or offset printing, or with a doctor knife, a slit coater, a roll coater, a curtain coater, or a knife coater, for example.

The sacrificial film 144a can be formed using an organic material such as polyvinyl alcohol (PVA), polyvinylbutyral, polyvinylpyrrolidone, polyethylene glycol, polyglycerin, pullulan, water-soluble cellulose, or an alcohol-soluble polyamide resin.

[Formation of Protective Film 146a]

Figure 5B:
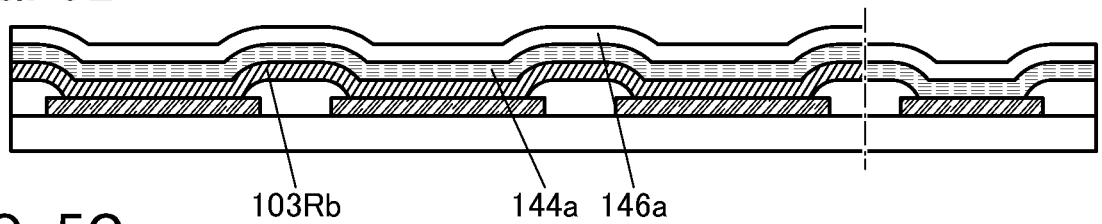

Next, the protective film 146a is formed over the sacrificial film 144a (FIG. 5B).

The protective film 146a is a film used as a hard mask when the sacrificial film 144a is etched later. In a later step of processing the protective film 146*a*, the sacrificial film 144*a* is exposed. Thus, the combination of films having high etching selectivity therebetween is selected for the sacrificial film 144*a* and the protective film 146*a*. It is thus possible to select a film that can be used for the protective film 146*a* depending on an etching condition of the sacrificial film 144*a* and an etching condition of the protective film 146*a*.

For example, in the case where dry etching using a gas containing fluorine (also referred to as a fluorine-based gas) is performed for the etching of the protective film 146*a*, the protective film 146*a* can be formed using silicon, silicon nitride, silicon oxide, tungsten, titanium, molybdenum, tantalum, tantalum nitride, an alloy containing molybdenum and niobium, an alloy containing molybdenum and tungsten, or the like. Here, a metal oxide film using IGZO, ITO, or the like is given as a film having high etching selectivity (that is, enabling low etching rate) in dry etching using the fluorine-based gas, and such a film can be used as the sacrificial film 144*a*.

Without being limited to the above, a material of the protective film 146*a* can be selected from a variety of materials depending on etching conditions of the sacrificial film 144*a* and the protective film 146*a*. For example, any of the films that can be used for the sacrificial film 144*a* can be used.

As the protective film 146*a*, a nitride film can be used, for example. Specifically, a nitride such as silicon nitride, aluminum nitride, hafnium nitride, titanium nitride, tantalum nitride, tungsten nitride, gallium nitride, or germanium nitride can be used.

As the protective film 146*a*, an oxide film can also be used. Typically, it is possible to use a film of an oxide or an oxynitride such as silicon oxide, silicon oxynitride, aluminum oxide, aluminum oxynitride, hafnium oxide, or hafnium oxynitride.

Alternatively, as the protective film 146*a*, an organic film that can be used for the EL film 103Rb or the like can be used. For example, the protective film 146*a* can be formed using the organic film that is used for the EL film 103Rb, an EL film 103Gb or an EL film 103Bb. Use of such an organic film is preferable because the same film-formation apparatus can be used for formation of the EL film 103Rb or the like.
[Formation of Resist Mask 143*a*]

Figure 5C:
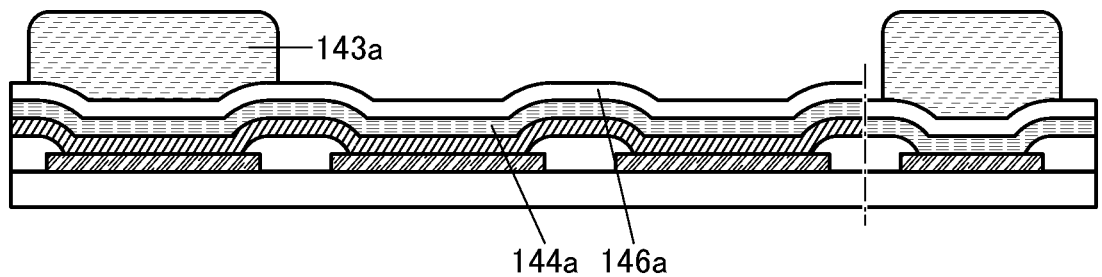

Then, the resist mask 143*a* is formed in positions over the protective film 146*a* that overlap with the first electrode 101R and the connection electrode 101C (FIG. 5C).

For the resist mask 143*a*, a resist material containing a photosensitive resin such as a positive type resist material or a negative type resist material can be used.

On the assumption that the resist mask 143*a* is formed over the sacrificial film 144*a* without the protective film 146*a* therebetween, there is a risk of dissolving the EL film 103Rb due to a solvent of the resist material if a defect such as a pinhole exists in the sacrificial film 144*a*. Such a defect can be prevented by using the protective film 146*a*.

In the case where a film that is unlikely to cause a defect such as a pinhole is used as the sacrificial film 144*a*, the resist mask 143*a* may be formed directly on the sacrificial film 144*a* without the protective film 146*a* therebetween.
[Etching of Protective Film 146*a*]

Next, part of the protective film 146*a* that is not covered with the resist mask 143*a* is removed by etching, so that a band-shaped protective layer 147*a* is formed. At that time, the protective layer 147*a* is formed also over the connection electrode 101C.

In the etching of the protective film 146*a*, an etching condition with high selectively is preferably employed so that the sacrificial film 144*a* is not removed by the etching. Either wet etching or dry etching can be performed for the etching of the protective film 146*a*. With use of dry etching, a reduction in a processing pattern of the protective film 146*a* can be inhibited.
[Removal of Resist Mask 143*a*]

Figure 5D:
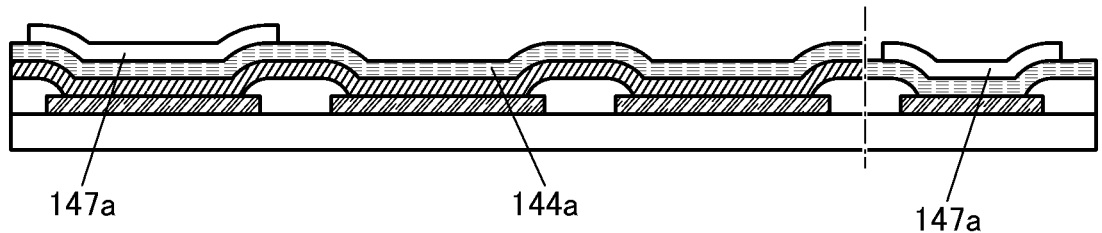

Then, the resist mask 143*a* is removed (FIG. 5D).

The removal of the resist mask 143*a* can be performed by wet etching or dry etching. It is particularly preferable to perform dry etching (also referred to as plasma ashing) using an oxygen gas as an etching gas to remove the resist mask 143*a*.

At this time, the removal of the resist mask 143*a* is performed in a state where the EL film 103Rb is covered with the sacrificial film 144*a*; thus, the EL film 103Rb is less likely to be affected by the removal. In particular, when the EL film 103Rb is exposed to oxygen, the electrical characteristics of the light-emitting device are adversely affected in some cases. Therefore, it is preferable that the EL film 103Rb be covered by the sacrificial film 144*a* when etching using an oxygen gas, such as plasma ashing, is performed.
[Etching of Sacrificial Film 144*a*]

Figure 5E:
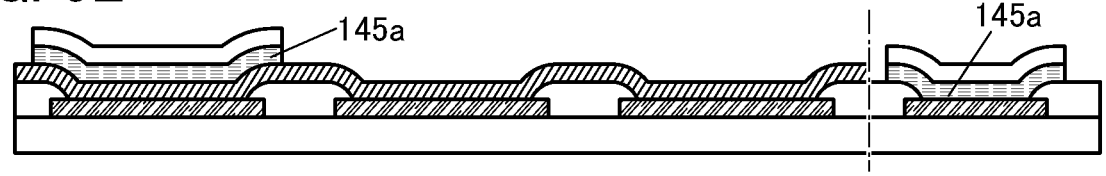

Next, part of the sacrificial film 144*a* that is not covered with the protective layer 147*a* is removed by etching with use of the protective layer 147*a* as a mask, so that a band-shaped sacrificial layer 145*a* is formed (FIG. 5E). At that time, the sacrificial layer 145*a* is formed also over the connection electrode 101C.

Either wet etching or dry etching can be performed for the etching of the sacrificial film 144*a*. With use of dry etching, a reduction in a processing pattern of the sacrificial film 144*a* can be inhibited.
[Etching of EL Film 103Rb and Protective Layer 147*a*]

Figure 5F:
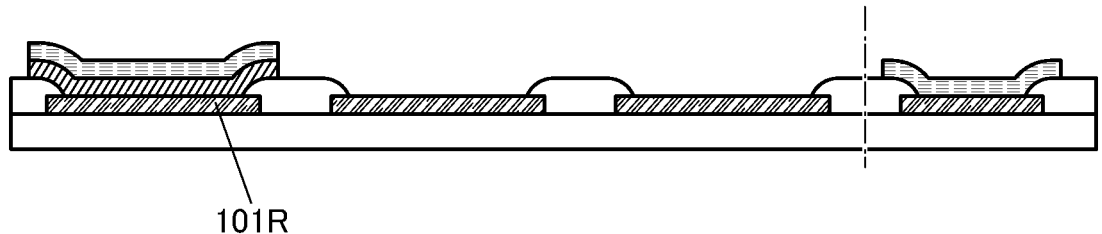

Next, the protective layer 147*a* and part of the EL film 103Rb that is not covered with the sacrificial layer 145*a* are removed by etching at the same time, so that the band-shaped EL layer 103R is formed (FIG. 5F). At that time, the protective layer 147*a* over the connection electrode 101C is also removed.

The EL film 103Rb and the protective layer 147*a* are preferably etched by the same treatment so that the process can be simplified to reduce the fabrication cost of the display device.

For the etching of the EL film 103Rb, it is particularly preferable to perform dry etching using an etching gas that does not contain oxygen as its main component. This is because the alteration of the EL film 103Rb is inhibited, and a highly reliable display device can be achieved. Examples of the etching gas that does not contain oxygen as its main component include $CF_4$, $C_4F_8$, $SF_6$, $CHF_3$, $Cl_2$, $H_2O$, $BCl_3$, or a rare gas such as $H_2$ or He. Alternatively, a mixed gas of the above gas and a dilution gas that does not contain oxygen can be used as the etching gas.

Note that the etching of the EL film 103Rb and the etching of the protective layer 147*a* may be performed separately. In that case, either the etching of the EL film 103Rb or the etching of the protective layer 147*a* may be performed first.

At this step, the EL layer 103R and the connection electrode 101C are covered with the sacrificial layer 145*a*.
[Formation of EL Film 103Gb]

Subsequently, the EL film 103Gb, which is to be the EL layer 103G, is formed over the sacrificial layer 145*a*, the insulating layer 121, the first electrode 101G, and the first electrode 101B. In that case, similarly to the EL film 103Rb, the EL film 103Gb is preferably not provided over the connection electrode 101C.

For the formation method of the EL film 103Gb, the above description of the EL film 103Rb can be referred to.

[Formation of Sacrificial Film 144b]

Then, the sacrificial film 144b is formed over the EL film 103Gb. The sacrificial film 144b can be formed in a manner similar to that for the sacrificial film 144a. In particular, the sacrificial film 144b and the sacrificial film 144a are preferably formed using the same material.

At that time, the sacrificial film 144a is formed also over the connection electrode 101C so as to cover the sacrificial layer 145a.

[Formation of Protective Film 146b]

Next, the protective film 146b is formed over the sacrificial film 144b. The protective film 146b can be formed in a manner similar to that for the protective film 146a. In particular, the protective film 146b and the protective film 146a are preferably formed using the same material.

[Formation of Resist Mask 143b]

Figure 6A:
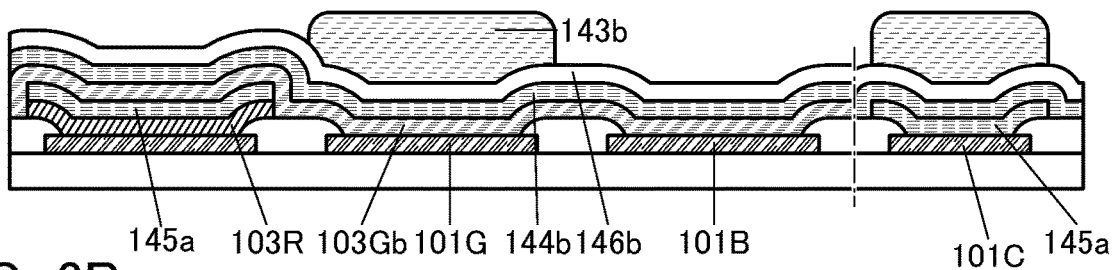
FIGS. 6A to 6F show a manufacturing method example of a display device.

Then, the resist mask 143b is formed in positions over the protective film 146b that overlap with the first electrode 101G and the connection electrode 101C (FIG. 6A).

The resist mask 143b can be formed in a manner similar to that for the resist mask 143a.

[Etching of Protective Film 146b]

Figure 6B:
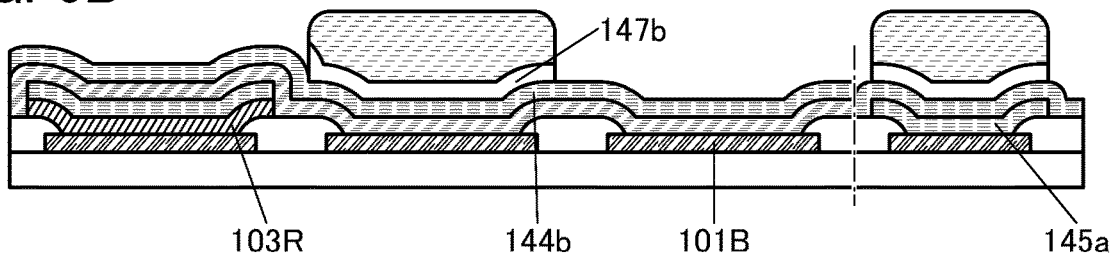

Next, part of the protective film 146b that is not covered with the resist mask 143b is removed by etching, so that a band-shaped protective layer 147b is formed (FIG. 6B). At that time, the protective layer 147b is formed also over the connection electrode 101C.

For the etching of the protective film 146b, the above description of the protective film 146a can be referred to.

[Removal of Resist Mask 143b]

Then, the resist mask 143b is removed. For the removal of resist mask 143b, the above description of the resist mask 143a can be referred to.

[Etching of Sacrificial Film 144b]

Next, part of the sacrificial film 144b that is not covered with the protective layer 147b is removed by etching with use of the protective layer 147b as a mask, so that a band-shaped sacrificial layer 145b is formed. At that time, the sacrificial layer 145b is formed also over the connection electrode 101C. The sacrificial layer 145a and the sacrificial layer 145b are stacked over the connection electrode 101C.

For the etching of the sacrificial film 144b, the above description of the sacrificial film 144a can be referred to.

[Etching of EL Film 103Gb and Protective Layer 147b]

Figure 6C:
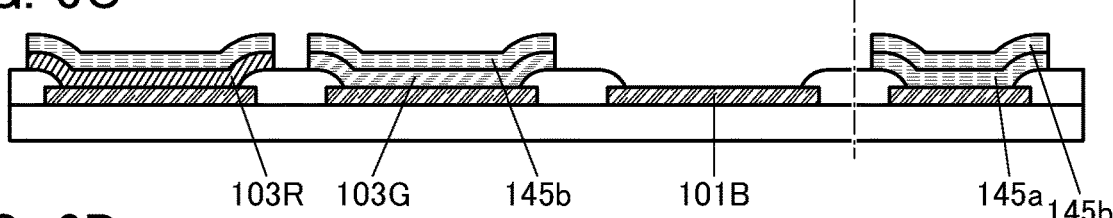

Next, the protective layer 147b and part of the EL film 103Gb that is not covered with the sacrificial layer 145b are removed by etching at the same time, so that the band-shaped EL layer 103G is formed (FIG. 6C). At that time, the protective layer 147b over the connection electrode 101C is also removed.

For the etching of the EL film 103Gb and the protective layer 147b, the above description of the EL film 103Rb and the protective layer 147a can be referred to.

At this time, the EL layer 103R is protected by the sacrificial layer 145a, and thus can be prevented from being damaged in the etching step of the EL film 103Gb.

In the above manner, the band-shaped EL layer 103R and the band-shaped EL layer 103G can be separately formed with highly accurate alignment.

[Formation of EL Layer 103B]

Figure 6D:
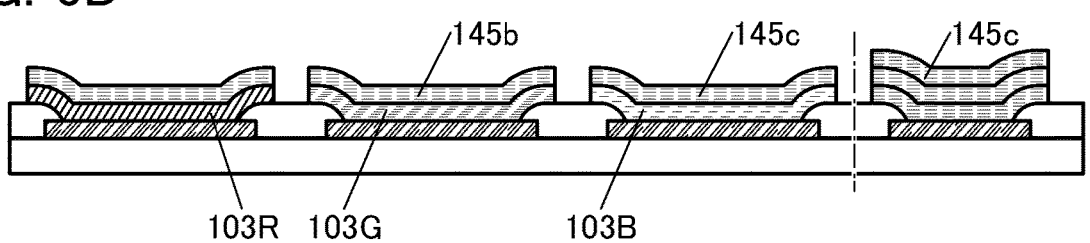

The above steps are performed on an EL film 103Bb (not illustrated), whereby the island-shaped EL layer 103B and an island-shaped sacrificial layer 145c can be formed (FIG. 6D).

That is, after the formation of the EL layer 103G, the EL film 103Bb, a sacrificial film 144c, a protective film 146c, and a resist mask 143c (each of which is not illustrated) are sequentially formed. After that, the protective film 146c is etched to form a protective layer 147c (not illustrated); then, the resist mask 143c is removed. Subsequently, the sacrificial film 144c is etched to form the sacrificial layer 145c. Then, the protective layer 147c and the EL film 103Bb are etched to form the band-shaped EL layer 103B.

After the EL layer 103B is formed, the sacrificial layer 145c is also formed over the connection electrode 101C. The sacrificial layer 145a, the sacrificial layer 145b, and the sacrificial layer 145c are stacked over the connection electrode 101C.

[Removal of Sacrificial Layer]

Figure 6E:
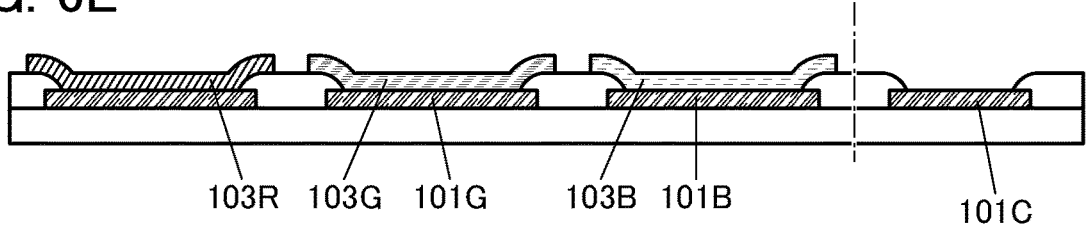

Next, the sacrificial layer 145a, the sacrificial layer 145b, and the sacrificial layer 145c are removed, whereby top surfaces of the EL layer 103R, the EL layer 103G, and the EL layer 103B are exposed (FIG. 6E). At that time, the top surface of the connection electrode 101C is also exposed.

At this time, the surface of the EL layer might be damaged to some extent by exposure to an etching gas or an etchant. For example, if patterning follows the formation of the electron-transport layer, a surface of the electron-transport layer might be damaged, leading to the degradation of electron-injection property. In view of this, using a material with a GSP_slope higher than or equal to 20 for one or both of the electron-transport layer and the hole-blocking layer improves the electron-injection property. Thus, the light-emitting device of one embodiment of the present invention can be favorably used for a light-emitting apparatus or a display device which is manufactured by a photoetching method.

The sacrificial layer 145a, the sacrificial layer 145b, and the sacrificial layer 145c can be removed by wet etching or dry etching. At this time, a method that causes damage to the EL layer 103R, the EL layer 103G, and the EL layer 103B as little as possible is preferably employed. In particular, a wet etching method is preferably used. For example, wet etching using a tetramethyl ammonium hydroxide (TMAH) solution, diluted hydrofluoric acid, oxalic acid, phosphoric acid, acetic acid, nitric acid, or a mixed solution thereof is preferably performed.

Alternatively, the sacrificial layer 145a, the sacrificial layer 145b, and the sacrificial layer 145c are preferably removed by being dissolved in a solvent such as water or alcohol. Examples of the alcohol in which the sacrificial layer 145a, the sacrificial layer 145b, and the sacrificial layer 145c can be dissolved include ethyl alcohol, methyl alcohol, isopropyl alcohol (IPA), and glycerin.

After the sacrificial layer 145a, the sacrificial layer 145b, and the sacrificial layer 145c are removed, drying treatment is preferably performed in order to remove water contained in the EL layer 103R, the EL layer 103G, and the EL layer 103B and water adsorbed on the surfaces of the EL layer 103R, the EL layer 103G, and the EL layer 103B. For example, heat treatment is preferably performed in an inert gas atmosphere or a reduced-pressure atmosphere. The heat treatment can be performed at a substrate temperature higher than or equal to 50° C. and lower than or equal to 200° C., preferably higher than or equal to 60° C. and lower than or equal to 150° C., and further preferably higher than or equal to 70° C. and lower than or equal to 120° C. The heat treatment is preferably performed in a reduced-pressure atmosphere because drying at a lower temperature is possible.

In the above manner, the EL layer 103R, the EL layer 103G, and the EL layer 103B can be separately formed.

[Formation of EL Layer 515]

Then, the EL layer 515 is formed to cover the EL layer 103R, the EL layer 103G, and the EL layer 103B. The EL layer 515 includes a layer that injects and transports electrons, such as an electron-injection layer.

The EL layer 515 can be formed in a manner similar to that for the EL film 103Rb or the like. In the case where the EL layer 515 is formed by an evaporation method, the EL layer 515 is preferably formed using a shielding mask so as not to be formed over the connection electrode 101C.

[Formation of Second Electrode 102]

Figure 6F:
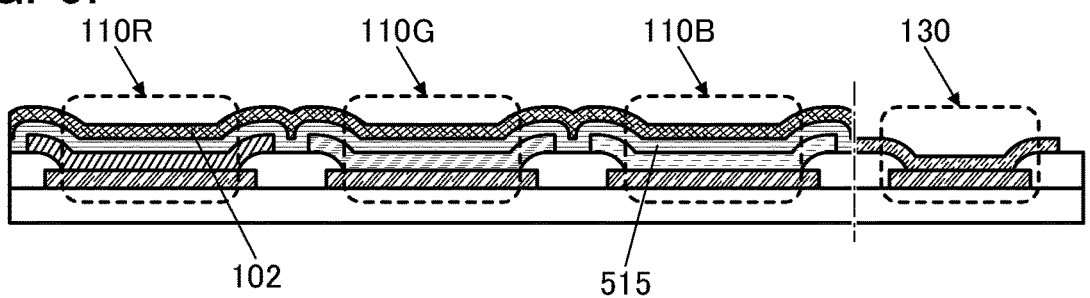

Then, the second electrode 102 is formed to cover the electron-injection layer 115 and the connection electrode 101C (FIG. 6F).

The second electrode 102 can be formed by a method such as an evaporation method or a sputtering method. Alternatively, a film formed by an evaporation method and a film formed by a sputtering method may be stacked. In that case, the second electrode 102 is preferably formed so as to cover a region where the electron-injection layer 115 is formed. That is, a structure in which end portions of the electron-injection layer 115 overlap with the second electrode 102 can be obtained. The second electrode 102 is preferably formed using a shielding mask.

The second electrode 102 is electrically connected to the connection electrode 101C outside a display region.

[Formation of Protective Layer]

Then, a protective layer is formed over the second electrode 102. An inorganic insulating film used for the protective layer is preferably formed by a sputtering method, a PECVD method, or an ALD method. In particular, an ALD method is preferable because a film deposited by ALD has good step coverage and is less likely to cause a defect such as pinhole. An organic insulating film is preferably formed by an inkjet method because a uniform film can be formed in a desired area.

In the above manner, the light-emitting apparatus of one embodiment of the present invention can be manufactured.

Although the second electrode 102 and the electron-injection layer 115 are formed so as to have different top surface shapes, they may be formed in the same region.

Embodiment 5

In this embodiment, a structure example of a display device of one embodiment of the present invention is described.

The display device in this embodiment can be a high-resolution display device or large-sized display device. Accordingly, the display device of this embodiment can be used for display portions of electronic devices such as a digital camera, a digital video camera, a digital photo frame, a mobile phone, a portable game console, a smart phone, a wristwatch terminal, a tablet terminal, a portable information terminal, and an audio reproducing device, in addition to display portions of electronic devices with a relatively large screen, such as a television device, a desktop or laptop personal computer, a monitor of a computer or the like, digital signage, and a large game machine such as a pachinko machine.

[Light-Emitting Apparatus 400A]

Figure 7:
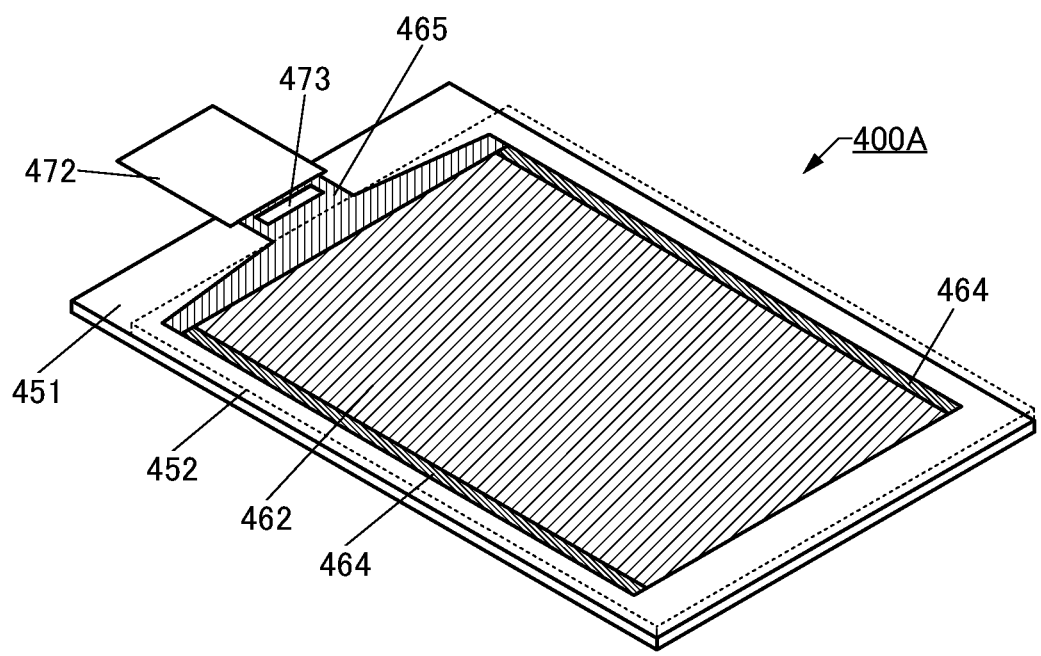
FIG. 7 is a perspective view of an example of a display device.

FIG. 7 is a perspective view of a light-emitting apparatus 400A, and FIG. 8A is a cross-sectional view of the light-emitting apparatus 400A.

The light-emitting apparatus 400A has a structure where a substrate 452 and a substrate 451 are bonded to each other. In FIGS. 8A and 8B, the substrate 452 is denoted by a dashed line.

The light-emitting apparatus 400A includes a display portion 462, a circuit 464, a wiring 465, and the like. FIGS. 8A and 8B illustrate an example in which an integrated circuit (IC) 473 and an FPC 472 are implemented on the light-emitting apparatus 400A. Thus, the structure illustrated in FIGS. 8A and 8B can be regarded as a display module including the light-emitting apparatus 400A, the IC, and the FPC.

As the circuit 464, a scan line driver circuit can be used, for example.

The wiring 465 has a function of supplying a signal and power to the display portion 462 and the circuit 464. The signal and power are input to the wiring 465 from the outside through the FPC 472 or input to the wiring 465 from the IC 473.

FIGS. 8A and 8B illustrate an example in which the IC 473 is provided over the substrate 451 by a chip on glass (COG) method, a chip on film (COF) method, or the like. An IC including a scan line driver circuit, a signal line driver circuit, or the like can be used as the IC 473, for example. Note that the light-emitting apparatuses 400A and the display module are not necessarily provided with an IC. The IC may be mounted on the FPC by a COF method or the like.

FIG. 8A illustrates an example of cross sections of part of a region including the FPC 472, part of the circuit 464, part of the display portion 462, and part of a region including an end portion of the light-emitting apparatus 400A.

The light-emitting apparatus 400A illustrated in FIG. 8A includes a transistor 201, a transistor 205, a light-emitting device 430a which emits red light, a light-emitting device 430b which emits green light, a light-emitting device 430c which emits blue light, and the like between the substrate 451 and the substrate 452.

The light-emitting device described in Embodiment 1 can be employed for the light-emitting device 430a, the light-emitting device 430b, and the light-emitting device 430c.

In the case where a pixel of the display device includes three kinds of subpixels including light-emitting devices emitting different colors from each other, the three subpixels can be of three colors of R, G, and B or of three colors of yellow (Y), cyan (C), and magenta (M). In the case where four subpixels are included, the four subpixels can be of four colors of R, G, B, and white (W) or of four colors of R, G, B, and Y.

The protective layer 416 and the substrate 452 are bonded to each other with the adhesive layer 442. A solid sealing structure, a hollow sealing structure, or the like can be employed to seal the light-emitting devices. In FIG. 8A, a hollow sealing structure is employed in which a space 443 surrounded by the substrate 452, the adhesive layer 442, and the substrate 451 is filled with an inert gas (e.g., nitrogen or argon). The adhesive layer 442 may overlap with the light-emitting device. The space 443 surrounded by the substrate 452, the adhesive layer 442, and the substrate 451 may be filled with a resin different from that of the adhesive layer 442.

The light-emitting devices 430a, 430b, and 430c each have an optical adjustment layer between the pixel electrode and the EL layer. The light-emitting device 430a includes an optical adjustment layer 426a, the light-emitting device 430b includes an optical adjustment layer 426b, and the light-emitting device 430c includes an optical adjustment layer 426c. Embodiment 1 can be referred to for the details of the light-emitting devices.

The pixel electrodes 411a, 411b, and 411c are each electrically connected to a conductive layer 222b included in the transistor 205 through an opening provided in an insulating layer 214.

End portions of the pixel electrode and the optical adjustment layer are covered with the insulating layer 421. The pixel electrode contains a material that reflects visible light, and the counter electrode contains a material that transmits visible light.

Light from the light-emitting device is emitted toward the substrate 452. For the substrate 452, a material having a high visible-light-transmitting property is preferably used.

The transistor 201 and the transistor 205 are formed over the substrate 451. These transistors can be fabricated using the same material in the same step.

An insulating layer 211, an insulating layer 213, an insulating layer 215, and an insulating layer 214 are provided in this order over the substrate 451. Part of the insulating layer 211 functions as a gate insulating layer of each transistor. Part of the insulating layer 213 functions as a gate insulating layer of each transistor. The insulating layer 215 is provided to cover the transistors. The insulating layer 214 is provided to cover the transistors and has a function of a planarization layer. Note that the number of gate insulating layers and the number of insulating layers covering the transistors are not limited and may each be one or two or more.

A material through which impurities such as water and hydrogen do not easily diffuse is preferably used for at least one of the insulating layers covering the transistors. This is because such an insulating layer can function as a barrier layer. Such a structure can effectively inhibit diffusion of impurities into the transistors from the outside and increase the reliability of a display device.

An inorganic insulating film is preferably used as each of the insulating layers 211, 213, and 215. As the inorganic insulating film, a silicon nitride film, a silicon oxynitride film, a silicon oxide film, a silicon nitride oxide film, an aluminum oxide film, or an aluminum nitride film can be used, for example. A hafnium oxide film, an yttrium oxide film, a zirconium oxide film, a gallium oxide film, a tantalum oxide film, a magnesium oxide film, a lanthanum oxide film, a cerium oxide film, a neodymium oxide film, or the like may be used. A stack including two or more of the above insulating films may also be used.

Here, an organic insulating film often has a lower barrier property than an inorganic insulating film. Therefore, the organic insulating film preferably has an opening in the vicinity of an end portion of the light-emitting apparatus 400A. This can inhibit entry of impurities from the end portion of the light-emitting apparatus 400A through the organic insulating film. Alternatively, the organic insulating film may be formed so that its end portion is positioned on the inner side compared to the end portion of the light-emitting apparatus 400A, to prevent the organic insulating film from being exposed at the end portion of the light-emitting apparatus 400A.

An organic insulating film is suitable for the insulating layer 214 functioning as a planarization layer. Examples of materials that can be used for the organic insulating film include an acrylic resin, a polyimide resin, an epoxy resin, a polyamide resin, a polyimide-amide resin, a siloxane resin, a benzocyclobutene-based resin, a phenol resin, and precursors of these resins.

In a region 228 illustrated in FIG. 8A, an opening is formed in the insulating layer 214. This can inhibit entry of impurities into the display portion 462 from the outside through the insulating layer 214 even when an organic insulating film is used as the insulating layer 214. Consequently, the reliability of the light-emitting apparatus 400A can be increased.

Each of the transistors 201 and 205, includes a conductive layer 221 functioning as a gate, the insulating layer 211 functioning as a gate insulating layer, a conductive layer 222a and a conductive layer 222b functioning as a source and a drain, a semiconductor layer 231, the insulating layer 213 functioning as a gate insulating layer, and a conductive layer 223 functioning as a gate. Here, a plurality of layers obtained by processing the same conductive film are shown with the same hatching pattern. The insulating layer 211 is positioned between the conductive layer 221 and the semiconductor layer 231. The insulating layer 213 is positioned between the conductive layer 223 and the semiconductor layer 231.

There is no particular limitation on the structure of the transistors included in the display device of this embodiment. For example, a planar transistor, a staggered transistor, or an inverted staggered transistor can be used. A top-gate transistor or a bottom-gate transistor can be used. Alternatively, gates may be provided above and below a semiconductor layer where a channel is formed.

The structure in which the semiconductor layer where a channel is formed is provided between two gates is used for the transistors 201 and 205. The two gates may be connected to each other and supplied with the same signal to operate the transistor. Alternatively, the threshold voltage of the transistor may be controlled by applying a potential for controlling the threshold voltage to one of the two gates and a potential for driving to the other of the two gates.

There is no particular limitation on the crystallinity of a semiconductor material used for the transistors, and any of an amorphous semiconductor, a single crystal semiconductor, and a semiconductor having crystallinity other than single crystal (a microcrystalline semiconductor, a polycrystalline semiconductor, or a semiconductor partly including crystal regions) may be used. It is preferable to use a semiconductor having crystallinity, in which case deterioration of the transistor characteristics can be inhibited.

It is preferable that a semiconductor layer of a transistor contain a metal oxide (also referred to as an oxide semiconductor). That is, a transistor including a metal oxide in its channel formation region (hereinafter, also referred to as an OS transistor) is preferably used for the display device of this embodiment. Alternatively, a semiconductor layer of a transistor may contain silicon. Examples of silicon include amorphous silicon and crystalline silicon (e.g., low-temperature polysilicon or single crystal silicon).

The semiconductor layer preferably contains indium, M (M is one or more of gallium, aluminum, silicon, boron, yttrium, tin, copper, vanadium, beryllium, titanium, iron, nickel, germanium, zirconium, molybdenum, lanthanum, cerium, neodymium, hafnium, tantalum, tungsten, and magnesium), and zinc, for example. Specifically, M is preferably one or more of aluminum, gallium, yttrium, and tin.

It is particularly preferable that an oxide containing indium (In), gallium (Ga), and zinc (Zn) (also referred to as IGZO) be used as the semiconductor layer.

When the semiconductor layer is an In-M-Zn oxide, the atomic ratio of In is preferably greater than or equal to the atomic ratio of M in the In-M-Zn oxide. Examples of the atomic ratio of the metal elements in such an In-M-Zn oxide are In:M:Zn=1:1:1, 1:1:1.2, 2:1:3, 3:1:2, 4:2:3, 4:2:4.1, 5:1:3, 5:1:6, 5:1:7, 5:1:8, 6:1:6, and 5:2:5 and a composition in the vicinity of any of the above atomic ratios. Note that the vicinity of the atomic ratio includes ±30% of an intended atomic ratio.

For example, in the case of describing an atomic ratio of In:Ga:Zn=4:2:3 or a composition in the vicinity thereof, the case is included in which with the atomic proportion of In being 4, the atomic proportion of Ga is greater than or equal to 1 and less than or equal to 3 and the atomic proportion of Zn is greater than or equal to 2 and less than or equal to 4. In the case of describing an atomic ratio of In:Ga:Zn=5:1:6 or a composition in the vicinity thereof, the case is included in which with the atomic proportion of In being 5, the atomic proportion of Ga is greater than 0.1 and less than or equal to 2 and the atomic proportion of Zn is greater than or equal to 5 and less than or equal to 7. In the case of describing an atomic ratio of In:Ga:Zn=1:1:1 or a composition in the vicinity thereof, the case is included in which with the atomic proportion of In being 1, the atomic proportion of Ga is greater than 0.1 and less than or equal to 2 and the atomic proportion of Zn is greater than 0.1 and less than or equal to 2.

The transistor included in the circuit 464 and the transistor included in the display portion 462 may have the same structure or different structures. One structure or two or more kinds of structures may be employed for a plurality of transistors included in the circuit 464. Similarly, one structure or two or more kinds of structures may be employed for a plurality of transistors included in the display portion 462.

A connection portion 204 is provided in a region of the substrate 451 where the substrate 452 does not overlap. In the connection portion 204, the wiring 465 is electrically connected to the FPC 472 through a conductive layer 466 and a connection layer 242. An example is illustrated in which the conductive layer 466 has a stacked-layer structure of a conductive film obtained by processing the same conductive film as the pixel electrode and a conductive film obtained by processing the same conductive film as the optical adjustment layer. On atop surface of the connection portion 204, the conductive layer 466 is exposed. Thus, the connection portion 204 and the FPC 472 can be electrically connected to each other through the connection layer 242.

A light-blocking layer 417 is preferably provided on the surface of the substrate 452 on the substrate 451 side. A variety of optical members can be arranged on the outer surface of the substrate 452. Examples of the optical members include a polarizing plate, a retardation plate, a light diffusion layer (e.g., a diffusion film), an anti-reflective layer, and a light-condensing film. Furthermore, an antistatic film preventing the attachment of dust, a water repellent film suppressing the attachment of stain, a hard coat film suppressing generation of a scratch caused by the use, an impact-absorbing layer, or the like may be arranged on the outer surface of the substrate 452.

When the protective layer 416 covering the light-emitting device is provided, which prevents an impurity such as water from entering the light-emitting device. As a result, the reliability of the light-emitting device can be enhanced.

In the region 228 in the vicinity of the end portion of the light-emitting apparatus 400A, the insulating layer 215 and the protective layer 416 are preferably in contact with each other through an opening in the insulating layer 214. In particular, the inorganic insulating film included in the insulating layer 215 and the inorganic insulating film included in the protective layer 416 are preferably in contact with each other. This can inhibit entry of impurities into the display portion 462 from the outside through the insulating layer 214. Consequently, the reliability of the light-emitting apparatus 400A can be enhanced.

FIG. 8B illustrates an example in which the protective layer 416 has a three-layer structure. In FIG. 8B, the protective layer 416 includes an inorganic insulating layer 416a over the light-emitting device 430c, an organic insulating layer 416b over the inorganic insulating layer 416a, and an inorganic insulating layer 416c over the organic insulating layer 416b.

An end portion of the inorganic insulating layer 416a and an end portion of the inorganic insulating layer 416c extend beyond an end portion of the organic insulating layer 416b and are in contact with each other. The inorganic insulating layer 416a is in contact with the insulating layer 215 (inorganic insulating layer) at the opening in the insulating layer 214 (organic insulating layer). Accordingly, the light-emitting device can be surrounded by the insulating layer 215 and the protective layer 416, whereby the reliability of the light-emitting device can be increased.

As described above, the protective layer 416 may have a stacked-layer structure of an organic insulating film and an inorganic insulating film. In that case, end portions of the inorganic insulating layers preferably extend beyond an end portion of the organic insulating layer.

For each of the substrates 451 and 452, glass, quartz, ceramic, sapphire, a resin, a metal, an alloy, a semiconductor or the like can be used. The substrate on the side from which light from the light-emitting device is extracted is formed using a material which transmits the light. When the substrates 451 and 452 are formed using a flexible material, the flexibility of the display device can be increased. Furthermore, a polarizing plate may be used as the substrate 451 or the substrate 452.

For each of the substrate 451 and the substrate 452, any of the following can be used, for example: polyester resins such as polyethylene terephthalate (PET) and polyethylene naphthalate (PEN), a polyacrylonitrile resin, an acrylic resin, a polyimide resin, a polymethyl methacrylate resin, a polycarbonate (PC) resin, a polyethersulfone (PES) resin, polyamide resins (e.g., nylon and aramid), a polysiloxane resin, a cycloolefin resin, a polystyrene resin, a polyamide-imide resin, a polyurethane resin, a polyvinyl chloride resin, a polyvinylidene chloride resin, a polypropylene resin, a polytetrafluoroethylene (PTFE) resin, an ABS resin, and cellulose nanofiber. Glass that is thin enough to have flexibility may be used for one or both of the substrate 451 and the substrate 452.

In the case where a circularly polarizing plate overlaps with the display device, a highly optically isotropic substrate is preferably used as the substrate included in the display device. A highly optically isotropic substrate has a low birefringence (in other words, a small amount of birefringence).

The absolute value of a retardation (phase difference) of a highly optically isotropic substrate is preferably less than or equal to 30 nm, further preferably less than or equal to 20 nm, still further preferably less than or equal to 10 nm.

Examples of the film having high optical isotropy include a triacetyl cellulose (TAC, also referred to as cellulose triacetate) film, a cycloolefin polymer (COP) film, a cycloolefin copolymer (COC) film, and an acrylic film.

When a film is used for the substrate and the film absorbs water, the shape of the display panel might be changed, e.g., creases are generated. Thus, for the substrate, a film with a low water absorption rate is preferably used. For example, the water absorption rate of the film is preferably 1% or lower, further preferably 0.1% or lower, still further preferably 0.01% or lower.

As the adhesive layer, any of a variety of curable adhesives such as a reactive curable adhesive, a thermosetting curable adhesive, an anaerobic adhesive, and a photocurable adhesive such as an ultraviolet curable adhesive can be used. Examples of these adhesives include an epoxy resin, an acrylic resin, a silicone resin, a phenol resin, a polyimide resin, an imide resin, a polyvinyl chloride (PVC) resin, a polyvinyl butyral (PVB) resin, and an ethylene vinyl acetate (EVA) resin. In particular, a material with low moisture permeability, such as an epoxy resin, is preferred. A two-component-mixture-type resin may be used. An adhesive sheet or the like may be used.

As the connection layer 242, an anisotropic conductive film (ACF), an anisotropic conductive paste (ACP), or the like can be used.

As materials for the gates, the source, and the drain of a transistor and conductive layers functioning as wirings and electrodes included in the display device, any of metals such as aluminum, titanium, chromium, nickel, copper, yttrium, zirconium, molybdenum, silver, tantalum, and tungsten, or an alloy containing any of these metals as its main component can be used. A single-layer structure or a stacked-layer structure including a film containing any of these materials can be used.

As a light-transmitting conductive material, a conductive oxide such as indium oxide, indium tin oxide, indium zinc oxide, zinc oxide, or zinc oxide containing gallium, or graphene can be used. It is also possible to use a metal material such as gold, silver, platinum, magnesium, nickel, tungsten, chromium, molybdenum, iron, cobalt, copper, palladium, or titanium; or an alloy material containing any of these metal materials. Alternatively, a nitride of the metal material (e.g., titanium nitride) or the like may be used. Note that in the case of using the metal material or the alloy material (or the nitride thereof), the thickness is preferably set small enough to transmit light. Alternatively, a stacked film of any of the above materials can be used for the conductive layers. For example, a stacked film of indium tin oxide and an alloy of silver and magnesium is preferably used because conductivity can be increased. They can also be used for conductive layers such as wirings and electrodes included in the display device, and conductive layers (e.g., a conductive layer functioning as a pixel electrode or a common electrode) included in a light-emitting device.

Examples of insulating materials that can be used for the insulating layers include a resin such as an acrylic resin and an epoxy resin, and an inorganic insulating material such as silicon oxide, silicon oxynitride, silicon nitride oxide, silicon nitride, and aluminum oxide.

[Light-Emitting Apparatus 400B]

FIG. 9A is a cross-sectional view of a light-emitting apparatus 400B. A perspective view of the light-emitting apparatus 400B is similar to that of the light-emitting apparatus 400A shown in FIG. 7. FIG. 9A illustrates an example of cross sections of part of a region including the FPC 472, part of the circuit 464, and part of the display portion 462 in the light-emitting apparatus 400B. FIG. 9A specifically shows an example of a cross section of a region including the light-emitting device 430b, which emits green light, and the light-emitting device 430c, which emits blue light, in the display portion 462. Note that portions similar to those in the light-emitting apparatus 400A are not described in some cases.

The light-emitting apparatus 400B illustrated in FIG. 9A includes a transistor 202, transistors 210, the light-emitting device 430b, the light-emitting device 430c, and the like between the substrate 453 and the substrate 454.

The substrate 454 and the protective layer 416 are bonded to each other with the adhesive layer 442. The adhesive layer 442 is provided so as to overlap with the light-emitting device 430b and the light-emitting device 430c; that is, the light-emitting apparatus 400B employs a solid sealing structure.

The substrate 453 and an insulating layer 212 are bonded to each other with an adhesive layer 455.

As a method for manufacturing the light-emitting apparatus 400B, first, a formation substrate provided with the insulating layer 212, the transistors, the light-emitting devices, and the like is bonded to the substrate 454 provided with the light-blocking layer 417 are bonded to each other with the adhesive layer 442. Then, the substrate 453 is attached to a surface exposed by separation of the formation substrate, whereby the components formed over the formation substrate are transferred to the substrate 453. The substrate 453 and the substrate 454 are preferably flexible. Accordingly, the light-emitting apparatus 400B can be highly flexible.

The inorganic insulating film that can be used as the insulating layer 211, the insulating layer 213, and the insulating layer 215 can be used as the insulating layer 212.

The pixel electrode is connected to the conductive layer 222b included in the transistor 210 through the opening provided in the insulating layer 214. The conductive layer 222b is connected to a low-resistance region 231n through an opening provided in the insulating layer 215 and the insulating layer 225. The transistor 210 has a function of controlling the driving of the light-emitting device.

An end portion of the pixel electrode is covered with the insulating layer 421.

Light from the light-emitting devices 430b and 430c is emitted toward the substrate 454. For the substrate 454, a material having a high visible-light-transmitting property is preferably used.

A connection portion 204 is provided in a region of the substrate 453 where the substrate 454 does not overlap. In the connection portion 204, the wiring 465 is electrically connected to the FPC 472 through a conductive layer 466 and a connection layer 242. The conductive layer 466 can be obtained by processing the same conductive film as the pixel electrode. Thus, the connection portion 204 and the FPC 472 can be electrically connected to each other through the connection layer 242.

A transistor 202 and a transistor 210 each include the conductive layer 221 functioning as a gate, the insulating layer 211 functioning as a gate insulating layer, a semiconductor layer including a channel formation region 231i and a pair of low-resistance regions 231n, the conductive layer 222a connected to one of the low-resistance regions 231n, the conductive layer 222b connected to the other low-resistance region 231n, an insulating layer 225 functioning as a gate insulating layer, the conductive layer 223 functioning as a gate, and the insulating layer 215 covering the conductive layer 223. The insulating layer 211 is positioned between the conductive layer 221 and the channel formation region 231i. The insulating layer 225 is positioned between the conductive layer 223 and the channel formation region 231i.

The conductive layer 222a and the conductive layer 222b are connected to the corresponding low-resistance regions 231n through openings provided in the insulating layer 215.

One of the conductive layers 222a and 222b serves as a source, and the other serves as a drain.

FIG. 9A illustrates an example in which the insulating layer 225 covers a top and side surfaces of the semiconductor layer. The conductive layer 222a and the conductive layer 222b are each connected to the corresponding low-resistance region 231n through openings provided in the insulating layer 225 and the insulating layer 215.

In a transistor 209 illustrated in FIG. 9B, the insulating layer 225 overlaps with the channel formation region 231i of the semiconductor layer 231 and does not overlap with the low-resistance regions 231n. The structure illustrated in FIG. 9B is obtained by processing the insulating layer 225 with the conductive layer 223 as a mask, for example. In FIG. 9B, the insulating layer 215 is provided to cover the insulating layer 225 and the conductive layer 223, and the conductive layer 222a and the conductive layer 222b are connected to the low-resistance regions 231n through the openings in the insulating layer 215. Furthermore, an insulating layer 218 covering the transistor may be provided.

At least part of any of the structure examples, the drawings corresponding thereto, and the like described in this embodiment can be implemented in combination with any of the other structure examples, the other drawings corresponding thereto, and the like as appropriate.

At least part of this embodiment can be implemented in combination with any of the other embodiments described in this specification, as appropriate.

Embodiment 6

In this embodiment, a structure example of a display device different from the above will be described.

The display device in this embodiment can be a high-resolution display device. Thus, the display device in this embodiment can be used for display portions of information terminals (wearable devices) such as watch-type or bracelet-type information terminals and display portions of wearable devices capable of being worn on ahead, such as a VR device such as a head mounted display and a glasses-type AR device.

[Display Module]

Figure 10A:
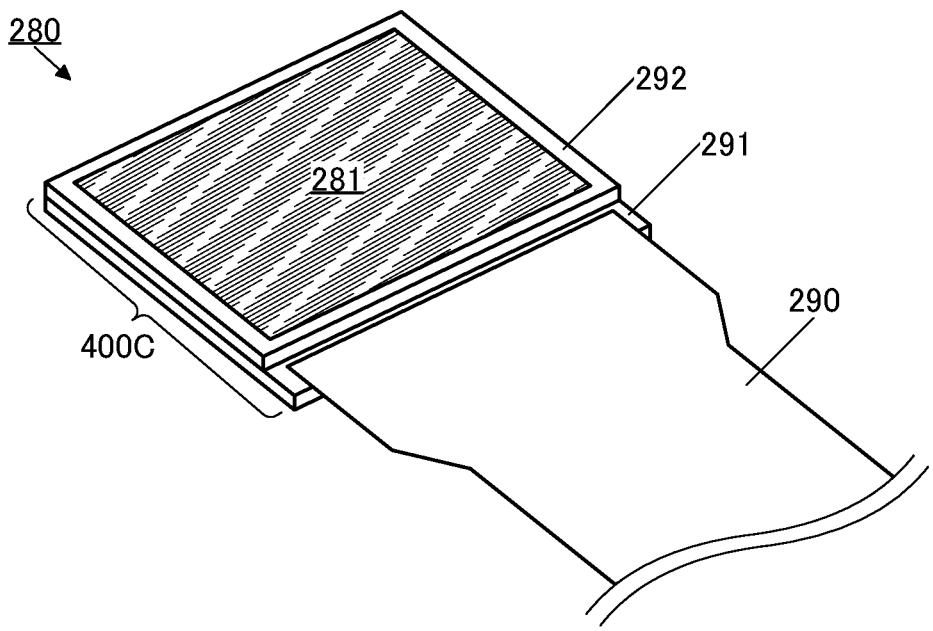
FIGS. 10A and 10B are perspective views showing an example of a display module.

FIG. 10A is a perspective view of a display module 280. The display module 280 includes the light-emitting apparatus 400C and an FPC 290. Note that the display device included in the display module 280 is not limited to the light-emitting apparatus 400C and may be a light-emitting apparatus 400D or a light-emitting apparatus 400E described later.

The display module 280 includes a substrate 291 and a substrate 292. The display module 280 includes a display portion 281. The display portion 281 is a region of the display module 280 where an image is displayed and is a region where light emitted from pixels provided in a pixel portion 284 described later can be seen.

Figure 10B:
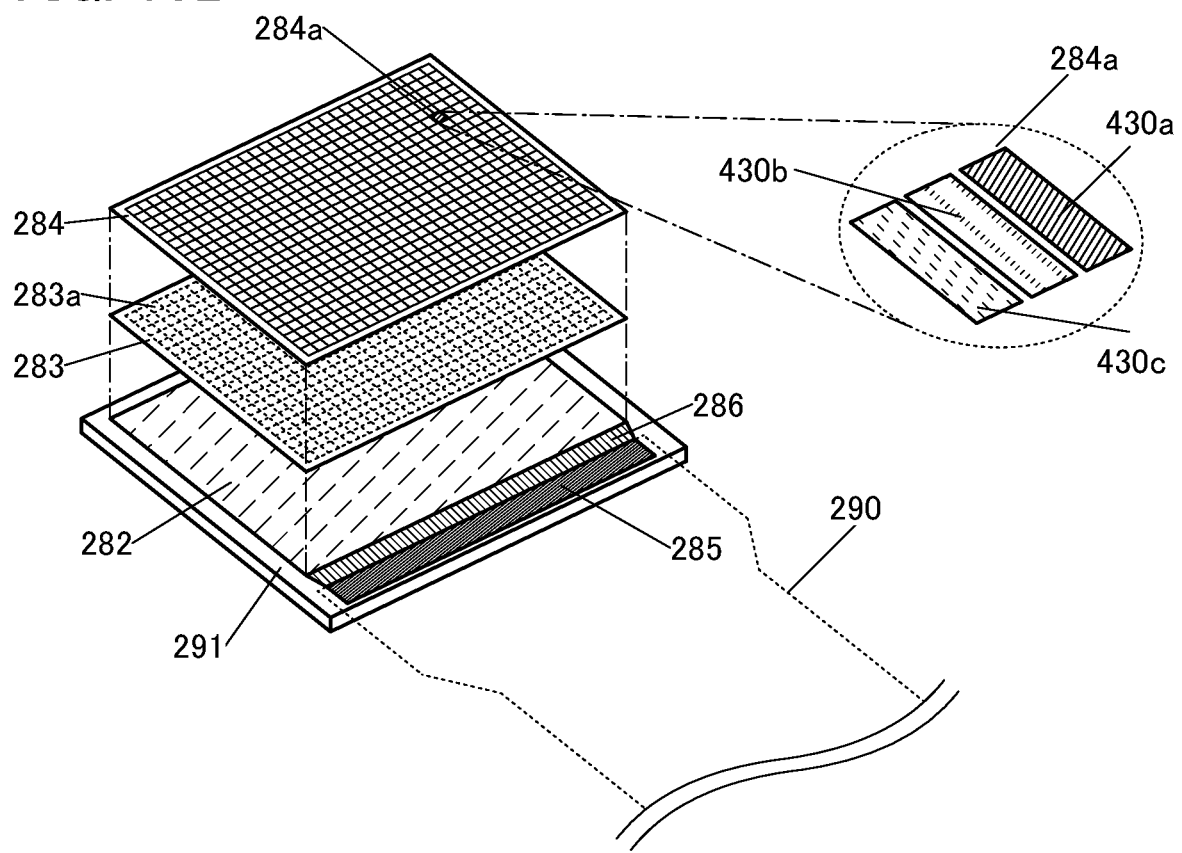

FIG. 10B is a perspective view schematically illustrating a structure on the substrate 291 side. Over the substrate 291, a circuit portion 282, a pixel circuit portion 283 over the circuit portion 282, and the pixel portion 284 over the pixel circuit portion 283 are stacked. In addition, a terminal portion 285 for connection to the FPC 290 is included in a portion not overlapping with the pixel portion 284 over the substrate 291. The terminal portion 285 and the circuit portion 282 are electrically connected to each other through a wiring portion 286 formed of a plurality of wirings.

The pixel portion 284 includes a plurality of pixels 284a arranged periodically. An enlarged view of one pixel 284a is illustrated on the right side in FIG. 10B. The pixel 284a includes the light-emitting devices 430a, 430b, and 430c whose emission colors are different from each other. The plurality of light-emitting devices may be arranged in a stripe pattern a as illustrated in FIG. 10B. With the stripe pattern that enables high-density arrangement of pixel circuits, a high-resolution display device can be provided. Alternatively, a variety of kinds of patterns such as a delta pattern or a pentile pattern can be employed.

The pixel circuit portion 283 includes a plurality of pixel circuits 283a arranged periodically.

One pixel circuit 283a is a circuit that controls light emission from three light-emitting devices included in one pixel 284a. One pixel circuit 283a may be provided with three circuits each of which controls light emission of one light-emitting device. For example, the pixel circuit 283a can include at least one selection transistor, one current control transistor (driving transistor), and a capacitor for one light-emitting device. A gate signal is input to a gate of the selection transistor, and a source signal is input to one of a source and a drain of the selection transistor. With such a structure, an active-matrix display device is achieved.

The circuit portion 282 includes a circuit for driving the pixel circuits 283a in the pixel circuit portion 283. For example, one or both of a gate line driver circuit and a source line driver circuit are preferably included. In addition, at least one of an arithmetic circuit, a memory circuit, a power supply circuit, and the like may be included.

The FPC 290 serves as a wiring for supplying a video signal or a power supply potential to the circuit portion 282 from the outside. An IC may be mounted on the FPC 290.

The display module 280 can have a structure in which one or both of the pixel circuit portion 283 and the circuit portion 282 are stacked below the pixel portion 284; thus, the aperture ratio (the effective display area ratio) of the display portion 281 can be significantly high. For example, the aperture ratio of the display portion 281 can be greater than or equal to 40% and less than 100%, preferably greater than or equal to 50% and less than or equal to 95%, and further preferably greater than or equal to 60% and less than or equal to 95%. Furthermore, the pixels 284a can be arranged extremely densely and thus the display portion 281 can have greatly high resolution. For example, the pixels 284a are preferably arranged in the display portion 281 with a resolution greater than or equal to 2000 ppi, preferably greater than or equal to 3000 ppi, further preferably greater than or equal to 5000 ppi, further more preferably greater than or equal to 6000 ppi, and less than or equal to 20000 ppi or less than or equal to 30000 ppi.

Such a display module 280 has extremely high resolution, and thus can be suitably used for a device for VR such as a head-mounted display or a glasses-type device for AR. For example, even in the case of a structure in which the display portion of the display module 280 is seen through a lens, pixels of the extremely-high-resolution display portion 281 included in the display module 280 are prevented from being seen when the display portion is enlarged by the lens, so that display providing a high sense of immersion can be performed. Without being limited thereto, the display module 280 can be suitably used for electronic devices including a relatively small display portion. For example, the display module 280 can be favorably used in a display portion of a wearable electronic device, such as a wrist watch.

[Light-Emitting Apparatus 400C]

Figure 11:
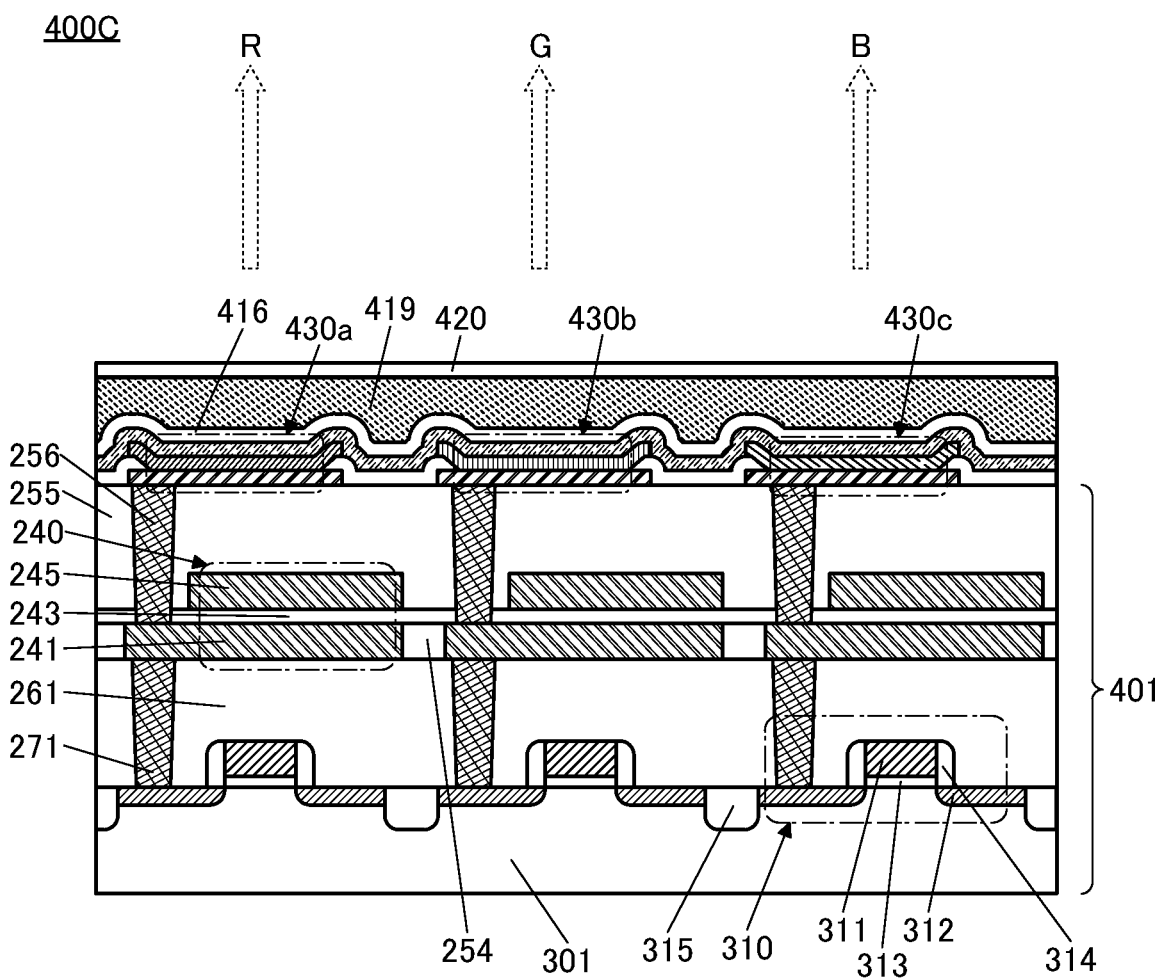
FIG. 11 is a cross-sectional view showing an example of a display device.

The light-emitting apparatus 400C illustrated in FIG. 11 includes a substrate 301, the light-emitting devices 430a, 430b, and 430c, a capacitor 240, and a transistor 310.

The substrate 301 corresponds to the substrate 291 illustrated in FIGS. 10A and 10B.

The transistor 310 is a transistor whose channel formation region is in the substrate 301. As the substrate 301, a semiconductor substrate such as a single crystal silicon substrate can be used, for example. The transistor 310 includes part of the substrate 301, a conductive layer 311, a low-resistance region 312, an insulating layer 313, and an insulating layer 314. The conductive layer 311 functions as a gate electrode. The insulating layer 313 is positioned between the substrate 301 and the conductive layer 311 and functions as a gate insulating layer. The low-resistance region 312 is a region where the substrate 301 is doped with an impurity, and functions as one of a source and a drain. The insulating layer 314 is provided to cover a side surface of the conductive layer 311 and functions as an insulating layer.

An element isolation layer 315 is provided between two adjacent transistors 310 to be embedded in the substrate 301.

Furthermore, an insulating layer 261 is provided to cover the transistor 310, and the capacitor 240 is provided over the insulating layer 261.

The capacitor 240 includes a conductive layer 241, a conductive layer 245, and an insulating layer 243 between the conductive layers 241 and 245. The conductive layer 241 functions as one electrode of the capacitor 240, the conductive layer 245 functions as the other electrode of the capacitor 240, and the insulating layer 243 functions as a dielectric of the capacitor 240.

The conductive layer 241 is provided over the insulating layer 261 and is embedded in an insulating layer 254. The conductive layer 241 is electrically connected to one of the source and the drain of the transistor 310 through a plug 271 embedded in the insulating layer 261. The insulating layer 243 is provided to cover the conductive layer 241. The conductive layer 245 is provided in a region overlapping with the conductive layer 241 with the insulating layer 243 therebetween.

The insulating layer 255 is provided to cover the capacitor 240, and the light-emitting device 430a, the light-emitting device 430b, the light-emitting device 430c, and the like are provided over the insulating layer 255. The protective layer 416 is provided over the light-emitting devices 430a, 430b, and 430c, and a substrate 420 is bonded to a top surface of the protective layer 416 with a resin layer 419.

The pixel electrode of the light-emitting device is electrically connected to one of the source and the drain of the transistor 310 through a plug 256 embedded in the insulating layer 255, the conductive layer 241 embedded in the insulating layer 254, and the plug 271 embedded in the insulating layer 261.

[Light-Emitting Apparatus 400D]

Figure 12:
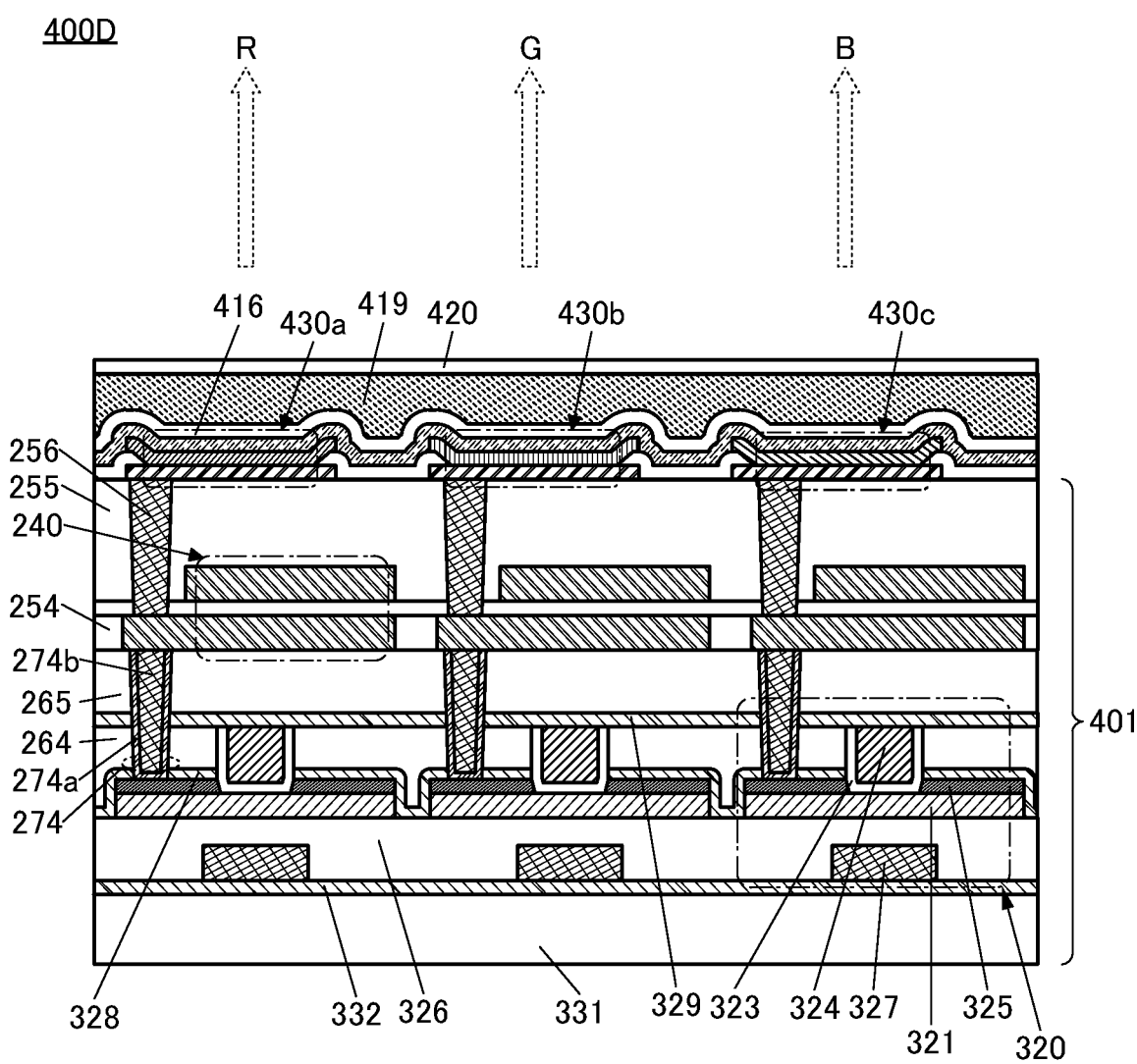
FIG. 12 is a cross-sectional view showing an example of a display device.

A light-emitting apparatus 400D illustrated in FIG. 12 is different from the light-emitting apparatus 400C mainly in a structure of the transistor. Note that portions similar to those in the light-emitting apparatus 400C are not be described in some cases.

A transistor 320 contains a metal oxide (also referred to as an oxide semiconductor) in a semiconductor layer where a channel is formed.

The transistor 320 includes a semiconductor layer 321, an insulating layer 323, a conductive layer 324, a pair of conductive layers 325, an insulating layer 326, and a conductive layer 327.

A substrate 331 corresponds to the substrate 291 in FIGS. 10A and 10B. A stacked structure including the substrate 331 and the components thereover (up to the insulating layer 255) corresponds to the layer 401 including the transistor in Embodiment 1. As the substrate 331, an insulating substrate or a semiconductor substrate can be used.

An insulating layer 332 is provided over the substrate 331. The insulating layer 332 functions as a barrier layer that prevents diffusion of impurities such as water or hydrogen from the substrate 331 into the transistor 320 and release of oxygen from the semiconductor layer 321 to the insulating layer 332 side. As the insulating layer 332, for example, a film in which hydrogen or oxygen is less likely to diffuse than in a silicon oxide film can be used. Examples of such a silicon oxide film include an aluminum oxide film, a hafnium oxide film, and a silicon nitride film.

The conductive layer 327 is provided over the insulating layer 332, and the insulating layer 326 is provided to cover the conductive layer 327. The conductive layer 327 functions as a first gate electrode of the transistor 320, and part of the insulating layer 326 functions as a first gate insulating layer. An oxide insulating film such as a silicon oxide film is preferably used as at least part of the insulating layer 326 that is in contact with the semiconductor layer 321. In addition, the top surface of the insulating layer 326 is preferably planarized.

The insulating layer 326 is provided over the semiconductor layer 321. A metal oxide film having semiconductor characteristics (also referred to as an oxide semiconductor film) is preferably used as the semiconductor layer 321. A material that can be used for the semiconductor layer 321 is described in detail later.

The pair of conductive layers 325 is provided on and in contact with the semiconductor layer 321, and functions as a source electrode and a drain electrode.

An insulating layer 328 is provided to cover top and side surfaces of the pair of conductive layers 325, a side surface of the semiconductor layer 321, and the like, and an insulating layer 264 is provided over the insulating layer 328. The insulating layer 328 functions as a barrier layer that prevents diffusion of impurities such as water or hydrogen from the interlayer insulating layer 264 and the like into the semiconductor layer 321 and release of oxygen from the semiconductor layer 321. As the insulating layer 328, an insulating film similar to the insulating layer 332 can be used.

An opening reaching the semiconductor layer 321 is provided in the insulating layers 328 and 264. The insulating layer 323 that is in contact with side surfaces of the insulating layers 264 and 328, a side surface of the conductive layer 325, and the top surface of the semiconductor layer 321 and the conductive layer 324 are embedded in the opening. The conductive layer 324 functions as a second gate electrode, and the insulating layer 323 functions as a second gate insulating layer.

The top surface of the conductive layer 324, the top surface of the insulating layer 323, and the top surface of the insulating layer 264 are planarized so that they are substantially level with each other, and insulating layers 329 and 265 are provided to cover these layers.

The insulating layers 264 and 265 each function as an interlayer insulating layer. The insulating layer 329 functions as a barrier layer that prevents diffusion of impurities such as water or hydrogen from the insulating layer 265 or the like to the transistor 320. As the insulating layer 329, an insulating film similar to the insulating layers 328 and 332 can be used.

A plug 274 electrically connected to one of the pair of conductive layers 325 is provided to be embedded in the insulating layers 265, 329, and 264. Here, the plug 274 preferably includes a conductive layer 274a that covers side surfaces of openings formed in the insulating layers 265, 329, 264, and 328 and part of a top surface of the conductive layer 325, and conductive layer 274b in contact with a top surface of the conductive layer 274a. As the conductive layer 274a, a conductive material in which hydrogen and oxygen are less likely to be diffused is preferably used.

The structure of the insulating layer 254 and the components thereof (up to the substrate 420) in the light-emitting apparatus 400D is similar to that of the light-emitting apparatus 400C.

[Light-Emitting Apparatus 400E]

Figure 13:
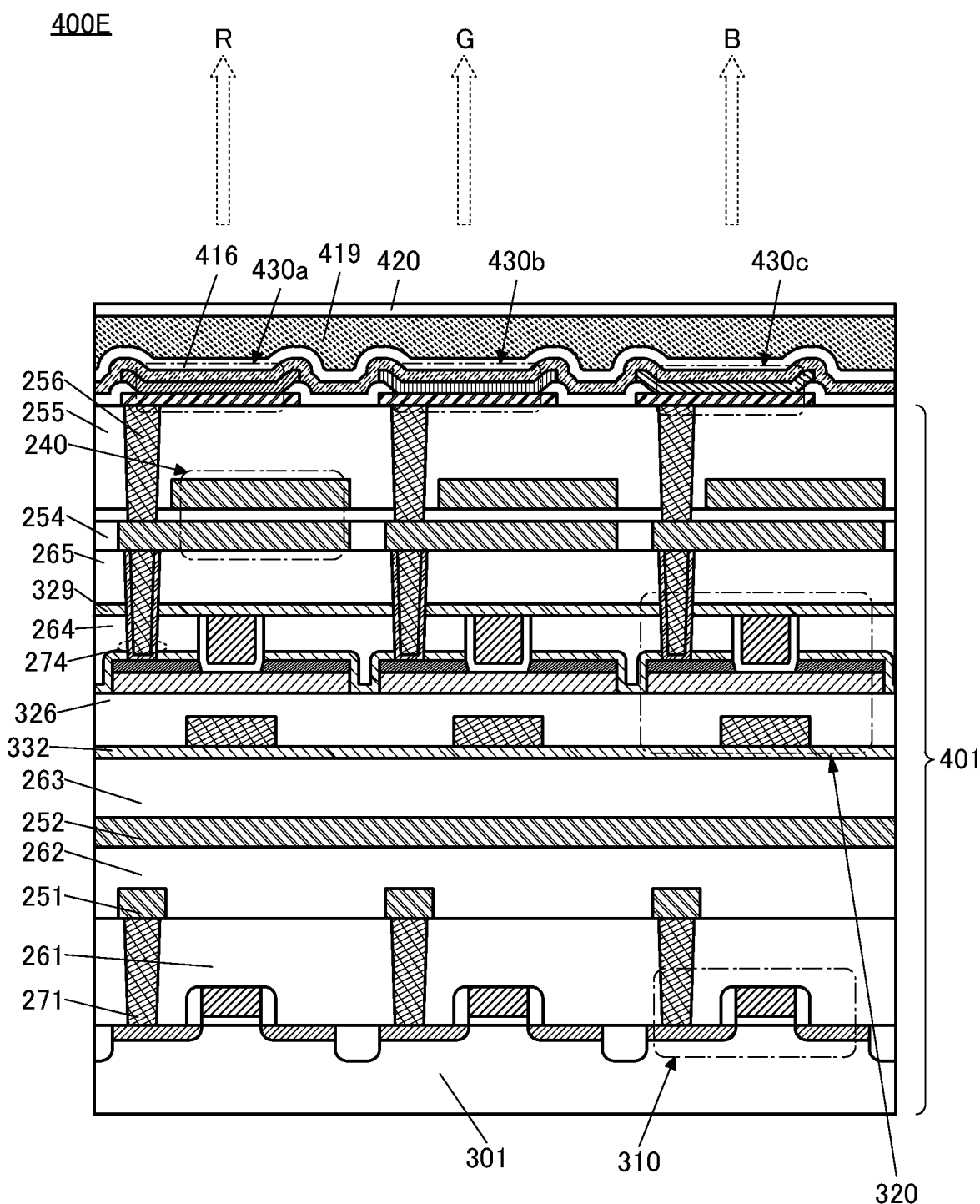
FIG. 13 is a cross-sectional view showing an example of a display device.

A light-emitting apparatus 400E illustrated in FIG. 13 has a structure in which the transistor 310 whose channel is formed in the substrate 301 and the transistor 320 including a metal oxide in the semiconductor layer where the channel is formed are stacked. Note that portions similar to those of the light-emitting apparatuses 400C and 400D are not described in some cases.

The insulating layer 261 is provided to cover the transistor 310, and a conductive layer 251 is provided over the insulating layer 261. The insulating layer 262 is provided so as to cover the conductive layer 251, and a conductive layer 252 is provided over the insulating layer 262. The conductive layers 251 and 252 each function as a wiring. An insulating layer 263 and the insulating layer 332 are provided to cover the conductive layer 252, and the transistor 320 is provided over the insulating layer 332. The insulating layer 265 is provided to cover the transistor 320, and the capacitor 240 is provided over the insulating layer 265. The capacitor 240 and the transistor 320 are electrically connected to each other through the plug 274.

The transistor 320 can be used as a transistor included in the pixel circuit. The transistor 310 can be used as a transistor included in the pixel circuit or a transistor included in a driver circuit (one or both of a gate driver and a source driver) for driving the pixel circuit. The transistor 310 and the transistor 320 can also be used as transistors included in a variety of circuits such as an arithmetic circuit and a memory circuit.

With such a structure, not only the pixel circuit but also the driver circuit or the like can be formed directly under the light-emitting device; thus, the display device can be downsized as compared with the case where the driver circuit is provided around a display portion.

At least part of any of the structure examples, the drawings corresponding thereto, and the like described in this embodiment can be implemented in combination with any of the other structure examples, the other drawings corresponding thereto, and the like as appropriate.

At least part of this embodiment can be implemented in combination with any of the other embodiments described in this specification, as appropriate.

Embodiment 7

In this embodiment, a high-definition display device will be described.

[Example of Structure of Pixel Circuit]

Examples of a pixel and a pixel layout suitable for a high-definition display device is described below.

Figure 14:
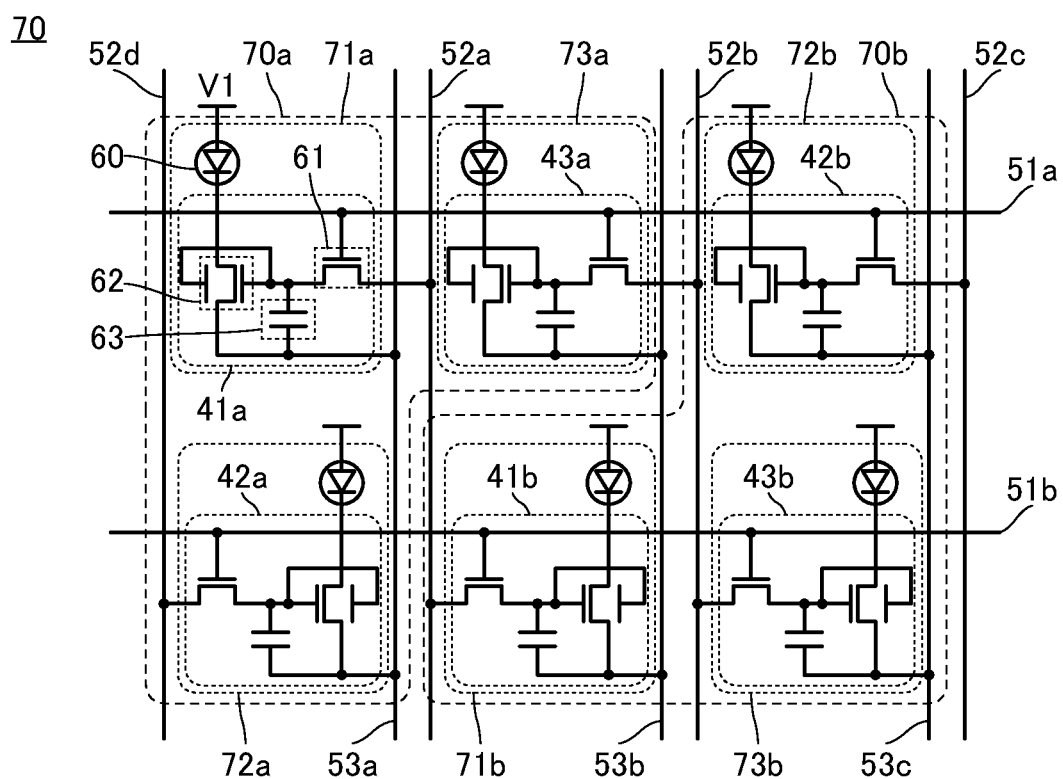
FIG. 14 shows a structure example of a display device.

FIG. 14 is an example of a circuit diagram of a pixel unit 70. The pixel unit 70 includes two pixels (a pixel 70a and a pixel 70b). In addition, the pixel unit 70 is connected to wirings 51a, 51b, 52a, 52b, 52c, 52d, 53a, 53b, and 53c and the like.

The pixel 70a includes subpixels 71a, 72a, and 73a. The pixel 70b includes subpixels 71b, 72b, and 73b. The subpixels 71a, 72a, and 73a include pixel circuits 41a, 42a, and 43a, respectively. The subpixels 71b, 72b, and 73b include pixel circuits 41b, 42b, and 43b, respectively.

Each subpixel includes a pixel circuit and a display element 60. For example, the subpixel 71a includes a pixel circuit 41a and the display element 60. A light-emitting element such as an organic EL element is used here as the display element 60.

The wirings 51a and 51b each serve as a scan line. The wirings 52a, 52b, 52c, and 52d each serve as a signal line (also referred to as a data line). The wirings 53a, 53b, and 53c each have a function of supplying a potential to the display element 60.

The pixel circuit 41a is electrically connected to the wirings 51a, 52a, and 53a. The pixel circuit 42a is electrically connected to the wirings 51b, 52d, and 53a. The pixel circuit 43a is electrically connected to the wirings 51a, 52b, and 53b. The pixel circuit 41b is electrically connected to the wirings 51b, 52a, and 53b. The pixel circuit 42b is electrically connected to the wirings 51a, 52c, and 53c. The pixel circuit 43b is electrically connected to the wirings 51b, 52b, and 53c.

With the structure shown in FIG. 14 in which two gate lines are connected to each pixel, the number of source lines can be reduced by half of the stripe arrangement. As a result, the number of terminals of the IC used as source driver circuits can be reduced by half and accordingly the number of components can be reduced.

A wiring functioning as a signal line is preferably connected to pixel circuits of the same color. For example, when a signal with an adjusted potential supplied to the wiring corrects for variation in luminance between pixels, the correction value may greatly vary between colors. Thus, when pixel circuits connected to one signal line correspond to the same color, the correction can be performed easily.

In addition, each pixel circuit includes a transistor 61, a transistor 62, and a capacitor 63. In the pixel circuit 41a, for example, a gate of the transistor 61 is electrically connected to the wiring 51a, one of a source and a drain of the transistor 61 is electrically connected to the wiring 52a, and the other of the source and the drain is electrically connected to a gate of the transistor 62 and one electrode of the capacitor 63. One of a source and a drain of the transistor 62 is electrically connected to one electrode of the display element 60, and the other of the source and the drain is electrically connected to the other electrode of the capacitor 63 and the wiring 53a. The other electrode of the display element 60 is electrically connected to a wiring to which a potential V1 is applied.

Note that the other pixel circuits are similar to the pixel circuit 41a except a wiring connected to the gate of the transistor 61, a wiring connected to the one of the source and the drain of the transistor 61, or a wiring connected to the other electrode of the capacitor 63 (see FIG. 14).

In FIG. 14, the transistor 61 serves as a selection transistor. The transistor 62 is in a series connection with the display element 60 to control a current flowing in the display element 60. The capacitor 63 has a function of holding the potential of a node connected to the gate of the transistor 62. Note that the capacitor 63 does not have to be intentionally provided in the case where an off-state leakage current of the transistor 61, a leakage current through the gate of the transistor 62, and the like are extremely small.

The transistor 62 preferably includes a first gate and a second gate electrically connected to each other as shown in FIG. 14. The amount of current that the transistor 62 can supply can be increased owing to the two gates. Such a structure is particularly preferable for a high-resolution display device because the amount of current can be increased without increasing the size, the channel width in particular, of the transistor 62.

Note that the number of gates of the transistor 62 may be one. This structure can be manufactured in a simpler process than the above structure because a step of forming the second gate is unnecessary. The transistor 61 may have two gates. This structure enables a reduction in size of the transistors. A first gate and a second gate of each transistor can be electrically connected to each other. Alternatively, the gates may be electrically connected to different wirings. In this case, threshold voltages of the transistors can be controlled by applying different potentials to the wirings.

The electrode of the display element 60 that is electrically connected to the transistor 62 corresponds to a pixel electrode. In FIG. 14, the one of the electrodes of the display element 60 that is electrically connected to the transistor 62 serves as a cathode, whereas the other electrode serves as an anode. This structure is particularly effective when the transistor 62 is an n-channel transistor. When the n-channel transistor 62 is on, the potential applied from the wiring 53a is a source potential; accordingly, the amount of current flowing in the transistor 62 can be constant regardless of variation or change in resistance of the display element 60. Alternatively, a p-channel transistor may be used as a transistor of a pixel circuit.

Embodiment 8

In this embodiment, a metal oxide (also referred to as an oxide semiconductor) that can be used in the OS transistor described in the above embodiment is described.

The metal oxide preferably contains at least indium or zinc. In particular, indium and zinc are preferably contained. In addition, aluminum, gallium, yttrium, tin, or the like is preferably contained. Furthermore, one or more kinds selected from boron, silicon, titanium, iron, nickel, germanium, zirconium, molybdenum, lanthanum, cerium, neodymium, hafnium, tantalum, tungsten, magnesium, cobalt, and the like may be contained.

The metal oxide can be formed by a sputtering method, a chemical vapor deposition (CVD) method such as a metal organic chemical vapor deposition (MOCVD) method, an atomic layer deposition (ALD) method, or the like.

<Classification of Crystal Structure>

Amorphous (including a completely amorphous structure), CAAC (c-axis-aligned crystalline), nc (nanocrystalline), CAC (cloud-aligned composite), single-crystal, and polycrystalline (poly crystal) structures can be given as examples of a crystal structure of an oxide semiconductor.

Note that a crystal structure of a film or a substrate can be evaluated with an X-ray diffraction (XRD) spectrum. For example, evaluation is possible using an XRD spectrum which is obtained by GIXD (Grazing-Incidence XRD) measurement. Note that a GIXD method is also referred to as a thin film method or a Seemann-Bohlin method.

For example, the XRD spectrum of the quartz glass substrate shows a peak with a substantially bilaterally symmetrical shape. On the other hand, the peak of the XRD spectrum of the IGZO film having a crystal structure has a bilaterally asymmetrical shape. The asymmetrical peak of the XRD spectrum clearly shows the existence of crystal in the film or the substrate. In other words, the crystal structure of the film or the substrate cannot be regarded as "amorphous" unless it has a bilaterally symmetrical peak in the XRD spectrum.

A crystal structure of a film or a substrate can also be evaluated with a diffraction pattern obtained by a nanobeam electron diffraction (NBED) method (such a pattern is also referred to as a nanobeam electron diffraction pattern). For example, a halo pattern is observed in the diffraction pattern of the quartz glass substrate, which indicates that the quartz glass substrate is in an amorphous state. Furthermore, not a halo pattern but a spot-like pattern is observed in the diffraction pattern of the IGZO film deposited at room temperature. Thus, it is suggested that the IGZO film deposited at room temperature is in an intermediate state, which is neither a crystal state nor an amorphous state, and it cannot be concluded that the IGZO film is in an amorphous state.

<<Structure of Oxide Semiconductor>>

Oxide semiconductors might be classified in a manner different from the above-described one when classified in terms of the structure. Oxide semiconductors are classified into a single crystal oxide semiconductor and a non-single-crystal oxide semiconductor, for example. Examples of the non-single-crystal oxide semiconductor include the above-described CAAC-OS and nc-OS. Other examples of the non-single-crystal oxide semiconductor include a polycrystalline oxide semiconductor, an amorphous-like oxide semiconductor (a-like OS), and an amorphous oxide semiconductor.

Here, the above-described CAAC-OS, nc-OS, and a-like OS are described in detail.

[CAAC-OS]

The CAAC-OS is an oxide semiconductor that has a plurality of crystal regions each of which has c-axis alignment in a particular direction. Note that the particular direction refers to the film thickness direction of a CAAC-OS film, the normal direction of the surface where the CAAC-OS film is formed, or the normal direction of the surface of the CAAC-OS film. The crystal region refers to a region having a periodic atomic arrangement. When an atomic arrangement is regarded as a lattice arrangement, the crystal region also refers to a region with a uniform lattice arrangement. The CAAC-OS has a region where a plurality of crystal regions are connected in the a-b plane direction, and the region has distortion in some cases. Note that distortion refers to a portion where the direction of a lattice arrangement changes between a region with a uniform lattice arrangement and another region with a uniform lattice arrangement in a region where a plurality of crystal regions are connected. That is, the CAAC-OS is an oxide semiconductor having c-axis alignment and having no clear alignment in the a-b plane direction.

Note that each of the plurality of crystal regions is formed of one or more fine crystals (crystals each of which has a maximum diameter of less than 10 nm). In the case where the crystal region is formed of one fine crystal, the maximum diameter of the crystal region is less than 10 nm. In the case where the crystal region is formed of a large number of fine crystals, the size of the crystal region may be approximately several tens of nanometers.

In the case of an In-M-Zn oxide (the element M is one or more kinds selected from aluminum, gallium, yttrium, tin, titanium, and the like), the CAAC-OS tends to have a layered crystal structure (also referred to as a stacked-layer structure) in which a layer containing indium (In) and oxygen (hereinafter, an In layer) and a layer containing the element M, zinc (Zn), and oxygen (hereinafter, an (M,Zn)

layer) are stacked. Indium and the element M can be replaced with each other. Therefore, indium may be contained in the (M,Zn) layer. In addition, the element M may be contained in the In layer. Note that Zn may be contained in the In layer. Such a layered structure is observed as a lattice image in a high-resolution transmission electron microscope (TEM) image, for example.

When the CAAC-OS film is subjected to structural analysis by Out-of-plane XRD measurement with an XRD apparatus using θ/2θ scanning, for example, a peak indicating c-axis alignment is detected at 2θ of 31° or around 31°. Note that the position of the peak indicating c-axis alignment (the value of 2θ) may change depending on the kind, composition, or the like of the metal element contained in the CAAC-OS.

For example, a plurality of bright spots are observed in the electron diffraction pattern of the CAAC-OS film. Note that one spot and another spot are observed point-symmetrically with a spot of the incident electron beam passing through a sample (also referred to as a direct spot) as the symmetric center.

When the crystal region is observed from the particular direction, a lattice arrangement in the crystal region is basically a hexagonal lattice arrangement; however, a unit lattice is not always a regular hexagon and is a non-regular hexagon in some cases. A pentagonal lattice arrangement, a heptagonal lattice arrangement, and the like are included in the distortion in some cases. Note that a clear grain boundary cannot be observed even in the vicinity of the distortion in the CAAC-OS. That is, formation of a crystal grain boundary is inhibited by the distortion of lattice arrangement. This is probably because the CAAC-OS can tolerate distortion owing to a low density of arrangement of oxygen atoms in the a-b plane direction, an interatomic bond distance changed by substitution of a metal atom, and the like.

Note that a crystal structure in which a clear grain boundary is observed is what is called polycrystal. It is highly probable that the grain boundary becomes a recombination center and captures carriers and thus decreases the on-state current and field-effect mobility of a transistor, for example. Thus, the CAAC-OS in which no clear grain boundary is observed is one of crystalline oxides having a crystal structure suitable for a semiconductor layer of a transistor. Note that Zn is preferably contained to form the CAAC-OS. For example, an In—Zn oxide and an In—Ga—Zn oxide are suitable because they can inhibit generation of a grain boundary as compared with an In oxide.

The CAAC-OS is an oxide semiconductor with high crystallinity in which no clear grain boundary is observed. Thus, in the CAAC-OS, a reduction in electron mobility due to the grain boundary is unlikely to occur. Moreover, since the crystallinity of an oxide semiconductor might be decreased by entry of impurities, formation of defects, or the like, the CAAC-OS can be regarded as an oxide semiconductor that has small amounts of impurities and defects (e.g., oxygen vacancies). Thus, an oxide semiconductor including the CAAC-OS is physically stable. Therefore, the oxide semiconductor including the CAAC-OS is resistant to heat and has high reliability. In addition, the CAAC-OS is stable with respect to high temperature in the manufacturing process (what is called thermal budget). Accordingly, the use of the CAAC-OS for the OS transistor can extend the degree of freedom of the manufacturing process.

[nc-OS]

In the nc-OS, a microscopic region (e.g., a region with a size greater than or equal to 1 nm and less than or equal to 10 nm, in particular, a region with a size greater than or equal to 1 nm and less than or equal to 3 nm) has a periodic atomic arrangement. In other words, the nc-OS includes a fine crystal. Note that the size of the fine crystal is, for example, greater than or equal to 1 nm and less than or equal to 10 nm, particularly greater than or equal to 1 nm and less than or equal to 3 nm; thus, the fine crystal is also referred to as a nanocrystal. Furthermore, there is no regularity of crystal orientation between different nanocrystals in the nc-OS. Thus, the orientation in the whole film is not observed. Accordingly, the nc-OS cannot be distinguished from an a-like OS or an amorphous oxide semiconductor by some analysis methods. For example, when an nc-OS film is subjected to structural analysis by Out-of-plane XRD measurement with an XRD apparatus using θ/2θ scanning, a peak indicating crystallinity is not detected. Furthermore, a diffraction pattern like a halo pattern is observed when the nc-OS film is subjected to electron diffraction (also referred to as selected-area electron diffraction) using an electron beam with a probe diameter larger than the diameter of a nanocrystal (e.g., larger than or equal to 50 nm). Meanwhile, in some cases, a plurality of spots in a ring-like region with a direct spot as the center are observed in the obtained electron diffraction pattern when the nc-OS film is subjected to electron diffraction (also referred to as nanobeam electron diffraction) using an electron beam with a probe diameter nearly equal to or smaller than the diameter of a nanocrystal (e.g., 1 nm or larger and 30 nm or smaller).

[a-Like OS]

The a-like OS is an oxide semiconductor having a structure between those of the nc-OS and the amorphous oxide semiconductor. The a-like OS contains a void or a low-density region. That is, the a-like OS has low crystallinity as compared with the nc-OS and the CAAC-OS. Moreover, the a-like OS has higher hydrogen concentration in the film than the nc-OS and the CAAC-OS.

<<Structure of Oxide Semiconductor>>

Next, the above-described CAC-OS is described in detail. Note that the CAC-OS relates to the material composition.

[CAC-OS]

The CAC-OS refers to one composition of a material in which elements constituting a metal oxide are unevenly distributed with a size greater than or equal to 0.5 nm and less than or equal to 10 nm, preferably greater than or equal to 1 nm and less than or equal to 3 nm, or a similar size, for example. Note that a state in which one or more metal elements are unevenly distributed and regions including the metal element(s) are mixed with a size greater than or equal to 0.5 nm and less than or equal to 10 nm, preferably greater than or equal to 1 nm and less than or equal to 3 nm, or a similar size in a metal oxide is hereinafter referred to as a mosaic pattern or a patch-like pattern.

In addition, the CAC-OS has a composition in which materials are separated into a first region and a second region to form a mosaic pattern, and the first regions are distributed in the film (this composition is hereinafter also referred to as a cloud-like composition). That is, the CAC-OS is a composite metal oxide having a composition in which the first regions and the second regions are mixed.

Note that the atomic ratios of In, Ga, and Zn to the metal elements contained in the CAC-OS in an In—Ga—Zn oxide are denoted by [In], [Ga], and [Zn], respectively. For example, the first region in the CAC-OS in the In—Ga—Zn oxide has [In] higher than that in the composition of the CAC-OS film. Moreover, the second region has [Ga] higher than that in the composition of the CAC-OS film. For example, the first region has higher [In] and lower [Ga] than the second region. Moreover, the second region has higher [Ga] and lower [In] than the first region.

Specifically, the first region contains indium oxide, indium zinc oxide, or the like as its main component. The second region contains gallium oxide, gallium zinc oxide, or the like as its main component. That is, the first region can be referred to as a region containing In as its main component. The second region can be referred to as a region containing Ga as its main component.

Note that a clear boundary between the first region and the second region cannot be observed in some cases.

In a material composition of a CAC-OS in an In—Ga—Zn oxide that contains In, Ga, Zn, and O, regions containing Ga as a main component are observed in part of the CAC-OS and regions containing In as a main component are observed in part thereof. These regions are randomly dispersed to form a mosaic pattern. Thus, it is suggested that the CAC-OS has a structure in which metal elements are unevenly distributed.

The CAC-OS can be formed by a sputtering method under a condition where a substrate is not heated, for example. Moreover, in the case of forming the CAC-OS by a sputtering method, any one or more selected from an inert gas (typically, argon), an oxygen gas, and a nitrogen gas are used as a deposition gas. The flow rate of the oxygen gas to the total flow rate of the deposition gas in deposition is preferably as low as possible, for example, the flow rate of the oxygen gas to the total flow rate of the deposition gas in deposition is higher than or equal to 0% and lower than 30%, preferably higher than or equal to 0% and lower than or equal to 10%.

For example, energy dispersive X-ray spectroscopy (EDX) is used to obtain EDX mapping, and according to the EDX mapping, the CAC-OS in the In—Ga—Zn oxide has a structure in which the region containing In as its main component (the first region) and the region containing Ga as its main component (the second region) are unevenly distributed and mixed.

Here, the first region has a higher conductivity than the second region. In other words, when carriers flow through the first region, the conductivity of a metal oxide is exhibited. Accordingly, when the first regions are distributed in a metal oxide as a cloud, high field-effect mobility ($\mu$) can be achieved.

The second region has a higher insulating property than the first region. In other words, when the second regions are distributed in a metal oxide, leakage current can be inhibited.

Thus, in the case where a CAC-OS is used for a transistor, by the complementary function of the conducting function due to the first region and the insulating function due to the second region, the CAC-OS can have a switching function (On/Off function). A CAC-OS has a conducting function in part of the material and has an insulating function in another part of the material; as a whole, the CAC-OS has a function of a semiconductor. Separation of the conducting function and the insulating function can maximize each function. Accordingly, when the CAC-OS is used for a transistor, high on-state current ($I_{on}$), high field-effect mobility ($\mu$), and excellent switching operation can be achieved.

A transistor using a CAC-OS has high reliability. Thus, the CAC-OS is most suitable for a variety of semiconductor devices such as display devices.

An oxide semiconductor has various structures with different properties. Two or more kinds among the amorphous oxide semiconductor, the polycrystalline oxide semiconductor, the a-like OS, the CAC-OS, the nc-OS, and the CAAC-OS may be included in an oxide semiconductor of one embodiment of the present invention.

<Transistor Including Oxide Semiconductor>

Next, the case where the above oxide semiconductor is used for a transistor is described.

When the above oxide semiconductor is used for a transistor, a transistor with high field-effect mobility can be achieved. In addition, a transistor having high reliability can be achieved.

An oxide semiconductor having a low carrier concentration is preferably used in a transistor. For example, the carrier concentration of an oxide semiconductor is lower than or equal to $1\times10^{17}$ cm$^{-3}$, preferably lower than or equal to $1\times10^{15}$ cm$^{-3}$, further preferably lower than or equal to $1\times10^{13}$ cm$^{-3}$, still further preferably lower than or equal to $1\times10^{11}$ cm$^{-3}$, yet further preferably lower than $1\times10^{10}$ cm$^{-3}$, and higher than or equal to $1\times10^{-9}$ cm$^{-3}$. In order to reduce the carrier concentration of an oxide semiconductor film, the impurity concentration in the oxide semiconductor film is reduced so that the density of defect states can be reduced. In this specification and the like, a state with a low impurity concentration and a low density of defect states is referred to as a highly purified intrinsic or substantially highly purified intrinsic state. Note that an oxide semiconductor having a low carrier concentration may be referred to as a highly purified intrinsic or substantially highly purified intrinsic oxide semiconductor.

A highly purified intrinsic or substantially highly purified intrinsic oxide semiconductor film has a low density of defect states and thus has a low density of trap states in some cases.

Charge trapped by the trap states in the oxide semiconductor takes a long time to disappear and might behave like fixed charge. Thus, a transistor whose channel formation region is formed in an oxide semiconductor with a high density of trap states has unstable electrical characteristics in some cases.

Accordingly, in order to obtain stable electrical characteristics of a transistor, reducing the impurity concentration in an oxide semiconductor is effective. In order to reduce the impurity concentration in the oxide semiconductor, it is preferable that the impurity concentration in an adjacent film be also reduced. Examples of impurities include hydrogen, nitrogen, an alkali metal, an alkaline earth metal, iron, nickel, and silicon.

<Impurity>

Here, the influence of each impurity in the oxide semiconductor is described.

When silicon or carbon, which is one of Group 14 elements, is contained in the oxide semiconductor, defect states are formed in the oxide semiconductor. Thus, the concentration of silicon or carbon in the oxide semiconductor and the concentration of silicon or carbon in the vicinity of an interface with the oxide semiconductor (the concentration obtained by secondary ion mass spectrometry (SIMS)) are each set lower than or equal to $2\times10^{18}$ atoms/cm$^3$, preferably lower than or equal to $2\times10^{17}$ atoms/cm$^3$.

When the oxide semiconductor contains an alkali metal or an alkaline earth metal, defect states are formed and carriers are generated in some cases. Thus, a transistor using an oxide semiconductor that contains an alkali metal or an alkaline earth metal is likely to have normally-on characteristics. Thus, the concentration of an alkali metal or an alkaline earth metal in the oxide semiconductor, which is obtained by SIMS, is lower than or equal to $1\times10^{18}$ atoms/cm$^3$, preferably lower than or equal to $2\times10^{16}$ atoms/cm$^3$.

Furthermore, when the oxide semiconductor contains nitrogen, the oxide semiconductor easily becomes n-type by generation of electrons serving as carriers and an increase in carrier concentration. As a result, a transistor using an oxide semiconductor containing nitrogen as a semiconductor is likely to have normally-on characteristics. When nitrogen is contained in the oxide semiconductor, a trap state is sometimes formed. This might make the electrical characteristics of the transistor unstable. Therefore, the concentration of nitrogen in the oxide semiconductor, which is obtained by SIMS, is set lower than $5\times10^{19}$ atoms/cm$^3$, preferably lower than or equal to $5\times10^{18}$ atoms/cm$^3$, further preferably lower than or equal to $1\times10^{18}$ atoms/cm$^3$, still further preferably lower than or equal to $5\times10^{17}$ atoms/cm$^3$.

Hydrogen contained in the oxide semiconductor reacts with oxygen bonded to a metal atom to be water, and thus forms an oxygen vacancy in some cases. Entry of hydrogen into the oxygen vacancy generates an electron serving as a carrier in some cases. Furthermore, bonding of part of hydrogen to oxygen bonded to a metal atom causes generation of an electron serving as a carrier in some cases. Thus, a transistor using an oxide semiconductor containing hydrogen is likely to have normally-on characteristics. Accordingly, hydrogen in the oxide semiconductor is preferably reduced as much as possible. Specifically, the hydrogen concentration in the oxide semiconductor, which is obtained by SIMS, is set lower than $1\times10^{20}$ atoms/cm$^3$, preferably lower than $1\times10^{19}$ atoms/cm$^3$, further preferably lower than $5\times10^{18}$ atoms/cm$^3$, still further preferably lower than $1\times10^{18}$ atoms/cm$^3$.

When an oxide semiconductor with sufficiently reduced impurities is used for the channel formation region of the transistor, stable electrical characteristics can be given.

At least part of this embodiment can be implemented in combination with any of the other embodiments described in this specification, as appropriate.

Embodiment 9

In this embodiment, electronic devices of one embodiment of the present invention will be described with reference to FIGS. 15A and 15B, FIGS. 16A to 16D, FIGS. 17A to 17F, and FIGS. 18A to 18F.

An electronic device in this embodiment includes the display device of one embodiment of the present invention. For the display device of one embodiment of the present invention, increases in resolution, definition, and sizes are easily achieved. Thus, the display device of one embodiment of the present invention can be used for display portions of a variety of electronic devices.

The display device of one embodiment of the present invention can be manufactured at low cost, which leads to a reduction in manufacturing cost of an electronic device.

Examples of the electronic devices include a digital camera, a digital video camera, a digital photo frame, a mobile phone, a portable game console, a portable information terminal, and an audio reproducing device, in addition to electronic devices with a relatively large screen, such as a television device, a desktop or laptop personal computer, a monitor of a computer or the like, digital signage, and a large game machine such as a pachinko machine.

In particular, a display device of one embodiment of the present invention can have a high resolution, and thus can be favorably used for an electronic device having a relatively small display portion. As such an electronic device, a watch-type or bracelet-type information terminal device (wearable device); and a wearable device worn on a head, such as a device for VR such as a head mounted display and a glasses-type device for AR can be given, for example. Examples of wearable devices includes a device for SR and a device for MR.

The resolution of the display device of one embodiment of the present invention is preferably as high as HD (number of pixels: 1280×720), FHD (number of pixels: 1920×1080), WQHD (number of pixels: 2560×1440), WQXGA (number of pixels: 2560×1600), 4K2K (number of pixels: 3840×2160), or 8K4K (number of pixels: 7680×4320). In particular, resolution of 4K2K, 8K4K, or higher is preferable. Furthermore, the pixel density (definition) of the display device of one embodiment of the present invention is preferably higher than or equal to 300 ppi, further preferably higher than or equal to 500 ppi, still further preferably higher than or equal to 1000 ppi, still further preferably higher than or equal to 2000 ppi, still further preferably higher than or equal to 3000 ppi, still further preferably higher than or equal to 5000 ppi, and yet further preferably higher than or equal to 7000 ppi. With such a display device with high resolution and high definition, the electronic device can have higher realistic sensation, sense of depth, and the like in personal use such as portable use and home use.

The electronic device in this embodiment can be incorporated along a curved surface of an inside wall or an outside wall of a house or a building or the interior or the exterior of a car.

The electronic device in this embodiment may include an antenna. With the antenna receiving a signal, the electronic device can display an image, information, and the like on a display portion. When the electronic device includes an antenna and a secondary battery, the antenna may be used for contactless power transmission.

The electronic device in this embodiment may include a sensor (a sensor having a function of sensing, detecting, or measuring force, displacement, position, speed, acceleration, angular velocity, rotational frequency, distance, light, liquid, magnetism, temperature, a chemical substance, sound, time, hardness, electric field, current, voltage, electric power, radiation, flow rate, humidity, gradient, oscillation, a smell, or infrared rays).

The electronic device in this embodiment can have a variety of functions. For example, the electronic device of one embodiment of the present invention can have a function of displaying a variety of data (a still image, a moving image, a text image, and the like) on the display portion, a touch panel function, a function of displaying a calendar, date, time, and the like, a function of executing a variety of software (programs), a wireless communication function, and a function of reading out a program or data stored in a recording medium.

Figure 15A:
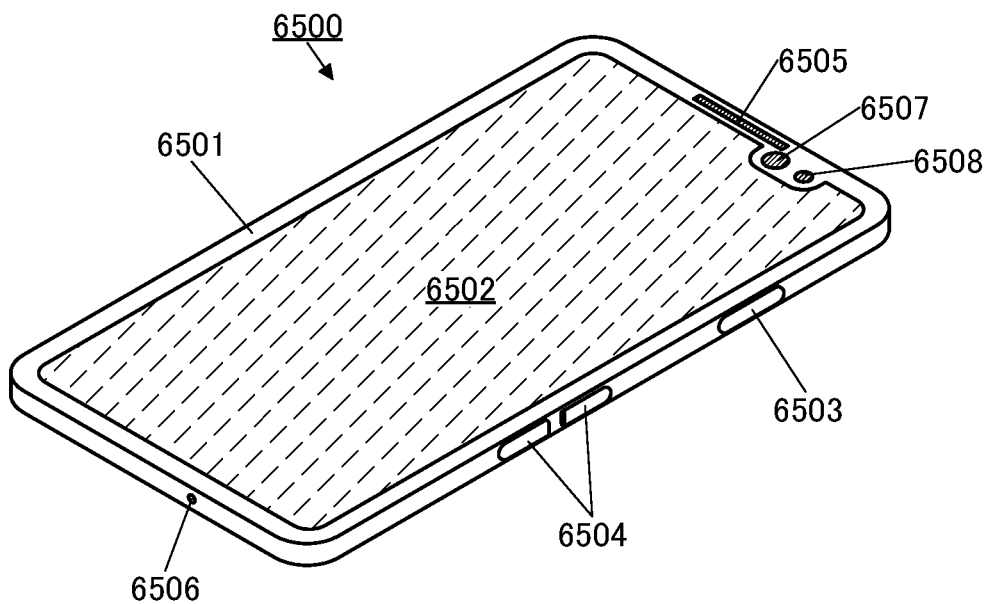
FIGS. 15A and 15B show an example of an electronic device.

An electronic device 6500 in FIG. 15A is a portable information terminal that can be used as a smartphone.

The electronic device 6500 includes a housing 6501, a display portion 6502, a power button 6503, buttons 6504, a speaker 6505, a microphone 6506, a camera 6507, a light source 6508, and the like. The display portion 6502 has a touch panel function.

The display device of one embodiment of the present invention can be used in the display portion 6502.

Figure 15B:
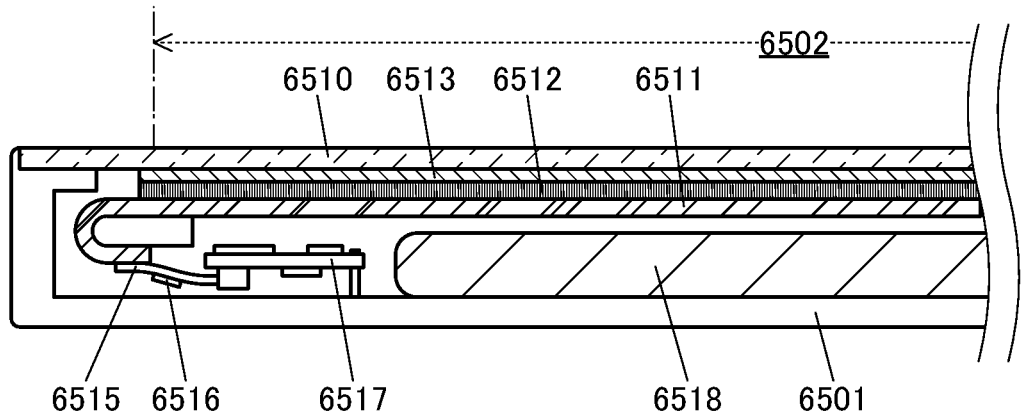

FIG. 15B is a schematic cross-sectional view including an end portion of the housing 6501 on the microphone 6506 side.

A protection member 6510 having a light-transmitting property is provided on a display surface side of the housing 6501, and a display panel 6511, an optical member 6512, a touch sensor panel 6513, a printed circuit board 6517, a battery 6518, and the like are provided in a space surrounded by the housing 6501 and the protection member 6510.

The display panel 6511, the optical member 6512, and the touch sensor panel 6513 are fixed to the protection member 6510 with an adhesive layer (not illustrated).

Part of the display panel 6511 is folded back in a region outside the display portion 6502, and an FPC 6515 is connected to the part that is folded back. An IC 6516 is mounted on the FPC 6515. The FPC 6515 is connected to a terminal provided on the printed circuit board 6517.

A flexible display of one embodiment of the present invention can be used as the display panel 6511. Thus, an extremely lightweight electronic device can be achieved. Since the display panel 6511 is extremely thin, the battery 6518 with high capacity can be mounted while h the thickness of the electronic device is controlled. Moreover, a part of the display panel 6511 is folded back so that a connection portion with the FPC 6515 is provided on the back side of the pixel portion, whereby an electronic device with a narrow bezel can be achieved.

Figure 16A:
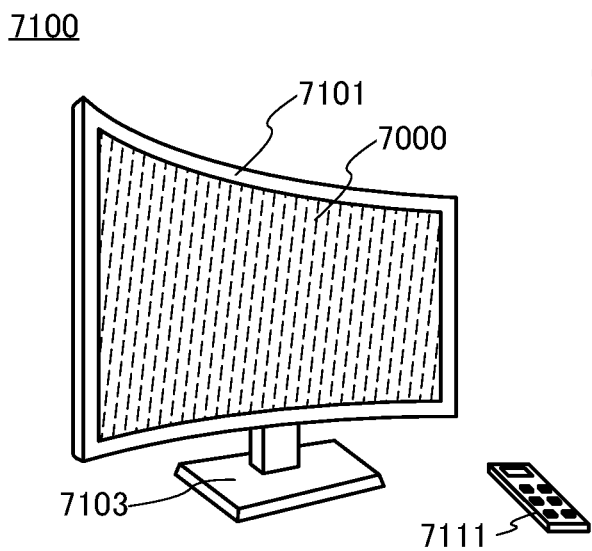
FIGS. 16A to 16D show examples of electronic devices.

FIG. 16A shows an example of a television device. In a television device 7100, a display portion 7000 is incorporated in a housing 7101. Here, the housing 7101 is supported by a stand 7103.

The display device of one embodiment of the present invention can be used for the display portion 7000.

Operation of the television device 7100 illustrated in FIG. 16A can be performed with an operation switch provided in the housing 7101 and a separate remote controller 7111. Alternatively, the display portion 7000 may include a touch sensor, and the television device 7100 may be operated by touch on the display portion 7000 with a finger or the like. The remote controller 7111 may be provided with a display portion for displaying information output from the remote controller 7111. With operation keys or a touch panel provided in the remote controller 7111, channels and volume can be operated and videos displayed on the display portion 7000 can be operated.

Note that the television device 7100 has a structure in which a receiver, a modem, and the like are provided. A general television broadcast can be received with the receiver. When the television device is connected to a communication network with or without wires via the modem, one-way (from a transmitter to a receiver) or two-way (between a transmitter and a receiver or between receivers, for example) data communication can be performed.

Figure 16B:
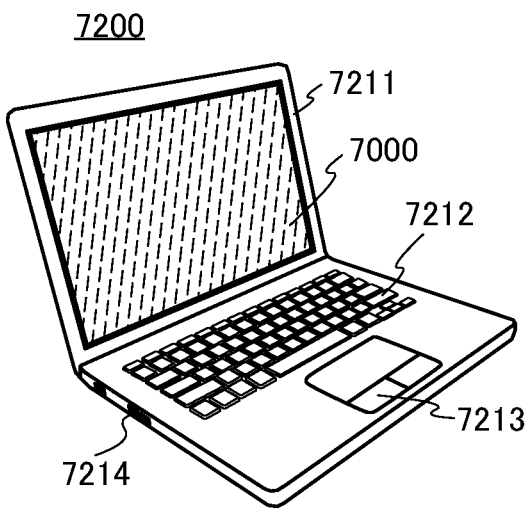

FIG. 16B illustrates an example of a laptop personal computer. The laptop personal computer 7200 includes a housing 7211, a keyboard 7212, a pointing device 7213, an external connection port 7214, and the like. In the housing 7211, the display portion 7000 is incorporated.

The display device of one embodiment of the present invention can be used for the display portion 7000.

Figure 16C:
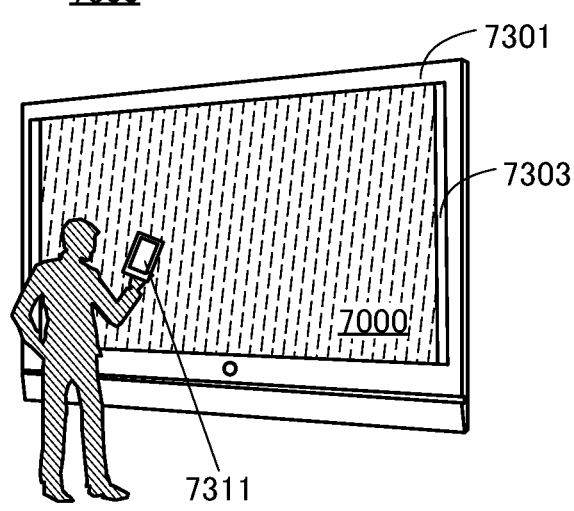
Figure 16D:
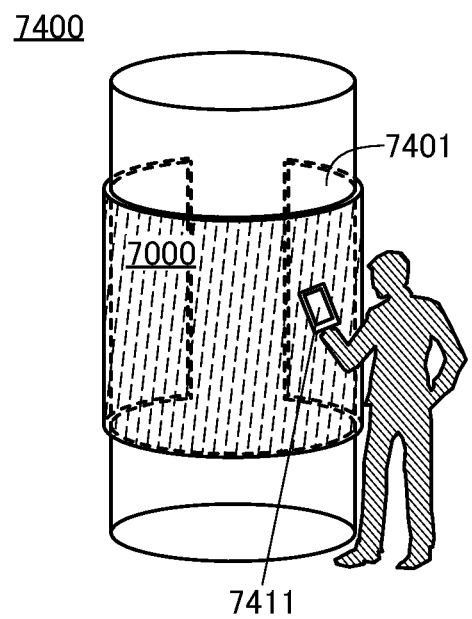

FIGS. 16C and 16D illustrate examples of digital signage.

Digital signage 7300 illustrated in FIG. 16C includes a housing 7301, the display portion 7000, a speaker 7303, and the like. The digital signage 7300 can also include an LED lamp, an operation key (including a power switch or an operation switch), a connection terminal, a variety of sensors, a microphone, and the like.

FIG. 16D is digital signage 7400 attached to a cylindrical pillar 7401. The digital signage 7400 includes the display portion 7000 provided along a curved surface of the pillar 7401.

The display device of one embodiment of the present invention can be used in the display portion 7000 illustrated in each of FIGS. 16C and 16D.

A larger area of the display portion 7000 can increase the amount of data that can be provided at a time. The larger display portion 7000 attracts more attention, so that the effectiveness of the advertisement can be increased, for example.

The use of a touch panel in the display portion 7000 is preferable because in addition to display of a still image or a moving image on the display portion 7000, intuitive operation by a user is possible. Moreover, for an application for providing information such as route information or traffic information, usability can be enhanced by intuitive operation.

As illustrated in FIGS. 16C and 16D, it is preferable that the digital signage 7300 or the digital signage 7400 can work with an information terminal 7311 or an information terminal 7411 such as a smartphone a user has through wireless communication. For example, information of an advertisement displayed on the display portion 7000 can be displayed on a screen of the information terminal 7311 or the information terminal 7411. By operation of the information terminal 7311 or the information terminal 7411, display on the display portion 7000 can be switched.

It is possible to make the digital signage 7300 or the digital signage 7400 execute a game with use of the screen of the information terminal 7311 or the information terminal 7411 as an operation means (controller). Thus, an unspecified number of users can join in and enjoy the game concurrently.

Figure 17A:
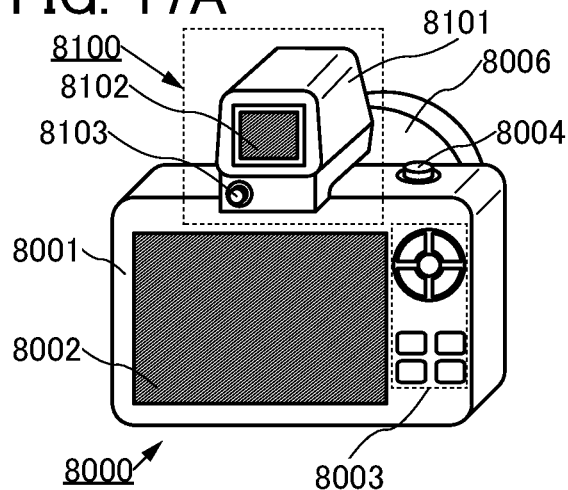
FIGS. 17A to 17F show structure examples of electronic devices.

FIG. 17A is an external view of a camera 8000 to which a finder 8100 is attached.

The camera 8000 includes a housing 8001, a display portion 8002, operation buttons 8003, a shutter button 8004, and the like. Furthermore, a detachable lens 8006 is attached to the camera 8000. Note that the lens 8006 and the housing may be integrated with each other in the camera 8000.

Images can be taken with the camera 8000 at the press of the shutter button 8004 or the touch of the display portion 8002 serving as a touch panel.

The housing 8001 includes a mount including an electrode, so that the finder 8100, a stroboscope, or the like can be connected to the housing.

The finder 8100 includes a housing 8101, a display portion 8102, a button 8103, and the like.

The housing 8101 is attached to the camera 8000 by a mount for engagement with the mount of the camera 8000. The finder 8100 can display a video received from the camera 8000 and the like on the display portion 8102.

The button 8103 functions as a power supply button or the like.

A display device of one embodiment of the present invention can be used in the display portion 8002 of the camera 8000 and the display portion 8102 of the finder 8100. Note that a finder may be incorporated in the camera 8000.

Figure 17B:
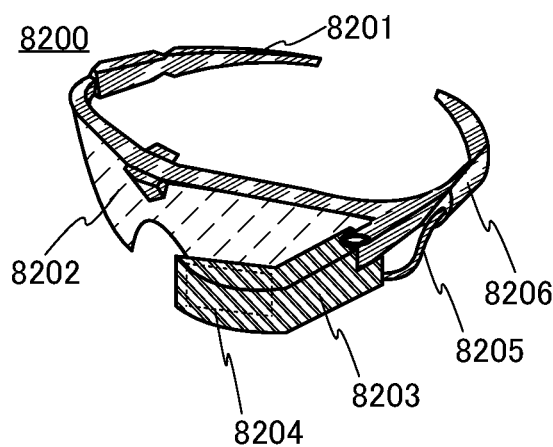

FIG. 17B is an external view of a head-mounted display 8200.

The head-mounted display 8200 includes a mounting portion 8201, a lens 8202, a main body 8203, a display portion 8204, a cable 8205, and the like. A battery 8206 is incorporated in the mounting portion 8201.

The cable 8205 supplies electric power from the battery 8206 to the main body 8203. The main body 8203 includes a wireless receiver or the like to receive image data and display it on the display portion 8204. The main body 8203 includes a camera, and data on the movement of the eyeballs or the eyelids of the user can be used as an input means.

The mounting portion 8201 may include a plurality of electrodes capable of sensing current flowing accompanying with the movement of the user's eyeball at a position in contact with the user to recognize the user's sight line. The mounting portion 8201 may also have a function of monitoring the user's pulse with use of current flowing in the electrodes. The mounting portion 8201 may include sensors such as a temperature sensor, a pressure sensor, and an acceleration sensor so that the user's biological information can be displayed on the display portion 8204 and an image displayed on the display portion 8204 can be changed in accordance with the movement of the user's head.

A display device of one embodiment of the present invention can be used in the display portion 8204.

Figure 17C:
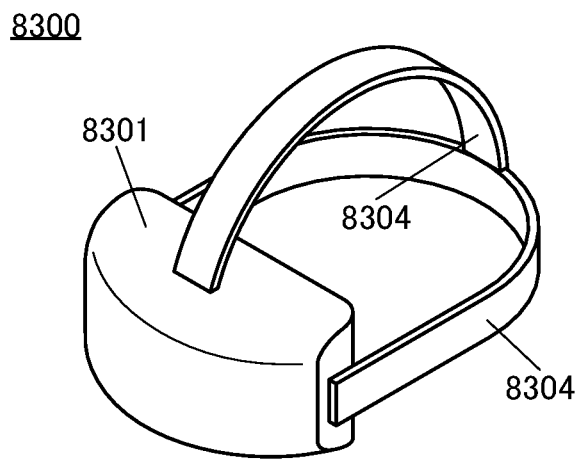
Figure 17D:
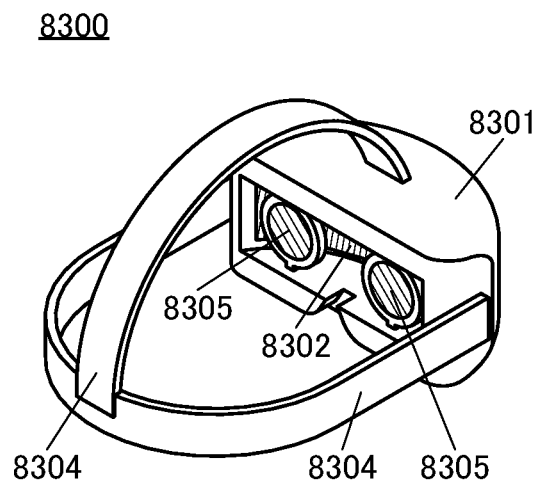
Figure 17E:
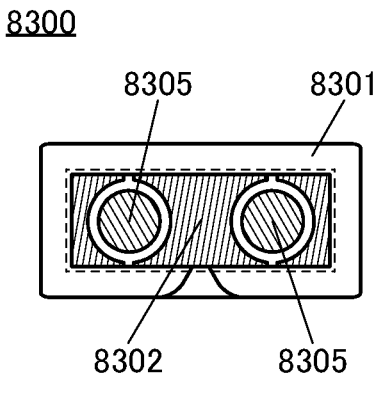

FIGS. 17C to 17E are external views of a head-mounted display 8300. The head-mounted display 8300 includes the housing 8301, the display portion 8302, the band-like fixing member 8304, and a pair of lenses 8305.

A user can see display on the display portion 8302 through the lenses 8305. The display portion 8302 is preferably curved because the user can feel high realistic sensation. Another image displayed in another region of the display portion 8302 is viewed through the lenses 8305, so that three-dimensional display using parallax or the like can be performed. Note that the number of the display portions 8302 is not limited to one; two display portions 8302 may be provided for user's respective eyes.

The display device of one embodiment of the present invention can be used for the display portion 8302. The display device of one embodiment of the present invention achieves extremely high resolution. For example, a pixel is not easily seen by the user even when the user sees display that is magnified by the use of the lenses 8305 as illustrated in FIG. 17E. In other words, a video with a strong sense of reality can be seen by the user with use of the display portion 8302.

Figure 17F:
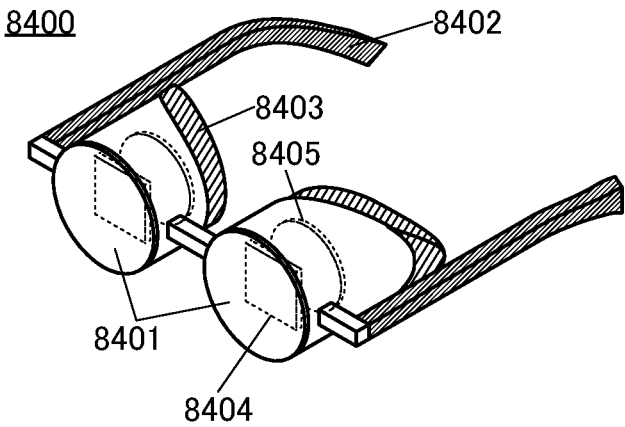

FIG. 17F is an external view of a goggle-type head-mounted display 8400. The head-mounted display 8400 includes a pair of housings 8401, a mounting portion 8402, and a cushion 8403. A display portion 8404 and a lens 8405 are provided in each of the pair of housings 8401. Furthermore, when the pair of display portions 8404 display different images, three-dimensional display using parallax can be performed.

A user can see display on the display portion 8404 through the lens 8405. The lens 8405 has a focus adjustment mechanism and can adjust the position according to the user's eyesight. The display portion 8404 is preferably a square or a horizontal rectangle. This can improve a realistic sensation.

The mounting portion 8402 preferably has plasticity and elasticity so as to be adjusted to fit the size of the user's face and not to slide down. In addition, part of the mounting portion 8402 preferably has a vibration mechanism functioning as a bone conduction earphone. Thus, audio devices such as an earphone and a speaker are not necessarily provided separately, and the user can enjoy images and sounds only when wearing the head-mounted display 8400. Note that the housing 8401 may have a function of outputting sound data by wireless communication.

The mounting portion 8402 and the cushion 8403 are portions in contact with the user's face (forehead, cheek, or the like). The cushion 8403 is in close contact with the user's face, so that light leakage can be prevented, which increases the sense of immersion. The cushion 8403 is preferably formed using a soft material so that the head-mounted display 8400 is in close contact with the user's face when being worn by the user. For example, a material such as rubber, silicone rubber, urethane, or sponge can be used. Furthermore, when a sponge or the like whose surface is covered with cloth, leather (natural leather or synthetic leather), or the like is used, a gap is unlikely to be generated between the user's face and the cushion 8403, whereby light leakage can be suitably prevented. Furthermore, using such a material is preferable because it has a soft texture and the user does not feel cold when wearing the device in a cold season, for example. The member in contact with user's skin, such as the cushion 8403 or the mounting portion 8402, is preferably detachable because cleaning or replacement can be easily performed.

Electronic devices illustrated in FIGS. 18A to 18F include a housing 9000, a display portion 9001, a speaker 9003, an operation key 9005 (including a power switch or an operation switch), a connection terminal 9006, a sensor 9007 (a sensor having a function of sensing, detecting, or measuring force, displacement, position, speed, acceleration, angular velocity, rotational frequency, distance, light, liquid, magnetism, temperature, a chemical substance, sound, time, hardness, electric field, current, voltage, electric power, radiation, flow rate, humidity, gradient, oscillation, a smell, or infrared rays), a microphone 9008, and the like.

The electronic devices illustrated in FIGS. 18A to 18F have a variety of functions. For example, the electronic device can have a function of displaying a variety of information (a still image, a moving image, a text image, and the like) on the display portion, a touch panel function, a function of displaying a calendar, date, time, and the like, a function of executing a variety of software (programs), a wireless communication function, and a function of reading out a program or data stored in a recording medium. Note that the functions of the electronic devices are not limited thereto, and the electronic devices can have a variety of functions. The electronic devices may include a plurality of display portions. The electronic devices may each be provided with a camera or the like and have a function of taking a still image or a moving image, a function of storing the taken image in a storage medium (an external storage medium or a storage medium incorporated in the camera), a function of displaying the taken image on the display portion, or the like.

The display device of one embodiment of the present invention can be used for the display portion 9001.

The electronic devices in FIGS. 18A to 18F are described in detail below.

Figure 18A:
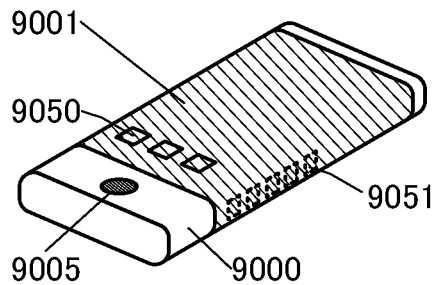
FIGS. 18A to 18F show structure examples of electronic devices.

FIG. 18A is a perspective view showing a portable information terminal 9101. For example, the portable information terminal 9101 can be used as a smartphone. Note that the portable information terminal 9101 may include the speaker 9003, the connection terminal 9006, the sensor 9007, or the like. The portable information terminal 9101 can display characters and image information on its plurality of surfaces. FIG. 18A illustrates an example in which three icons 9050 are displayed. Furthermore, information 9051 indicated by dashed rectangles can be displayed on another surface of the display portion 9001. Examples of the information 9051 include notification of reception of an e-mail, an SNS message, or an incoming call, the title and sender of an e-mail, an SNS message, or the like, the date, the time, remaining battery, and the reception strength of an antenna. Alternatively, the icon 9050 or the like may be displayed at the position where the information 9051 is displayed.

Figure 18B:
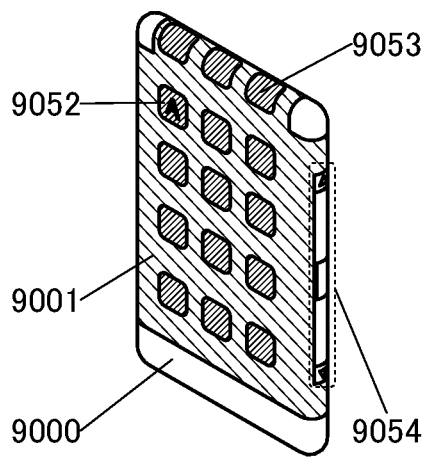

FIG. 18B is a perspective view showing a portable information terminal 9102. The portable information terminal 9102 has a function of displaying information on three or more surfaces of the display portion 9001. Here, information 9052, information 9053, and information 9054 are displayed on different surfaces. For example, a user of the portable information terminal 9102 can check the information 9053 displayed such that it can be seen from above the portable information terminal 9102, with the portable information terminal 9102 put in a breast pocket of his/her clothes. Thus, the user can see the display without taking out the portable information terminal 9102 from the pocket and decide whether to answer the call, for example.

Figure 18C:
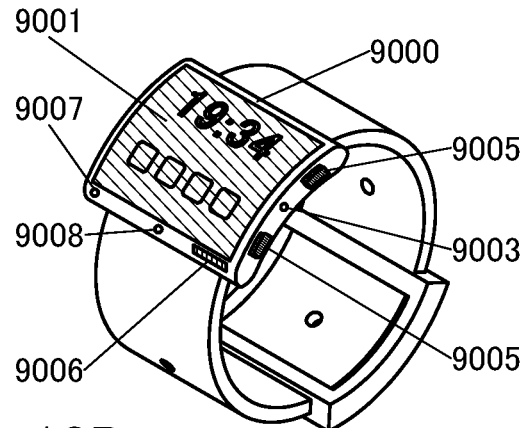

FIG. 18C is a perspective view illustrating a watch-type portable information terminal 9200. For example, the portable information terminal 9200 can be used as a Smartwatch (registered trademark). The display surface of the display portion 9001 is curved, and an image can be displayed on the curved display surface. Mutual communication between the portable information terminal 9200 and, for example, a headset capable of wireless communication enables hands-free calling. With the connection terminal 9006, the portable information terminal 9200 can perform mutual data transmission with another information terminal and charging. Note that the charging operation may be performed by wireless power feeding.

Figure 18D:
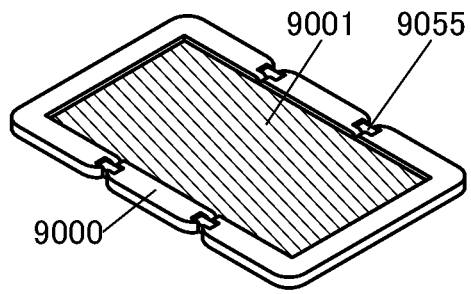
Figure 18E:
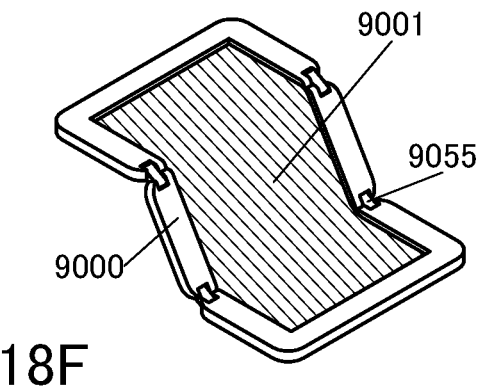
Figure 18F:
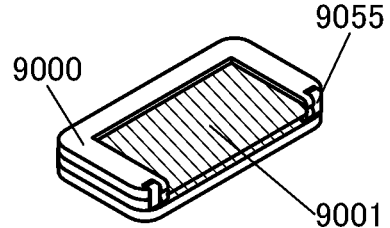

FIGS. 18D to 18F are perspective views illustrating a foldable portable information terminal 9201. FIG. 18D is a perspective view of an opened state of the portable information terminal 9201, FIG. 18F is a perspective view of a folded state thereof, and FIG. 18E is a perspective view of a state in the middle of change from one of FIGS. 18D and 18F to the other. The portable information terminal 9201 is highly portable when folded. When the portable information terminal 9201 is opened, a seamless large display region is highly browsable. The display portion 9001 of the portable information terminal 9201 is supported by three housings 9000 joined together by hinges 9055. For example, the display portion 9001 can be folded with a radius of curvature greater than or equal to 0.1 mm and less than or equal to 150 mm.

At least part of any of the structure examples, the drawings corresponding thereto, and the like described in this embodiment can be implemented in combination with any of the other structure examples, the other drawings corresponding thereto, and the like as appropriate.

At least part of this embodiment can be implemented in combination with any of the other embodiments described in this specification, as appropriate.

Example 1

In this example, light-emitting devices of one embodiment of the present invention will be described in detail. Structural formulae of typical organic compounds used in this example are shown below.

[Chemical Formula 4]

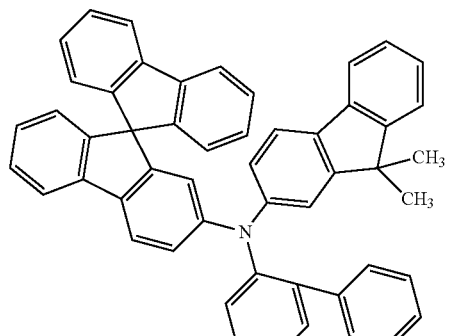

oFBiSF(2)

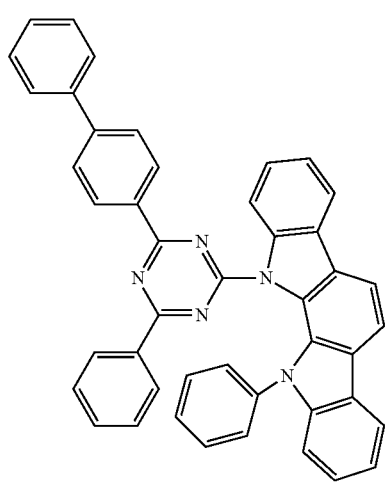

BP-Icz(II)Tzn

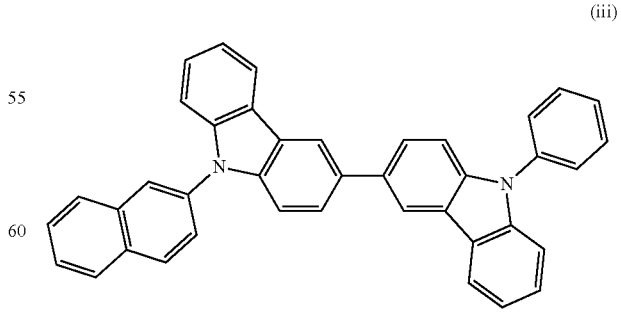

βNCCP

-continued
(v)
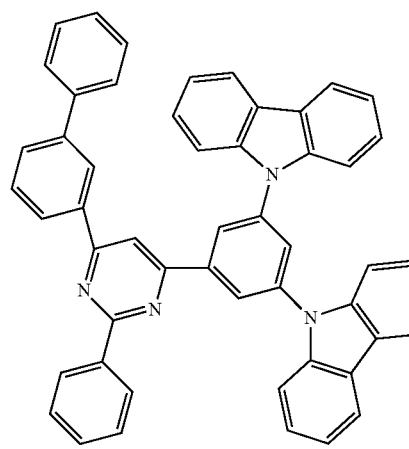
6mBP-4Cz2PPm
(iv)
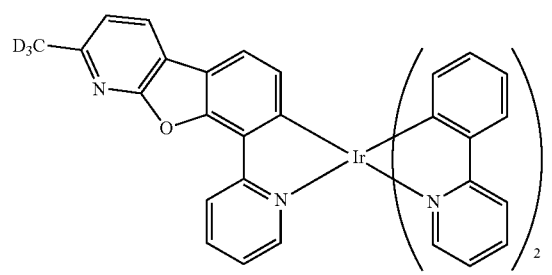
[Ir(ppy)₂(mbfpypy-d3)]
(vi)
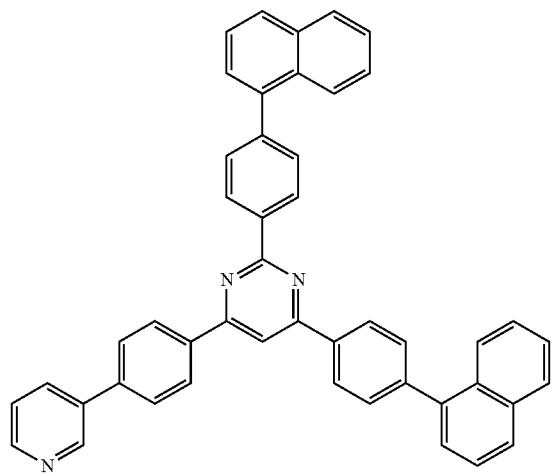
2,4NP-6PyPPm
(vii)
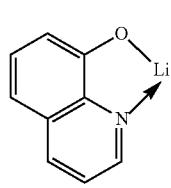
Liq
-continued
(viii)
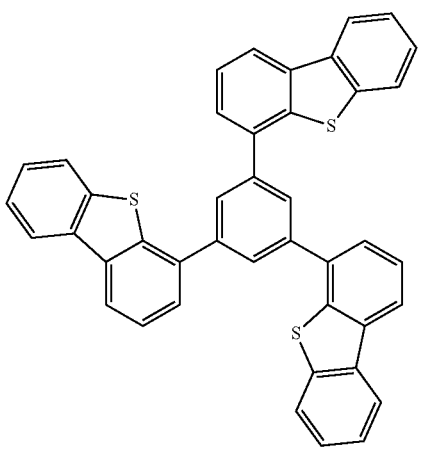
DBT3P-II
[Chemical Formula 5]
(I)
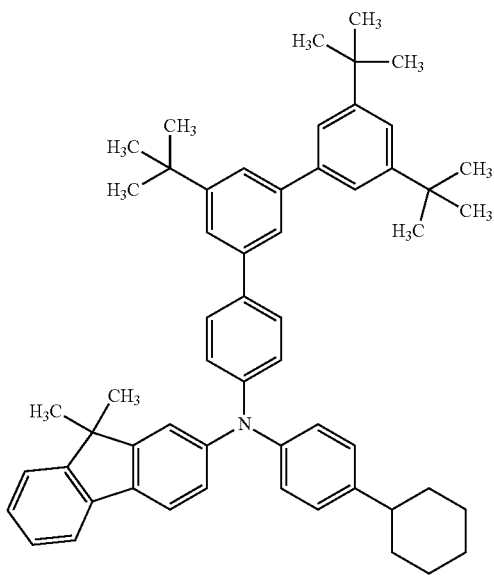
mmtBumTPchPAF-04

-continued
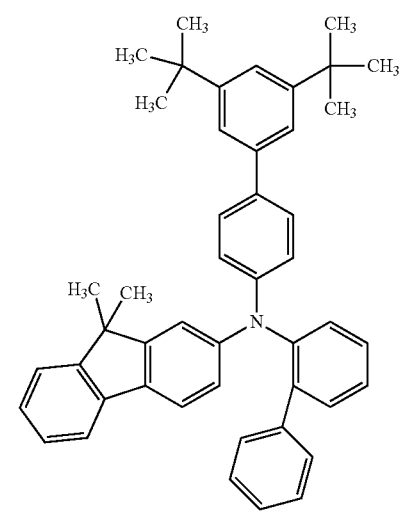
mmtBuBioFBi (II)
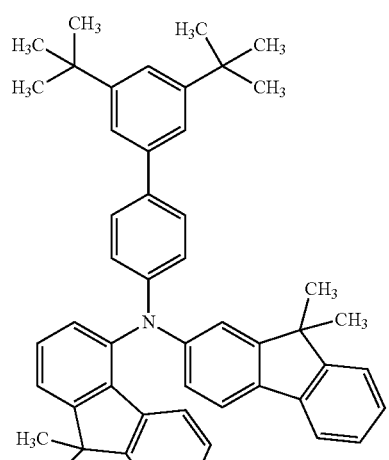
mmtBuBiFF-02 (III)
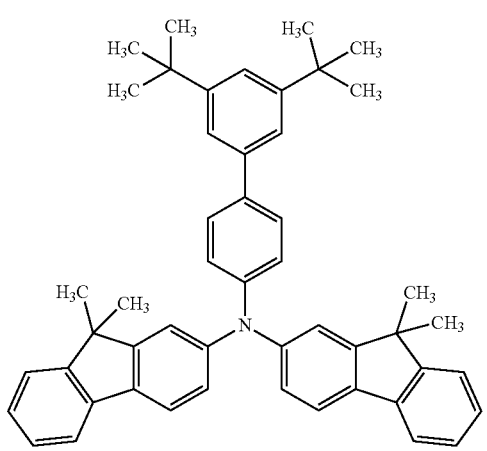
mmtBuBiFF (IV)
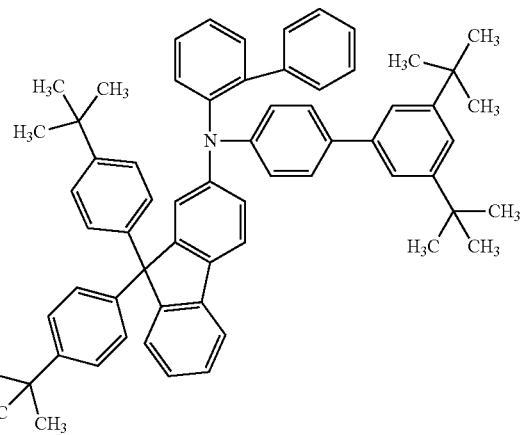
mmtBuBioBitBu2FLP(2) (V)
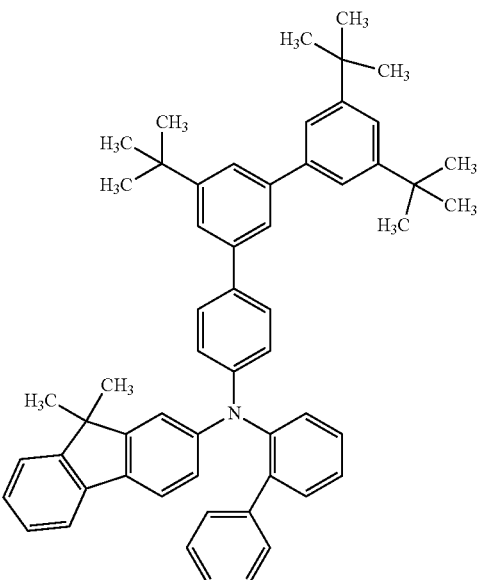
FrBBiFLP (VI)
mmtBumTPoFBi-04 (VII)

(Fabrication Method of Light-Emitting Device D1)

As a reflective electrode, silver (Ag) was deposited to a thickness of 100 nm by a sputtering method, and then, as a transparent electrode, indium tin oxide containing silicon oxide (ITSO) was deposited to a thickness of 10 nm by a sputtering method, whereby the first electrode 101 was formed. The electrode area was set to 4 mm$^2$ (2 mm×2 mm). Note that ITSO forms a transparent electrode serving as an anode. The transparent electrode and the reflective electrode can be collectively regarded as the first electrode 101.

Next, in pretreatment for forming the light-emitting device over a substrate, a surface of the substrate was washed with water and baked at 200° C. for one hour, and then UV ozone treatment was performed for 370 seconds.

After that, the substrate was transferred into a vacuum evaporation apparatus where the pressure was reduced to approximately 10$^{-4}$ Pa, vacuum baking was performed at 170° C. for 30 minutes in a heating chamber of the vacuum evaporation apparatus, and then the substrate was cooled down for approximately 30 minutes.

Next, the substrate provided with the first electrode 101 was fixed to a substrate holder provided in the vacuum evaporation apparatus such that the surface on which the first electrode 101 was formed faced downward. Then, N-(1,1'-biphenyl-2-yl)-N-(9,9-dimethylfluoren-2-yl)-9,9'-spirobi[9H-fluoren]-2-amine (abbreviation: oFBiSF(2)) represented by Structural Formula (i) and a fluorine-containing electron acceptor material with a molecular weight of 672 (OCHD-003) were deposited on the first electrode 101 to a thickness of 10 nm by co-evaporation using resistance heating such that the weight ratio of oFBiSF(2) to OCHD-003 was 1:0.04, whereby the hole-injection layer 111 was formed.

Next, over the hole-injection layer 111, oFBiSF(2) was deposited by evaporation to a thickness of 120 nm to form a first hole-transport layer. Then, N-(3",5',5"-tri-tert-butyl-1,1':3',1"-terphenyl-4-yl)-N-(4-cyclohexylphenyl)-9,9-dimethyl-9H-fluoren-2-amine (abbreviation: mmtBumTPch-PAF-04) represented by Structural Formula (I) was deposited by evaporation to a thickness of 40 nm to form a second hole-transport layer. Note that the second hole-transport layer also functions as an electron-blocking layer.

Over the second hole-transport layer, 11-(4-[1,1'-biphenyl]-4-yl-6-phenyl-1,3,5-triazin-2-yl)-11,12-dihydro-12-phenyl-indolo[2,3-a]carbazole (abbreviation: BP-Icz(II)Tzn) represented by Structural Formula (ii), 9-(2-naphthyl)-9'-phenyl-9H,9'H-3,3'-bicarbazole (abbreviation: βNCCP) represented by Structural Formula (iii), and [2-d3-methyl-(2-pyridinyl-κN)benzofuro[2,3-b]pyridine-xC]bis[2-(2-pyridinyl-κN)phenyl-κC]iridium(III) (abbreviation: [Ir(ppy)$_2$(mbfpypy-d3)]) represented by Structural Formula (iv) were deposited by co-evaporation to a thickness of 40 nm such that the weight ratio of BP-Icz(II)Tzn to βNCCP and [Ir(ppy)$_2$(mbfpypy-d3)] was 0.5:0.5:0.1, whereby the light-emitting layer 113 was formed.

Next, 6-(1,1'-biphenyl-3-yl)-4-[3,5-bis(9H-carbazol-9-yl)phenyl]-2phenylpyrimidine (abbreviation: 6mBP-4Cz2PPm) represented by Structural Formula (v) was deposited by evaporation over the light-emitting layer 113 to a thickness of 10 nm, whereby a hole-blocking layer was formed.

After that, 2,4-bis[4-(1-naphthyl)phenyl]-6-[4-(pyridin-3yl)phenyl]pyrimidine (abbreviation: 2,4NP-6PyPPm2) represented by Structural Formula (vi) and 8-quinolinolato-lithium (abbreviation: Liq) represented by Structural Formula (vii) were deposited by co-evaporation to a thickness of 25 nm such that the weight ratio of 2,4NP-6PyPPm2 to Liq was 0.5:0.5, whereby the electron-transport layer 114 was formed.

After the electron-transport layer 114 was formed, lithium fluoride (LiF) was deposited to a thickness of 1 nm by evaporation to form the electron-injection layer 115, and lastly silver (Ag) and magnesium (Mg) were deposited to a thickness of 15 nm by co-evaporation such that the volume ratio of Ag to Mg was 10:1 to form the second electrode 102, whereby Light-emitting device D1 was fabricated. The second electrode 102 is a transflective electrode having a function of reflecting light and a function of transmitting light; thus, the light-emitting device of this example is a top emission device in which light is extracted through the second electrode 102. Over the second electrode 102, 4,4',4"-(benzene-1,3,5-triyl)tri(dibenzothiophene) (abbreviation: DBT3P-II) represented by Structural Formula (viii) was deposited by evaporation to a thickness of 70 nm to form a cap layer so that light extraction efficiency can be improved.

(Fabrication Method of Light-Emitting Device D2)

Light-emitting device D2 was fabricated in the same manner as Light-emitting device D1 except that the thickness of the first hole-transport layer was 125 nm and that the second hole-transport layer (electron-blocking layer) was formed with N-3',5'-ditertiarybutyl-1,1'-biphenyl-4-yl-N-1,1'-biphenyl-2-yl-9,9-dimethyl-9H-fluoren-2-amine (abbreviation: mmtBuBioFBi) represented by Structural Formula (II).

(Fabrication Method of Light-Emitting Device D3)

Light-emitting device D3 was fabricated in the same manner as Light-emitting device D1 except that the thickness of the first hole-transport layer was 125 nm and that the second hole-transport layer (electron-blocking layer) was formed with N-(3',5'-di-tert-butyl-1,1'-biphenyl-4-yl)-N-(9,9-dimethyl-9H-fluoren-4-yl)-9,9-dimethyl-9H-fluoren-2-amine (abbreviation: mmtBuBiFF-02) represented by Structural Formula (III).

(Fabrication Method of Light-Emitting Device D4)

Light-emitting device D4 was fabricated in the same manner as Light-emitting device D1 except that the thickness of the first hole-transport layer was 125 nm and that the second hole-transport layer (electron-blocking layer) was formed with N-(3',5',-di-tert-butyl-1,1'-biphenyl-4-yl)-bis(9,9-dimethyl-9H-fluoren)-2,2'-amine (abbreviation: mmtBuBiFF) represented by Structural Formula (IV).

(Fabrication Method of Light-Emitting Device D5)

Light-emitting device D5 was fabricated in the same manner as Light-emitting device D1 except that the thickness of the first hole-transport layer was 125 nm and that the second hole-transport layer (electron-blocking layer) was formed with N-(1,1'-biphenyl-2-yl)-N-[(3',5'-di-tert-butyl)-1,1'-biphenyl-4-yl)-9,9-bis-(4-tert-butylphenyl)-9H-fluoren-2-amine (abbreviation: mmtBuBioBitBu2FLP(2)) represented by Structural Formula (V).

(Fabrication Method of Light-Emitting Device CDT)

Light-emitting device CD1 was fabricated in the same manner as Light-emitting device D1 except that the second hole-transport layer (electron-blocking layer) was formed with N-[4-(4-dibenzofuranyl)phenyl]-N-[4-(9-phenyl-9H-fluoren-9-yl)phenyl]-[1,1'-biphenyl]-4-amine (abbreviation: FrBBiFLP) represented by Structural Formula (VI).

(Fabrication Method of Light-Emitting Device CD2)

Light-emitting device CD2 was fabricated in the same manner as Light-emitting device D1 except that the thickness of the first hole-transport layer was 125 nm and that the second hole-transport layer (electron-blocking layer) was formed with N-(3",5',5"-tri-tert-butyl-1,1':3',1"-terphenyl-4- yl)-N-(1,1'-biphenyl-2-yl)-9,9-dimethyl-9H-fluoren-2-amine (abbreviation: mmtBumTPoFBi-04) represented by Structural Formula (VII).

The element structure of the above-described light-emitting devices and the GSP_slopes of the materials of the electron-blocking layers are listed in the following tables.

TABLE 3

| | | Thickness (nm) | Structure |
|---|---|---|---|
| Cap layer | | 70 | DBT3P-II |
| Second electrode | | 15 | Ag:Mg (10:1) |
| Electron-injection layer | | 1 | LiF |
| Electron-transport layer | | 25 | 2,4NP-6PyPPm: Liq (0.5:0.5) |
| Hole-blocking layer | | 10 | 6mBP-4Cz2PPm |
| Light-emitting layer | | 40 | BP-Icz(II)Tzn:βNCCP: Ir(ppy)$_2$(mbfpypy-d$_3$) (0.5:0.5:0.10) |
| Electron-blocking layer | | 40 | *2 |
| Hole-transport layer | | *1 | oFBiSF(2) |
| Hole-injection layer | | 10 | oFBiSF(2): OCHD-003 (1:0.04) |
| First electrode | Transparent electrode | 10 | ITSO |
| | Reflective electrode | 100 | Ag |

In the materials forming the light-emitting layer, BP-Icz (II)Tzn has the lowest LUMO level, which is −2.99 eV. The LUMO levels of the electron-blocking materials in Light-emitting devices D1 to D5 are each higher than −2.99 eV by 0.5 eV or more, indicating the sufficient electron-blocking properties of Light-emitting devices D1 to D5.

The light-emitting devices were sealed using a glass substrate in a glove box containing a nitrogen atmosphere so as not to be exposed to the air (a sealing material was applied to surround the device and UV treatment and heat treatment at 80° C. for one hour were performed at the time of sealing). Then, the initial characteristics of the light-emitting devices were measured. Note that particular treatment for improving outcoupling efficiency was not performed on the glass substrate over which the light-emitting device was formed.

Figure 19:
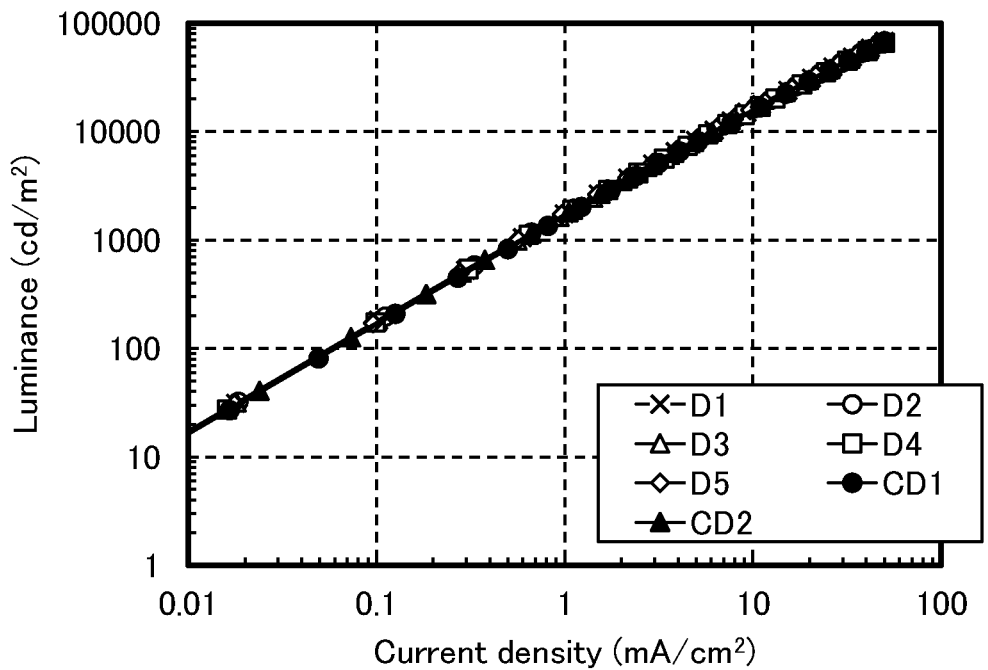
FIG. 19 shows the luminance-current density characteristics of Light-emitting devices D1 to D5, CD1, and CD2.
Figure 20:
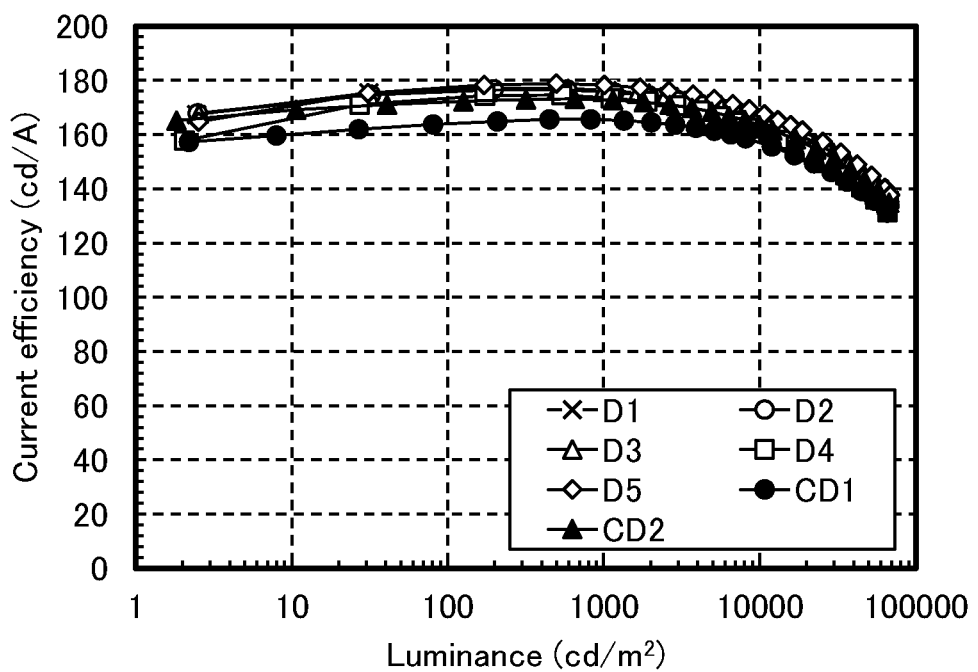
FIG. 20 shows the current efficiency-luminance characteristics of Light-emitting devices D1 to D5, CD1, and CD2.
Figure 21:
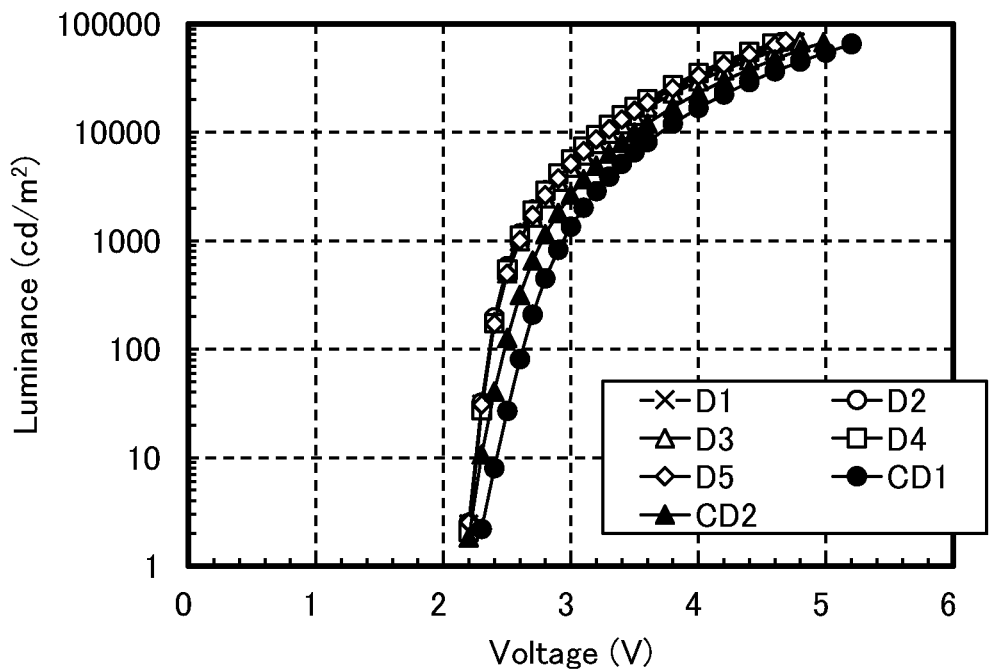
FIG. 21 shows the luminance-voltage characteristics of Light-emitting devices D1 to D5, CD1, and CD2.
Figure 22:
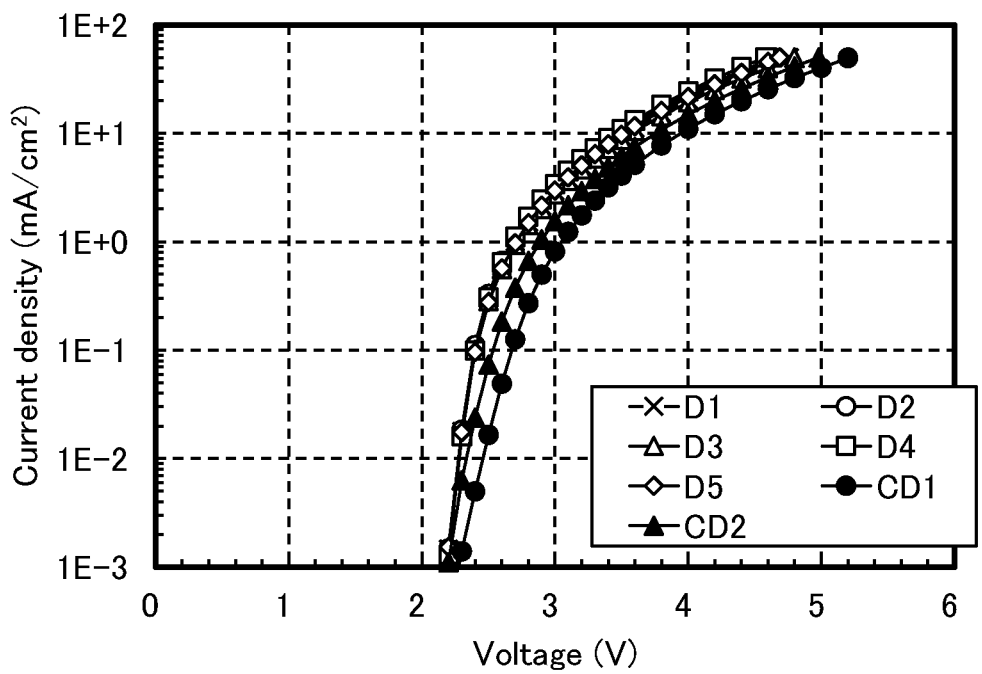
FIG. 22 shows the current density-voltage characteristics of Light-emitting devices D1 to D5, CD1, and CD2.
Figure 23:
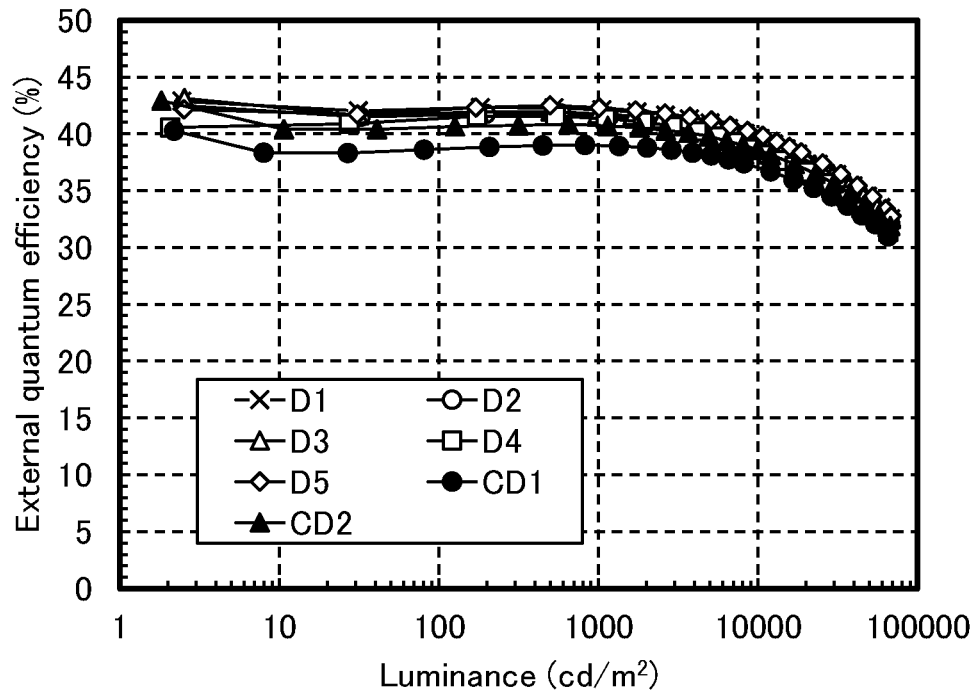
FIG. 23 shows the external quantum efficiency-luminance characteristics of Light-emitting devices D1 to D5, CD1, and CD2.
Figure 24:
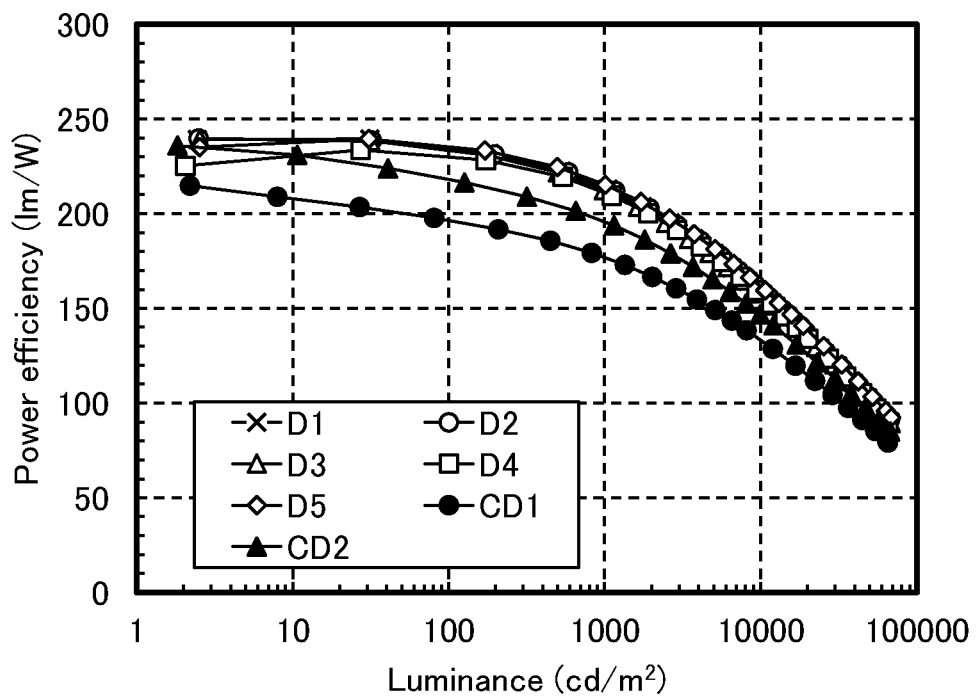
FIG. 24 shows the power efficiency-luminance characteristics of Light-emitting devices D1 to D5, CD1, and CD2.
Figure 25:
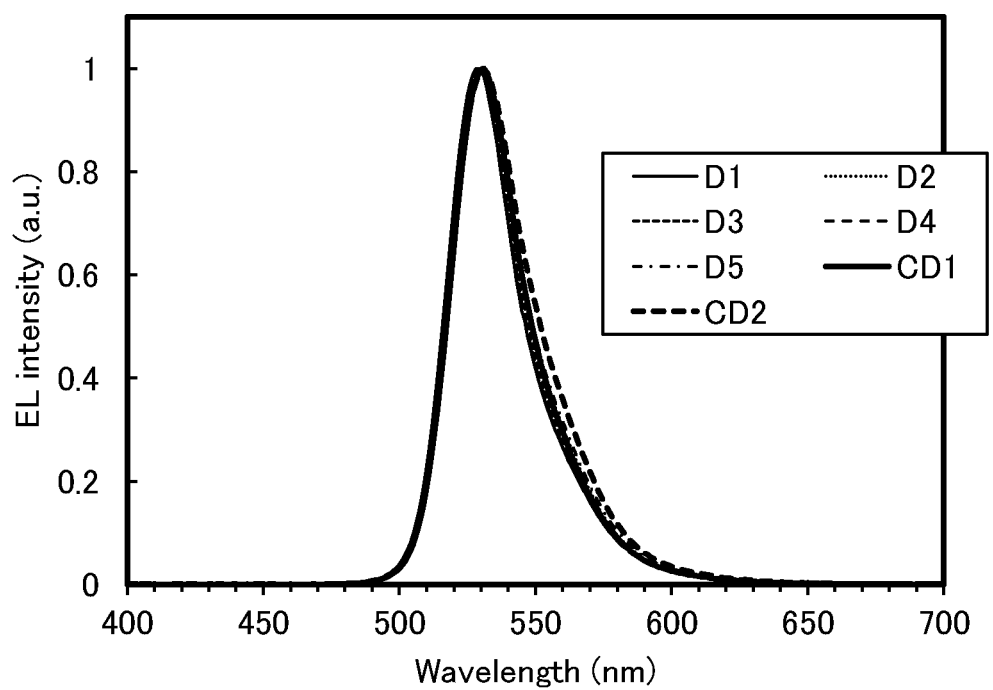
FIG. 25 shows the emission spectra of Light-emitting devices D1 to D5, CD1, and CD2.

FIG. 19 shows the luminance-current density characteristics of the light-emitting devices. FIG. 20 shows the current efficiency-luminance characteristics of the light-emitting devices. FIG. 21 shows the luminance-voltage characteristics of the light-emitting devices. FIG. 22 shows the current density-voltage characteristics of the light-emitting devices. FIG. 23 shows the external quantum efficiency-luminance characteristics of the light-emitting devices. FIG. 24 shows the power efficiency-luminance characteristics of the light-emitting devices. FIG. 25 shows the emission spectrum of the light-emitting devices. Table 5 shows the main characteristics of the light-emitting devices at a luminance of approximately 1000 cd/m$^2$. Luminance, CIE chromaticity, and emission spectra were measured at

TABLE 4

| Light-emitting device | *1 | *2 | GSP (mV/nm) | Refractive index 530 nm | Refractive index 633 nm | LUMO (eV) |
|---|---|---|---|---|---|---|
| D1 | 120 | mmtBumTPchPAF-04 | 33.9 | 1.68 | 1.65 | −2.00 |
| D2 | 125 | mmtBuBioFBi | 25.5 | 1.69 | 1.66 | −2.10 |
| D3 | 125 | mmtBuBiFF-02 | 27.2 | 1.68 | 1.65 | −2.01 |
| D4 | 125 | mmtBuBiFF | 39.7 | 1.73 | 1.70 | −2.20 |
| D5 | 125 | mmtBuBioBitBu2FLP(2) | 37.3 | 1.67 | 1.65 | −1.90 |
| CD1 | 120 | FrBBiFLP | 12.8 | 1.82 | 1.78 | −2.24 |
| CD2 | 125 | mmtBumTPoFBi-04 | 16.7 | 1.69 | 1.66 | −2.00 |

As shown in Table 4, a transport material with a GSP_slope higher than or equal to 20 is used in the electron-blocking layer of each of Light-emitting devices D1 to D5, and a transport material with a GSP_slope lower than or equal to 20 mV/nm is used in each of Light-emitting devices CDT and CD2. Note that the electron-blocking layer can also regarded as part of the hole-transport layer.

normal temperature with a spectroradiometer (SR-UL1R produced by TOPCON TECHNOHOUSE CORPORATION). The external quantum efficiency is the reference value calculated from the measured luminance and emission spectra, on the assumption that the light-emitting devices had Lambertian light-distribution characteristics.

TABLE 5

| Light-emitting device | Voltage (V) | Current (mA) | Current density (mA/cm$^2$) | Chromaticity x | Chromaticity y | Current efficiency (cd/A) | Power efficiency (lm/W) | External quantum efficiency (%) |
|---|---|---|---|---|---|---|---|---|
| D1 | 2.6 | 0.02 | 0.6 | 0.24 | 0.72 | 176.3 | 213 | 42 |
| D2 | 2.6 | 0.03 | 0.7 | 0.25 | 0.71 | 175.5 | 212 | 42 |
| D3 | 2.6 | 0.02 | 0.6 | 0.25 | 0.72 | 175.8 | 212 | 42 |
| D4 | 2.6 | 0.03 | 0.6 | 0.24 | 0.72 | 173.4 | 210 | 41 |
| D5 | 2.6 | 0.02 | 0.6 | 0.25 | 0.71 | 178.2 | 215 | 42 |
| CD1 | 2.9 | 0.02 | 0.5 | 0.25 | 0.71 | 165.6 | 179 | 39 |
| CD2 | 2.8 | 0.03 | 0.7 | 0.26 | 0.70 | 172.7 | 194 | 41 |

FIG. 19 to FIG. 25 and Table 5 show that Light-emitting devices D1 to D5 each including the transport material with a GSP_slope higher than or equal to 20 have favorable characteristics with lower driving voltage and higher emission efficiency than Light-emitting devices CD1 and CD2 each including the transport material with a GSP_slope lower than or equal to 20.

Example 2

In this example, light-emitting devices of one embodiment of the present invention will be described in detail. Structural formulae of typical organic compounds used in this example are shown below.

[Chemical Formula 6]

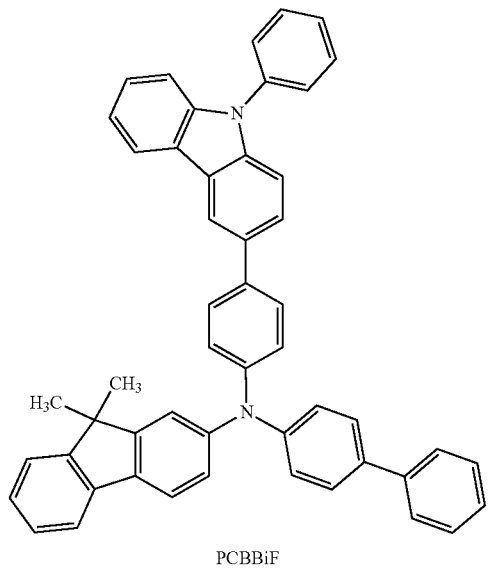

(viii)

PCBBiF

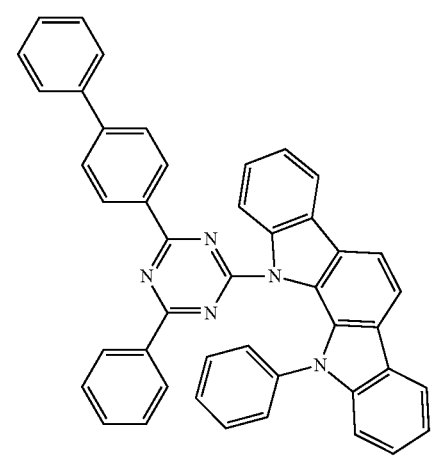

(ii)

BP-Icz(II)Tzn

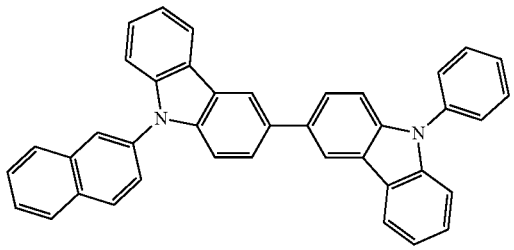

(iii)

β NCCP

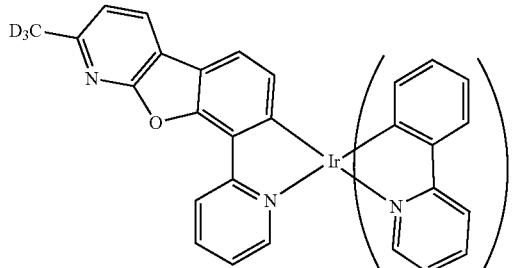

(iv)

[Ir(ppy)₂(mbfpypy-d3)]

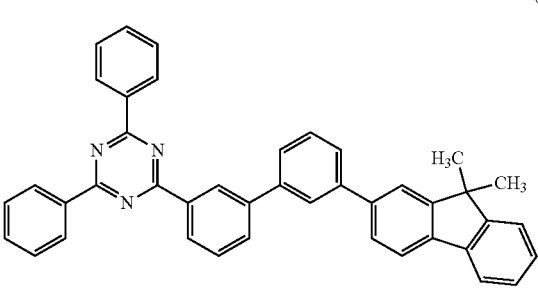

(ix)

mFBPTzn

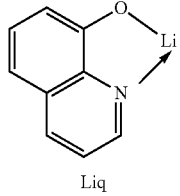

(vii)

Liq

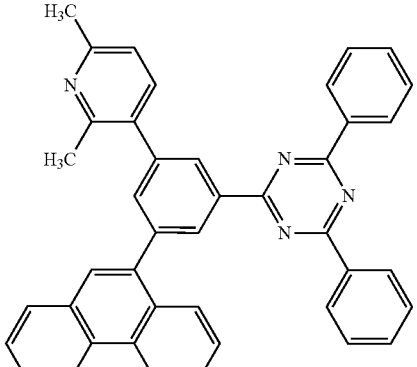

(x)

mPn-mDMePyPTzn (viii)
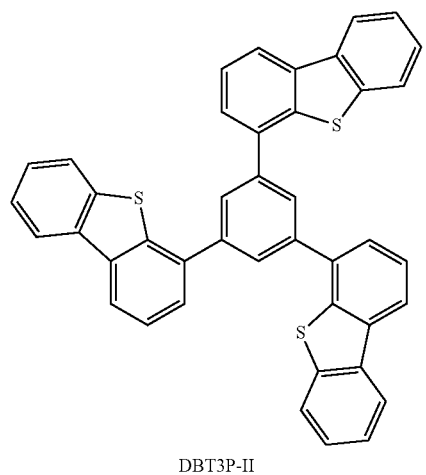
DBT3P-II
[Chemical Formula 7]
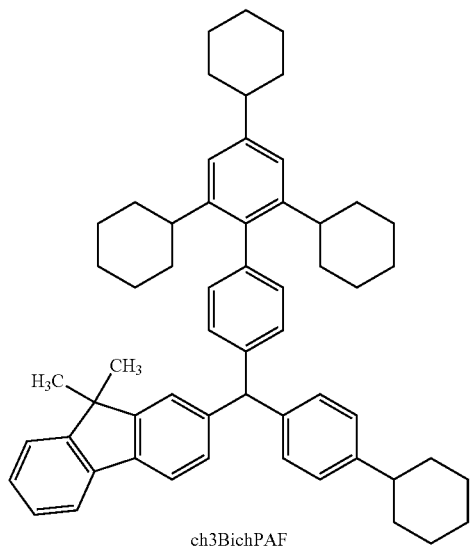
ch3BichPAF
(IX)
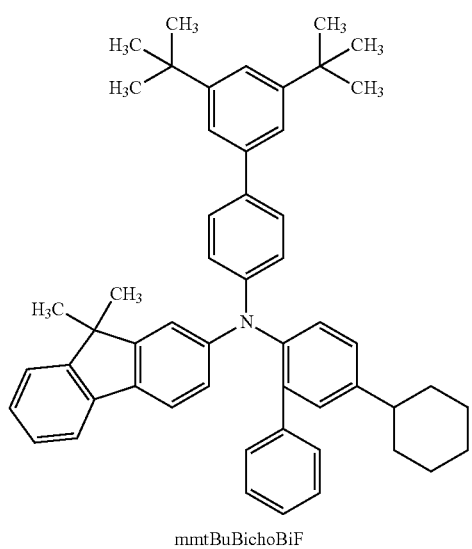
mmtBuBichoBiF
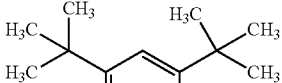
(III)
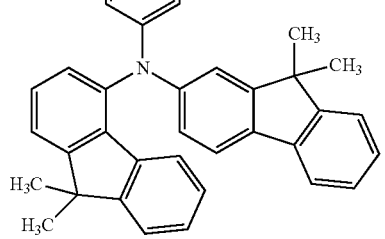
mmtBuBiFF-02
(X)
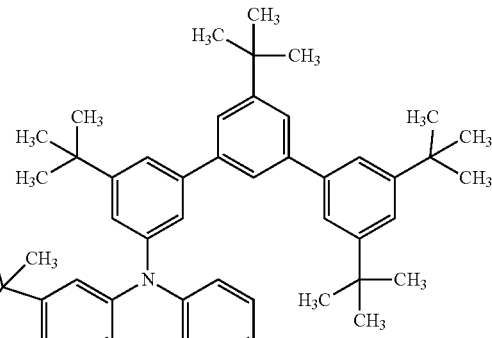
mmtBumTPoFBi-02
(V)
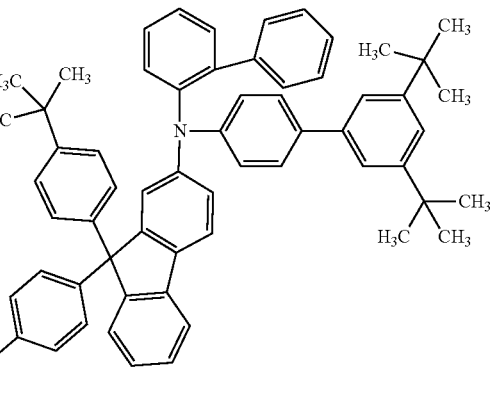
mmtBuBioBitBu2FLP(2)

(XI)

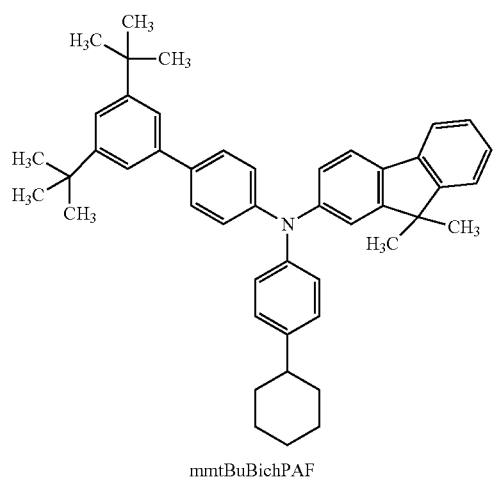

mmtBuBichPAF (IV)

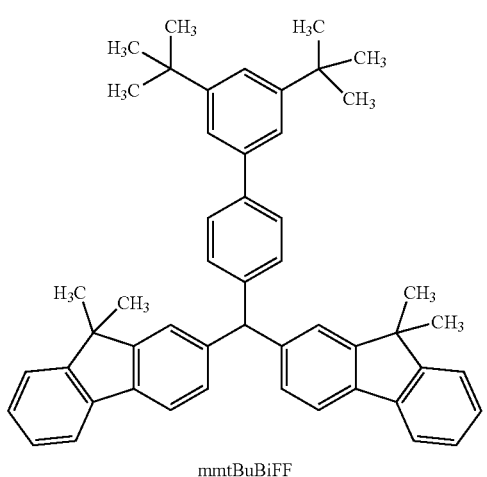

mmtBuBiFF (XII)

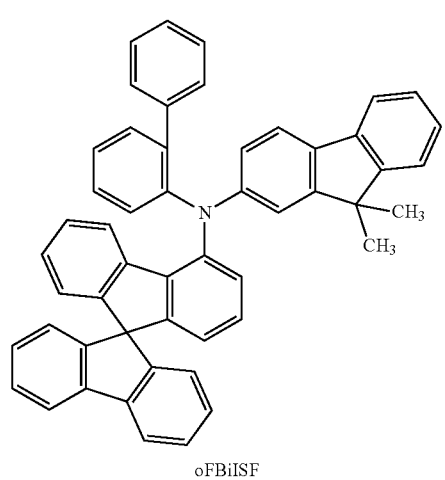

oFBiISF (XIII)

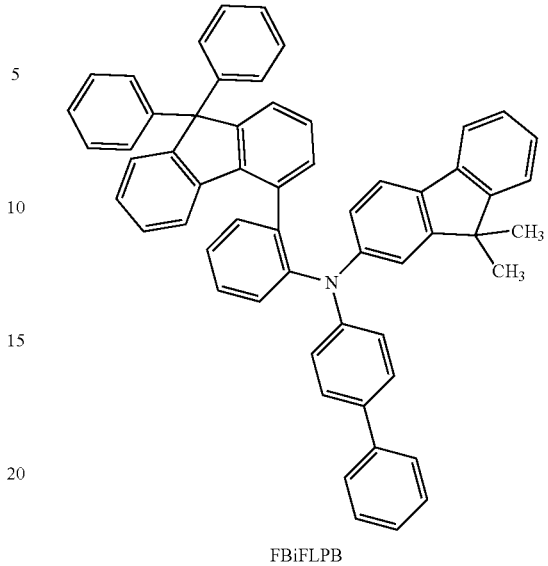

FBiFLPB (Fabrication Method of Light-Emitting Device D11)

As a reflective electrode, silver (Ag) was deposited to a thickness of 100 nm by a sputtering method, and then, as a transparent electrode, indium tin oxide containing silicon oxide (ITSO) was deposited to a thickness of 10 nm by a sputtering method, whereby the first electrode 101 was formed. The electrode area was set to 4 mm² (2 mm×2 mm). Note that ITSO forms a transparent electrode, and the transparent electrode and the reflective electrode can be collectively regarded as the first electrode 101.

Next, in pretreatment for forming the light-emitting device over a substrate, a surface of the substrate was washed with water and baked at 200° C. for one hour, and then UV ozone treatment was performed for 370 seconds.

After that, the substrate was transferred into a vacuum evaporation apparatus where the pressure was reduced to approximately $10^{-4}$ Pa, vacuum baking was performed at 170° C. for 30 minutes in a heating chamber of the vacuum evaporation apparatus, and then the substrate was cooled down for approximately 30 minutes.

Next, the substrate provided with the first electrode 101 was fixed to a substrate holder provided in the vacuum evaporation apparatus such that the surface on which the first electrode 101 was formed faced downward. Then, N-(1,1'-biphenyl-4-yl)-N-[4-(9-phenyl-9H-carbazol-3-yl)phenyl]-9,9-dimethyl-9H-fluoren-2-amine (abbreviation: PCBBiF) represented by Structural Formula (viii) and a fluorine-containing electron acceptor material with a molecular weight of 672 (OCHD-003) were deposited on the first electrode 101 to a thickness of 10 nm by co-evaporation using resistance heating such that the weight ratio of PCBBiF to OCHD-003 was 1:0.04, whereby the hole-injection layer 111 was formed.

Next, over the hole-injection layer 111, PCBBiF was deposited by evaporation to a thickness of 115 nm to form a first hole-transport layer 112. Then, N-2',4',6'-tritertiary-butyl-1,1'-biphenyl-4-yl-N-(4-cyclohexylphenyl)-9,9-dimethyl-9H-fluoren-2-amine (abbreviation: ch3BichPAF) represented by Structural Formula (VIII) was deposited by evaporation to a thickness of 40 nm to form the second hole-transport layer. Note that the second hole-transport layer also functions as an electron-blocking layer.

Over the second hole-transport layer, 11-(4-[1,1'-biphenyl]-4-yl-6-phenyl-1,3,5-triazin-2-yl)-11,12-dihydro-12-phenyl-indolo[2,3-a]carbazole (abbreviation: BP-Icz(II)Tzn) represented by Structural Formula (ii), 9-(2-naphthyl)-9'-phenyl-9H,9'H-3,3'-bicarbazole (abbreviation: βNCCP) represented by Structural Formula (iii), and [2-d3-methyl-(2-pyridinyl-κN)benzofuro[2,3-b]pyridine-xC]bis[2-(2-pyridinyl-κN)phenyl-κC]iridium(III) (abbreviation: [Ir(ppy)$_2$(mbfpypy-d3)]) represented by Structural Formula (iv) were deposited by co-evaporation to a thickness of 40 nm such that the weight ratio of BP-Icz(II)Tzn to βNCCP and [Ir(ppy)$_2$(mbfpypy-d3)] was 0.5:0.5:0.1, whereby the light-emitting layer 113 was formed.

Next, 2-[3'-(9,9-dimethyl-9H-fluoren-2-yl)-1,1'-biphenyl-3-yl]-4,6-diphenyl-1,3,5-triazine (abbreviation: mFBPTzn) represented by Structural Formula (ix) was deposited by evaporation over the light-emitting layer 113 to a thickness of 10 nm, whereby a hole-blocking layer was formed.

After that, 2-[3-(2,6-dimethyl-3-pyridinyl)-5-(9-phenanthrenyl)phenyl]-4,6-diphenyl-1,3,5-triazine (abbreviation: mPn-mDMePyPTzn) represented by Structural Formula (x) and 8-quinolinolato-lithium (abbreviation: Liq) represented by Structural Formula (vii) were deposited by co-evaporation to a thickness of 25 nm such that the weight ratio of mPn-mDMePyPTzn to Liq was 0.5:0.5, whereby the electron-transport layer 114 was formed.

After the electron-transport layer 114 was formed, lithium fluoride (LiF) was deposited to a thickness of 1 nm by evaporation to form the electron-injection layer 115, and lastly silver (Ag) and magnesium (Mg) were deposited to a thickness of 15 nm by co-evaporation such that the volume ratio of Ag to Mg was 10:1 to form the second electrode 102, whereby Light-emitting device D11 was fabricated. The second electrode 102 is a transflective electrode having a function of reflecting light and a function of transmitting light; thus, the light-emitting device of this example is a top emission device in which light is extracted through the second electrode 102. Over the second electrode 102, 4,4',4''-(benzene-1,3,5-triyl)tri(dibenzothiophene) (abbreviation: DBT3P-II) represented by Structural Formula (viii) was deposited by evaporation to a thickness of 70 nm to form a cap layer so that light extraction efficiency can be improved.

(Fabrication Method of Light-Emitting Device D12)

Light-emitting device D12 was fabricated in the same manner as Light-emitting device D11 except that the thickness of the first hole-transport layer was 110 nm and that the second hole-transport layer (electron-blocking layer) was formed with N-3',5'-di-tert-buty-1,1'-biphenyl-4-yl)-N-(5-cyclohexyl-1,1'-biphenyl-2-yl)-9,9-dimethyl-9H-fluoren-2-amine (abbreviation: mmtBuBichoBiF) represented by Structural Formula (IX).

(Fabrication Method of Light-Emitting Device D13)

Light-emitting device D13 was fabricated in the same manner as Light-emitting device D11 except that the thickness of the first hole-transport layer was 110 nm and that the second hole-transport layer (electron-blocking layer) was formed with N-(3',5'-di-tert-butyl-1,1'-biphenyl-4-yl)-N-(9,9-dimethyl-9H-fluoren-4-yl)-9,9-dimethyl-9H-fluoren-2-amine (abbreviation: mmtBuBiFF-02) represented by Structural Formula (III).

(Fabrication Method of Light-Emitting Device D14)

Light-emitting device D14 was fabricated in the same manner as Light-emitting device D11 except that the thickness of the first hole-transport layer was 110 nm and that the second hole-transport layer (electron-blocking layer) was formed with N-(1,1'-biphenyl-2-yl)-N-(3,3'',5',5''-tetra-tert-butyl-1,1':3',1''-terphenyl-5-yl)-9,9-dimethyl-9H-fluoren-2-amine (abbreviation: mmtBumTPoFBi-02) represented by Structural Formula (X).

(Fabrication Method of Light-Emitting Device D15)

Light-emitting device D15 was fabricated in the same manner as Light-emitting device D11 except that the thickness of the first hole-transport layer was 110 nm and that the second hole-transport layer (electron-blocking layer) was formed with N-[(3',5'-ditertiarybutyl)-1,1'-biphenyl-4-yl]-N-(4-cyclohexylphenyl)-9,9-dimethyl-9H-fluoren-2-amine (abbreviation: mmtBuBichPAF) represented by Structural Formula (XI).

(Fabrication Method of Light-Emitting Device D16)

Light-emitting device D16 was fabricated in the same manner as Light-emitting device D11 except that the thickness of the first hole-transport layer was 120 nm and that the second hole-transport layer (electron-blocking layer) was formed with N-(1,1'-biphenyl-2-yl)-N-[(3',5'-di-tert-butyl)-1,1'-biphenyl-4-yl)-9,9-bis-(4-tert-butylphenyl)-9H-fluoren-2-amine (abbreviation: mmtBuBioBitBu2FLP(2)) represented by Structural Formula (V).

(Fabrication Method of Light-Emitting Device D17)

Light-emitting device D17 was fabricated in the same manner as Light-emitting device D11 except that the second hole-transport layer (electron-blocking layer) was formed with N-(3',5',-di-tert-butyl-1,1'-biphenyl-4-yl)-bis(9,9-dimethyl-9H-fluoren)-2,2'-amine (abbreviation: mmtBuBiFF) represented by Structural Formula (IV).

(Fabrication Method of Light-Emitting Device CD11)

Light-emitting device CD11 was fabricated in the same manner as Light-emitting device D11 except that the thickness of the first hole-transport layer was 110 nm and that the second hole-transport layer (electron-blocking layer) was formed with N-(1,1'-biphenyl-2-yl)-N-(9,9-dimethyl-9H-fluoren-2-yl)-9,9'-spirobi[9H-fluoren]-4-amine (abbreviation: oFBiSF) represented by Structural Formula (XII).

(Fabrication Method of Light-Emitting Device CD12)

Light-emitting device CD12 was fabricated in the same manner as Light-emitting device D11 except that the second hole-transport layer (electron-blocking layer) was formed using N-[2-(9,9-diphenyl-9H-fluoren-4-yl)phenyl]-N-(1,1'-biphenyl-4-yl)-9,9-dimethyl-9H-fluoren-2-amine (abbreviation: FBiFLPB) represented by Structural Formula (XIII).

The element structure of the above-described light-emitting devices and the GSP_slopes of the materials of the electron-blocking layers are listed in the following tables.

TABLE 6

| | | Thickness (nm) | Structure |
|---|---|---|---|
| Cap layer | | 70 | DBT3P-II |
| Second electrode | | 15 | Ag:Mg (10:1) |
| Electron-injection layer | | 1 | LiF |
| Electron-transport layer | | 25 | mPn-mDMePyPTzn: Liq (0.5:0.5) |
| Hole-blocking layer | | 10 | mFBPTzn |
| Light-emitting layer | | 40 | BP-Icz(II)Tzn:βNCCP: Ir(ppy)$_2$(mbfpypy-d$_3$) (0.5:0.5:0.10) |
| Electron-blocking layer | | 40 | *4 |
| Hole-transport layer | | *3 | PCBBiF |
| Hole-injection layer | | 10 | PCBBiF: OCHD-003 (1:0.04) |
| First electrode | Transparent electrode | 10 | ITSO |
| | Reflective electrode | 100 | Ag |

TABLE 7

| Light-emitting device | *3 | *4 | GSP (mV/nm) | Refractive index 530 nm | Refractive index 633 nm | LUMO (eV) |
|---|---|---|---|---|---|---|
| D11 | 115 | ch3BichPAF | 22.0 | 1.66 | 1.64 | −2.00 |
| D12 | 110 | mmtBuBichoBiF | 25.3 | 1.69 | 1.66 | −2.11 |
| D13 | 110 | mmtBuBiFF-02 | 27.0 | 1.68 | 1.65 | −2.01 |
| D14 | 110 | mmtBumTPoFBi-02 | 31.9 | 1.66 | 1.64 | −2.02 |
| D15 | 110 | mmtBuBichPAF | 31.6 | 1.68 | 1.65 | −1.98 |
| D16 | 120 | mmtBuBioBitBu2FLP(2) | 37.3 | 1.66 | 1.64 | −1.90 |
| D17 | 115 | mmtBuBiFF | 39.7 | 1.68 | 1.65 | −2.20 |
| CD11 | 110 | oFBiSF | 11.3 | 1.67 | 1.65 | −2.05 |
| CD12 | 115 | FBiFLPB | 18.6 | 1.73 | 1.70 | −2.11 |

As shown in Table 7, a transport material with a GSP_slope higher than or equal to 20 mV/nm is used in the electron-blocking layer of each of Light-emitting devices D11 to D17, and a transport material with a GSP_slope lower than or equal to 20 mV/nm is used in each of Light-emitting devices CD11 and CD12. Note that the electron-blocking layer can also regarded as part of the hole-transport layer.

In the materials forming the light-emitting layer, BP-Icz (II)Tzn has the lowest LUMO level, which is −2.99 eV. The LUMO levels of the electron-blocking materials in Light-emitting devices D11 to D17 are each higher than −2.99 eV by 0.5 eV or more, indicating the sufficient electron-blocking properties of Light-emitting devices D11 to D17.

The GSP_slope of PCBBiF used in the first hole-transport layer is 17.3 mV/nm, which is lower than that of the second hole-transport layer (electron-blocking layer) and also lower than 20 mV/nm.

The light-emitting devices were sealed using a glass substrate in a glove box containing a nitrogen atmosphere so as not to be exposed to the air (a sealing material was applied to surround the device and UV treatment and heat treatment at 80° C. for one hour were performed at the time of sealing). Then, the initial characteristics of the light-emitting devices were measured. Note that particular treatment for improving outcoupling efficiency was not performed on the glass substrate over which the light-emitting device was formed.

Figure 26:
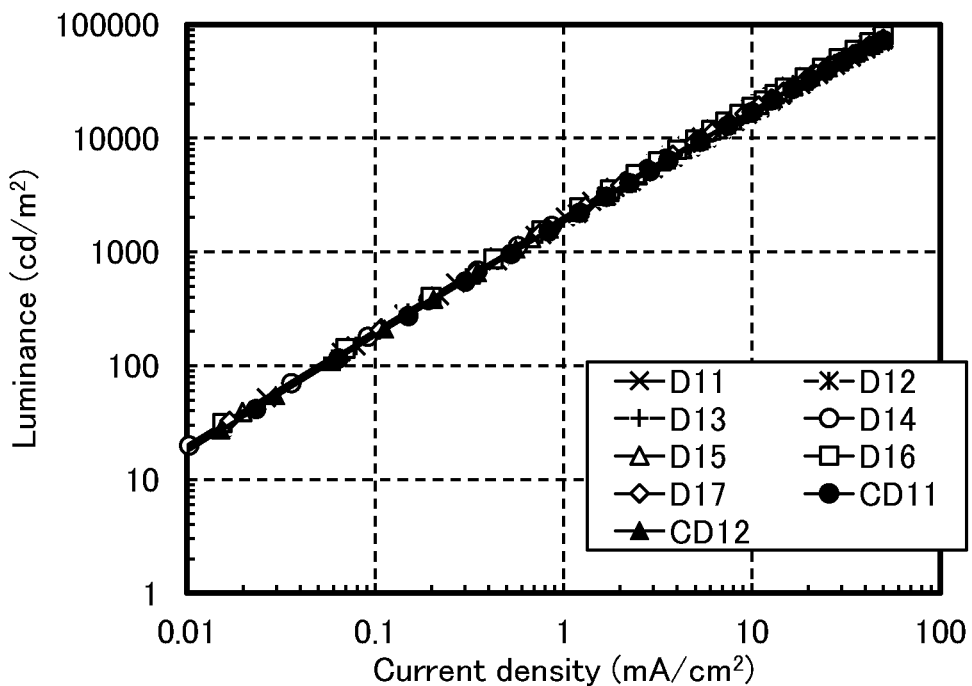
FIG. 26 shows the luminance-current density characteristics of Light-emitting devices D11 to D17, CD11, and CD12.
Figure 27:
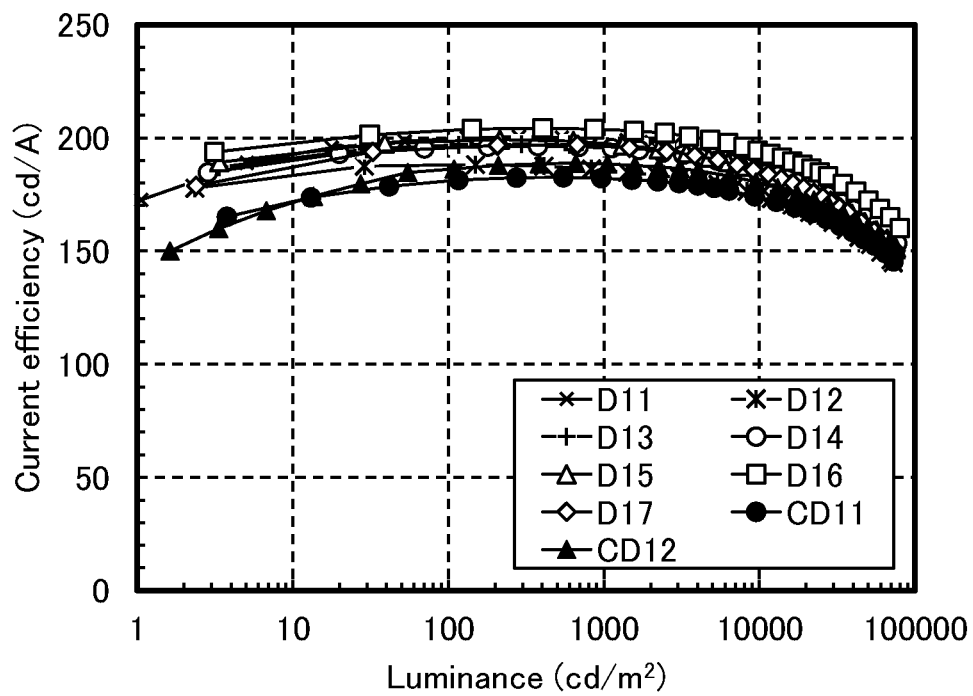
FIG. 27 shows the current efficiency-luminance characteristics of Light-emitting devices D11 to D17, CD11, and CD12.
Figure 28:
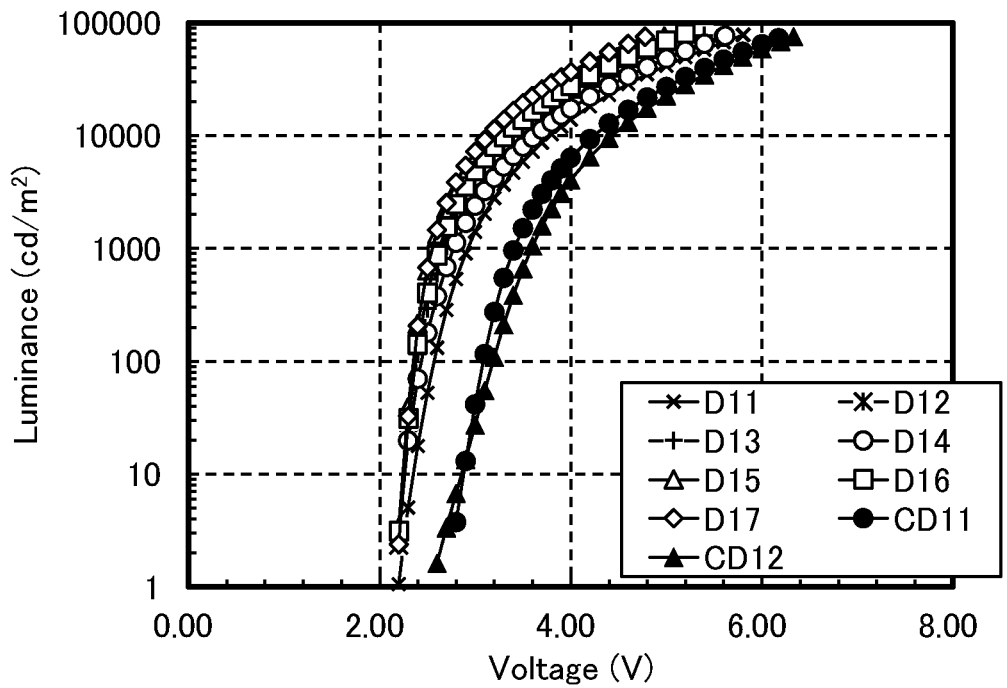
FIG. 28 shows the luminance-voltage characteristics of Light-emitting devices D11 to D17, CD11, and CD12.
Figure 29:
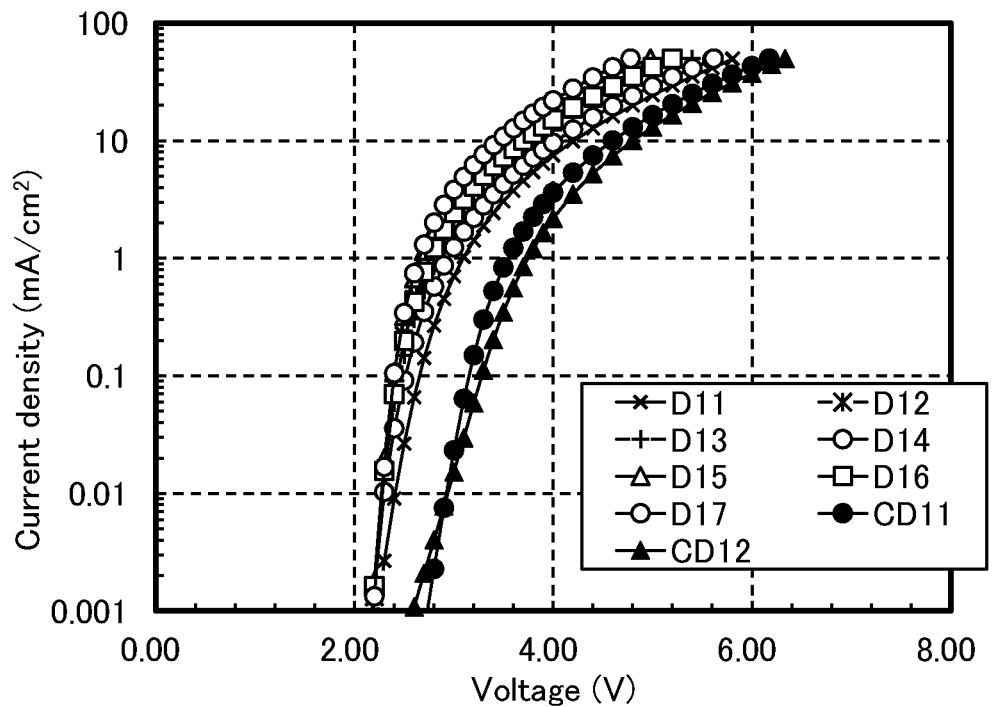
FIG. 29 shows the current density-voltage characteristics of Light-emitting devices D11 to D17, CD11, and CD12.
Figure 30:
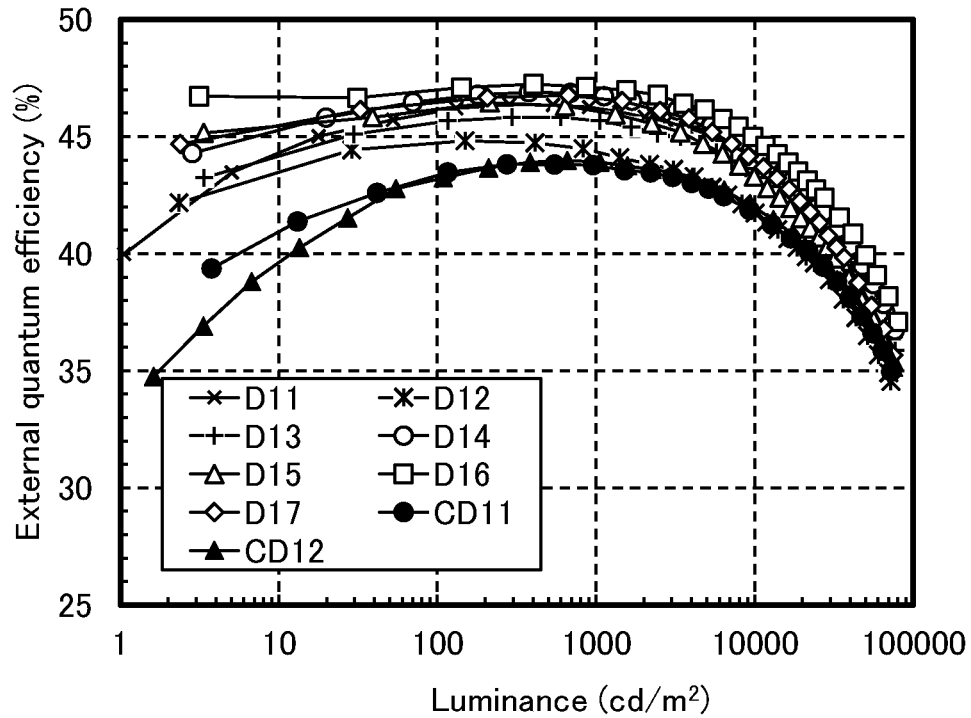
FIG. 30 shows the external quantum efficiency-luminance characteristics of Light-emitting devices D11 to D17, CD11, and CD12.
Figure 31:
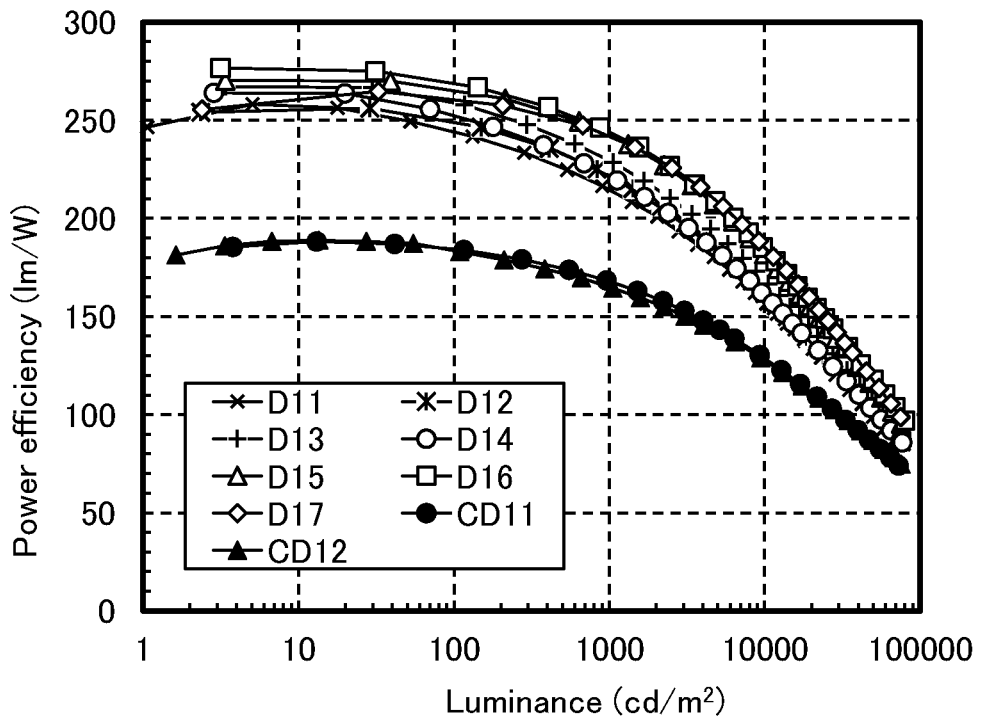
FIG. 31 shows the power efficiency-luminance characteristics of Light-emitting devices D11 to D17, CD11, and CD12.
Figure 32:
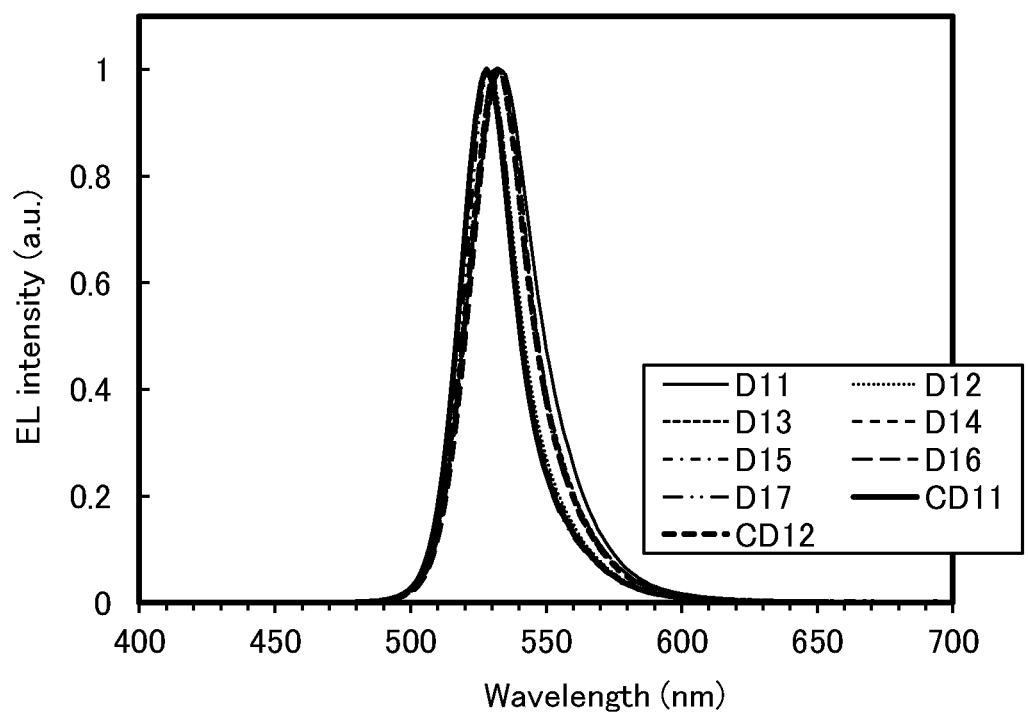
FIG. 32 shows the emission spectra of Light-emitting devices D11 to D17, CD11, and CD12.

FIG. 26 shows the luminance-current density characteristics of the light-emitting devices. FIG. 27 shows the current efficiency-luminance characteristics of the light-emitting devices. FIG. 28 shows the luminance-voltage characteristics of the light-emitting devices. FIG. 29 shows the current density-voltage characteristics of the light-emitting devices. FIG. 30 shows the external quantum efficiency-luminance characteristics of the light-emitting devices. FIG. 31 shows the power efficiency-luminance characteristics of the light-emitting devices. FIG. 32 shows the emission spectrum of the light-emitting devices. Table 8 shows the main characteristics of the light-emitting devices at a luminance of approximately 1000 cd/m$^2$. Luminance, CIE chromaticity, and emission spectra were measured at normal temperature with a spectroradiometer (SR-UL1R produced by TOPCON TECHNOHOUSE CORPORATION). The external quantum efficiency is the reference value calculated from the measured luminance and emission spectra, on the assumption that the light-emitting devices had Lambertian light-distribution characteristics.

TABLE 8

| Light-emitting device | Voltage (V) | Current (mA) | Current density (mA/cm$^2$) | Chromaticity x | Chromaticity y | Current efficiency (cd/A) | Power efficiency (lm/W) | External quantum efficiency (%) |
|---|---|---|---|---|---|---|---|---|
| D11 | 2.9 | 0.02 | 0.5 | 0.24 | 0.72 | 199.8 | 216 | 46 |
| D12 | 2.6 | 0.02 | 0.4 | 0.21 | 0.74 | 186.3 | 225 | 44 |
| D13 | 2.7 | 0.02 | 0.5 | 0.24 | 0.73 | 196.4 | 229 | 46 |
| D14 | 2.8 | 0.02 | 0.6 | 0.21 | 0.74 | 195.4 | 219 | 47 |
| D15 | 2.6 | 0.03 | 0.7 | 0.23 | 0.73 | 196.8 | 238 | 46 |
| D16 | 2.6 | 0.02 | 0.4 | 0.24 | 0.73 | 203.9 | 246 | 47 |
| D17 | 2.5 | 0.01 | 0.3 | 0.21 | 0.75 | 196.9 | 247 | 47 |
| CD11 | 3.4 | 0.02 | 0.5 | 0.21 | 0.75 | 182.1 | 168 | 44 |
| CD12 | 3.6 | 0.02 | 0.6 | 0.23 | 0.73 | 188.4 | 164 | 44 |

FIG. 26 to FIG. 32 and Table 8 show that Light-emitting devices D11 to D17 each including the transport material with a GSP_slope higher than or equal to 20 have favorable characteristics with lower driving voltage and higher emission efficiency than Light-emitting devices CD11 and CD12 each including the transport material with a GSP_slope lower than or equal to 20.

Example 3

Synthesis Example 1

In this example, a synthesis method of N-2',4',6'-tricyclohexyl-1,1'-biphenyl-4-yl-N-(4-cyclohexylphenyl)-9,9-dimethyl-9H-fluoren-2-amine (abbreviation: ch3BichPAF), which is the organic compound of one embodiment of the present invention, is described. A structure of ch3BichPAF is shown below.

[Chemical Formula 8]

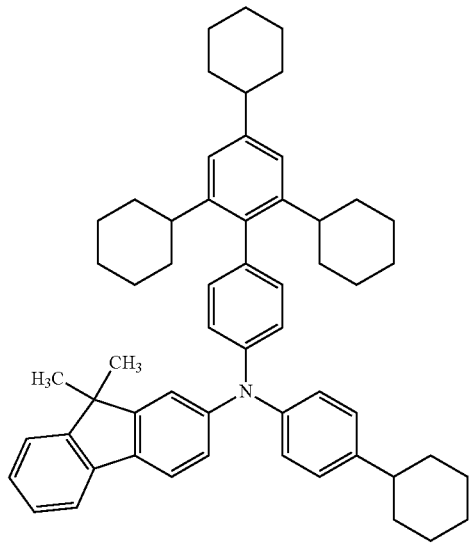

Step 1: Synthesis of 4'-chloro-2,4,6-tricyclohexyl-1,1'-biphenyl

In a three-neck flask were put 5.0 g (12 mmol) of 1-bromo-2,4,6-tricyclohexylbenzene, 2.0 g (13 mmol) of 4-chlorophenylboronic acid, 5.1 g (37 mmol) of potassium carbonate, 62 mL of toluene, 16 mL of ethanol, and 20 mL of tap water. The mixture was degassed under reduced pressure, and then the air in the flask was replaced with nitrogen. Then, 0.30 mg (0.25 mmol) of tetrakis(triphenylphosphine)palladium(0) was added, and the mixture was heated at 80° C. for approximately 10 hours. After that, the temperature of the flask was lowered to room temperature, and the mixture was separated into an organic layer and an aqueous layer. Magnesium sulfate was added to this solution to eliminate moisture, whereby the organic layer was concentrated. The obtained hexane solution was purified by silica gel column chromatography, whereby 3.2 g of a target white oily solid was obtained in a yield of 60%.

[Chemical Formula 9]

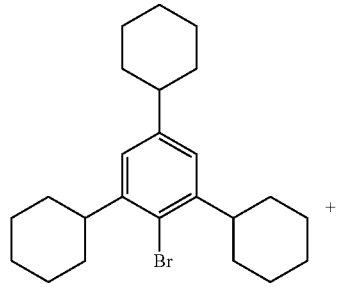

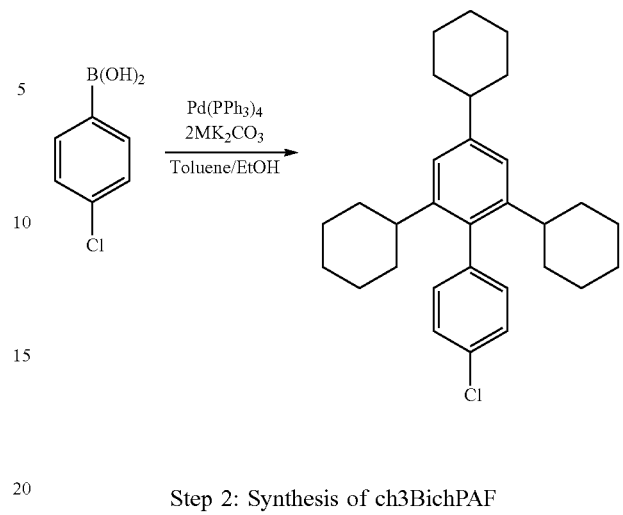

Step 2: Synthesis of ch3BichPAF

In a three-neck flask were put 1.7 g (3.9 mmol) of 4'-2,4,6-tricyclohexyl-1,1'-biphenyl obtained in Step 1, 1.4 g (3.9 mmol) of N-(4-cyclohexylphenyl)-N-(9,9-dimethyl-9H-fluoren-2-yl)amine, 1.1 g (12 mmol) of sodium-tert-butoxide, and 15 mL of toluene. The mixture was degassed under reduced pressure, the air in the flask was replaced with nitrogen, 45 mg (0.11 mmol) of bis(dibenzylideneacetone)palladium(0) and 47 mg (0.23 mmol) of tri-tert-butylphosphine were added thereto, and the mixture was heated at 80° C. for approximately 2 hours. After that, the temperature of the flask was lowered to approximately 60° C., approximately 1 mL of water was added, a precipitated solid was separated by filtration, and the solid was washed with toluene. The filtrate was concentrated, and the obtained toluene solution was purified by silica gel column chromatography. The obtained solution was concentrated to give a condensed toluene solution. Ethanol was added to this toluene solution and the toluene solution was concentrated under reduced pressure, whereby an ethanol suspension was obtained. The precipitate was filtrated at approximately 20° C., and the obtained solid was dried at approximately 80° C. under reduced pressure, whereby 2.4 g of a target white solid was obtained in a yield of 80%.

[Chemical Formula 10]

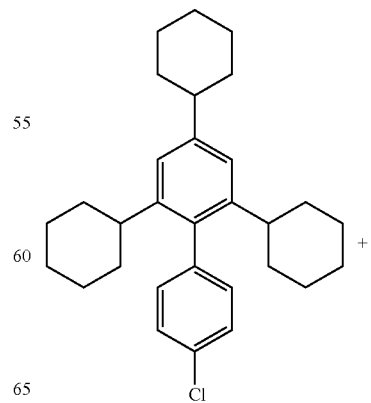

-continued

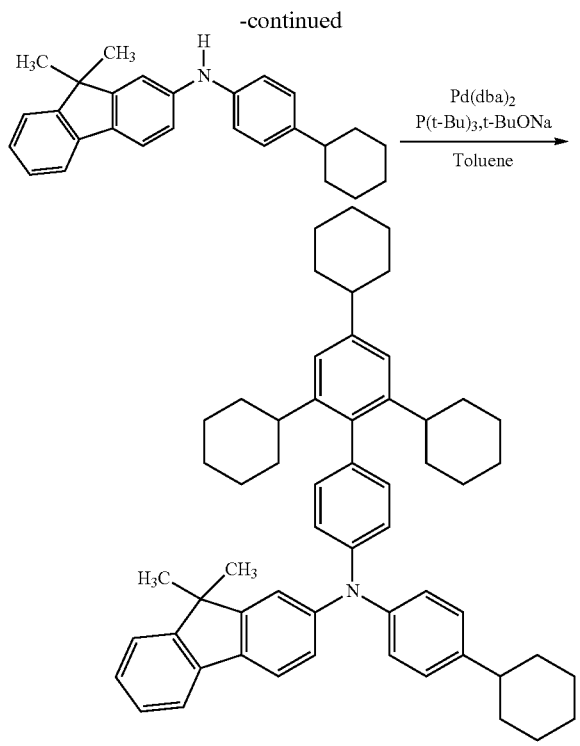

Figure 33:
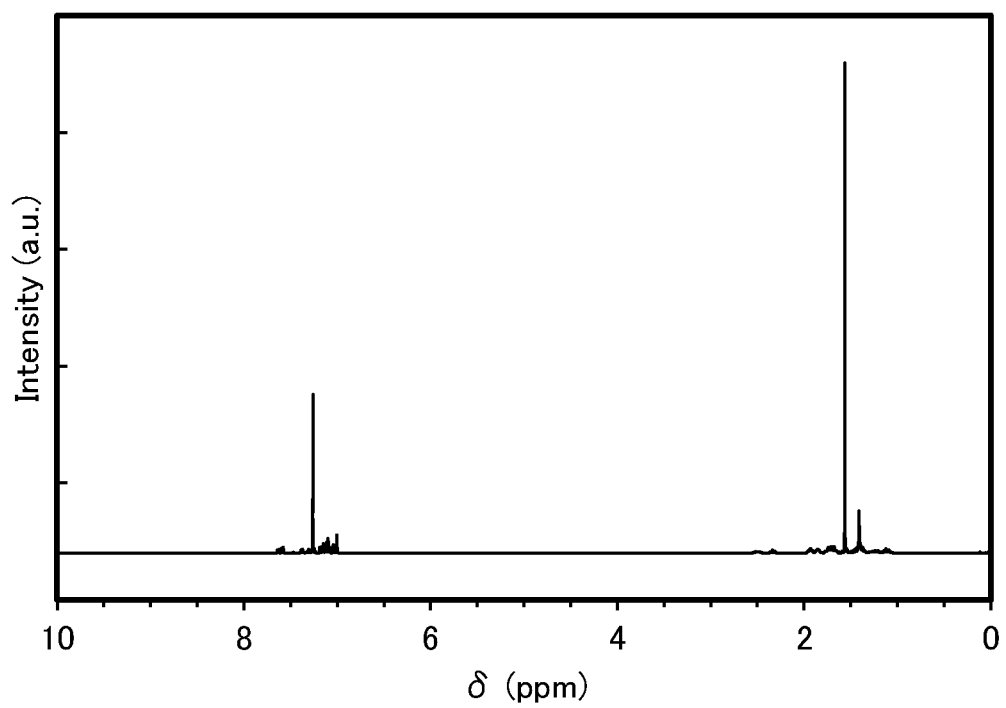
FIG. 33 shows the $^1$H-NMR spectrum of ch3BichPAF.

Analysis results by nuclear magnetic resonance (¹H-NMR) spectroscopy of the white solid obtained in Step 3 are shown in FIG. 33 and the numerical data is described below. These show that N-2',4',6'-tricyclohexyl-1,1'-biphenyl-4-yl-N-(4-cyclohexylphenyl)-9,9-dimethyl-9H-fluoren-2-amine was synthesized.

¹H-NMR. δ (CDCl$_3$): 7.63 (d, 1H, J=7.4 Hz), 7.58 (d, 1H, J=8.0 Hz), 7.38 (d, 1H, J=7.5 Hz), 7.30 (d, 1H, J=1.6 Hz), 7.18 (d, 1H, J=1.8 Hz), 7.13-7.17 (m, 3H), 7.08-7.12 (m, 5H), 7.03 (d, 2H, J=8.0 Hz), 7.00 (s, 2H), 2.48-2.54 (m, 2H), 2.31-2.36 (m, 2H), 1.92-1.96 (m, 4H), 1.85-1.87 (m, 4H), 1.66-1.74 (m, 13H), 1.44-1.55 (m, 5H), 1.35-1.41 (m, 12H), 1.21-1.32 (m, 4H), 1.07-1.18 (m, 4H).

Then, 2.4 g of the obtained white solid was purified by a train sublimation method. The purification by sublimation was conducted by heating at 265° C. under a pressure of 2.9 Pa with a flow rate of an argon gas of 10 mL/min. After the purification by sublimation, 2.1 g of a pale yellowish white solid was obtained at a collection rate of 88%.

Figure 34:
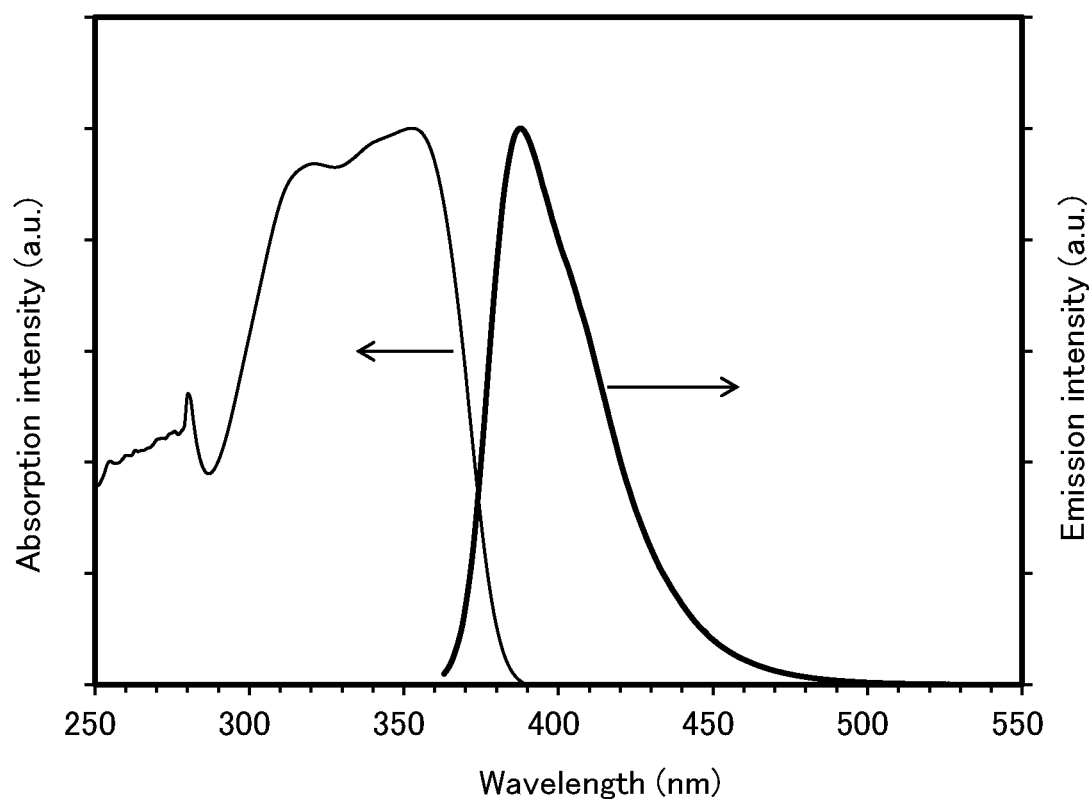
FIG. 34 shows the ultraviolet-visible absorption spectrum and emission spectrum of ch3BichPAF in a toluene solution.

Next, an ultraviolet-visible absorption spectrum (hereinafter, simply referred to as an absorption spectrum) of ch3BichPAF in a toluene solution and an emission spectrum thereof were measured. The absorption spectrum was measured at room temperature with an ultraviolet-visible light spectrophotometer (V-550, produced by JASCO Corporation) in a state where the toluene solution was put in a quartz cell. The emission spectrum was measured with a fluorescence spectrophotometer (FP-8600, produced by JASCO Corporation) at room temperature in a state where the toluene solution was put in a quartz cell. FIG. 34 shows measurement results of the absorption spectrum and the emission spectrum. The horizontal axis represents the wavelength and the vertical axes represent the absorbance and emission intensity. In FIG. 34, two solid lines are shown; the thin line represents the absorption spectrum, and the thick line represents the emission spectrum. The absorbance shown in FIG. 34 is a result obtained by subtraction of an absorption spectrum of only toluene in a quartz cell from the measured absorption spectrum of the toluene solution in the quartz cell.

As shown in FIG. 34, the organic compound ch3BichPAF has an emission peak at 388 nm.

Next, the glass transition temperature (hereinafter referred to as "Tg") of ch3BichPAF was measured. Note that the Tg was measured with a differential scanning calorimeter (Pyris 1 DSC produced by PerkinElmer Japan Co., Ltd.) in a state where a powder was put on an aluminum cell. As a result, the Tg was 124° C.

Example 4

Synthesis Example 2

In this example, a synthesis method of N-3',5'-di-t-butyl-biphenyl-4-yl)-N-(4-cyclohexyl-biphenyl-2-yl)-9,9-dimethyl-9H-fluoren-2-amine (abbreviation: mmtBuBichoBiF), which is the organic compound of one embodiment of the present invention, is described. A structure of mmtBuBicho-BiF is shown below.

[Chemical Formula 11]

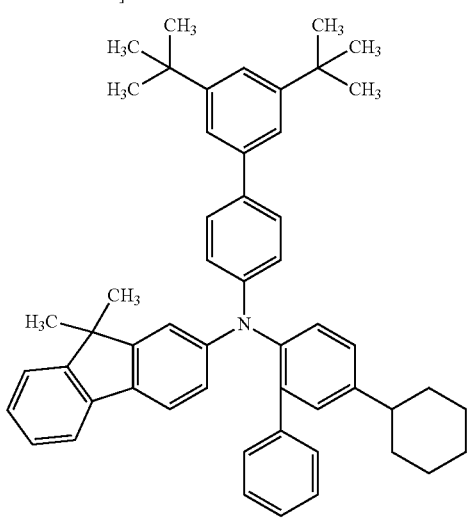

Step 1: Synthesis of 5-bromo-2-chlorobiphenyl

In a three-neck flask were put 15.0 g (50 mmol) of 5-bromo-2-chloroiodobenzene, 6.7 g (55 mmol) of phenylboronic acid, 20.7 g (150 mmol) of potassium carbonate, 125 mL of toluene, 32 mL of ethanol, and 50 mL of water. The mixture was degassed under reduced pressure, and then the air in the flask was replaced with nitrogen. Then, 580 mg (0.50 mmol) of tetrakis(triphenylphosphine)palladium(0) was added to this mixture, and the mixture was stirred at approximately 80° C. for approximately 8 hours under a nitrogen stream. After that, the temperature of the flask was lowered to room temperature, and the mixture was separated into an organic layer and an aqueous layer. The obtained organic layer was washed with water, and then separated. Then, 6 g of magnesium sulfate was added to this organic layer, followed by filtration and washing with toluene. This toluene solution was concentrated, and the obtained oily substance was purified by silica gel column chromatography. The solution was concentrated and dried under reduced pressure, whereby 12.8 g of a target colorless oily substance was obtained in a yield of 95%. The synthesis scheme of 5-bromo-2-chlorobiphenyl in Step 1 is shown below.

[Chemical Formula 12]

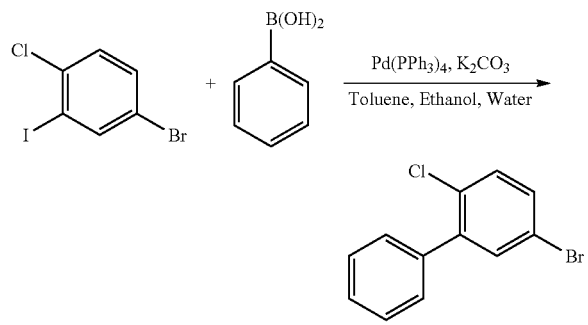

Step 2: Synthesis of 2-chloro-5-cyclohexylbiphenyl

In a three-neck flask was put 5.4 g (20 mmol) of 5-bromo-2-chlorobiphenyl obtained in Step 1, and the air in the flask was made into a vacuum state and replaced with nitrogen. To this flask was added 100 mL of dehydrated THF, and the mixture was heated and stirred at approximately 50° C. under a nitrogen stream. To this flask were added 183 mg (0.20 mmol) of tris(dibenzylidineacetone)dipalladium and 167 mg (0.40 mmol) of 2-dicyclohexylphosphino-2'-4'-6'-triisopropylbiphenyl (registered trademark: Xphos), and the flask was heated to a temperature of approximately 65° C. Then, 22 mL (22 mmol) of a 1.0 mol/L THF solution of cyclohexylmagnesium was slowly added dropwise to the mixture. This reaction solution was heated and refluxed at 65° C. for approximately 1 hour. After that, the temperature of the flaks was returned to room temperature, approximately 50 mL of water was added, and the mixture was separated into an organic layer and an aqueous layer. This aqueous layer was extracted with approximately 50 mL of ethyl acetate and this extraction was repeated twice, so that organic layers were obtained. The obtained organic layers were all combined and washed with saturated brine. Magnesium sulfate was added to this solution for drying, and filtration was performed. The obtained filtrate was concentrated, and the obtained oily substance was purified by silica column chromatography. The obtained solution was concentrated. The obtained viscous oily substance was dried under reduced pressure, whereby 3.6 g of a target colorless viscous oily substance was obtained in a yield of 66%. The synthesis scheme of 2-chloro-5-cyclohexylbiphenyl in Step 2 is shown below.

[Chemical Formula 13]

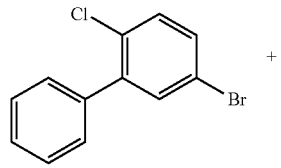

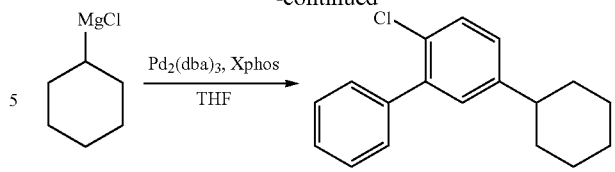

Step 3: Synthesis of 3',5'-di-t-butyl-4-bromobiphenyl

In a three-neck flask were put 35.1 g (150 mmol) of 3',5'-di-t-butylphenylboronic acid, 50.9 g (180 mmol) of 4-bromoiodobenzene, 62.2 g (450 mmol) of potassium carbonate, 500 mL of toluene, 125 mL of ethanol, and 225 mL of water. The mixture was degassed under reduced pressure, and then the air in the flask was replaced with nitrogen. Then, 3.47 g (3.0 mmol) of tetrakis(triphenylphosphine)palladium(0) was added to this mixture, and the mixture was stirred at approximately 80° C. for approximately 5 hours under a nitrogen stream. After that, the temperature of the flask was lowered to approximately 60° C., approximately 1 mL of water was added, a precipitated solid was separated by filtration, and the solid was washed with toluene. The filtrate was concentrated, and the obtained toluene solution was purified by silica gel column chromatography. The obtained solution was concentrated to give a condensed hexane solution. Ethanol was added to this hexane solution and the hexane solution was concentrated under reduced pressure, whereby an ethanol suspension was obtained. The precipitate was filtrated at approximately −10° C., and the obtained solid was dried at approximately 70° C. under reduced pressure, whereby 44.3 g of a target white solid was obtained in a yield of 86%. The synthesis scheme of 3',5'-di-t-butyl-4-bromobiphenyl in Step 3 is shown below.

[Chemical Formula 14]

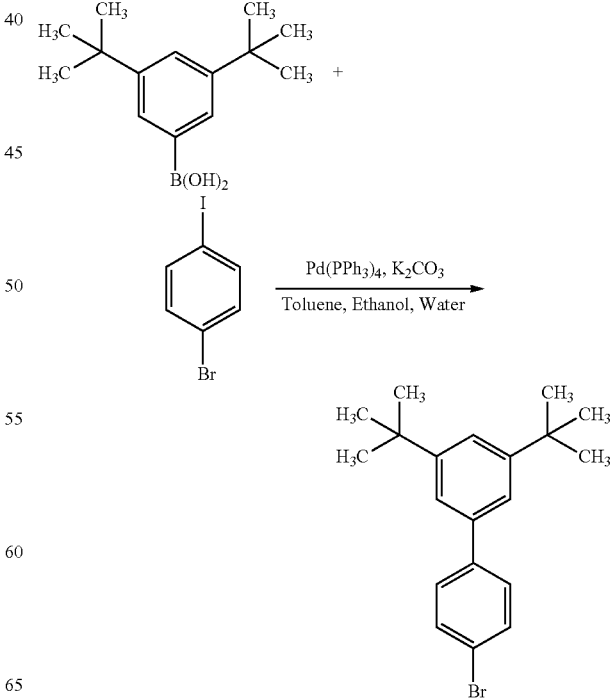

Step 4: Synthesis of N-(3',5'-di-t-butylbiphenyl-4yl)-9,9-dimethyl-9H-fluoren-2-amine In a three-neck flask were put 5.2 g (15 mmol) of 3',5'-di-t-butyl-4-bromobiphenyl synthesized in Step 3, 3.1 g (15 mmol) of 9,9-dimethyl-9H-fluoren-2-amine, 4.3 g (45 mmol) of sodium-tert-butoxide, and 75 mL of xylene. The mixture was degassed under reduced pressure, and then the air in the flask was replaced with nitrogen. Then, 55 mg (0.15 mmol) of allylpalladium(II) chloride dimer (abbreviation: [(Allyl)PdCl]$_2$) and 212 mg (0.60 mmol) of di-tert-butyl(1-methyl-2,2-diphenylcyclopropyl)phosphine (abbreviation: cBRIDP (registered trademark)) were added to this mixture, and the mixture was stirred at 120° C. under a nitrogen stream for approximately 5 hours. After that, the temperature of the flask was lowered to approximately 60° C., approximately 1 mL of water was added, a precipitated solid was separated by filtration, and the solid was washed with toluene. The filtrate was concentrated, and the obtained toluene solution was purified by silica gel column chromatography. The obtained solution was concentrated and the obtained oily substance was dried under reduced pressure, whereby 6.2 g of a target brown viscous oil was obtained in a yield of 88%. The synthesis scheme of N-(3',5'-di-t-butylbiphenyl-4yl)-9,9-dimethyl-9H-fluoren-2-amine in Step 4 is shown below.

Step 5: Synthesis of mmtBuBichoBiF

In a three-neck flask were put 4.7 g (10 mmol) of N-(3',5'-di-t-butylbiphenyl-4yl)-9,9-dimethyl-9H-fluoren-2-amine synthesized in Step 4, 2.7 g (10 mmol) of 2-chloro-5-cyclohexylbiphenyl synthesized in Step 2, 2.9 g (30 mmol) of sodium-tert-butoxide, and 50 mL of xylene. The mixture was degassed under reduced pressure, and then the air in the flask was replaced with nitrogen. Then, 56 mg (0.15 mmol) of allylpalladium(II) chloride dimer (abbreviation: [(Allyl)PdCl]2) and 212 mg (0.60 mmol) of di-tert-butyl(1-methyl-2,2-diphenylcyclopropyl)phosphine (abbreviation: cBRIDP (trademark)) were added to this mixture, and the mixture was stirred at 120° C. under a nitrogen stream for approximately 15 hours. After that, the temperature of the flask was lowered to approximately 60° C., approximately 1 mL of water was added, a precipitated solid was separated by filtration, and the solid was washed with toluene. The filtrate was concentrated, and the obtained toluene solution was purified by silica gel column chromatography. The obtained solution was concentrated, ethanol was added thereto, and the mixture was concentrated under reduced pressure, whereby an ethanol suspension was obtained. The precipitate was filtrated at approximately −10° C., and the obtained solid was dried at approximately 80° C. under reduced pressure, whereby 4.2 g of a target pale yellowish white solid was obtained in a yield of 60%. The synthesis scheme of Step 5 is shown below.

[Chemical Formula 15]

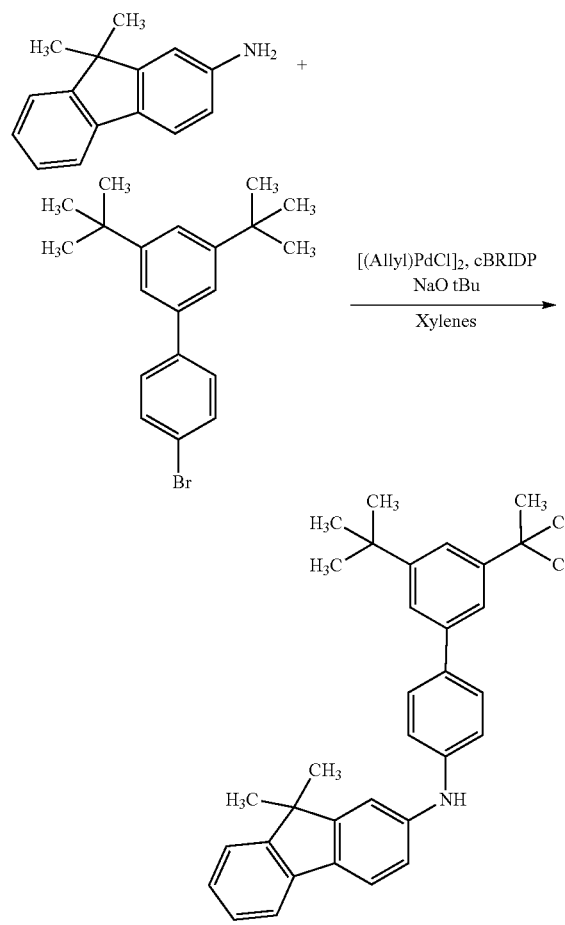

[Chemical Formula 16]

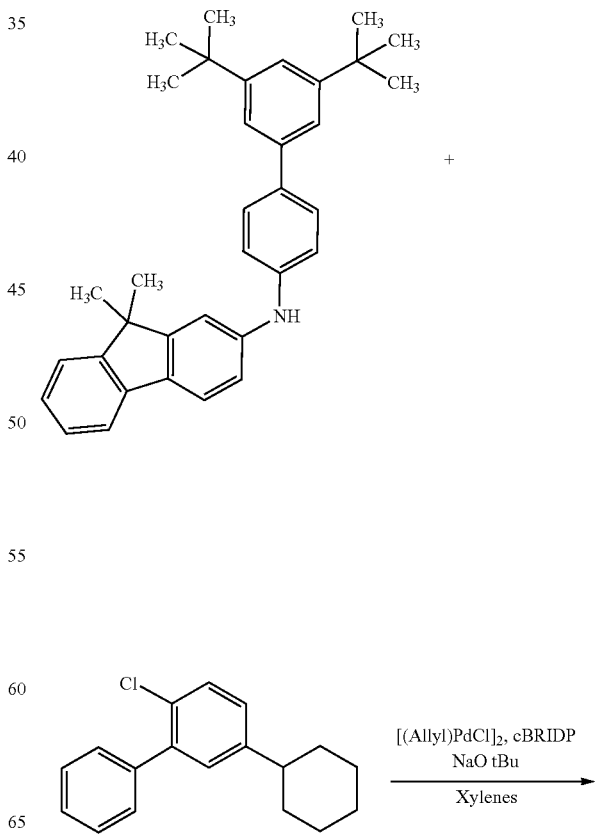

-continued

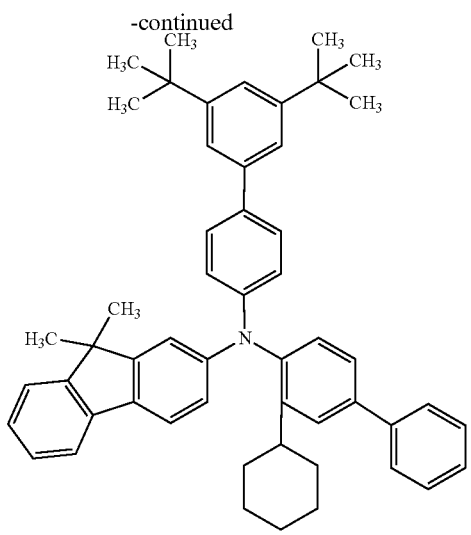

Figure 35:
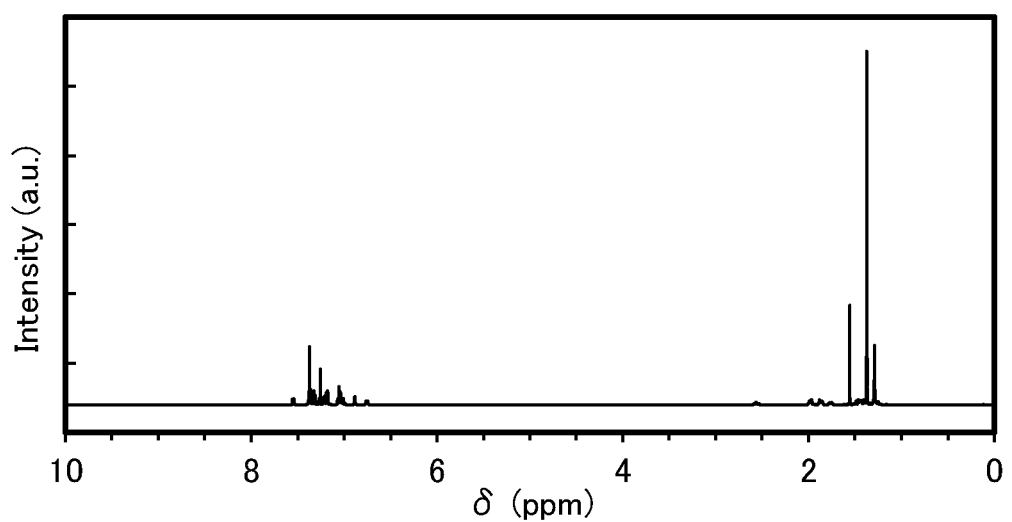
FIG. 35 shows the $^1$H-NMR spectrum of mmtBuBichoBiF.

Analysis results by nuclear magnetic resonance ($^1$H-NMR) spectroscopy of the white solid obtained in Step 2 are shown in FIG. 35 and the numerical data is described below. These show that mmtBuBichoBiF was synthesized in Step 5.

$^1$H-NMR. δ (CDCl$_3$): 7.55 (d, 1H, J=7.5 Hz), 7.35-7.39 (m, 6H), 7.33 (t, 2H, J=7.5 Hz), 7.27 (td, 2H, J=1.5 Hz, 7 Hz), 7.20-7.24 (m, 2H), 7.16-7.20 (m, 3H), 6.98-7.08 (m, 5H), 6.88 (d, 1H, J=1.5 Hz), 6.76 (dd, 1H, J=2.0 Hz, 8.5 Hz), 2.52-2.60 (m, 1H), 1.98 (d, 2H, 12 Hz), 1.87 (d, 2H, J=13 Hz), 1.76 (d, 1H, J=12.5 Hz), 1.39-1.53 (brm, 4H), 1.37 (s, 18H), 1.29 (s, 6H), 1.20-1.27 (m, 1H).

Then, 4.0 g of the obtained white solid was purified by a train sublimation method. The purification by sublimation was conducted by heating at 258° C. under a pressure of 3.0 Pa with a flow rate of an argon gas of 15.9 mL/min. After the purification by sublimation, 3.8 g of a pale yellowish white solid was obtained at a collection rate of 94%.

Figure 36:
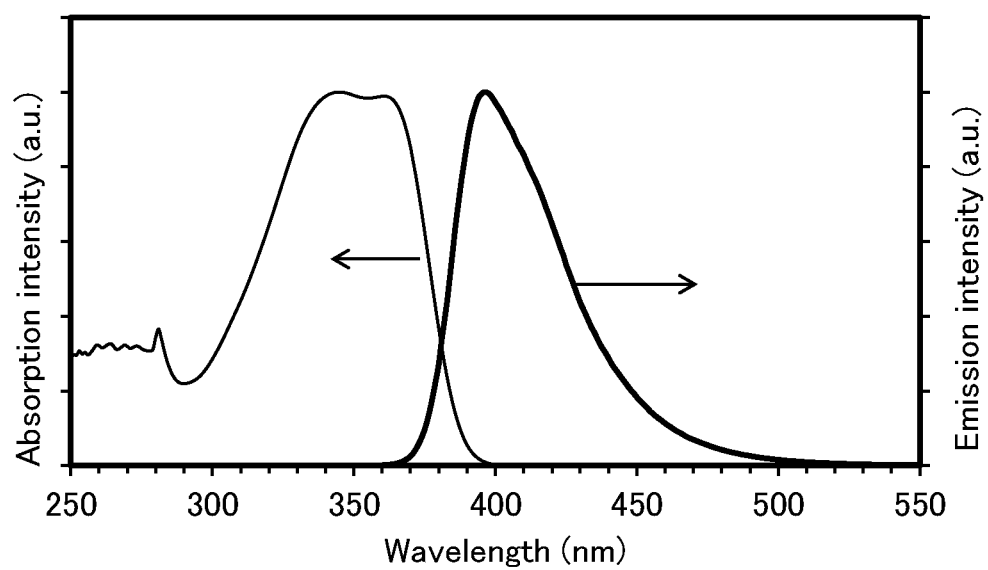
FIG. 36 shows the ultraviolet-visible absorption spectrum and emission spectrum of mmtBuBichoBiF in a toluene solution.

Next, an ultraviolet-visible absorption spectrum (hereinafter, simply referred to as an absorption spectrum) of mmtBuBichoBiF in a toluene solution and an emission spectrum thereof were measured. The absorption spectrum was measured at room temperature with an ultraviolet-visible light spectrophotometer (V-550, produced by JASCO Corporation) in a state where the toluene solution was put in a quartz cell. The emission spectrum was measured with a fluorescence spectrophotometer (FP-8600, produced by JASCO Corporation) at room temperature in a state where the toluene solution was put in a quartz cell. FIG. 36 shows measurement results of the absorption spectrum and the emission spectrum. The horizontal axis represents the wavelength and the vertical axes represent the absorbance and emission intensity. In FIG. 36, two solid lines are shown; the thin line represents the absorption spectrum, and the thick line represents the emission spectrum. The absorbance shown in FIG. 36 is a result obtained by subtraction of an absorption spectrum of only toluene in a quartz cell from the measured absorption spectrum of the toluene solution in the quartz cell.

As shown in FIG. 36, the organic compound mmtBuBichoBiF has emission peaks at 344 nm and 364 nm.

Next, mmtBuBichoBiF obtained in this example was analyzed by liquid chromatography mass spectrometry (LC/MS).

In the LC/MS analysis, liquid chromatography (LC) separation was performed with UltiMate 3000 produced by Thermo Fisher Scientific K.K., and mass spectrometry (MS) was performed with Q Exactive produced by Thermo Fisher Scientific K.K.

In the LC separation, a given column was used at a column temperature of 40° C., and solution sending was performed in such a manner that an appropriate solvent was selected, the sample was prepared by dissolving mmtBuBichoBiF in an organic solvent at an arbitrary concentration, and the injection amount was 5.0 μL.

By a PRM method, MS$^2$ measurement of m/z=707.45 corresponding to the exact mass of mmtBuBichoBiF was performed. For setting of the PRM, the mass range of a target ion was set to m/z=707.45±2.0 (isolation window=4) and detection was performed in a positive mode. The measurement was performed with energy (normalized collision energy: NCE) for accelerating a target ion in a collision cell set to 60. The obtained MS spectrum is shown in FIG. 37.

Figure 37:
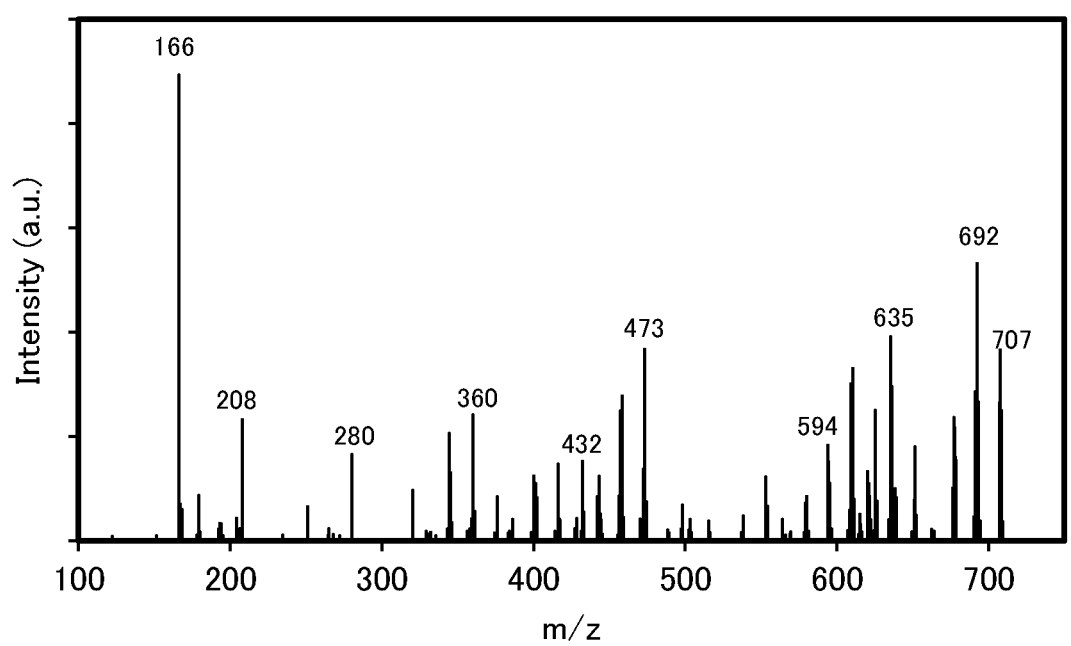
FIG. 37 shows the MS spectrum of mmtBuBichoBiF.

FIG. 37 shows that product ions of mmtBuBichoBiF are mainly detected at m/z of around 707. Note that the result in FIG. 37 shows characteristics derived from mmtBumBioBiF and therefore can be regarded as important data for identifying mmtBumBioBiF contained in a mixture.

FIG. 37 shows that fragment ions of mmtBuBichoBiF are mainly detected at m/z of around 473. Note that the result in FIG. 37 shows characteristics derived from mmtBuBichoBiF and therefore can be regarded as important data for identifying mmtBuBichoBiF contained in a mixture.

Next, the glass transition temperature (hereinafter referred to as "Tg") of mmtBuBichoBiF was measured. Note that the Tg was measured with a differential scanning calorimeter (Pyris 1 DSC produced by PerkinElmer Japan Co., Ltd.) in a state where a powder was put on an aluminum cell. As a result, the Tg was 115° C.

Reference Example 1

Reference Synthesis Example 1

In this reference example, a method for synthesizing N-(4-cyclohexylphenyl)-N-(3",5',5"-tri-tert-butyl-1,1':3',1"-terphenyl-4-yl)-9,9-dimethyl-9H-fluoren-2-amine (abbreviation: mmtBumTPchPAF-04), which is the organic compound used in the example, will be described. The structural formula of mmtBumTPchPAF-04 is shown below.

[Chemical Formula 17]

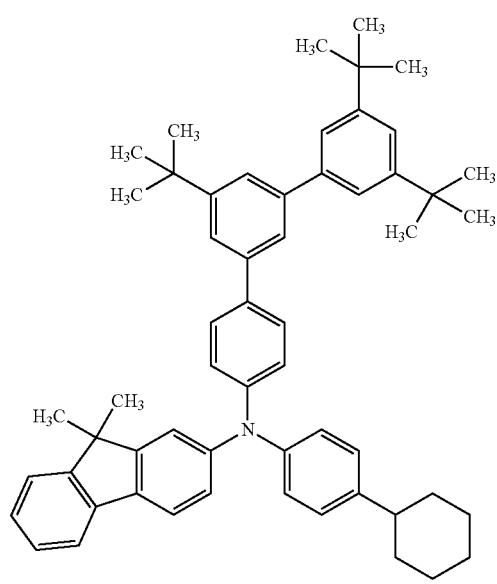

Step 1: Synthesis of 4-bromo-3",5',5"-tri-tert-butyl-1,1':3',1"-terphenyl

In a three-neck flask were put 9.0 g (20.1 mmol) of 2-(3',5,5'-tri-tert-butyl[1,1'-biphenyl]-3-yl)-4,4,5,5-tetramethyl-1,3,2-dioxaborolane, 6.8 g (24.1 mmol) of 1-bromo-4-iodobenzene, 8.3 g (60.3 mmol) of potassium carbonate, 100 mL of toluene, 40 mL of ethanol, and 30 mL of tap water. The mixture was degassed under reduced pressure, and then the air in the flask was replaced with nitrogen. Then, 91 mg (0.40 mmol) of palladium acetate and 211 mg (0.80 mmol) of triphenylphosphine were added, and the mixture was heated at 80° C. for approximately 4 hours. After that, the temperature of the flask was lowered to room temperature, and the mixture was separated into an organic layer and an aqueous layer. Magnesium sulfate was added to this solution to eliminate moisture, whereby this solution was concentrated. The obtained hexane solution was purified by silica gel column chromatography, whereby 6.0 g of a target white solid was obtained in a yield of 62.5%. The synthesis scheme of 4-bromo-3",5',5"-tri-tert-butyl-1,1':3',1"-terphenyl of Step 1 is shown below.

[Chemical Formula 18]

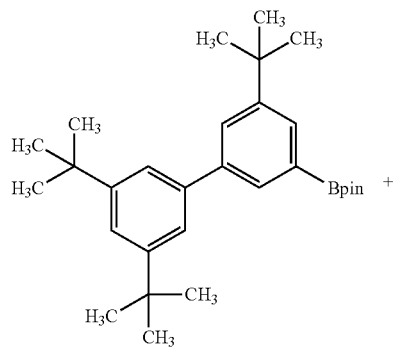

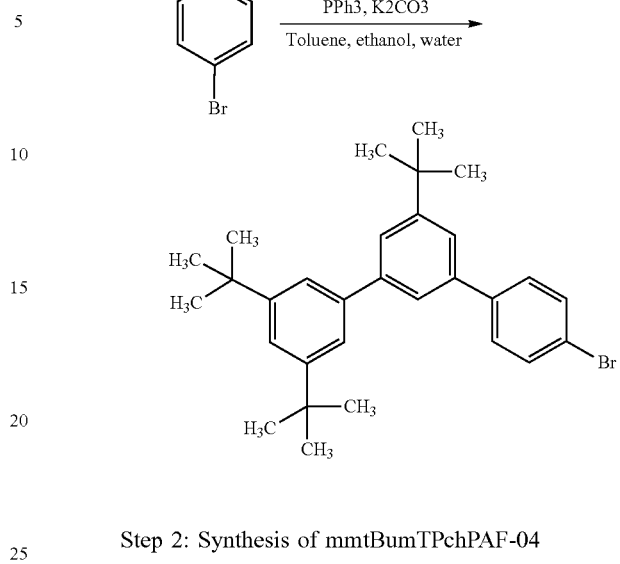

Step 2: Synthesis of mmtBumTPchPAF-04

In a three-neck flask were put 3.0 g (6.3 mmol) of 4-bromo-3",5',5"-tri-tert-butyl-1,1':3',1"-terphenyl obtained in Step 1, 2.3 g (6.3 mmol) of N-(4-cyclohexylphenyl)-N-(9,9-dimethyl-9H-fluoren-2-yl)amine, 1.8 g (18.9 mmol) of sodium-tert-butoxide, and 32 mL of toluene. The mixture was degassed under reduced pressure, the air in the flask was replaced with nitrogen, 72 mg (0.13 mmol) of bis(dibenzylideneacetone)palladium(0) and 76 mg (0.38 mmol) of tri-tert-butylphosphine were added thereto, and the mixture was heated at 80° C. for approximately 2 hours. After that, the temperature of the flask was lowered to approximately 60° C., approximately 1 mL of water was added, a precipitated solid was separated by filtration, and the solid was washed with toluene. The filtrate was concentrated, and the obtained toluene solution was purified by silica gel column chromatography. The obtained solution was concentrated to give a condensed toluene solution. Ethanol was added to this toluene solution and the toluene solution was concentrated under reduced pressure, whereby an ethanol suspension was obtained. The precipitate in the ethanol suspension was filtrated at approximately 20° C., and the obtained solid was dried at approximately 80° C. under reduced pressure, whereby 4.1 g of a target white solid was obtained in a yield of 85%. The synthesis scheme of mmtBumTPchPAF-04 is shown below.

[Chemical Formula 19]

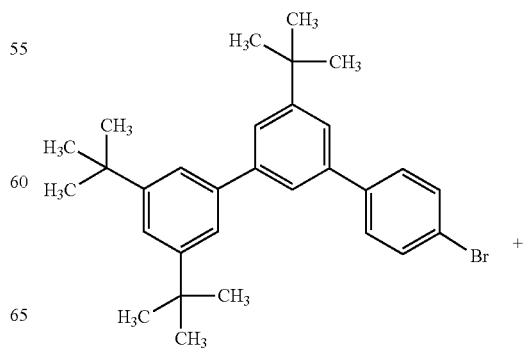

-continued

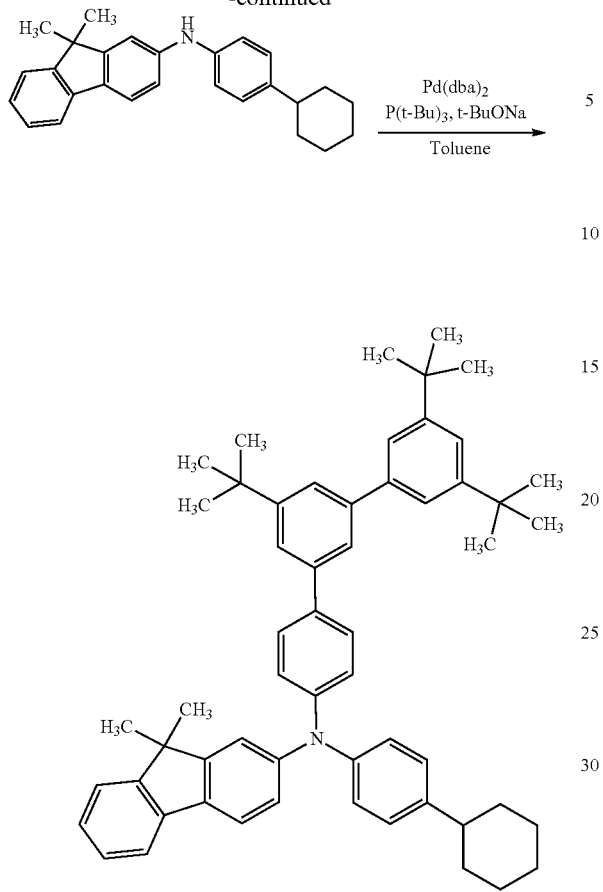

Analysis results by nuclear magnetic resonance spectroscopy (¹H-NMR) of the white solid obtained in Step 2 are shown below. The results show that mmtBumTPchPAF-04 was synthesized in this synthesis example.

¹H-NMR. δ (CDCl$_3$): 7.63 (d, 1H, J=7.5 Hz), 7.52-7.59 (m, 7H), 7.44-7.45 (m, 4H), 7.39 (d, 1H, J=7.4 Hz), 7.31 (dd, 1H, J=7.4 Hz), 7.19 (d, 2H, J=6.6 Hz), 7.12 (m, 4H), 7.07 (d, 1H, J=9.7 Hz), 2.48 (brm, 1H), 1.84-1.93 (brm, 4H), 1.74-1.76 (brm, 1H), 1.43 (s, 18H), 1.39 (brm, 19H), 1.24-1.30 (brm, 1H).

Reference Example 2

Reference Synthesis Example 2

In this reference example, a method for synthesizing N-(3',5'-ditertiarybutyl-1,1'-biphenyl-4-yl)-N-(1,1'-biphenyl-2-yl)-9,9-dimethyl-9H-fluoren-2-amine (abbreviation: mmtBuBioFBi), which is the organic compound used in the example, will be described. The structural formula of mmtBuBioFBi is shown below.

[Chemical Formula 20]

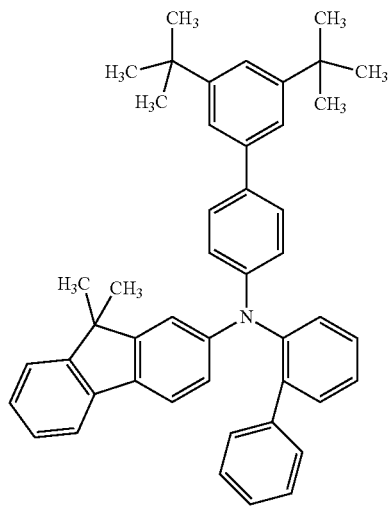

In a three-neck flask were put 2.22 g (7.4 mmol) of 4-chloro-3',5'-di-tert-butyl-1,1'-biphenyl, 2.94 g (8.1 mmol) of 2-(2-biphenylyl)amino-9,9-dimethylfluorene, 2.34 g (24.4 mmol) of sodium-tert-butoxide, and 37 mL of xylene. The mixture was degassed under reduced pressure, and then the air in the flask was replaced with nitrogen. To this mixture, 107.6 mg (0.31 mmol) of di-t-butyl(1-methyl-2,2-diphenylcyclopropyl)phosphine (abbreviation: cBRIDP (registered trademark)) and 28.1 mg (0.077 mmol) of allylpalladium chloride dimer were added. This mixture was heated at 100° C. for approximately 4 hours. After that, the temperature of the flask was lowered to approximately 70° C., and approximately 4 mL of water was added to the mixture, so that a solid was precipitated. The precipitated solid was separated by filtration. The filtrate was concentrated, and the obtained solution was purified by silica gel column chromatography. The obtained solution was concentrated. After that, ethanol was added thereto and the obtained solution was concentrated again; this process was performed three times to obtain an ethanol suspension. After that, recrystallization was performed on the ethanol suspension. The precipitate was cooled to approximately −10° C. and then filtrated, and the obtained solid was dried at approximately 130° C. under reduced pressure, whereby 2.07 g of a target white solid was obtained in a yield of 45%. The synthesis scheme of this synthesis example is shown below.

[Chemical Formula 21]

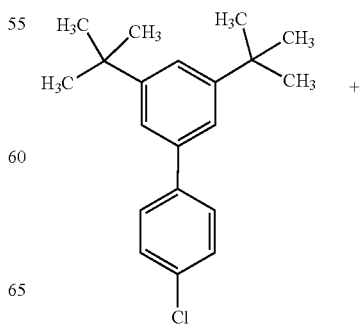

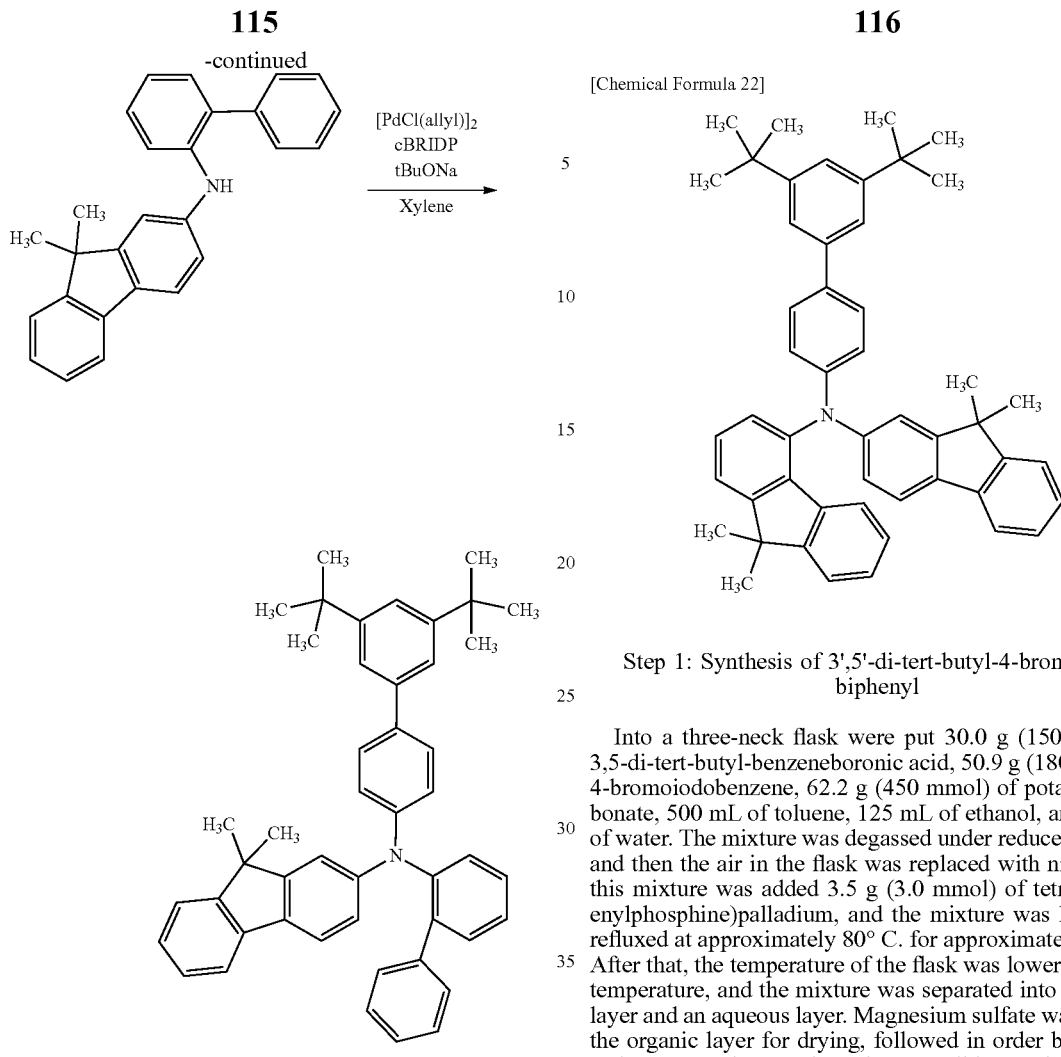

Analysis results by nuclear magnetic resonance ($^1$H-NMR) spectroscopy of the white solid obtained in this synthesis example are shown below. The results show that mmtBuBioFBi was synthesized in this synthesis example.

$^1$H-NMR (CDCl$_3$, 500 MHz): δ=1.29 (s, 6H), 1.38 (s, 18H), 6.76 (dd, J$_1$=8.0 Hz, J$_2$=2.0 Hz, 1H), 6.87 (d, J=2.5 Hz, 1H), 7.00-7.08 (m, 5H), 7.18-7.23 (m, 3H), 7.27-7.43 (m, 12H), 7.55 (d, J=7.5 Hz, 1H).

Reference Example 3

Reference Synthesis Example 3

In this reference example, a method for synthesizing N-(3',5'-di-tert-butyl-1,1'-biphenyl-4-yl)-N-(9,9-dimethyl-9H-fluoren-4-yl)-9,9-dimethyl-9H-fluoren-2-amine (abbreviation: mmtBuBiFF-02), which is the organic compound used in the example, is described. The structure of mmtBu-BiFF-02 is shown below.

[Chemical Formula 22]

Step 1: Synthesis of 3',5'-di-tert-butyl-4-bromo-1,1'-biphenyl

Into a three-neck flask were put 30.0 g (150 mmol) of 3,5-di-tert-butyl-benzeneboronic acid, 50.9 g (180 mmol) of 4-bromoiodobenzene, 62.2 g (450 mmol) of potassium carbonate, 500 mL of toluene, 125 mL of ethanol, and 225 mL of water. The mixture was degassed under reduced pressure, and then the air in the flask was replaced with nitrogen. To this mixture was added 3.5 g (3.0 mmol) of tetrakis(triphenylphosphine)palladium, and the mixture was heated and refluxed at approximately 80° C. for approximately 5 hours. After that, the temperature of the flask was lowered to room temperature, and the mixture was separated into an organic layer and an aqueous layer. Magnesium sulfate was added to the organic layer for drying, followed in order by filtration and concentration, so that a brown solid was obtained. The obtained solid was purified by silica gel column chromatography. The obtained solution was concentrated and dried for hardening. After that, hexane was added for recrystallization. The mixed solution in which a white solid was precipitated was cooled with ice and then filtrated. The obtained solid was dried at approximately 100° C. in a vacuum, whereby 44.3 g of a target white solid was obtained in a yield of 86%. The synthesis scheme of Step 1 is shown below.

[Chemical Formula 23]

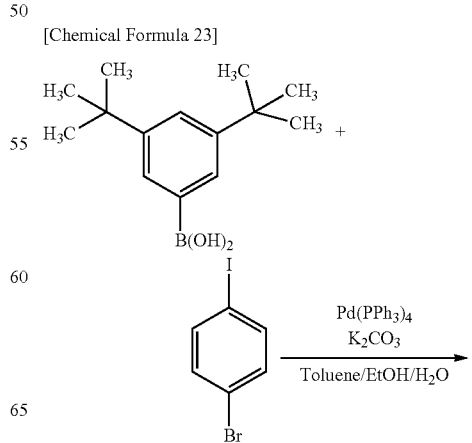

-continued

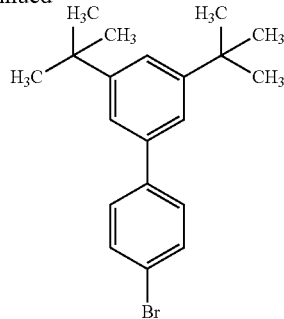

Step 2: Synthesis of N-(9,9-dimethyl-9H-fluoren-4-yl)-9,9-dimethyl-9H-fluoren-2-amine In a three-neck flask were put 4.22 g (20.2 mmol) of 2-amino-9,9-dimethyl-9H-fluorene, 5.08 g (18.6 mmol) of 4-bromo-9,9-dimethyl-9H-fluorene, 6.60 g (68.7 mmol) of sodium-tert-butoxide, and 90.0 mL of xylene. The mixture was degassed under reduced pressure, and then the air in the flask was replaced with nitrogen. The mixture was stirred while being heated to approximately 40° C. Then, 78.5 mg (0.215 mmol) of allylpalladium(II) chloride dimer (abbreviation: (AllylPdCl)$_2$) and 307 mg (0.748 mmol) of 2-dicyclohexylphosphino-2',6'-dimethoxybiphenyl (abbreviation: SPhos) were added, and the mixture was heated at 100° C. for approximately 6 hours. After that, the temperature of the flask was lowered to approximately 60° C., and approximately 1 mL of water was added to the mixture, so that a solid was precipitated. The precipitated solid was separated by filtration. The filtrate was concentrated, and the obtained solution was purified by silica gel column chromatography. The obtained solution was concentrated to give 7.50 g of a target reddish brown oily substance in a yield of 100%. The synthesis scheme of Step 2 is shown below.

[Chemical Formula 24]

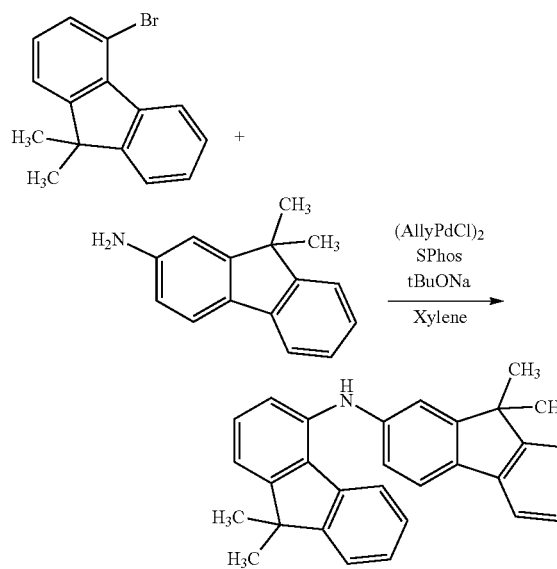

Step 3: Synthesis of mmtBuBiFF-02

In a three-neck flask were put 2.73 g (0.680 mmol) of N-(9,9-dimethyl-9H-fluoren-4-yl)-9,9-dimethyl-9H-fluoren-2-amine, 2.36 g (0.683 mmol) of 3',5'-di-tert-butyl-4-bromo-1,1'-biphenyl, 1.94 g (2.02 mmol) of sodium-tert-butoxide, and 37.0 mL of xylene. The mixture was degassed under reduced pressure, and then the air in the flask was replaced with nitrogen. Then, 29.0 mg (0.079 mmol) of allylpalladium(II) chloride dimer (abbreviation: (AllylPdCl)$_2$) and 88.2 mg (0.250 mmol) of di-tert-butyl(1-methyl-2,2-diphenylcyclopropyl)phosphine (abbreviation: cBRIDP (registered trademark)) were added, and the mixture was heated at 100° C. for approximately 6 hours. After that, the temperature of the mixture was lowered to approximately 60° C., and approximately 1 mL of water was added to the mixture, so that a solid was precipitated. The precipitated solid was separated by filtration. The filtrate was concentrated, and the obtained condensed solution was purified by silica gel column chromatography. The obtained solution was concentrated to give a condensed toluene solution. The toluene solution was dropped into ethanol for reprecipitation. The precipitate was filtrated at approximately 10° C. and the obtained solid was dried at approximately 100° C. under reduced pressure, whereby 3.21 g of a target white solid was obtained in a yield of 71%. The synthesis scheme of Step 3 is shown below.

[Chemical Formula 25]

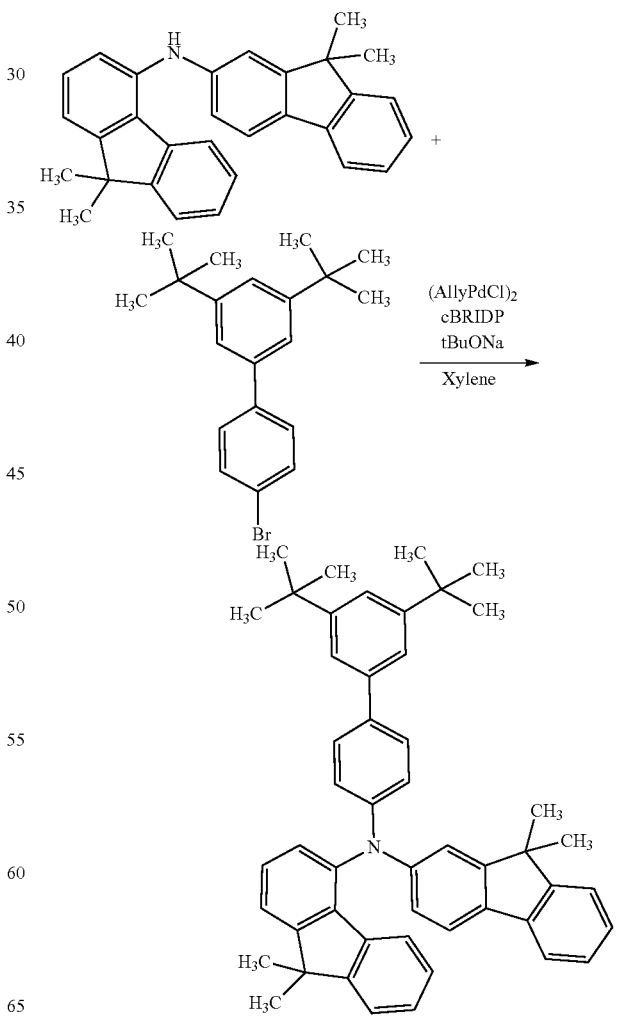

Analysis results by nuclear magnetic resonance (¹H-NMR) spectroscopy of the white solid obtained in Step 3 are shown below. The results show that N-(3',5'-di-tert-butyl-1,1'-biphenyl-4-yl)-N-(9,9-dimethyl-9H-fluoren-4-yl)-9,9-dimethyl-9H-fluoren-2-amine (abbreviation: mmtBuBiFF-02) was synthesized in this synthesis example.

¹H-NMR (500 MHz, DMSO-$d_6$): δ=7.66-7.62 (m, 3H), 7.58-7.52 (m, 4H), 7.47-7.43 (m, 2H), 7.37 (s, 2H), 7.33 (br, 2H), 7.28 (t, 1H, J=7.0 Hz), 7.22 (dt, 2H, J=7.3 Hz, 3.5 Hz), 7.13 (d, 1H, J=7.0 Hz), 6.89 (dd, 1H, J=8.0 Hz, 1.5 Hz), 1.50 (br, 6H), 1.36 (br, 6H), 1.31 (s, 18H), 1.28 (br, 6H).

Reference Example 4

Reference Synthesis Example 4

In this reference example, a method for synthesizing N-(3',5',-di-tert-butyl-1,1'-biphenyl-4-yl)-bis(9,9-dimethyl-9H-fluoren)-2,2'-amine (abbreviation: mmtBuBiFF), which is the organic compound used in the example, will be described. The structure of mmtBuBiFF is shown below.

[Chemical Formula 26]

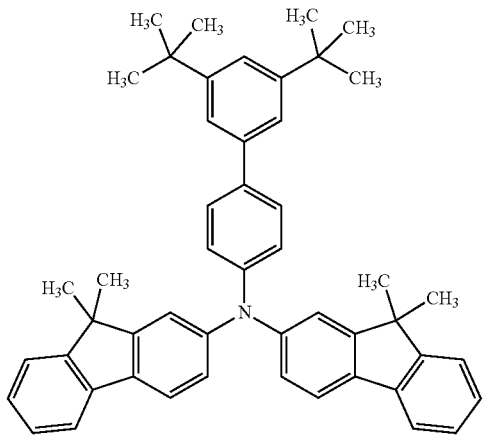

Step 1: Synthesis of 3',5'-di-tert-butyl-4-chloro-1,1'-biphenyl

In a three-neck flask were put 30.0 g (114 mmol) of 3,5-di-tert-butyl-1-bromobenzene, 19.2 g (123 mmol) of 4-chlorophenylboronic acid, 46.1 g (334 mmol) of potassium carbonate, 550 mL of toluene, 140 mL of ethanol, and 160 mL of water. The mixture was degassed under reduced pressure, and then the air in the flask was replaced with nitrogen. Then, 251 mg (1.12 mmol) of palladium acetate and 695 mg (2.28 mmol) of tris(2-methylphenyl)phosphine were added, and the mixture was heated and refluxed at 90° C. for approximately 5 hours. After that, the temperature of the flask was lowered to room temperature, and the mixture was separated into an organic layer and an aqueous layer. Magnesium sulfate was added to this organic layer to eliminate moisture, and then a solution separated by filtration was concentrated to give a condensed brown solution. The obtained solution was purified by silica gel column chromatography. The obtained solution was concentrated and dried for hardening. After that, hexane was added for recrystallization. The mixed solution in which a white solid was precipitated was cooled with ice and filtrated. The obtained solid was dried at approximately 100° C. in a vacuum, whereby 29.6 g of a target white solid was obtained in a yield of 88%. The synthesis scheme of Step 1 is shown below.

[Chemical Formula 27]

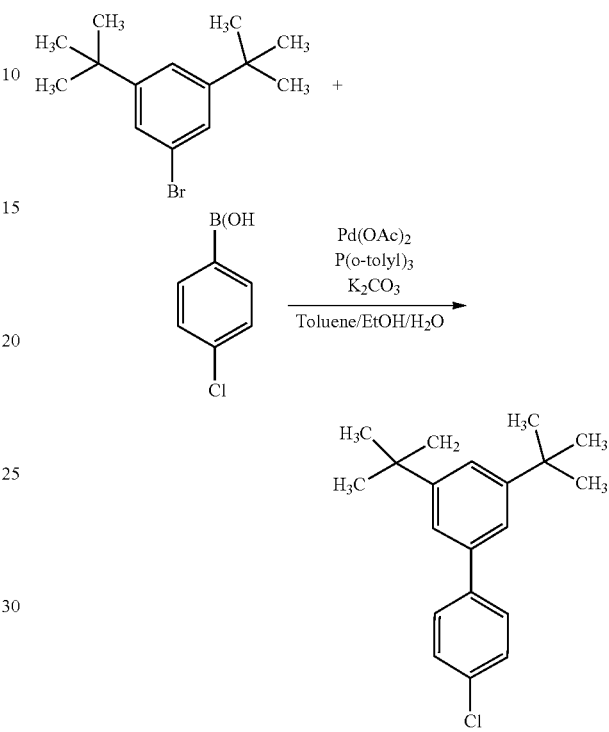

Step 2: Synthesis of mmtBuBiFF

In a three-neck flask were put 30.4 g (75.7 mmol) of bis(9,9-dimethyl-9H-fluoren-2-yl)amine, 22.8 g (75.8 mmol) of 3',5'-di-tert-butyl-4-chloro-1,1'-biphenyl, 21.9 g (228 mmol) of sodium-tert-butoxide, and 380 mL of xylene. The mixture was degassed under reduced pressure, and then the air in the flask was replaced with nitrogen. The mixture was stirred while being heated to approximately 60° C. Then, 283 mg (0.773 mmol) of allylpalladium(II) chloride dimer (abbreviation: (AllylPdCl)₂) and 1.05 g (2.98 mmol) of di-tert-butyl(1-methyl-2,2-diphenylcyclopropyl)phosphine (abbreviation: cBRIDP (registered trademark)) were added, and the mixture was heated at 100° C. for approximately 5 hours. After that, the temperature of the mixture was lowered to approximately 60° C., and approximately 2 mL of water was added to the mixture, so that a solid was precipitated. The precipitated solid was separated by filtration to give a filtrate. The filtrate was concentrated, and the obtained solution was purified by silica gel column chromatography. The obtained solution was concentrated to give a condensed toluene solution. The toluene solution was dropped into ethanol for reprecipitation. The precipitate was collected by filtration at approximately 10° C. and the obtained solid was dried at approximately 100° C. under reduced pressure, whereby 44.2 g of a target white solid was obtained in a yield of 88%. The synthesis scheme of Step 2 is shown below.

[Chemical Formula 28]

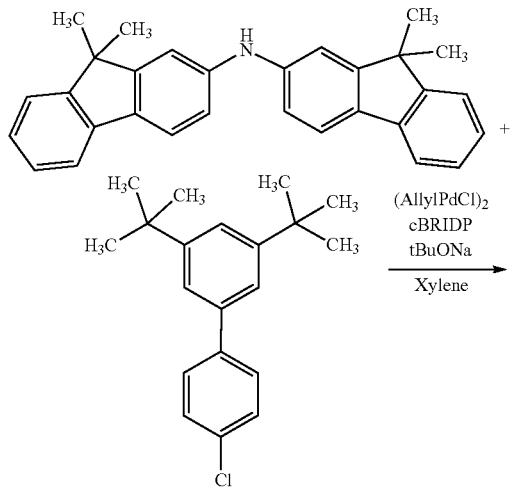

[Chemical Formula 29]

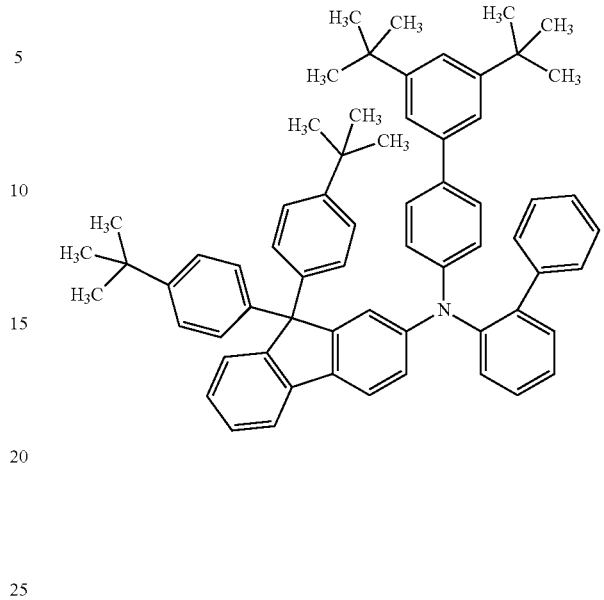

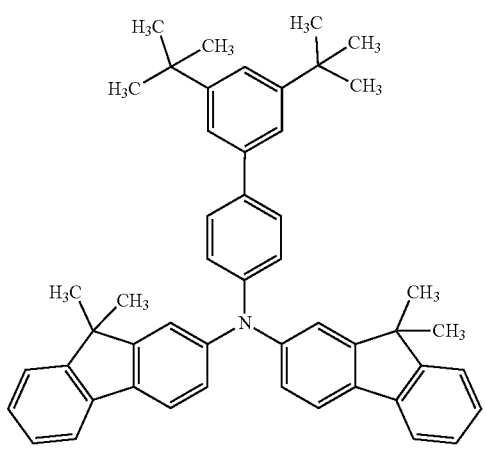

Analysis results by nuclear magnetic resonance spectroscopy ($^1$H-NMR) of the white solid obtained in Step 2 are shown below. The results reveal that N-(3',5',-di-tert-butyl-1,1'-biphenyl-4-yl)-bis(9,9-dimethyl-9H-fluoren)-2,2'-amine (abbreviation: mmtBuBiFF) was obtained in this example.

$^1$H-NMR (500 MHz, DMSO-$d_6$): δ=7.75 (t, 4H, J=7.8 Hz), 7.62 (d, 2H, J=9.0 Hz), 7.51 (d, 2H, J=5.0 Hz), 7.42 (s, 2H), 7.38 (s, 1H), 7.34-7.25 (m, 6H), 7.18 (d, 2H, J=8.0 Hz, 2.0 Hz), 7.03 (dd, 2H, J=8.0 Hz, 2.0 Hz), 1.37 (s, 12H), 1.34 (s, 18H).

Reference Example 5

Reference Synthesis Example 5

In this synthesis example, a method for synthesizing N-(1,1'-biphenyl-2-yl)-N-[(3',5'-di-tert-butyl)-1,1'-biphenyl-4-yl)-9,9-bis-(4-tert-butylphenyl)-9H-fluoren-2-amine (abbreviation: mmtBuBioBitBu2FLP(2)), which is the organic compound used in the example, will be described. The structure of mmtBuBioBitBu2FLP(2) is shown below.

Step 1: Synthesis of bis(4-tert-butylphenyl)-(3-chloro-6-phenylphenyl)methanol

Into a three-neck flask was put 9.98 g (33.9 mmol) of 4,4'-di-tert-butylbenzophenone, and the air in the flask was replaced with nitrogen. Into this flask was added 34.0 mL of tetrahydrofuran (THF), and then the mixture was stirred to obtain a 4,4'-di-tert-butylbenzophenone THF solution. Into another three-neck flask was put 8.26 g (30.9 mmol) of 2-bromo-4'-chloro-1,1'-biphenyl, and the air in the flask was replaced with nitrogen. Into this flask was added 152 mL of THF, the mixture was stirred while being cooled down to approximately −80° C., and then 23.5 mL (37.6 mmol) of n-butyllithium (a 1.6 mol/L hexane solution) was dropped into this mixture with a syringe. After the dropping, the mixture was stirred for one hour. After the stirring, 34.0 mL of the 4,4'-di-tert-butylbenzophenone THF solution prepared earlier was dropped into this solution with a syringe. After the dropping, the temperature was returned to room temperature and the mixture was stirred for one hour. After the stirring, approximately 25 mL of dilute hydrochloric acid (2.0 mol/L) was added to this solution, followed by stirring for one hour. After the stirring, the aqueous layer of this mixture was subjected to extraction with ethyl acetate, and a solution of the extract and the organic layer were combined and washed with a saturated aqueous solution of sodium hydrogen carbonate and saturated brine. The organic layer was dried with magnesium sulfate, and after the drying, this mixture was gravity-filtered. The obtained solution was concentrated and dried for hardening. Then, toluene was added to obtain a condensed toluene solution. The toluene solution was dropped into ethanol for reprecipitation. The precipitate was filtered at approximately 10° C. and the obtained solid was dried at approximately 40° C. under reduced pressure, whereby 12.2 g of a target pale brown solid was obtained in a yield of 82%. The synthesis scheme is shown below.

[Chemical Formula 30]

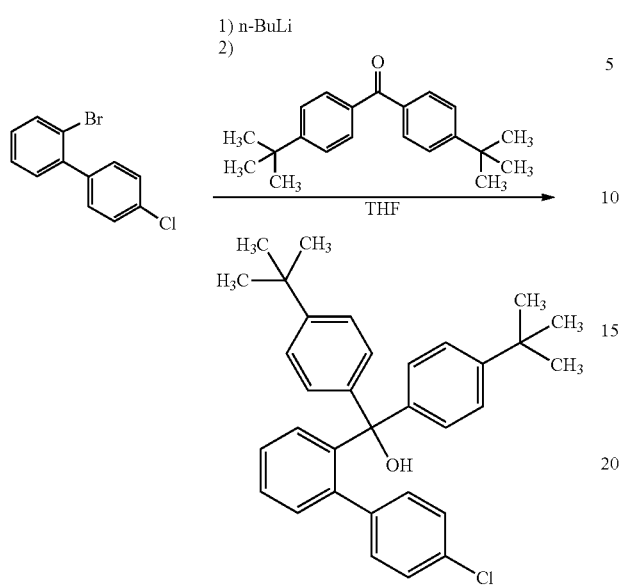

Step 2: Synthesis of 2-chloro-9,9-bis(4-tert-butylphenyl)-9H-fluorene

Into a three-neck flask were added 12.2 g (25.3 mmol) of bis(4-tert-butylphenyl)-(3-chloro-6-phenylphenyl)methanol, 211 mg (1.23 mmol) of p-toluene sulfonic acid monohydrate, and 126 mL of toluene. The mixture was stirred while being heated at approximately 120° C. for approximately 5 hours. After that, the temperature of the flask was lowered to room temperature, 21.5 mL of a saturated aqueous solution of sodium hydrogen carbonate was added to this mixture, and the mixture was stirred for approximately one hour. After the stirring, an organic layer and an aqueous layer were separated, and the organic layer was washed with saturated brine. The organic layer was concentrated, and the obtained solution was purified by silica gel column chromatography. The obtained solution was concentrated to give a condensed toluene solution. The toluene solution was dropped into ethanol for reprecipitation. The precipitate was filtrated at approximately 10° C., and the obtained solid was dried at approximately 100° C. under reduced pressure, whereby 11.3 g of a target white solid was obtained in a yield of 97%. The synthesis scheme is shown below.

[Chemical Formula 31]

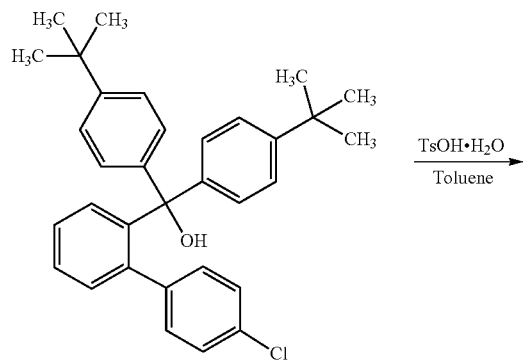

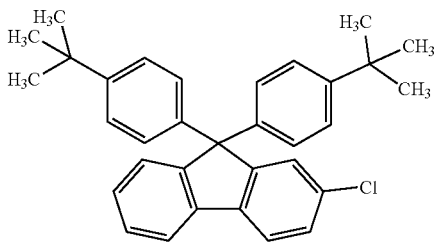

Step 3: Synthesis of 3',5'-di-tert-butyl-4-bromo-1,1'-biphenyl

Into a three-neck flask were put 30.0 g (150 mmol) of 3,5-di-tert-butyl-benzeneboronic acid, 50.9 g (180 mmol) of 4-bromoiodobenzene, 62.2 g (450 mmol) of potassium carbonate, 500 mL of toluene, 125 mL of ethanol, and 225 mL of water. The mixture was degassed under reduced pressure, and then the air in the flask was replaced with nitrogen. To this mixture was added 3.5 g (3.0 mmol) of tetrakis(triphenylphosphine)palladium, and the mixture was heated and refluxed at approximately 80° C. for approximately 5 hours. After that, the temperature of the flask was lowered to room temperature, and the mixture was separated into an organic layer and an aqueous layer. Magnesium sulfate was added to the organic layer for drying, followed in order by filtration and concentration, so that a brown solid was obtained. The obtained solid was purified by silica gel column chromatography. The obtained solution was concentrated and dried for hardening. After that, hexane was added for recrystallization. The mixed solution in which a white solid was precipitated was cooled with ice and then filtrated. The obtained solid was dried at approximately 100° C. in a vacuum, whereby 44.3 g of a target white solid was obtained in a yield of 86%. The synthesis scheme is shown below.

[Chemical Formula 32]

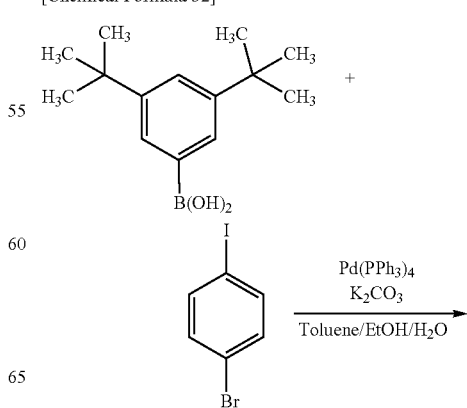

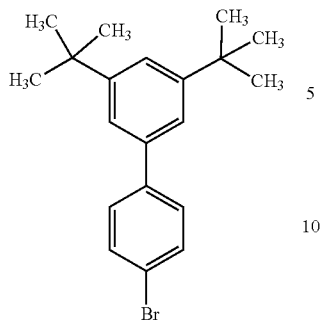

Step 4: Synthesis of 3',5'-di-tert-butyl-1,1'-biphenyl-4-amine

Into a three-neck flask were put 36.9 g (107 mmol) of 3',5'-di-tert-butyl-4-bromo-1,1'-biphenyl and 530 mL of toluene. The mixture was degassed under reduced pressure, and then the air in the flask was replaced with nitrogen. To this mixture was added 2.76 g (5.40 mmol) of bis(tri-tert-butylphosphine)palladium, and the mixture was stirred while being cooled down to approximately −15° C. Then, 120 mL (120 mmol) of lithium bis(trimethylsilyl)amide (abbreviation: LiHMDS) (a 1.0 mol/L toluene solution) was dropped with a syringe. After that, the mixture was stirred while being heated at 120° C. for approximately 3 hours. Subsequently, the temperature of the flask was lowered to room temperature, 100 mL of water was added to the mixture, and then the mixture was stirred for approximately one hour. After the stirring, an organic layer and an aqueous layer were separated, and the organic layer was washed with a saturated aqueous solution of sodium hydrogen carbonate and saturated brine. The organic layer was concentrated, and the obtained solution was purified by silica gel column chromatography. The obtained solution was concentrated to give 29.0 g of a target pale brown solid in a yield of 99%. The synthesis scheme is shown below.

[Chemical Formula 33]

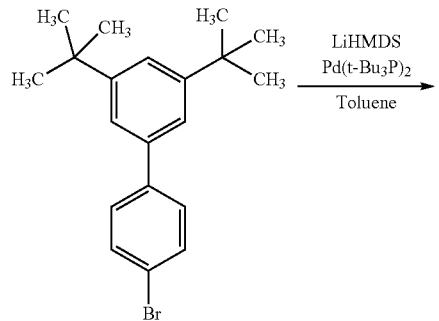

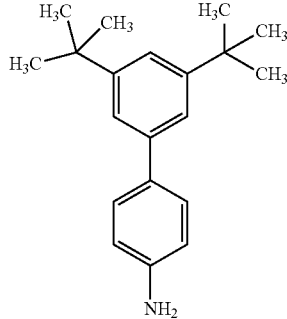

Step 5: Synthesis of N-[3',5'-di-tert-butyl-1,1'-biphenyl-3-yl]-9,9-bis(4-tert-butylphenyl)-9H-fluoren-2-amine Into a three-neck flask were put 3.64 g (12.9 mmol) of 3',5'-di-tert-butyl-1,1'-biphenyl-4-amine, 5.95 g (12.8 mmol) of 2-chloro-9,9-bis(4-tert-butylphenyl)-9H-fluorene, 3.62 g (37.7 mmol) of sodium-tert-butoxide, and 64.0 mL of xylene. The mixture was degassed under reduced pressure, and then the air in the flask was replaced with nitrogen. The mixture was stirred while being heated to approximately 60° C. Then, 56.2 mg (0.154 mmol) of allylpalladium(II) chloride dimer (abbreviation: (AllylPdCl)$_2$) and 216 mg (0.526 mmol) of 2-dicyclohexylphosphino-2',6'-dimethoxybiphenyl (abbreviation: SPhos) were added, and the mixture was stirred while being heated at 90° C. for approximately 6 hours. After that, the temperature of the flask was lowered to approximately 60° C., and approximately 1 mL of water was added to the mixture, so that a solid was precipitated. The precipitated solid was separated by filtration to obtain a solution. The filtrate was concentrated, and the obtained solution was purified by silica gel column chromatography. The obtained solution was concentrated to give 7.75 g of a target pale brown solid in a yield of 85%. The synthesis scheme is shown below.

[Chemical Formula 34]

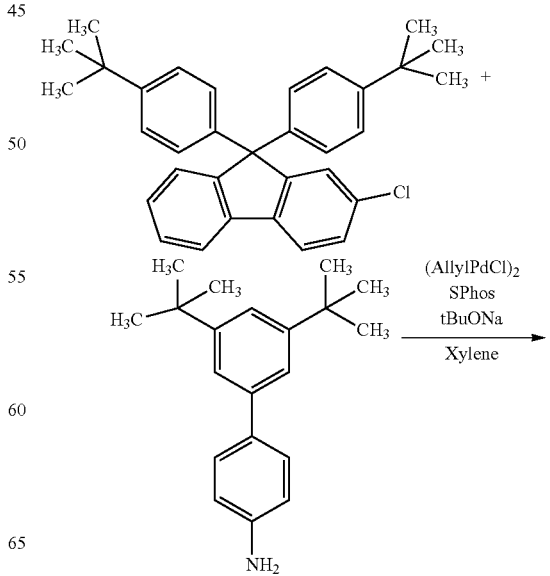

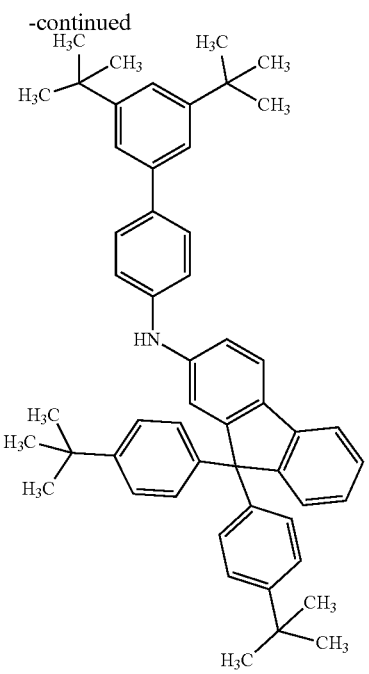

Step 6: Synthesis of mmtBuBioBitBu2FLP(2)

Into a three-neck flask were put 3.50 g (150 mmol) of N-[3',5'-di-tert-butyl-1,1'-biphenyl-3-yl]-9,9-bis(4-tert-butylphenyl)-9H-fluoren-2-amine, 1.17 g (180 mmol) of 2-bromo-1,1'-biphenyl, 1.41 g (37.7 mmol) of sodium-tert-butoxide, and 24.5 mL of mesitylene. The mixture was degassed under reduced pressure, and then the air in the flask was replaced with nitrogen. The mixture was stirred while being heated to approximately 60° C. Then, 20.1 mg (0.154 mmol) of allylpalladium(II) chloride dimer (abbreviation: (AllylPdCl)$_2$) and 64.7 mg (0.204 mmol) of di-tert-butyl(1-methyl-2,2-diphenylcyclopropyl)phosphine (abbreviation: cBRIDP (registered trademark)) were added, and the mixture was stirred while being heated at 140° C. for approximately 6 hours. After that, the temperature of the flask was lowered to approximately 60° C., and approximately 1 mL of water was added to the mixture, so that a solid was precipitated. The precipitated solid was separated by filtration to obtain a solution. The filtrate was concentrated, and the obtained solution was purified by silica gel column chromatography. The obtained solution was concentrated to give 2.91 g of a target pale brown solid in a yield of 69%. The synthesis scheme is shown below.

[Chemical Formula 35]

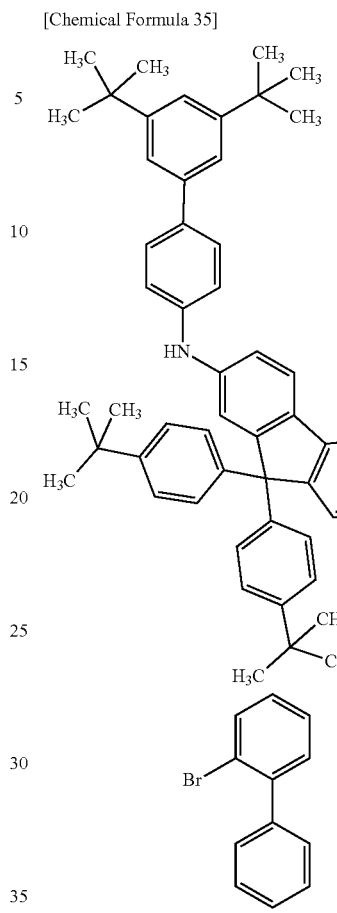

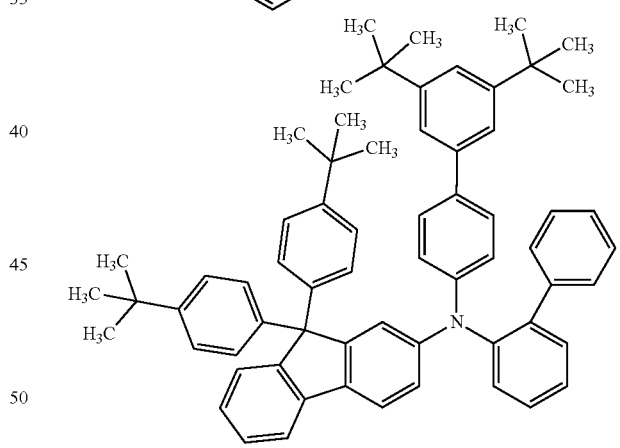

Analysis results by nuclear magnetic resonance ($^1$H-NMR) spectroscopy of the white solid obtained in Step 6 are shown below. The results show that N-(1,1'-biphenyl-2-yl)-N-[(3',5'-di-tert-butyl)-1,1'-biphenyl-4-yl]-9,9-bis(4-tert-butylphenyl)-9H-fluoren-2-amine (abbreviation: mmtBuBioBitBu2FLP(2)) was synthesized in this synthesis example.

$^1$H-NMR (500 MHz, DMSO-d$_6$): δ=7.68 (d, 1H, J=7.5 Hz), 7.49 (d, 1H, J=8.0 Hz), 7.45 (dt, 1H, J=7.5 Hz, 1.0 Hz), 7.40-7.34 (m, 7H), 7.32-7.25 (m, 7H), 7.19 (t, 1H, J=7.5 Hz), 7.10-7.03 (m, 3H), 6.95 (d, 2H, J=7.5 Hz), 6.90 (d, 2H, J=8.5 Hz), 6.82 (d, 4H, J=8.0 Hz), 6.70 (d, 1H, J=2.0 Hz), 6.54 (dd, 1H, J=8.5 Hz, 1.5 Hz), 1.33 (s, 18H), 1.26 (s, 18H).

Reference Example 6

In this reference example, a method for synthesizing N-(1,1'-biphenyl-2-yl)-N-(3",5',5"-tri-tert-butyl-1,1':3',1"-terphenyl-4-yl)-9,9-dimethyl-9H-fluoren-2-amine (abbreviation: mmtBumTPoFBi-04), which is the organic compound used in the example, will be described. The structural formula of mmtBumTPoFBi-04 is shown below.

[Chemical Formula 36]

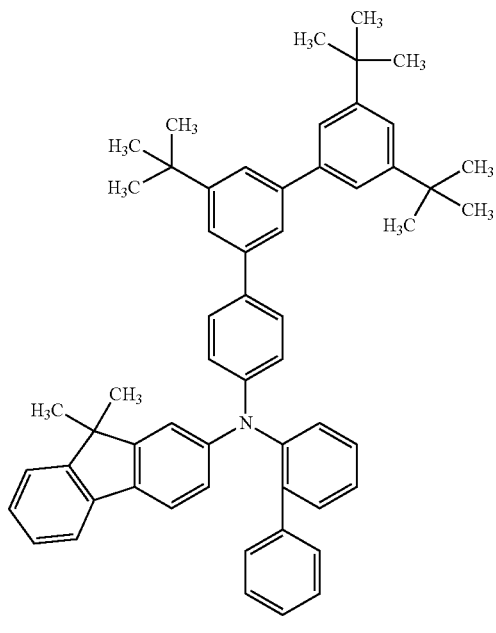

[Chemical Formula 37]

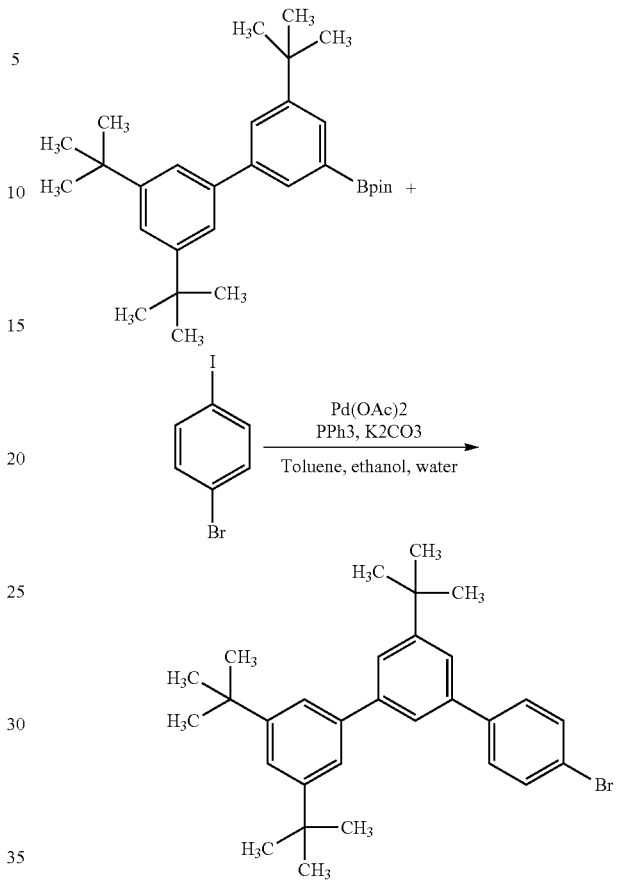

Step 1: Synthesis of 4-bromo-3",5',5"-tri-tert-butyl-1,1':3',1"-terphenyl

In a three-neck flask were put 9.0 g (20.1 mmol) of 2-(3',5,5'-tri-tert-butyl[1,1'-biphenyl]-3-yl)-4,4,5,5-tetramethyl-1,3,2-dioxaborolane, 6.8 g (24.1 mmol) of 1-bromo-4-iodobenzene, 8.3 g (60.3 mmol) of potassium carbonate, 100 mL of toluene, 40 mL of ethanol, and 30 mL of tap water. The mixture was degassed under reduced pressure, and then the air in the flask was replaced with nitrogen. Then, 91 mg (0.40 mmol) of palladium acetate and 211 mg (0.80 mmol) of triphenylphosphine were added, and the mixture was heated at 80° C. for approximately 4 hours. After that, the temperature of the flask was lowered to room temperature, and the mixture was separated into an organic layer and an aqueous layer. Magnesium sulfate was added to this solution to eliminate moisture, whereby this solution was concentrated. The obtained hexane solution was purified by silica gel column chromatography, whereby 6.0 g of a target white solid was obtained in a yield of 62.5%. The synthesis scheme of 4-bromo-3",5',5"-tri-tert-butyl-1,1':3',1"-terphenyl of Step 1 is shown below.

Step 2: Synthesis of mmtBumTPoFBi-04

In a three-neck flask were put 3.0 g (6.3 mmol) of 4-bromo-3",5',5"-tri-tert-butyl-1,1':3',1"-terphenyl, 2.3 g (6.3 mmol) of N-(1,1'-biphenyl-4-yl)-N-phenyl-9,9-dimethyl-9H-fluoren-2-amine, 1.8 g (18.9 mmol) of sodium-tert-butoxide, and 32 mL of toluene. The mixture was degassed under reduced pressure, the air in the flask was replaced with nitrogen, 72 mg (0.13 mmol) of bis(dibenzylideneacetone)palladium(0) and 76 mg (0.38 mmol) of tri-tert-butylphosphine were added thereto, and the mixture was heated at 120° C. for approximately 8 hours. After that, the temperature of the mixture was lowered to approximately 60° C., approximately 1 mL of water was added, a precipitated solid was separated by filtration, and the solid was washed with toluene. The filtrate was concentrated, and the obtained toluene solution was purified by silica gel column chromatography. The obtained solution was concentrated to give a condensed toluene solution. Ethanol was added to this toluene solution and the toluene solution was concentrated under reduced pressure, whereby an ethanol suspension was obtained. The precipitate was filtrated at approximately 20° C., and the obtained solid was dried at approximately 80° C. under reduced pressure, whereby 3.6 g of a target white solid was obtained in a yield of 75%. The synthesis scheme of Step 2 is shown below. The synthesis scheme of mmtBumTPoFBi-04 of Step 4 is shown below.

131

[Chemical Formula 38]

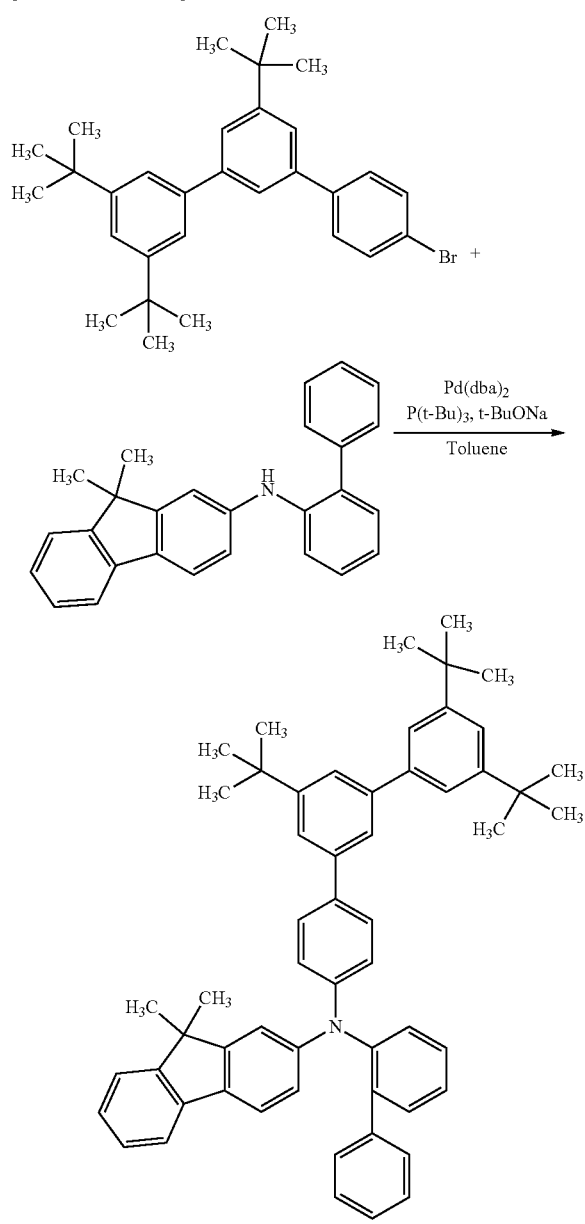

Analysis results by nuclear magnetic resonance spectroscopy ($^1$H-NMR) of the white solid obtained in Step 2 are shown below. The results reveal that mmtBumTPoFBi-04 was obtained in this example.

$^1$H-NMR. δ (CDCl$_3$): 7.54-7.56 (m, 1H), 7.53 (dd, 1H, J=1.7 Hz), 7.50 (dd, 1H, J=1.7 Hz), 7.27-7.47 (m, 13H), 7.23 (dd, 1H, J=6.3 Hz, 1.2 Hz), 7.18-7.19 (m, 2H), 7.08-7.00 (m, 5H), 6.88 (d, 1H, J=1.7 Hz), 6.77 (dd, 1H, J=8.0 Hz, 2.3 Hz), 1.42 (s, 9H), 1.39 (s, 18H), 1.29 (s, 6H).

Reference Example 7

Reference Synthesis Example

In this reference example, a method for synthesizing N-(1,1'-biphenyl-2-yl)-N-(3,3",5',5"-tetra-tert-butyl-1,1':3',1"-terphenyl-5-yl)-9,9-dimethyl-9H-fluoren-2-amine (abbreviation: mmtBumTPoFBi-02), which is the organic compound used in the example, will be described. The structural formula of mmtBumTPoFBi-02 is shown below.

132

[Chemical Formula 39]

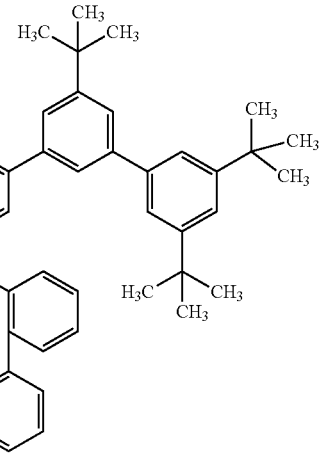

Step 1: Synthesis of 3-bromo-3',5,5'-tri-tert-butylbiphenyl

In a three-neck flask were put 37.2 g (128 mmol) of 1,3-dibromo-5-tert-butylbenzene, 20.0 g (85 mmol) of 3,5-di-tert-butylphenylboronic acid, 35.0 g (255 mmol) of potassium carbonate, 570 mL of toluene, 170 mL of ethanol, and 130 mL of tap water. The mixture was degassed under reduced pressure, and then the air in the flask was replaced with nitrogen. Then, 382 mg (1.7 mmol) of palladium acetate and 901 mg (3.4 mmol) of triphenylphosphine were added, and the mixture was heated at 40° C. for approximately 5 hours. After that, the temperature of the flask was lowered to room temperature, and the mixture was separated into an organic layer and an aqueous layer. Magnesium sulfate was added to this organic layer to eliminate moisture, whereby the organic layer was concentrated. The obtained solution was purified by silica gel column chromatography, whereby 21.5 g of a target colorless oily substance was obtained in a yield of 63%. The synthesis scheme of Step 1 is shown below.

[Chemical Formula 40]

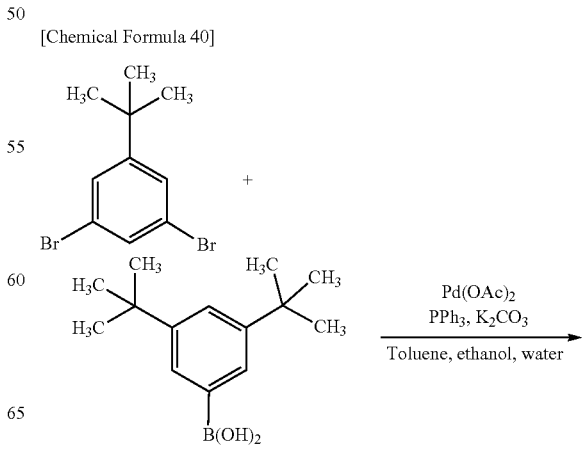

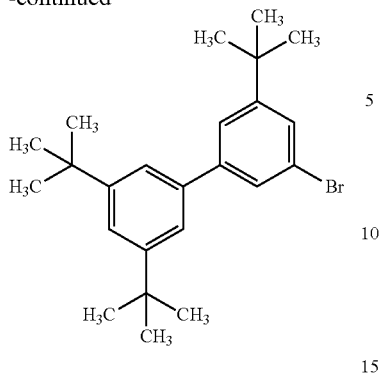

<Step 2: Synthesis of 2-(3',5,5'-tri-tert-butyl[1,1'-biphenyl]-3-yl)-4,4,5,5-tetramethyl-1,3,2-dioxaborolane In a three-neck flask were put 15.0 g (38 mmol) of 3-bromo-3',5,5'-tri-tert-butylbiphenyl obtained in Step 1, 10.5 g (41 mmol) of 4,4,4',4',5,5,5',5-octamethyl-2,2'-bi-1,3,2-dioxaborolane, 11.0 g (113 mmol) of potassium acetate, and 125 mL of N,N-dimethylformamide. The mixture was degassed under reduced pressure, the air in the flask was replaced with nitrogen, 1.5 g (1.9 mmol) of [1,1'-bis(diphenylphosphino)ferrocene]dichloropalladium(II) was added thereto, and the mixture was heated at 100° C. for approximately 3 hours. Then, the temperature of the flask was lowered to room temperature, the mixture was separated into an organic layer and an aqueous layer, and extraction was performed with ethyl acetate. Magnesium sulfate was added to the solution of the extract to eliminate moisture, whereby the solution of the extract was concentrated. A toluene solution of the obtained mixture was purified by silica gel column chromatography, and the resulting solution was concentrated to give a condensed toluene solution. Ethanol was added to this toluene solution and the toluene solution was concentrated under reduced pressure, whereby an ethanol suspension was obtained. The precipitate was filtrated at approximately 20° C., and the obtained solid was dried at approximately 80° C. under reduced pressure, whereby 13.6 g of a target white solid was obtained in a yield of 81%. The synthesis scheme of Step 2 is shown below.

[Chemical Formula 41]

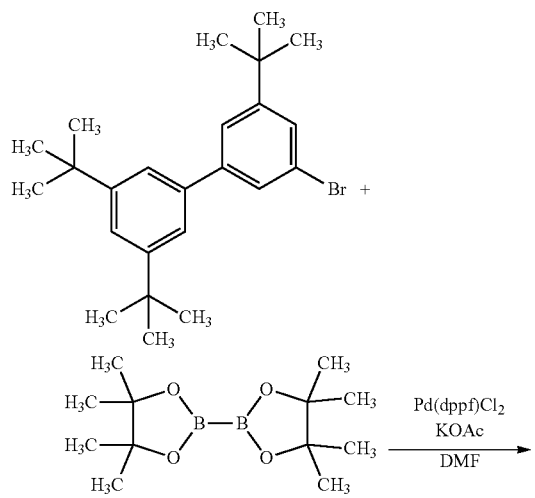

Step 3: Synthesis of 3-bromo-3",5,5',5"-tetra-tert-butyl-1,1':3',1"-terphenyl

In a three-neck flask were put 5.0 g (11.1 mmol) of 2-(3',5,5'-tri-tert-butyl[1,1'-biphenyl]-3-yl)-4,4,5,5-tetramethyl-1,3,2-dioxaborolane, 4.8 g (16.7 mmol) of 1,3-dibromo-5-tert-butylbenzene, 4.6 g (33.3 mmol) of potassium carbonate, 56 mL of toluene, 22 mL of ethanol, and 17 mL of tap water. The mixture was degassed under reduced pressure, and then the air in the flask was replaced with nitrogen. Then, 50 mg (0.22 mmol) of palladium acetate and 116 mg (0.44 mmol) of triphenylphosphine were added, and the mixture was heated at 80° C. for approximately 10 hours. After that, the temperature of the flask was lowered to room temperature, and the mixture was separated into an organic layer and an aqueous layer. Magnesium sulfate was added to this solution to eliminate moisture, whereby this solution was concentrated. The obtained hexane solution was purified by silica gel column chromatography, whereby 3.0 g of a target white solid was obtained in a yield of 51.0%. The synthesis scheme of 3-bromo-3",5,5',5"-tetra-tert-butyl-1,1':3',1"-terphenyl of Step 3 is shown below.

[Chemical Formula 42]

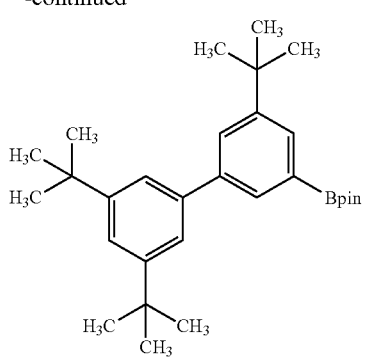

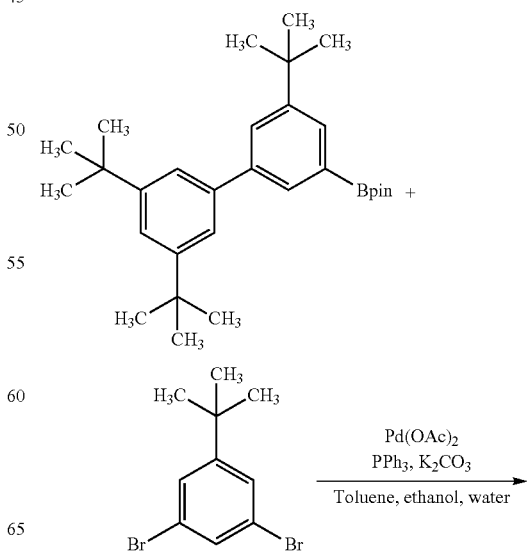

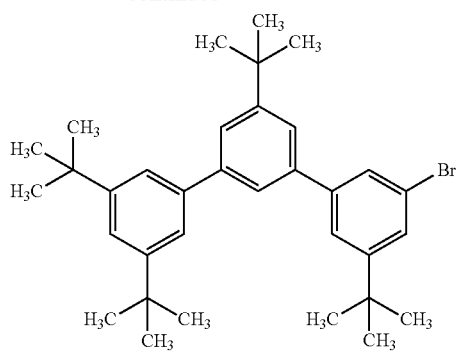

Step 4: Synthesis of mmtBumTPoFBi-02

In a three-neck flask were put 5.8 g (10.9 mmol) of 3-bromo-3",5,5',5"-tetra-tert-butyl-1,1':3',1"-terphenyl obtained in Step 3, 3.9 g (10.9 mmol) of N-(1,1'-biphenyl-4-yl)-N-phenyl-9,9-dimethyl-9H-fluoren-2-amine, 3.1 g (32.7 mmol) of sodium-tert-butoxide, and 55 mL of toluene. The mixture was degassed under reduced pressure, the air in the flask was replaced with nitrogen, 64 mg (0.11 mmol) of bis(dibenzylideneacetone)palladium(0) and 132 mg (0.65 mmol) of tri-tert-butylphosphine were added thereto, and the mixture was heated at 80° C. for approximately 2 hours. After that, the temperature of the flask was lowered to approximately 60° C., approximately 1 mL of water was added, a precipitated solid was separated by filtration, and the solid was washed with toluene. The filtrate was concentrated, and the obtained toluene solution was purified by silica gel column chromatography. The obtained solution was concentrated to give a condensed toluene solution. Ethanol was added to this toluene solution and the toluene solution was concentrated under reduced pressure, whereby an ethanol suspension was obtained. The precipitate was filtered at approximately 20° C., and the obtained solid was dried at approximately 80° C. under reduced pressure, whereby 8.1 g of a target white solid was obtained in a yield of 91%. The synthesis scheme of mmtBumTPoFBi-02 is shown below.

[Chemical Formula 43]

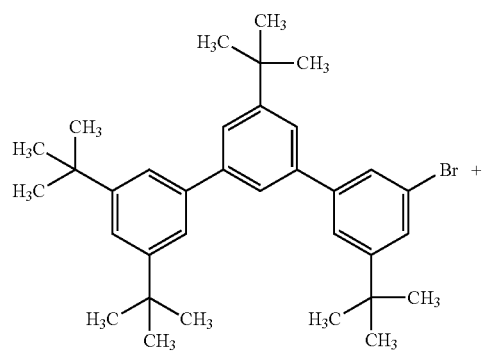

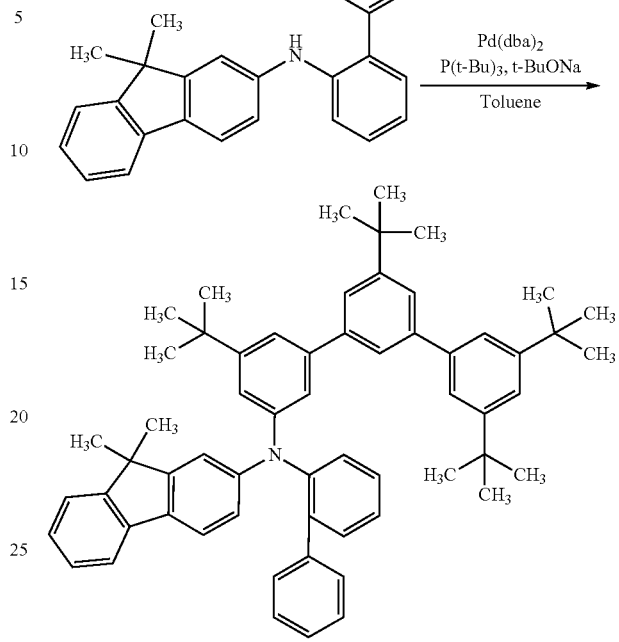

Analysis results by nuclear magnetic resonance ($^1$H-NMR) spectroscopy of the white solid obtained in the above step are shown below. The results show that mmtBumT-PoFBi-02 was synthesized.

$^1$H-NMR. δ (CDCl$_3$): 7.56 (d, 1H, J=7.4 Hz), 7.50 (dd, 1H, J=1.7 Hz), 7.33-7.46 (m, 11H), 7.27-7.29 (m, 2H), 7.22 (dd, 1H, J=2.3 Hz), 7.15 (d, 1H, J=6.9 Hz), 6.98-7.07 (m, 7H), 6.93 (s, 1H), 6.84 (d, 1H, J=6.3 Hz), 1.38 (s, 9H), 1.37 (s, 18H), 1.31 (s, 6H), 1.20 (s, 9H).

This application is based on Japanese Patent Application Serial No. 2021-081940 filed with Japan Patent Office on May 13, 2021, the entire contents of which are hereby incorporated by reference.

What is claimed is:

1. A hole transport layer material for a light-emitting device,
   wherein a GSP_slope that is a potential gradient of a surface potential of an evaporated film of the hole transport layer material is higher than or equal to 20 mV/nm.

2. The hole transport layer material for a light-emitting device, according to claim 1,
   wherein the GSP_slope is lower than or equal to 100 mV/nm.

3. The hole transport layer material for a light-emitting device, according to claim 1,
   wherein an ordinary ray refractive index of the hole transport layer material with respect to light with a wavelength of 450 nm is higher than or equal to 1.50 and lower than or equal to 1.75.

4. The hole transport layer material for a light-emitting device, according to claim 1,
   wherein an ordinary ray refractive index of the hole transport layer material with respect to light with a wavelength of 633 nm is higher than or equal to 1.45 and lower than or equal to 1.70.

5. The hole transport layer material for a light-emitting device, according to claim 1,
wherein a glass transition temperature (Tg) of the hole transport layer material is higher than or equal to 100° C.

6. The hole transport layer material for a light-emitting device, according to claim 1, wherein the hole transport layer material comprises at least three substituents selected from a chain alkyl group having 2 to 5 carbon atoms and a cycloalkyl group having 6 to 12 carbon atoms.

7. The hole transport layer material for a light-emitting device, according to claim 6,
wherein the chain alkyl group is a chain alkyl group having a branch formed of 3 to 5 carbon atoms.

8. The hole transport layer material for a light-emitting device, according to claim 6,
wherein the chain alkyl group is a t-butyl group.

9. The hole transport layer material for a light-emitting device, according to claim 1,
wherein a percentage of carbon atoms forming bonds by $sp^3$ hybrid orbitals in a total number of carbon atoms in a molecule is higher than or equal to 23% and lower than or equal to 55%.

10. The hole transport layer material for a light-emitting device, according to claim 1,
wherein an integral value of signals lower than 4 ppm exceeds an integral value of signals at 4 ppm or higher in a 1H-NMR measurement of the hole transport layer material.

11. The hole transport layer material for a light-emitting device, according to claim 1,
wherein the hole transport layer material has a hole-transport property.

12. The hole transport layer material for a light-emitting device, according to claim 11,
wherein the hole transport layer material is arylamine.

13. The hole transport layer material for a light-emitting device, according to claim 11,
wherein, when the hole transport layer material comprises a condensed aromatic hydrocarbon ring, the condensed aromatic hydrocarbon ring is a bicyclic condensed aromatic ring or a tricyclic condensed aromatic ring and a total number of condensed aromatic hydrocarbon rings in a molecule of the hole transport layer material is one or two.

14. The hole transport layer material for a light-emitting device, according to claim 11,
wherein the hole transport layer material comprises two or less fluorene skeletons in a molecule.

15. An electron blocking layer material comprising the hole transport layer material according to claim 11.

16. A light-emitting device comprising:
an anode;
a cathode; and
an EL layer between the anode and the cathode,
wherein the EL layer comprises a hole-transport layer and a light-emitting layer,
wherein the hole-transport layer is positioned between the anode and the light-emitting layer,
wherein the hole-transport layer is not in contact with the anode,
wherein the hole-transport layer comprises a hole transport layer material, and
wherein a GSP_slope that is a potential gradient of a surface potential of an evaporated film of the hole transport layer material is higher than or equal to 20 mV/nm.

17. The light-emitting device according to claim 16,
wherein the hole-transport layer is in contact with the light-emitting layer.

18. An electronic device comprising:
the light-emitting device according to claim 16; and
at least one of a sensor, an operation button, a speaker, and a microphone.

19. A light-emitting apparatus comprising:
the light-emitting device according to claim 16; and
at least one of a transistor and a substrate.

20. A lighting device comprising:
the light-emitting device according to claim 16; and
a housing.

21. A light-emitting device comprising:
an anode;
a cathode; and
an EL layer between the anode and the cathode,
wherein the EL layer comprises a hole-injection layer, a hole-transport layer, an electron-blocking layer, and a light-emitting layer,
wherein the hole-injection layer, the hole-transport layer, and the electron-blocking layer are positioned between the anode and the light-emitting layer,
wherein the electron-blocking layer is in contact with the light-emitting layer,
wherein the hole-injection layer is in contact with the anode,
wherein the hole-transport layer comprises a hole transport layer material,
wherein the electron-blocking layer comprises an electron blocking layer material, and
wherein a GSP_slope of an evaporated film of the hole transport layer material is lower than a GSP slope of an evaporated film of the electron blocking layer material.

* * * * *